(12) United States Patent
Kontermann et al.

(10) Patent No.: US 12,378,323 B2
(45) Date of Patent: *Aug. 5, 2025

(54) IgM AND IgE HEAVY CHAIN DOMAIN 2 AS COVALENTLY LINKED HOMODIMERIZATION MODULES FOR THE GENERATION OF FUSION PROTEINS WITH DUAL SPECIFICITY

(71) Applicant: UNIVERSITÄT STUTTGART, Stuttgart (DE)

(72) Inventors: Roland Kontermann, Nurtingen (DE); Oliver Seifert, Stuttgart (DE); Aline Plappert, Stuttgart (DE)

(73) Assignee: UNIVERSITAT STUTTGART, Stuttgart (DE)

( * ) Notice: Subject to any disclaimer, the term of this patent is extended or adjusted under 35 U.S.C. 154(b) by 438 days.

This patent is subject to a terminal disclaimer.

(21) Appl. No.: 17/092,423

(22) Filed: Nov. 9, 2020

(65) Prior Publication Data

US 2021/0139606 A1     May 13, 2021

Related U.S. Application Data

(63) Continuation of application No. 15/645,892, filed on Jul. 10, 2017, now Pat. No. 10,875,928, which is a continuation of application No. 14/391,930, filed as application No. PCT/EP2013/001126 on Apr. 16, 2013, now abandoned.

(30) Foreign Application Priority Data

Apr. 16, 2012  (WO) ................. PCT/EP2012/056938

(51) Int. Cl.

| | | |
|---|---|---|
| C07K 16/32 | (2006.01) | |
| A61K 39/395 | (2006.01) | |
| C07K 14/435 | (2006.01) | |
| C07K 14/52 | (2006.01) | |
| C07K 14/525 | (2006.01) | |
| C07K 16/28 | (2006.01) | |
| C07K 16/46 | (2006.01) | |

(52) U.S. Cl.
CPC .......... *C07K 16/32* (2013.01); *A61K 39/3955* (2013.01); *C07K 14/435* (2013.01); *C07K 14/52* (2013.01); *C07K 14/525* (2013.01); *C07K 16/2863* (2013.01); *C07K 16/468* (2013.01); *C07K 2317/24* (2013.01); *C07K 2317/31* (2013.01); *C07K 2317/35* (2013.01); *C07K 2317/524* (2013.01); *C07K 2317/622* (2013.01); *C07K 2317/64* (2013.01); *C07K 2317/73* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 7,754,208 B2 | 7/2010 | Ledbettter et al. | |
| 8,980,266 B2 | 3/2015 | Eckelman et al. | |
| 10,301,368 B2 * | 5/2019 | Sahin | A61P 35/00 |
| 10,875,928 B2 * | 12/2020 | Kontermann | C07K 14/525 |
| 11,142,558 B2 * | 10/2021 | Fischer | C07K 14/525 |
| 2006/0171942 A1 | 8/2006 | Saxon et al. | |
| 2008/0050374 A1 | 2/2008 | Cho et al. | |
| 2008/0227958 A1 * | 9/2008 | Thompson | C07K 16/00 |
| | | | 530/387.3 |
| 2010/0233079 A1 | 9/2010 | Jakob et al. | |
| 2012/0276099 A1 | 11/2012 | Poppe et al. | |

FOREIGN PATENT DOCUMENTS

| | | |
|---|---|---|
| JP | S59-044399 | 3/1984 |
| WO | WO 92/03569 | 3/1992 |
| WO | WO 2000/25722 | 5/2000 |
| WO | WO 2000/47740 | 8/2000 |
| WO | WO 01/87982 | 11/2001 |
| WO | WO 2002/072605 | 9/2002 |
| WO | WO 2002/088317 | 11/2002 |
| WO | WO 2005/017148 | 2/2005 |
| WO | WO 2008/012543 | 1/2008 |
| WO | WO 2008/151088 | 12/2008 |
| WO | WO 2010/010051 | 1/2010 |
| WO | WO 2011/064257 | 6/2011 |

OTHER PUBLICATIONS

Zhang et al., J Biol Chemistry 267(33): 24069-24076 (Year: 1992).*
Hofmann et al., Journal of American Chemical Society 140: 167-175 (Year: 2018).*
Piche-Nicholas et al., MABS 10(1): 81-94 (Year: 2018).*
Colman, "Effects of amino acid sequence changes on antibody-antigen interactions." Research in Immunology, 145(1):33-35 (Jan. 1994).
Hellman et al. "Profound reduction in alergen sensitivity following treatment with a novel allergy vaccine," European Journal of Immunology, 24(2): 415-420 (1994).
MacCallum et al., "Antibody-antigen Interactions: Contact Analysis and Binding Site Topography" J. Mol. Biol., 262:732-745 (1996).
Rudikoff et al., "Single amino acid substitution altering antigen-binding specificity" Proc. Natl. Acad. Sci. USA, 79(6):1979-83 (Mar. 1982).
Sayers et al., "Combining proteasome inhibition with TNF-related apoptosis-inducing ligand (Apo2L/TRAIL) for cancer therapy" Cancer Immunol Immunother 55: 76-84 (2006).

(Continued)

*Primary Examiner* — Phuong Huynh
(74) *Attorney, Agent, or Firm* — McDonnell Boehnen Hulbert & Berghoff LLP

(57) ABSTRACT

The present invention provides a polypeptides comprising a heavy chain domain 2 (HD2) from IgM or IgE and at least one pharmaceutically active moiety, complexes thereof and their use for therapy and prophylaxis.

25 Claims, 47 Drawing Sheets

Specification includes a Sequence Listing.

(56) References Cited

OTHER PUBLICATIONS

Seifert et al., "The IgM CH2 domain as covalently linked homodimerization module for the generation of fusion proteins with dual specificity," Protein Engineering, Deign and Selection, 25(10): 603-612 (2012).
Vernersson et al., "Generation of therapeutic antibody responses against IgE through vaccination," FASEB Journal 16(8): 875-877 (2002).
Vie et al., Human fusion proteins between interleukin 2 and IgM heavy chain are cytotoxic fore cells expressing the Interleukin 2 receptor, PNAS, 89(23): 11337-11341 (1992).
Wang et al., "Sythetic IgE peptide vaccine for immunotherapy of allergy," Vaccine, 21(15): 1580-1590 (2003).
Wu et al., Humanization of a murine monoclonal antibody by simultaneous optimization of framework and CDR residues J. Mol. Biol. 294:151-162 (1999).
The International Search Report for International Application No. PCT/EP2013/001126, mailed Jun. 18, 2013.
Lloyd et al., Protein Engineering, Design & Selection 22:159-168 (Year: 2009).
Edwards et al., J Mol Biol 334(1):103-118 (Year: 2003).
Dorrington et al., Immunological Rev., 1978, vol. 41, p. 3-25.
Gieffers et al., Cancer Research, Apr. 15, 2012, vol. 72, No. 8, Abstract 3856.
Siegemund et al., Cell Death and Disease, 2012, vol. 3, e295, p. 1-11, published online Apr. 12, 2012.

\* cited by examiner

Fig. 2 human MHD2

AELPPKVSVFVPPRDGFFGNPRKSKLICQATGFSPRQIQVSWLREGKQVGSGVTTDQVQAEA
                              |  intradomain
                              |  disulfide bond
KESGPTTYKVTSTLTIKESDWLGQSMFTCRVDHRGLTFQQNASSMCVPD
                                            |         |
                                         N-glycan  interchain
                                                   disulfide bond human EHD2 interchain
                  disulfide bond                N-glycan
                        |                          |
DFTPPTVKILQSSCDGGGHFPPTIQLLCLVSGYTPGTINITWLEDGQVMDVDLSTASTTQEG
                              |  intradomain
                              |  disulfide bond
    ELASTQSELTLSQKHWLSDRTYTCQVTYQGHTFEDSTKKCADSN
                                 |
                             interchain
                           disulfide bond

Alignment human MHD2 and human EHD2

MHD2   AELPPKVSVFVPPRDGFFGNPRKSKLICQATGFSPRQIQVSWLREGKQVGSGVTTD
       | | :      ||       |     |:|   :|::|  |:::||  :|  :    ::|
EHD2   DFTPPTVKILQSSCDGGGHFPPTIQLLCLVSGYTPGTINITWLEDGQVMDVDLSTA

MHD2   QVQAEAKESGPTTYKVTSTLTIKESDWLGQSMFTCRVDHRGLTFQQNASSMCVPD
       |          |  ||:      ||       :|| |     |  ||
EHD2   STTQEGELAS-----TQSELTLSQKHWLSDRTYTCQVTYQGHTFEDSTKKCADSN

Fig. 3
a)
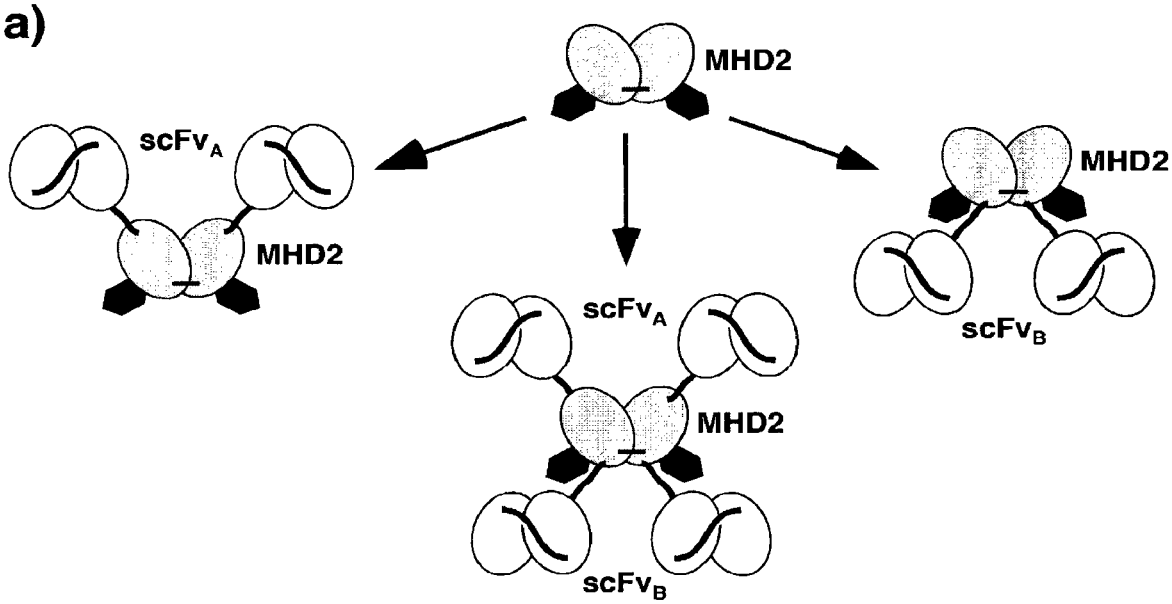
b)
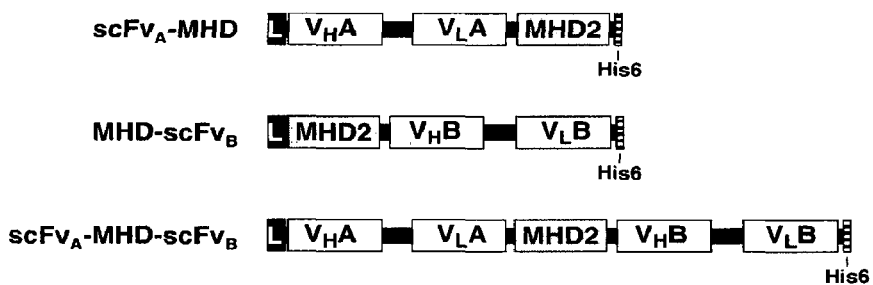
c)
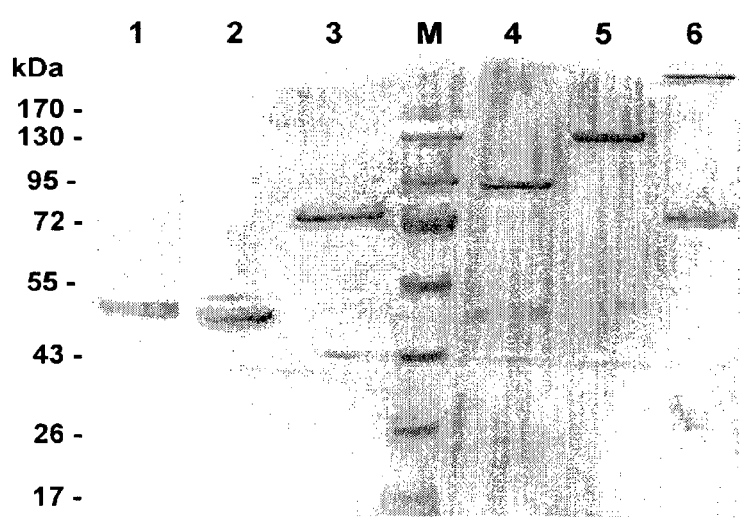

Fig. 4
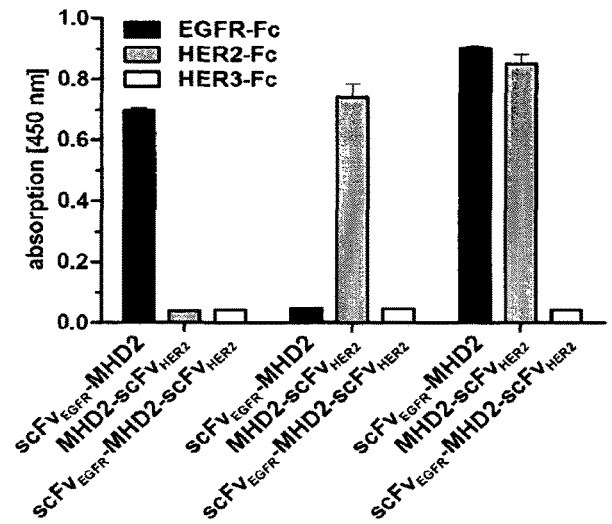
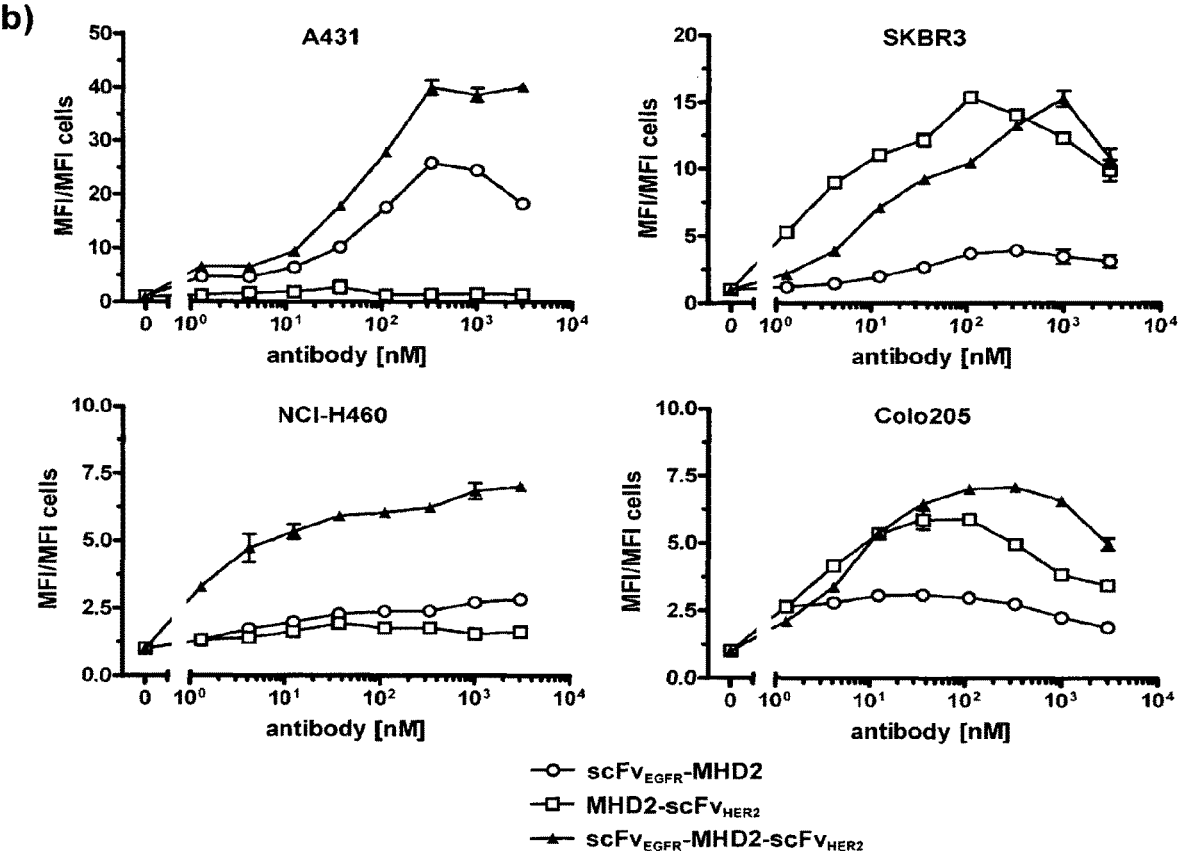

Figure 5:
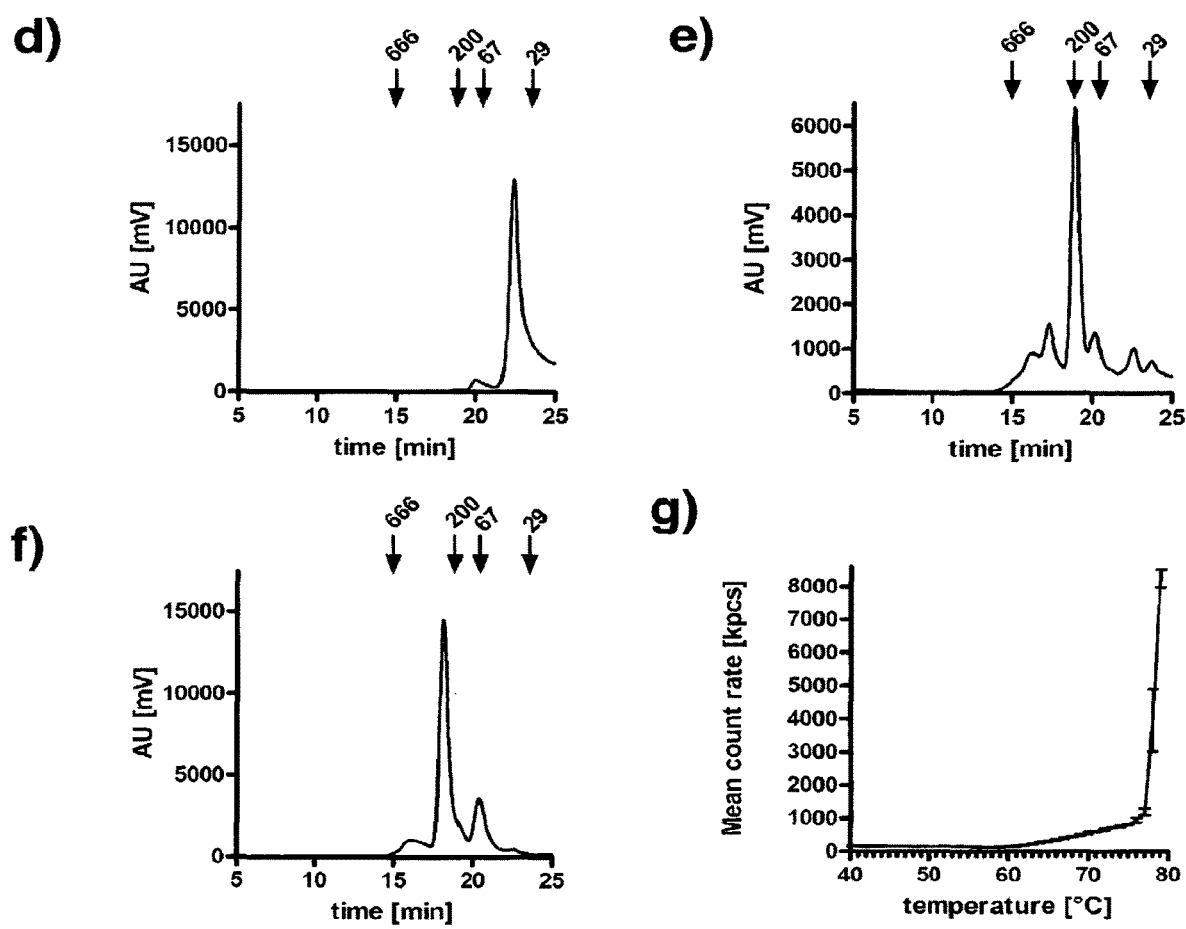

Fig. 5
a) 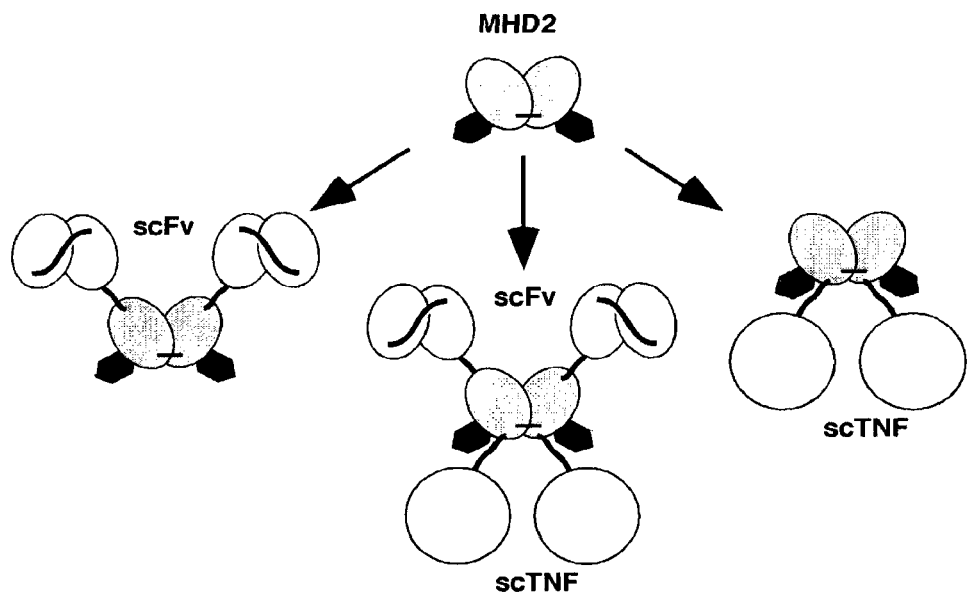
b) 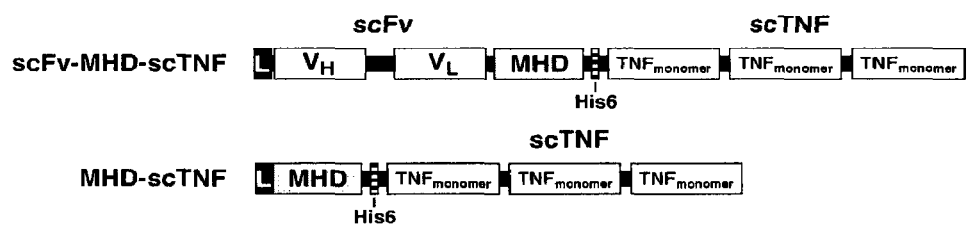
c) 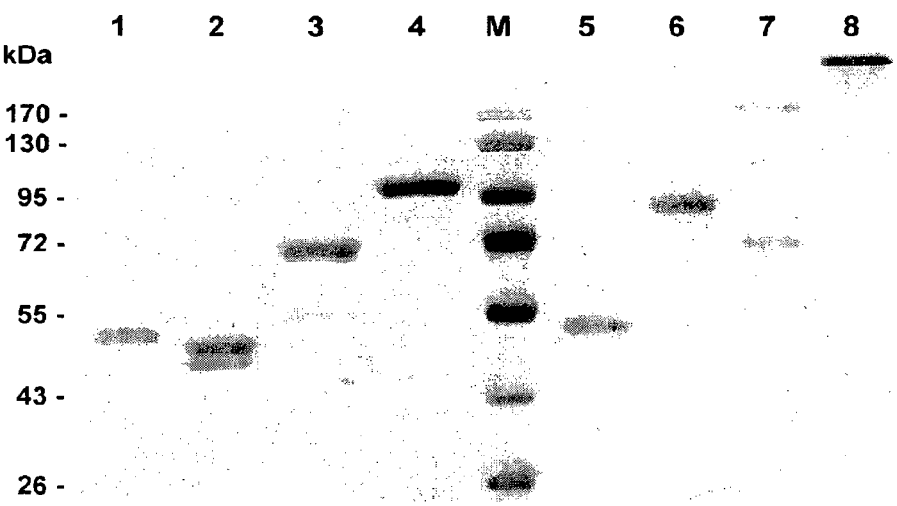

Figure 6:
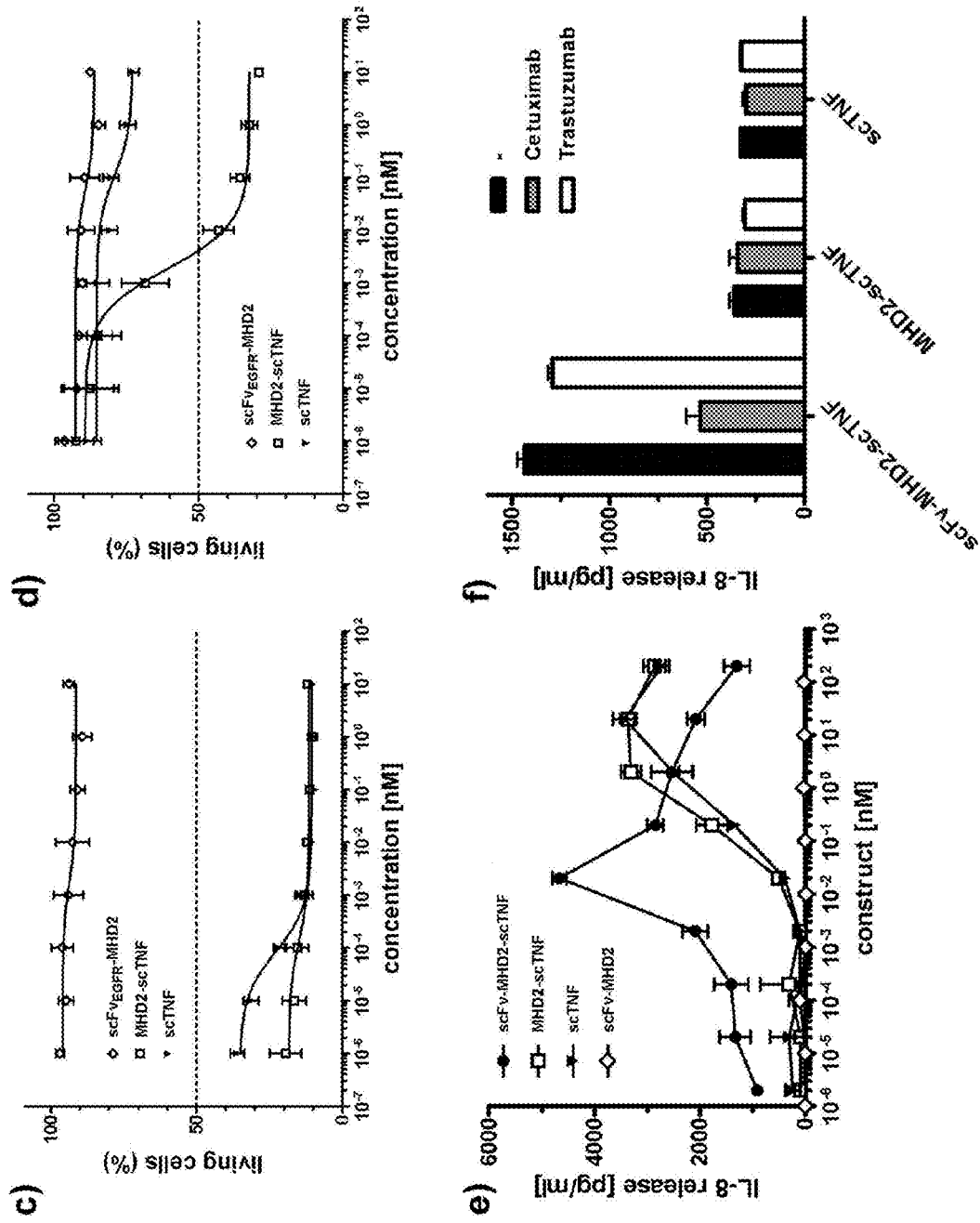

Fig. 6
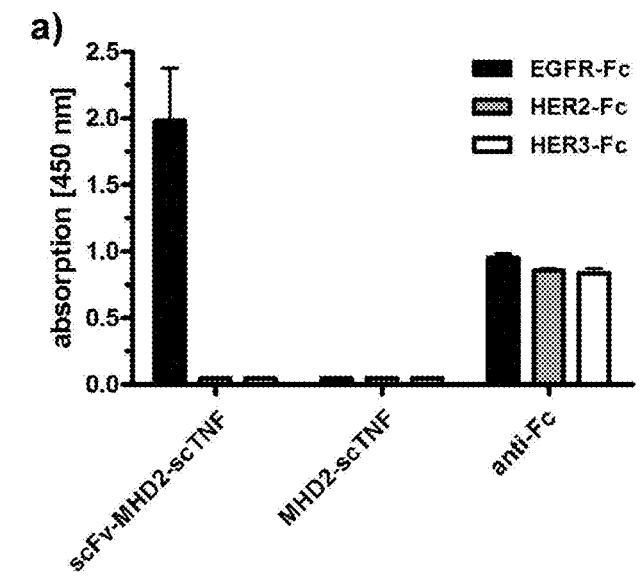
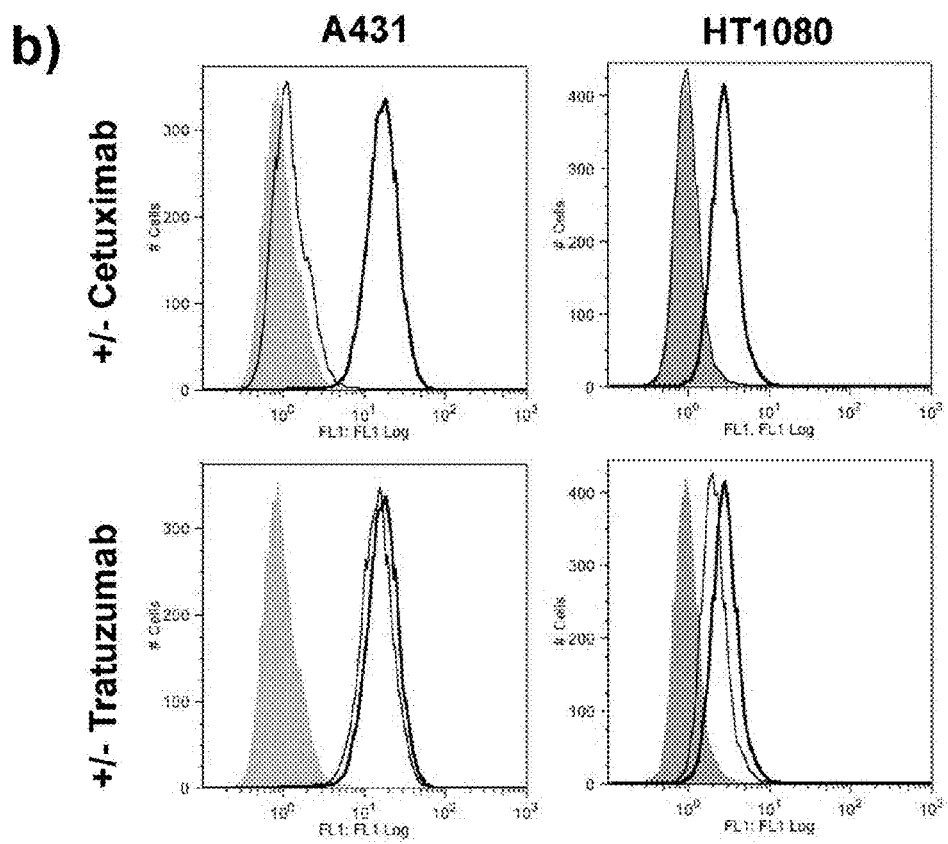

Fig. 7
a) 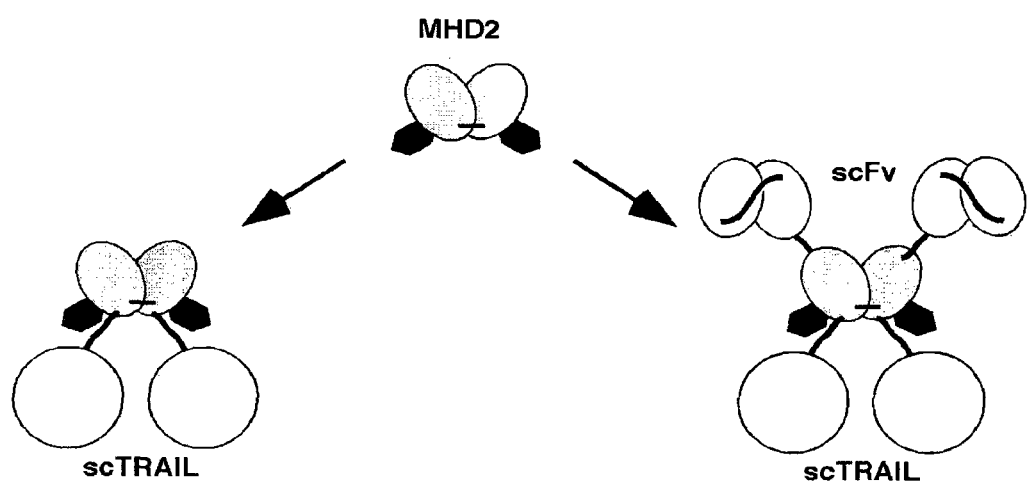
b) 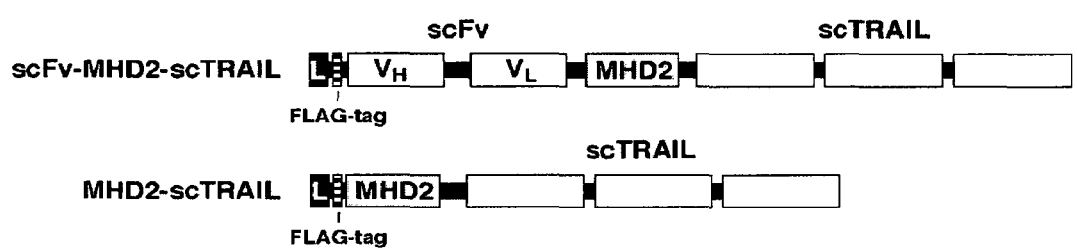
c) 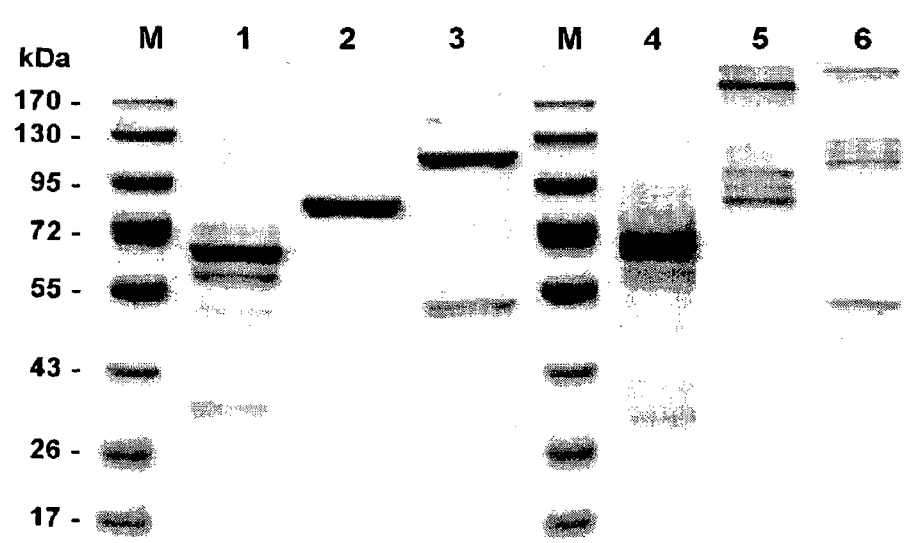

Fig. 9
a) 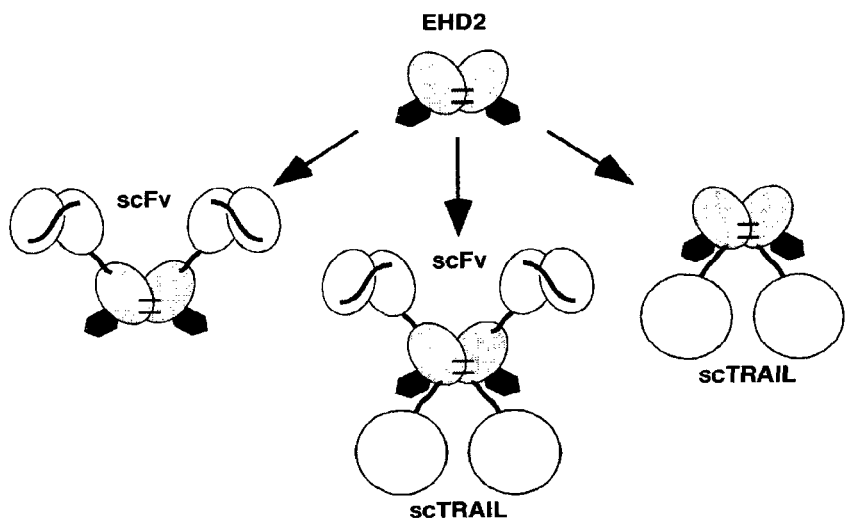
b) 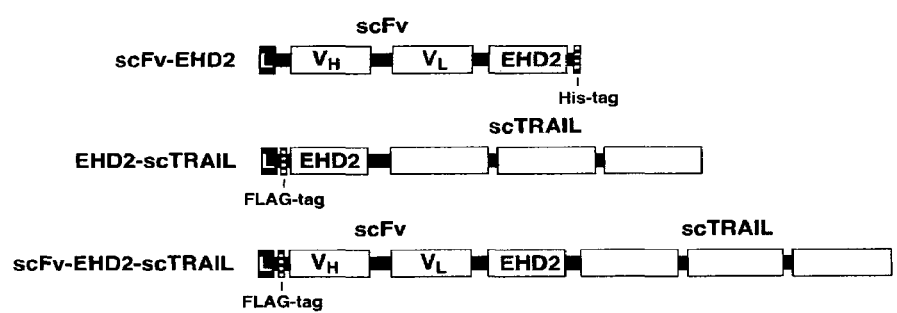
c) 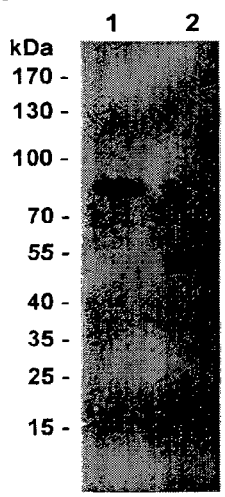
d) 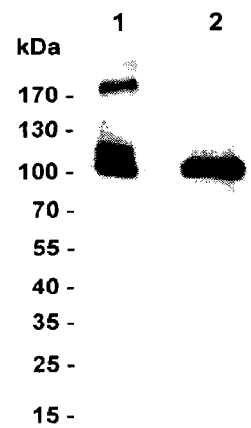
e) 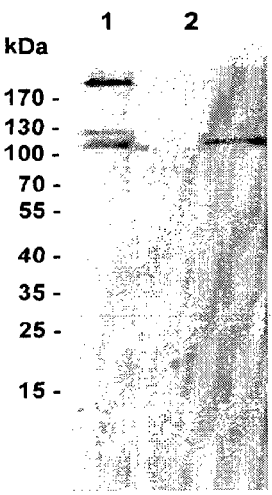

Fig. 11

```
anti-HER2 scFvs (4D5)

ATG AAA TAC CTA TTG CCT ACG GCA GCC GCT GGA TTG TTA TTA CTC GCG GCC CAG CCG GCC   < 60
 M   K   Y   L   L   P   T   A   A   A   G   L   L   L   L   A   A   Q   P   A
ATG GCC GAA GTG CAG CTC GTC GAA AGT GGC GGT GGA CTT GTG CAG CCT GGC GGT TCC CTC   < 120
 M   A   E   V   Q   L   V   E   S   G   G   G   L   V   Q   P   G   G   S   L
AGA CTG TCC TGT GCC GCG TCA GGC TTC AAC ATC AAG GAC ACG TAC ATC CAC TGG GTG AGG   < 180
 R   L   S   C   A   A   S   G   F   N   I   K   D   T   Y   I   H   W   V   R
CAA GCT CCT GGA AAG GGC TTG GAG TGG GTC GCT AGG ATC TAC CCG ACG AAC GGC TAC ACC   < 240
 Q   A   P   G   K   G   L   E   W   V   A   R   I   Y   P   T   N   G   Y   T
AGG TAC GCT GAC TCA GTG AAG GGA AGG TTC ACG ATC AGT GCA GAC ACC AGC AAG AAC ACC   < 300
 R   Y   A   D   S   V   K   G   R   F   T   I   S   A   D   T   S   K   N   T
GCA TAC CTC CAA ATG AAC TCC CTG AGA GCC GAG GAC ACC GCC GTG TAC TAC TGC TCT CGT   < 360
 A   Y   L   Q   M   N   S   L   R   A   E   D   T   A   V   Y   Y   C   S   R
TGG GGT GGA GAT GGC TTC TAC GCT ATG GAC TAC TGG GGT CAA GGC ACA CTG GTG ACC GTG   < 420
 W   G   G   D   G   F   Y   A   M   D   Y   W   G   Q   G   T   L   V   T   V
TCC AGT GGT GGC GGA GGC AGT GGC GGA GGT GGC TCA GGA GGC GGA ACC GGT GAC ATC CAG   < 480
 S   S   G   G   G   G   S   G   G   G   G   S   G   G   T   G   D   I   Q
ATG ACC CAG TCA CCC TCA AGC CTC AGT GCC AGC GTC GGA GAT AGA GTG ACC ATA ACG TGC   < 540
 M   T   Q   S   P   S   S   L   S   A   S   V   G   D   R   V   T   I   T   C
CGA GCT TCT CAG GAT GTG AAC ACG GCA GTG GCT TGG TAT CAG CAA AAG CCT GGG AAA GCC   < 600
 R   A   S   Q   D   V   N   T   A   V   A   W   Y   Q   Q   K   P   G   K   A

CCA AAG CTG CTC ATC TAC TCC GCA TCC TTC CTG TAT AGC GGA GTT CCA TCT AGG TTC TCA   < 660
 P   K   L   L   I   Y   S   A   S   F   L   Y   S   G   V   P   S   R   F   S
GGC TCT AGG TCT GGG ACC GAC TTC ACG CTG ACG ATC TCC TCC CTG CAA CCT GAG GAC TTC   < 720
 G   S   R   S   G   T   D   F   T   L   T   I   S   S   L   Q   P   E   D   F
GCC ACG TAC TAC TGC CAG CAG CAC TAC ACG ACT CCT CCA ACC TTC GGT CAG GGA ACG AAG   < 780
 A   T   Y   Y   C   Q   Q   H   Y   T   T   P   P   T   F   G   Q   G   T   K
GTC GAG ATC AAG CGT
 V   E   I   K   R
```

Fig. 12

```
anti-EGFR scFvs (hu225)

ATG AAA TAC CTA TTG CCT ACG GCA GCC GCT GGA TTG TTA TTA CTC GCG GCC CAG CCG GCC   < 60
 M   K   Y   L   L   P   T   A   A   A   G   L   L   L   L   A   A   Q   P   A
ATG GCG GAA GTG CAG CTG GTT GAA AGC GGC GGT GGT CTG GTT CAG CCG GGT GGC AGC CTG   < 120
 M   A   E   V   Q   L   V   E   S   G   G   G   L   V   Q   P   G   G   S   L
CGT CTG AGC TGT GCG GCG AGC GGC TTT AGC CTG ACC AAC TAT GGC GTG CAT TGG GTG CGT   < 180
 R   L   S   C   A   A   S   G   F   S   L   T   N   Y   G   V   H   W   V   R
CAG GCA CCG GGC AAA GGC CTG GAA TGG CTG GGC GTG ATT TGG AGC GGC GGC AAC ACC GAT   < 240
 Q   A   P   G   K   G   L   E   W   L   G   V   I   W   S   G   G   N   T   D
TAT AAC ACC CCG TTT ACC AGC CGT TTT ACC ATT AGC CGT GAT AAC AGC AAA AAC ACC CTG   < 300
 Y   N   T   P   F   T   S   R   F   T   I   S   R   D   N   S   K   N   T   L
TAT CTG CAG ATG AAC AGC CTG CGT GCG GAA GAT ACC GCG GTG TAT TAT TGC GCG CGT GCG   < 360
 Y   L   Q   M   N   S   L   R   A   E   D   T   A   V   Y   Y   C   A   R   A
CTG ACC TAT TAT GAT TAC GAA TTT GCG TAT TGG GGC CAG GGC ACC ACC GTT ACG GTC TCG   < 420
 L   T   Y   Y   D   Y   E   F   A   Y   W   G   Q   G   T   T   V   T   V   S
AGC GGT GGC GGT GGT AGC GGT GGT GGC GGC TCT GGC GGT GGT GGA TCC GAT ATT CAG CTG   < 480
 S   G   G   G   G   S   G   G   G   G   S   G   G   G   G   S   D   I   Q   L
ACC CAG AGC CCG AGC TTT CTG AGC GCG AGC GTG GGC GAT CGT GTT ACC ATT ACC TGT CGT   < 540
 T   Q   S   P   S   F   L   S   A   S   V   G   D   R   V   T   I   T   C   R
GCA AGC CAG AGC ATT GGC ACC AAC ATT CAT TGG TAT CAG CAG AAA CCG GGC AAA GCG CCG   < 600
 A   S   Q   S   I   G   T   N   I   H   W   Y   Q   Q   K   P   G   K   A   P
AAA CTG CTG ATT AAA TAT GCG AGC GAA AGC ATT AGC GGC GTG CCG AGC CGT TTT AGC GGC   < 660
 K   L   L   I   K   Y   A   S   E   S   I   S   G   V   P   S   R   F   S   G
AGC GGT AGC GGC ACC GAA TTT ACC CTG ACC ATT AGC AGC CTG CAG CCG GAA GAT TTT GCG   < 720
 S   G   S   G   T   E   F   T   L   T   I   S   S   L   Q   P   E   D   F   A
ACC TAT TAT TGC CAG CAG AAC AAC AAC TGG CCG ACC ACC TTT GGT GCG GGC ACC AAA CTG   < 780
 T   Y   Y   C   Q   Q   N   N   N   W   P   T   T   F   G   A   G   T   K   L
GAA ATT AAA CGT
 E   I   K   R
```

Fig. 13 scTNF

```
TCT TCT CGT ACC CCG TCT GAC AAA CCG GTT GCT CAC GTT GTT GCA AAC CCG CAG GCT GAA   < 60
 S   S   R   T   P   S   D   K   P   V   A   H   V   V   A   N   P   Q   A   E
GGT CAA CTG CAA TGG CTG AAC CGT CGT GCT AAC GCT CTG CTG GCT AAC GGT GTT GAA CTG   < 120
 G   Q   L   Q   W   L   N   R   R   A   N   A   L   L   A   N   G   V   E   L
CGT GAC AAC CAG CTG GTT GTT CCG TCT GAA GGC CTG TAC CTG ATC TAC TCC CAG GTT CTG   < 180
 R   D   N   Q   L   V   V   P   S   E   G   L   Y   L   I   Y   S   Q   V   L
TTC AAA GGC CAG GGC TGC CCG TCC ACC CAC GTT CTG CTG ACC CAC ACC ATC TCT CGT ATC   < 240
 F   K   G   Q   G   C   P   S   T   H   V   L   L   T   H   T   I   S   R   I
GCT GTT TCC TAC CAG ACC AAA GTA AAC CTG CTG TCT GCA ATC AAA TCT CCG TGC CAG CGT   < 300
 A   V   S   Y   Q   T   K   V   N   L   L   S   A   I   K   S   P   C   Q   R
GAA ACC CCG GAA GGT GCT GAA GCT AAA CCG TGG TAC GAA CCG ATC TAC CTG GGT GGC GTT   < 360
 E   T   P   E   G   A   E   A   K   P   W   Y   E   P   I   Y   L   G   G   V
TTT CAA CTG GAG AAA GGT GAC CGT CTG TCT GCA GAA ATT AAC CGT CCG GAC TAC CTG GAC   < 420
 F   Q   L   E   K   G   D   R   L   S   A   E   I   N   R   P   D   Y   L   D
TTC GCA GAA TCT GGT CAG GTT TAC TTC GGT ATC ATA GCG CTG GGT GGA GGT GGT TCC TCT   < 480
 F   A   E   S   G   Q   V   Y   F   G   I   I   A   L   G   G   G   G   S   S
TCT CGT ACC CCG TCT GAC AAA CCG GTT GCT CAC GTT GTT GCA AAC CCG CAG GCT GAA GGT   < 540
 S   R   T   P   S   D   K   P   V   A   H   V   V   A   N   P   Q   A   E   G
CAA CTG CAA TGG CTG AAC CGT CGT GCT AAC GCT CTG CTG GCT AAC GGT GTT GAA CTG CGT   < 600
 Q   L   Q   W   L   N   R   R   A   N   A   L   L   A   N   G   V   E   L   R
GAC AAC CAG CTG GTT GTT CCG TCT GAA GGC CTG TAC CTG ATC TAC TCC CAG GTT CTG TTC   < 660
 D   N   Q   L   V   V   P   S   E   G   L   Y   L   I   Y   S   Q   V   L   F
AAA GGC CAG GGC TGC CCG TCC ACC CAC GTT CTG CTG ACC CAC ACC ATC TCT CGT ATC GCT   < 720
 K   G   Q   G   C   P   S   T   H   V   L   L   T   H   T   I   S   R   I   A
GTT TCC TAC CAG ACC AAA GTA AAC CTG CTG TCT GCA ATC AAA TCT CCG TGC CAG CGT GAA   < 780
 V   S   Y   Q   T   K   V   N   L   L   S   A   I   K   S   P   C   Q   R   E
ACC CCG GAA GGT GCT GAA GCT AAA CCG TGG TAC GAA CCG ATC TAC CTG GGT GGC GTT TTT   < 840
 T   P   E   G   A   E   A   K   P   W   Y   E   P   I   Y   L   G   G   V   F
CAA CTG GAG AAA GGT GAC CGT CTG TCT GCA GAA ATT AAC CGT CCG GAC TAC CTG GAC TTC   < 900
 Q   L   E   K   G   D   R   L   S   A   E   I   N   R   P   D   Y   L   D   F
GCA GAA TCT GGT CAG GTT TAC TTC GGT ATC ATC GCT CTG GGT GGT GGA GGA TCC TCT TCT   < 960
 A   E   S   G   Q   V   Y   F   G   I   I   A   L   G   G   G   G   S   S   S
CGT ACC CCG TCT GAC AAA CCG GTT GCT CAC GTT GTT GCA AAC CCG CAG GCT GAA GGT CAA   < 1020
 R   T   P   S   D   K   P   V   A   H   V   V   A   N   P   Q   A   E   G   Q
CTG CAA TGG CTG AAC CGT CGT GCT AAC GCT CTG CTG GCT AAC GGT GTT GAA CTG CGT GAC   < 1080
 L   Q   W   L   N   R   R   A   N   A   L   L   A   N   G   V   E   L   R   D
AAC CAG CTG GTT GTT CCG TCT GAA GGC CTG TAC CTG ATC TAC TCC CAG GTT CTG TTC AAA   < 1140
 N   Q   L   V   V   P   S   E   G   L   Y   L   I   Y   S   Q   V   L   F   K
GGC CAG GGC TGC CCG TCC ACC CAC GTT CTG CTG ACC CAC ACC ATC TCT CGT ATC GCT GTT   < 1200
 G   Q   G   C   P   S   T   H   V   L   L   T   H   T   I   S   R   I   A   V
TCC TAC CAG ACC AAA GTA AAC CTG CTG TCT GCA ATC AAA TCT CCG TGC CAG CGT GAA ACC   < 1260
 S   Y   Q   T   K   V   N   L   L   S   A   I   K   S   P   C   Q   R   E   T
CCG GAA GGT GCT GAA GCT AAA CCG TGG TAC GAA CCG ATC TAC CTG GGT GGC GTT TTT CAA   < 1320
 P   E   G   A   E   A   K   P   W   Y   E   P   I   Y   L   G   G   V   F   Q
CTG GAG AAA GGT GAC CGT CTG TCT GCA GAA ATT AAC CGT CCG GAC TAC CTG GAC TTC GCA   < 1380
 L   E   K   G   D   R   L   S   A   E   I   N   R   P   D   Y   L   D   F   A
GAA TCT GGT CAG GTT TAC TTC GGT ATC ATC GCT CTG
 E   S   G   Q   V   Y   F   G   I   I   A   L
```

Fig. 14

```
scTRAIL

ACG CGT GGC ACC AGC GAG GAA ACC ATT AGC ACC GTC CAG GAA AAG CAG CAG AAC ATC AGC    < 60
 T   R   G   T   S   E   E   T   I   S   T   V   Q   E   K   Q   Q   N   I   S
CCC CTG GTC CGG GAG AGA GGC CCC CAG AGA GTC GCC GCC CAC ATC ACC GGC ACC CGG GGC    < 120
 P   L   V   R   E   R   G   P   Q   R   V   A   A   H   I   T   G   T   R   G
AGA AGC AAC ACC CTG AGC AGC CCC AAC AGC AAG AAC GAG AAG GCC CTG GGC CGG AAG ATC    < 180
 R   S   N   T   L   S   S   P   N   S   K   N   E   K   A   L   G   R   K   I
AAC AGC TGG GAG AGC AGC AGA AGC GGC CAC AGC TTT CTG AGC AAC CTG CAC CTG CGG AAC    < 240
 N   S   W   E   S   S   R   S   G   H   S   F   L   S   N   L   H   L   R   N
GGC GAG CTG GTC ATC CAC GAG AAG GGC TTC TAC TAC ATC TAC AGC CAG ACC TAC TTC AGA    < 300
 G   E   L   V   I   H   E   K   G   F   Y   Y   I   Y   S   Q   T   Y   F   R
TTC CAA GAA GAG ATC AAA GAG AAC ACC AAG AAC GAC AAG CAG ATG GTG CAG TAC ATC TAC    < 360
 F   Q   E   E   I   K   E   N   T   K   N   D   K   Q   M   V   Q   Y   I   Y
AAG TAC ACC AGC TAC CCC GAC CCC ATC CTG CTG ATG AAG TCC GCC CGG AAC AGC TGC TGG    < 420
 K   Y   T   S   Y   P   D   P   I   L   L   M   K   S   A   R   N   S   C   W
TCC AAG GAC GCC GAG TAC GGC CTG TAC AGC ATC TAC CAG GGC GGC ATC TTC GAG CTG AAA    < 480
 S   K   D   A   E   Y   G   L   Y   S   I   Y   Q   G   G   I   F   E   L   K
GAG AAC GAC CGG ATC TTC GTG AGC GTG ACC AAC GAG CAC CTG ATC GAC ATG GAC CAC GAG    < 540
 E   N   D   R   I   F   V   S   V   T   N   E   H   L   I   D   M   D   H   E
GCC AGC TTT TTC GGC GCA TTC CTG GTC GGC GGA GGG GGA TCC GGC GGA GGA AGC ACC TCC    < 600
 A   S   F   F   G   A   F   L   V   G   G   G   G   S   G   G   G   S   T   S
GAA GAG ACT ATC TCT ACA GTC CAG GAA AAA CAG CAG AAT ATC TCC CCT CTC GTG CGG GAG    < 660
 E   E   T   I   S   T   V   Q   E   K   Q   Q   N   I   S   P   L   V   R   E
CGG GGA CCT CAG CGG GTG GCC CAT ATT ACA GGC ACA AGA GGC CGG TCC AAC ACC CTG    < 720
 R   G   P   Q   R   V   A   H   I   T   G   T   R   G   R   S   N   T   L
TCC TCC CCC AAC TCT AAG AAT GAA AAG GCC CTC GGG AGA AAG ATC AAC TCC TGG GAG TCC    < 780
 S   S   P   N   S   K   N   E   K   A   L   G   R   K   I   N   S   W   E   S
AGC CGC TCC GGC CAC TCC TTT CTG TCC AAT CTG CAC CTG AGA AAT GGG GAG CTG GTC ATT    < 840
 S   R   S   G   H   S   F   L   S   N   L   H   L   R   N   G   E   L   V   I
CAC GAA AAG GGG TTT TAC TAT ATC TAC TCT CAG ACA TAC TTT AGG TTT CAG GAA GAA ATT    < 900
 H   E   K   G   F   Y   Y   I   Y   S   Q   T   Y   F   R   F   Q   E   E   I
AAA GAA AAT ACA AAG AAT GAT AAA CAG ATG GTC CAG TAT ATC TAT AAA TAC ACT TCC TAC    < 960
 K   E   N   T   K   N   D   K   Q   M   V   Q   Y   I   Y   K   Y   T   S   Y
CCT GAT CCT ATT CTG CTG ATG AAA AGC GCC AGA AAC AGC TGT TGG AGC AAG GAT GCC GAA   < 1020
 P   D   P   I   L   L   M   K   S   A   R   N   S   C   W   S   K   D   A   E
TAT GGG CTC TAC TCT ATC TAC CAG GGG GGG ATT TTT GAA CTT AAG GAG AAT GAC AGA ATC   < 1080
 Y   G   L   Y   S   I   Y   Q   G   G   I   F   E   L   K   E   N   D   R   I
TTT GTG TCT GTG ACA AAT GAG CAT CTG ATT GAT ATG GAT CAC GAA GCC TCA TTC TTT GGA   < 1140
 F   V   S   V   T   N   E   H   L   I   D   M   D   H   E   A   S   F   F   G
GCC TTT CTT GTG GGA GGG GGC GGA TCT GGT GGC GGA TCC ACC TCT GAG GAA ACA ATA TCC   < 1200
 A   F   L   V   G   G   G   S   G   G   G   S   T   S   E   E   T   I   S
ACC GTC CAG GAG AAG CAA CAA AAC ATT TCC CCC CTC GTG CGC GAA CGG GGC CCA CAG AGG   < 1260
 T   V   Q   E   K   Q   Q   N   I   S   P   L   V   R   E   R   G   P   Q   R
GTC GCC GCT CAC ATT ACA GGG ACC AGG GGC CGC AGC AAT ACC CTG TCC AGC CCG AAC TCC   < 1320
 V   A   A   H   I   T   G   T   R   G   R   S   N   T   L   S   S   P   N   S
AAA AAT GAG AAA GCG CTG GGG CGG AAG ATT AAT TCC TGG GAA AGC TCC AGA AGC GGG CAC   < 1380
 K   N   E   K   A   L   G   R   K   I   N   S   W   E   S   S   R   S   G   H
TCC TTC CTC AGC AAT CTG CAT CTG CGC AAC GGG GAA CTC GTG ATT CAT GAG AAG GGA TTC   < 1440
 S   F   L   S   N   L   H   L   R   N   G   E   L   V   I   H   E   K   G   F
TAT TAT ATC TAT TCC CAG ACA TAC TTC CGC TTC CAA GAG GAA ATT AAA GAG AAC ACT AAA   < 1500
 Y   Y   I   Y   S   Q   T   Y   F   R   F   Q   E   E   I   K   E   N   T   K
AAC GAT AAA CAA ATG GTT CAA TAC ATC TAC AAA TAT ACC TCT TAC CCA GAT CCC ATC CTC   < 1560
 N   D   K   Q   M   V   Q   Y   I   Y   K   Y   T   S   Y   P   D   P   I   L
CTC ATG AAG AGT GCC AGA AAC TCC TGC TGG TCT AAG GAT GCG GAA TAC GGA TTG TAC TCC   < 1620
 L   M   K   S   A   R   N   S   C   W   S   K   D   A   E   Y   G   L   Y   S
ATC TAT CAA GGG GGA ATC TTT GAG TTG AAA GAA AAT GAT CGC ATT TTC GTG TCC GTC ACG   < 1680
 I   Y   Q   G   G   I   F   E   L   K   E   N   D   R   I   F   V   S   V   T
AAT GAG CAC CTC ATA GAC ATG GAT CAT GAA GCG AGT TTC TTC GGG GCT TTC CTC GTG GGT   < 1740
 N   E   H   L   I   D   M   D   H   E   A   S   F   F   G   A   F   L   V   G
TGA
 *
```

Fig. 15 scFv_EGFR-MHD2

```
ATG GAG ACA GAC ACA CTC CTG CTA TGG GTA CTG CTG CTC TGG GTT CCA GGT TCC ACT GGT   < 60
 M   E   T   D   T   L   L   L   W   V   L   L   L   W   V   P   G   S   T   G
GAC GCG GCC CAG CCG GCC ATG GCG GAA GTG CAG CTG GTT GAA AGC GGC GGT GGT CTG GTT   < 120
 D   A   A   Q   P   A   M   A   E   V   Q   L   V   E   S   G   G   G   L   V
CAG CCG GGT GGC AGC CTG CGT CTG AGC TGT GCG GCG AGC GGC TTT AGC CTG ACC AAC TAT   < 180
 Q   P   G   G   S   L   R   L   S   C   A   A   S   G   F   S   L   T   N   Y
GGC GTG CAT TGG GTG CGT CAG GCA CCG GGC AAA GGC CTG GAA TGG CTG GGC GTG ATT TGG   < 240
 G   V   H   W   V   R   Q   A   P   G   K   G   L   E   W   L   G   V   I   W
AGC GGC GGC AAC ACC GAT TAT AAC ACC CCG TTT ACC AGC CGT TTT ACC ATT AGC CGT GAT   < 300
 S   G   G   N   T   D   Y   N   T   P   F   T   S   R   F   T   I   S   R   D
AAC AGC AAA AAC ACC CTG TAT CTG CAG ATG AAC AGC CTG CGT GCG GAA GAT ACC GCG GTG   < 360
 N   S   K   N   T   L   Y   L   Q   M   N   S   L   R   A   E   D   T   A   V
TAT TAT TGC GCG CGT GCG CTG ACC TAT TAT GAT TAC GAA TTT GCG TAT TGG GGC CAG GGC   < 420
 Y   Y   C   A   R   A   L   T   Y   Y   D   Y   E   F   A   Y   W   G   Q   G
ACC ACC GTT ACG GTC TCG AGC GGT GGC GGT GGT AGC GGT GGT GGC GGC TCT GGC GGT GGT   < 480
 T   T   V   T   V   S   S   G   G   G   G   S   G   G   G   G   S   G   G   G
GGA TCC GAT ATT CAG CTG ACC CAG AGC CCG AGC TTT CTG AGC GCG AGC GTG GGC GAT CGT   < 540
 G   S   D   I   Q   L   T   Q   S   P   S   F   L   S   A   S   V   G   D   R
GTT ACC ATT ACC TGT CGT GCA AGC CAG AGC ATT GGC ACC AAC ATT CAT TGG TAT CAG CAG   < 600
 V   T   I   T   C   R   A   S   Q   S   I   G   T   N   I   H   W   Y   Q   Q
AAA CCG GGC AAA GCG CCG AAA CTG CTG ATT AAA TAT GCG AGC GAA AGC ATT AGC GGC GTG   < 660
 K   P   G   K   A   P   K   L   L   I   K   Y   A   S   E   S   I   S   G   V
CCG AGC CGT TTT AGC GGC AGC GGT AGC GGC ACC GAA TTT ACC CTG ACC ATT AGC AGC CTG   < 720
 P   S   R   F   S   G   S   G   S   G   T   E   F   T   L   T   I   S   S   L
CAG CCG GAA GAT TTT GCG ACC TAT TAT TGC CAG CAG AAC AAC AAC TGG CCG ACC ACC TTT   < 780
 Q   P   E   D   F   A   T   Y   Y   C   Q   Q   N   N   N   W   P   T   T   F
GGT GCG GGC ACC AAA CTG GAA ATT AAA CGT GGA AGC TTA GGA GGC TCT GGC GGA GCC GAG   < 840
 G   A   G   T   K   L   E   I   K   R   G   S   L   G   G   S   G   G   A   E
CTG CCC CCT AAG GTG TCC GTG TTC GTG CCC CCC AGG GAC GGC TTC TTC GGC AAC CCC AGA   < 900
 L   P   P   K   V   S   V   F   V   P   P   R   D   G   F   F   G   N   P   R
AAG AGC AAG CTG ATC TGC CAG GCC ACC GGC TTC AGC CCC AGA CAG ATC CAG GTG TCC TGG   < 960
 K   S   K   L   I   C   Q   A   T   G   F   S   P   R   Q   I   Q   V   S   W
CTG CGC GAG GGC AAA CAG GTC GGA AGC GGC GTG ACC ACC GAC CAG GTG CAG GCC GAG GCC   < 1020
 L   R   E   G   K   Q   V   G   S   G   V   T   T   D   Q   V   Q   A   E   A
AAA GAG AGC GGC CCC ACC ACC TAC AAA GTG ACC AGC ACC CTG ACC ATC AAA GAG TCC GAC   < 1080
 K   E   S   G   P   T   T   Y   K   V   T   S   T   L   T   I   K   E   S   D
TGG CTG GGC CAG AGC ATG TTC ACC TGT CGG GTG GAC CAC CGG GGC CTG ACC TTC CAG CAG   < 1140
 W   L   G   Q   S   M   F   T   C   R   V   D   H   R   G   L   T   F   Q   Q
AAC GCC AGC TCT ATG TGC GTG CCC GAC GGC GGA GGG TCC GGC GGA GGT ACC GGA TCC GAA   < 1200
 N   A   S   S   M   C   V   P   D   G   G   G   S   G   G   G   T   G   S   E
TTC GCG GCC GCC CAC CAT CAT CAC CAT CAC TGA
 F   A   A   A   H   H   H   H   H   *
```

Fig. 16

MHD2 - scFv_HER2

```
ATG GAG ACA GAC ACA CTC CTG CTA TGG GTA CTG CTG CTC TGG GTT CCA GGT TCC ACT GGT    < 60
 M   E   T   D   T   L   L   L   W   V   L   L   L   W   V   P   G   S   T   G
GAC GCG GCC CAG CCG GCC AGC GCT GGC GCC GGA AGC TTA GGA GGC TCT GGC GGA GCC GAG    < 120
 D   A   A   Q   P   A   S   A   G   A   G   S   L   G   G   S   G   G   A   E
CTG CCC CCT AAG GTG TCC GTG TTC GTG CCC CCC AGG GAC GGC TTC TTC GGC AAC CCC AGA    < 180
 L   P   P   K   V   S   V   F   V   P   P   R   D   G   F   F   G   N   P   R
AAG AGC AAG CTG ATC TGC CAG GCC ACC GGC TTC AGC CCC AGA CAG ATC CAG GTG TCC TGG    < 240
 K   S   K   L   I   C   Q   A   T   G   F   S   P   R   Q   I   Q   V   S   W
CTG CGC GAG GGC AAA CAG GTC GGA AGC GGC GTG ACC ACC GAC CAG GTG CAG GCC GAG GCC    < 300
 L   R   E   G   K   Q   V   G   S   G   V   T   T   D   Q   V   Q   A   E   A
AAA GAG AGC GGC CCC ACC ACC TAC AAA GTG ACC AGC ACC CTG ACC ATC AAA GAG TCC GAC    < 360
 K   E   S   G   P   T   T   Y   K   V   T   S   T   L   T   I   K   E   S   D
TGG CTG GGC CAG AGC ATG TTC ACC TGT CGG GTG GAC CAC CGG GGC CTG ACC TTC CAG CAG    < 420
 W   L   G   Q   S   M   F   T   C   R   V   D   H   R   G   L   T   F   Q   Q
AAC GCC AGC TCT ATG TGC GTG CCC GAC GGC GGA GGG TCC GGC GGA GGT ACC GGA TCC GGC    < 480
 N   A   S   S   M   C   V   P   D   G   G   G   S   G   G   G   T   G   S   G
GGA GAA GTG CAG CTC GTC GAA AGT GGC GGT GGA CTT GTG CAG CCT GGC GGT TCC CTC AGA    < 540
 G   E   V   Q   L   V   E   S   G   G   G   L   V   Q   P   G   G   S   L   R
CTG TCC TGT GCC GCG TCA GGC TTC AAC ATC AAG GAC ACG TAC ATC CAC TGG GTG AGG CAA    < 600
 L   S   C   A   A   S   G   F   N   I   K   D   T   Y   I   H   W   V   R   Q
GCT CCT GGA AAG GGC TTG GAG TGG GTC GCT AGG ATC TAC CCG ACG AAC GGC TAC ACC AGG    < 660
 A   P   G   K   G   L   E   W   V   A   R   I   Y   P   T   N   G   Y   T   R
TAC GCT GAC TCA GTG AAG GGA AGG TTC ACG ATC AGT GCA GAC ACC AGC AAG AAC ACC GCA    < 720
 Y   A   D   S   V   K   G   R   F   T   I   S   A   D   T   S   K   N   T   A
TAC CTC CAA ATG AAC TCC CTG AGA GCC GAG GAC ACC GCC GTG TAC TAC TGC TCT CGT TGG    < 780
 Y   L   Q   M   N   S   L   R   A   E   D   T   A   V   Y   Y   C   S   R   W
GGT GGA GAT GGC TTC TAC GCT ATG GAC TAC TGG GGT CAA GGC ACA CTG GTG ACC GTG TCC    < 840
 G   G   D   G   F   Y   A   M   D   Y   W   G   Q   G   T   L   V   T   V   S
AGT GGT GGC GGA GGC AGT GGC GGA GGT GGC TCA GGA GGC GGA ACC GGT GAC ATC CAG ATG    < 900
 S   G   G   G   G   S   G   G   G   G   S   G   G   G   T   G   D   I   Q   M
ACC CAG TCA CCC TCA AGC CTC AGT GCC AGC GTC GGA GAT AGA GTG ACC ATA ACG TGC CGA    < 960
 T   Q   S   P   S   S   L   S   A   S   V   G   D   R   V   T   I   T   C   R
GCT TCT CAG GAT GTG AAC ACG GCA GTG GCT TGG TAT CAG CAA AAG CCT GGG AAA GCC CCA    < 1020
 A   S   Q   D   V   N   T   A   V   A   W   Y   Q   Q   K   P   G   K   A   P
AAG CTG CTC ATC TAC TCC GCA TCC TTC CTG TAT AGC GGA GTT CCA TCT AGG TTC TCA GGC    < 1080
 K   L   L   I   Y   S   A   S   F   L   Y   S   G   V   P   S   R   F   S   G
TCT AGG TCT GGG ACC GAC TTC ACG CTG ACG ATC TCC TCC CTG CAA CCT GAG GAC TTC GCC    < 1140
 S   R   S   G   T   D   F   T   L   T   I   S   S   L   Q   P   E   D   F   A
ACG TAC TAC TGC CAG CAG CAC TAC ACG ACT CCT CCA ACC TTC GGT CAG GGA ACG AAG GTC    < 1200
 T   Y   Y   C   Q   Q   H   Y   T   T   P   P   T   F   G   Q   G   T   K   V
GAG ATC AAG CGT GCG GCC GCC CAC CAT CAT CAC CAT CAC TAA
 E   I   K   R   A   A   A   H   H   H   H   H   H   *
```

Fig. 17

Fig. 18

MHD2-scTNF

```
ATG GAG ACA GAC ACA CTC CTG CTA TGG GTA CTG CTG CTC TGG GTT CCA GGT TCC ACT GGT   < 60
 M   E   T   D   T   L   L   L   W   V   L   L   L   W   V   P   G   S   T   G
GAC GCG GCC CAG CCG GCC AGC GCT GGC GCC GGA AGC TTA GGA GGC TCT GGC GGA GCC GAG   < 120
 D   A   A   Q   P   A   S   A   G   A   G   S   L   G   G   S   G   G   A   E
CTG CCC CCT AAG GTG TCC GTG TTC GTG CCC CCC AGG GAC GGC TTC TTC GGC AAC CCC AGA   < 180
 L   P   P   K   V   S   V   F   V   P   P   R   D   G   F   F   G   N   P   R
AAG AGC AAG CTG ATC TGC CAG GCC ACC GGC TTC AGC CCC AGA CAG ATC CAG GTG TCC TGG   < 240
 K   S   K   L   I   C   Q   A   T   G   F   S   P   R   Q   I   Q   V   S   W
CTG CGC GAG GGC AAA CAG GTC GGA AGC GGC GTG ACC ACC GAC CAG GTG CAG GCC GAG GCC   < 300
 L   R   E   G   K   Q   V   G   S   G   V   T   T   D   Q   V   Q   A   E   A
AAA GAG AGC GGC CCC ACC ACC TAC AAA GTG ACC AGC ACC CTG ACC ATC AAA GAG TCC GAC   < 360
 K   E   S   G   P   T   T   Y   K   V   T   S   T   L   T   I   K   E   S   D
TGG CTG GGC CAG AGC ATG TTC ACC TGT CGG GTG GAC CAC CGG GGC CTG ACC TTC CAG CAG   < 420
 W   L   G   Q   S   M   F   T   C   R   V   D   H   R   G   L   T   F   Q   Q
AAC GCC AGC TCT ATG TGC GTG CCC GAC GGC GGA GGG TCC GGC GGA GGT ACC GGA TCC GAA   < 480
 N   A   S   S   M   C   V   P   D   G   G   G   S   G   G   G   T   G   S   E
TTC ATG AGA GGA TCG CAT CAC CAT CAC CAT CAC GGA TCA GCG TCG TCT TCT TCT CGT ACC   < 540
 F   M   R   G   S   H   H   H   H   H   H   G   S   A   S   S   S   S   R   T
CCG TCT GAC AAA CCG GTT GCT CAC GTT GTT GCA AAC CCG CAG GCT GAA GGT CAA CTG CAA   < 600
 P   S   D   K   P   V   A   H   V   V   A   N   P   Q   A   E   G   Q   L   Q
TGG CTG AAC CGT CGT GCT AAC GCT CTG CTG GCT AAC GGT GTT GAA CTG CGT GAC AAC CAG   < 660
 W   L   N   R   R   A   N   A   L   L   A   N   G   V   E   L   R   D   N   Q
CTG GTT GTT CCG TCT GAA GGC CTG TAC CTG ATC TAC TCC CAG GTT CTG TTC AAA GGC CAG   < 720
 L   V   V   P   S   E   G   L   Y   L   I   Y   S   Q   V   L   F   K   G   Q
GGC TGC CCG TCC ACC CAC GTT CTG CTG ACC CAC ACC ATC TCT CGT ATC GCT GTT TCC TAC   < 780
 G   C   P   S   T   H   V   L   L   T   H   T   I   S   R   I   A   V   S   Y
CAG ACC AAA GTA AAC CTG CTG TCT GCA ATC AAA TCT CCG TGC CAG CGT GAA ACC CCG GAA   < 840
 Q   T   K   V   N   L   L   S   A   I   K   S   P   C   Q   R   E   T   P   E
GGT GCT GAA GCT AAA CCG TGG TAC GAA CCG ATC TAC CTG GGT GGC GTT TTT CAA CTG GAG   < 900
 G   A   E   A   K   P   W   Y   E   P   I   Y   L   G   G   V   F   Q   L   E
AAA GGT GAC CGT CTG TCT GCA GAA ATT AAC CGT CCG GAC TAC CTG GAC TTC GCA GAA TCT   < 960
 K   G   D   R   L   S   A   E   I   N   R   P   D   Y   L   D   F   A   E   S
GGT CAG GTT TAC TTC GGT ATC ATA GCG CTG GGT GGA GGT GGT TCC TCT TCT CGT ACC CCG   < 1020
 G   Q   V   Y   F   G   I   I   A   L   G   G   G   G   S   S   S   R   T   P
TCT GAC AAA CCG GTT GCT CAC GTT GTT GCA AAC CCG CAG GCT GAA GGT CAA CTG CAA TGG   < 1080
 S   D   K   P   V   A   H   V   V   A   N   P   Q   A   E   G   Q   L   Q   W
CTG AAC CGT CGT GCT AAC GCT CTG CTG GCT AAC GGT GTT GAA CTG CGT GAC AAC CAG CTG   < 1140
 L   N   R   R   A   N   A   L   L   A   N   G   V   E   L   R   D   N   Q   L
GTT GTT CCG TCT GAA GGC CTG TAC CTG ATC TAC TCC CAG GTT CTG TTC AAA GGC CAG GGC   < 1200
 V   V   P   S   E   G   L   Y   L   I   Y   S   Q   V   L   F   K   G   Q   G
TGC CCG TCC ACC CAC GTT CTG CTG ACC CAC ACC ATC TCT CGT ATC GCT GTT TCC TAC CAG   < 1260
 C   P   S   T   H   V   L   L   T   H   T   I   S   R   I   A   V   S   Y   Q
ACC AAA GTA AAC CTG CTG TCT GCA ATC AAA TCT CCG TGC CAG CGT GAA ACC CCG GAA GGT   < 1320
 T   K   V   N   L   L   S   A   I   K   S   P   C   Q   R   E   T   P   E   G
GCT GAA GCT AAA CCG TGG TAC GAA CCG ATC TAC CTG GGT GGC GTT TTT CAA CTG GAG AAA   < 1380
 A   E   A   K   P   W   Y   E   P   I   Y   L   G   G   V   F   Q   L   E   K
GGT GAC CGT CTG TCT GCA GAA ATT AAC CGT CCG GAC TAC CTG GAC TTC GCA GAA TCT GGT   < 1440
 G   D   R   L   S   A   E   I   N   R   P   D   Y   L   D   F   A   E   S   G
CAG GTT TAC TTC GGT ATC ATC GCT CTG GGT GGT GGA GGA TCC TCT TCT CGT ACC CCG TCT   < 1500
 Q   V   Y   F   G   I   I   A   L   G   G   G   G   S   S   S   R   T   P   S
GAC AAA CCG GTT GCT CAC GTT GTT GCA AAC CCG CAG GCT GAA GGT CAA CTG CAA TGG CTG   < 1560
 D   K   P   V   A   H   V   V   A   N   P   Q   A   E   G   Q   L   Q   W   L
AAC CGT CGT GCT AAC GCT CTG CTG GCT AAC GGT GTT GAA CTG CGT GAC AAC CAG CTG GTT   < 1620
 N   R   R   A   N   A   L   L   A   N   G   V   E   L   R   D   N   Q   L   V
GTT CCG TCT GAA GGC CTG TAC CTG ATC TAC TCC CAG GTT CTG TTC AAA GGC CAG GGC TGC   < 1680
 V   P   S   E   G   L   Y   L   I   Y   S   Q   V   L   F   K   G   Q   G   C
CCG TCC ACC CAC GTT CTG CTG ACC CAC ACC ATC TCT CGT ATC GCT GTT TCC TAC CAG ACC   < 1740
 P   S   T   H   V   L   L   T   H   T   I   S   R   I   A   V   S   Y   Q   T
AAA GTA AAC CTG CTG TCT GCA ATC AAA TCT CCG TGC CAG CGT GAA ACC CCG GAA GGT GCT   < 1800
 K   V   N   L   L   S   A   I   K   S   P   C   Q   R   E   T   P   E   G   A
GAA GCT AAA CCG TGG TAC GAA CCG ATC TAC CTG GGT GGC GTT TTT CAA CTG GAG AAA GGT   < 1860
 E   A   K   P   W   Y   E   P   I   Y   L   G   G   V   F   Q   L   E   K   G
GAC CGT CTG TCT GCA GAA ATT AAC CGT CCG GAC TAC CTG GAC TTC GCA GAA TCT GGT CAG   < 1920
 D   R   L   S   A   E   I   N   R   P   D   Y   L   D   F   A   E   S   G   Q
GTT TAC TTC GGT ATC ATC GCT CTG TGA
 V   Y   F   G   I   I   A   L   *
```

Fig. 19

Fig. 20

MHD2-scTRAIL

```
ATG GAC TGG ACC TGG CGC GTG TTT TGC CTG CTC GCC GTG GCT CCT GGG GCC CAC AGC CTC    < 60
 M   D   W   T   W   R   V   F   C   L   L   A   V   A   P   G   A   H   S   L
GAC GAT TAC AAA GAC GAT GAC GAT AAA GAA TTC GCC GAG CTG CCC CCT AAG GTG TCC GTG    < 120
 D   D   Y   K   D   D   D   D   K   E   F   A   E   L   P   P   K   V   S   V
TTC GTG CCC CCC AGG GAC GGC TTC TTC GGC AAC CCC AGA AAG AGC AAG CTG ATC TGC CAG    < 180
 F   V   P   P   R   D   G   F   F   G   N   P   R   K   S   K   L   I   C   Q
GCC ACC GGC TTC AGC CCC AGA CAG ATC CAG GTG TCC TGG CTG CGC GAG GGC AAA CAG GTC    < 240
 A   T   G   F   S   P   R   Q   I   Q   V   S   W   L   R   E   G   K   Q   V
GGA AGC GGC GTG ACC ACC GAC CAG GTG CAG GCC GAG GCC AAA GAG AGC GGC CCC ACC ACC    < 300
 G   S   G   V   T   T   D   Q   V   Q   A   E   A   K   E   S   G   P   T   T
TAC AAA GTG ACC AGC ACC CTG ACC ATC AAA GAG TCC GAC TGG CTG GGC CAG AGC ATG TTC    < 360
 Y   K   V   T   S   T   L   T   I   K   E   S   D   W   L   G   Q   S   M   F
ACC TGT CGG GTG GAC CAC CGG GGC CTG ACC TTC CAG CAG AAC GCC AGC TCT ATG TGC GTG    < 420
 T   C   R   V   D   H   R   G   L   T   F   Q   Q   N   A   S   S   M   C   V
CCC GAC GAA TTC ACG CGT GGC ACC AGC GAG GAA ACC ATT AGC ACC GTC CAG GAA AAG CAG    < 480
 P   D   E   F   T   R   G   T   S   E   E   T   I   S   T   V   Q   E   K   Q
CAG AAC ATC AGC CCC CTG GTC CGG GAG AGA GGC CCC CAG AGA GTC GCC GCC CAC ATC ACC    < 540
 Q   N   I   S   P   L   V   R   E   R   G   P   Q   R   V   A   A   H   I   T
GGC ACC CGG GGC AGA AGC AAC ACC CTG AGC AGC CCC AAC AGC AAG AAC GAG AAG GCC CTG    < 600
 G   T   R   G   R   S   N   T   L   S   S   P   N   S   K   N   E   K   A   L
GGC CGG AAG ATC AAC AGC TGG GAG AGC AGC AGA AGC GGC CAC AGC TTT CTG AGC AAC CTG    < 660
 G   R   K   I   N   S   W   E   S   S   R   S   G   H   S   F   L   S   N   L
CAC CTG CGG AAC GGC GAG CTG GTC ATC CAC GAG AAG GGC TTC TAC TAC ATC TAC AGC CAG    < 720
 H   L   R   N   G   E   L   V   I   H   E   K   G   F   Y   Y   I   Y   S   Q
ACC TAC TTC AGA TTC CAA GAA GAG ATC AAA GAG AAC ACC AAG AAC GAC AAG CAG ATG GTG    < 780
 T   Y   F   R   F   Q   E   E   I   K   E   N   T   K   N   D   K   Q   M   V
CAG TAC ATC TAC AAG TAC ACC AGC TAC CCC GAC CCC ATC CTG CTG ATG AAG TCC GCC CGG    < 840
 Q   Y   I   Y   K   Y   T   S   Y   P   D   P   I   L   L   M   K   S   A   R
AAC AGC TGC TGG TCC AAG GAC GCC GAG TAC GGC CTG TAC AGC ATC TAC CAG GGC GGC ATC    < 900
 N   S   C   W   S   K   D   A   E   Y   G   L   Y   S   I   Y   Q   G   G   I
TTC GAG CTG AAA GAG AAC CGG ATC TTC GTG AGC GTG ACC AAC GAG CAC CTG ATC GAC        < 960
 F   E   L   K   E   N   R   I   F   V   S   V   T   N   E   H   L   I   D
ATG GAC CAC GAG GCC AGC TTT TTC GGC GCA TTC CTG GTC GGC GGA GGG GGA TCC GGC GGA    < 1020
 M   D   H   E   A   S   F   F   G   A   F   L   V   G   G   G   G   S   G   G
GGA AGC ACC TCC GAA GAG ACT ATC TCT ACA GTC CAG GAA AAA CAG CAG AAT ATC TCC CCT    < 1080
 G   S   T   S   E   E   T   I   S   T   V   Q   E   K   Q   Q   N   I   S   P
CTC GTG CGG GAG CGG GGA CCT CAG CGG GTG GCC GCC CAT ATT ACA GGC ACA AGA GGC CGG    < 1140
 L   V   R   E   R   G   P   Q   R   V   A   A   H   I   T   G   T   R   G   R
TCC AAC ACC CTG TCC TCC CCC AAC TCT AAG AAT GAA AAG GCC CTC GGG AGA AAG ATC AAC    < 1200
 S   N   T   L   S   S   P   N   S   K   N   E   K   A   L   G   R   K   I   N
TCC TGG GAG TCC AGC CGC TCC GGC CAC TCC TTT CTG TCC AAT CTG CAC CTG AGA AAT GGG    < 1260
 S   W   E   S   S   R   S   G   H   S   F   L   S   N   L   H   L   R   N   G
GAG CTG GTC ATT CAC GAA AAG GGG TTT TAC TAT ATC TAC TCT CAG ACA TAC TTT AGG TTT    < 1320
 E   L   V   I   H   E   K   G   F   Y   Y   I   Y   S   Q   T   Y   F   R   F
CAG GAA GAA ATT AAA GAA AAT ACA AAG AAT GAT AAA CAG ATG GTC CAG TAT ATC TAT AAA    < 1380
 Q   E   E   I   K   E   N   T   K   N   D   K   Q   M   V   Q   Y   I   Y   K
TAC ACT TCC TAC CCT GAT CCT ATT CTG CTG ATG AAA AGC GCC AGA AAC AGC TGT TGG AGC    < 1440
 Y   T   S   Y   P   D   P   I   L   L   M   K   S   A   R   N   S   C   W   S
AAG GAT GCC GAA TAT GGG CTC TAC TCT ATC TAC CAG GGG GGG ATT TTT GAA CTT AAG GAG    < 1500
 K   D   A   E   Y   G   L   Y   S   I   Y   Q   G   G   I   F   E   L   K   E
AAT GAC AGA ATC TTT GTG TCT GTG ACA AAT GAG CAT CTG ATT GAT ATG GAT CAC GAA GCC    < 1560
 N   D   R   I   F   V   S   V   T   N   E   H   L   I   D   M   D   H   E   A
TCA TTC TTT GGA GCC TTT CTT GTG GGA GGG GGC GGA TCT GGT GGC GGA TCC ACC TCT GAG    < 1620
 S   F   F   G   A   F   L   V   G   G   G   G   S   G   G   G   S   T   S   E
GAA ACA ATA TCC ACC GTC CAG GAG AAG CAA CAA AAT ATT TCC CCC CTC GTG CGC GAA CGG    < 1680
 E   T   I   S   T   V   Q   E   K   Q   Q   N   I   S   P   L   V   R   E   R
GGC CCA CAG AGG GTC GCC GCT CAC ATT ACA GGG ACC AGG GGC CGC AGC AAT ACC CTG TCC    < 1740
 G   P   Q   R   V   A   A   H   I   T   G   T   R   G   R   S   N   T   L   S
AGC CCG AAC TCC AAA AAT GAG AAA GCG CTG GGG CGG AAG ATT AAT TCC TGG GAA AGC TCC    < 1800
 S   P   N   S   K   N   E   K   A   L   G   R   K   I   N   S   W   E   S   S
AGA AGC GGG CAC TCC TTC CTC AGC AAT CTG CAT CTG CGC AAC GGG GAA CTC GTG ATT CAT    < 1860
 R   S   G   H   S   F   L   S   N   L   H   L   R   N   G   E   L   V   I   H
GAG AAG GGA TTC TAT TAT ATC TAT TCC CAG ACA TAC TTC CGC TTC CAA GAG GAA ATT AAA    < 1920
 E   K   G   F   Y   Y   I   Y   S   Q   T   Y   F   R   F   Q   E   E   I   K
GAG AAC ACT AAA AAC GAT AAA CAA ATG GTT CAA TAC ATC TAC AAA TAT ACC TCT TAC CCA    < 1980
 E   N   T   K   N   D   K   Q   M   V   Q   Y   I   Y   K   Y   T   S   Y   P
GAT CCC ATC CTC CTC ATG AAG AGT GCC AGA AAC TCC TGC TGG TCT AAG GAT GCG GAA TAC    < 2040
 D   P   I   L   L   M   K   S   A   R   N   S   C   W   S   K   D   A   E   Y
GGA TTG TAC TCC ATC TAT CAA GGG GGA ATC TTT GAG TTG AAA GAA AAT GAT CGC ATT TTC    < 2100
 G   L   Y   S   I   Y   Q   G   G   I   F   E   L   K   E   N   D   R   I   F
GTG TCC GTC ACG AAT GAG CAC CTC ATA GAC ATG GAT CAT GAA GCG AGT TTC TTC GGG GCT    < 2160
 V   S   V   T   N   E   H   L   I   D   M   D   H   E   A   S   F   F   G   A
TTC CTC GTG GGT TGA
 F   L   V   G   *
```

Fig. 21

Fig. 22

Fig. 23 scFvEGFR-EHD2

```
ATG GAG ACA GAC ACA CTC CTG CTA TGG GTA CTG CTG CTC TGG GTT CCA GGT TCC ACT GGT   < 60
 M   E   T   D   T   L   L   L   W   V   L   L   L   W   V   P   G   S   T   G
GAC GCG GCC CAG CCG GCC ATG GCG GAA GTG CAG CTG GTT GAA AGC GGC GGT GGT CTG GTT   < 120
 D   A   A   Q   P   A   M   A   E   V   Q   L   V   E   S   G   G   G   L   V
CAG CCG GGT GGC AGC CTG CGT CTG AGC TGT GCG GCG AGC GGC TTT AGC CTG ACC AAC TAT   < 180
 Q   P   G   G   S   L   R   L   S   C   A   A   S   G   F   S   L   T   N   Y
GGC GTG CAT TGG GTG CGT CAG GCA CCG GGC AAA GGC CTG GAA TGG CTG GGC GTG ATT TGG   < 240
 G   V   H   W   V   R   Q   A   P   G   K   G   L   E   W   L   G   V   I   W
AGC GGC GGC AAC ACC GAT TAT AAC ACC CCG TTT ACC AGC CGT TTT ACC ATT AGC CGT GAT   < 300
 S   G   G   N   T   D   Y   N   T   P   F   T   S   R   F   T   I   S   R   D
AAC AGC AAA AAC ACC CTG TAT CTG CAG ATG AAC AGC CTG CGT GCG GAA GAT ACC GCG GTG   < 360
 N   S   K   N   T   L   Y   L   Q   M   N   S   L   R   A   E   D   T   A   V
TAT TAT TGC GCG CGT GCG CTG ACC TAT TAT GAT TAC GAA TTT GCG TAT TGG GGC CAG GGC   < 420
 Y   Y   C   A   R   A   L   T   Y   Y   D   Y   E   F   A   Y   W   G   Q   G
ACC ACC GTT ACG GTC TCG AGC GGT GGC GGT GGT AGC GGT GGT GGC GGC TCT GGC GGT GGT   < 480
 T   T   V   T   V   S   S   G   G   G   G   S   G   G   G   G   S   G   G   G
GGA TCC GAT ATT CAG CTG ACC CAG AGC CCG AGC TTT CTG AGC GCG AGC GTG GGC GAT CGT   < 540
 G   S   D   I   Q   L   T   Q   S   P   S   F   L   S   A   S   V   G   D   R
GTT ACC ATT ACC TGT CGT GCA AGC CAG AGC ATT GGC ACC AAC ATT CAT TGG TAT CAG CAG   < 600
 V   T   I   T   C   R   A   S   Q   S   I   G   T   N   I   H   W   Y   Q   Q
AAA CCG GGC AAA GCG CCG AAA CTG CTG ATT AAA TAT GCG AGC GAA AGC ATT AGC GGC GTG   < 660
 K   P   G   K   A   P   K   L   L   I   K   Y   A   S   E   S   I   S   G   V
CCG AGC CGT TTT AGC GGC AGC GGT AGC GGC ACC GAA TTT ACC CTG ACC ATT AGC AGC CTG   < 720
 P   S   R   F   S   G   S   G   S   G   T   E   F   T   L   T   I   S   S   L
CAG CCG GAA GAT TTT GCG ACC TAT TAT TGC CAG CAG AAC AAC AAC TGG CCG ACC ACC TTT   < 780
 Q   P   E   D   F   A   T   Y   Y   C   Q   Q   N   N   N   W   P   T   T   F
GGT GCG GGC ACC AAA CTG GAA ATT AAA CGT GGA AGC TTA GGC GGC TCT GGC GGC GAT TTC   < 840
 G   A   G   T   K   L   E   I   K   R   G   S   L   G   G   S   G   G   D   F
ACC CCC CCC ACA GTG AAG ATC CTC CAG AGC AGC TGT GAC GGC GGA GGC CAC TTC CCA CCT   < 900
 T   P   P   T   V   K   I   L   Q   S   S   C   D   G   G   H   F   P   P
ACC ATC CAG CTG CTG TGT CTG GTG TCC GGC TAC ACC CCC GGC ACC ATC AAC ATC ACC TGG   < 960
 T   I   Q   L   L   C   L   V   S   G   Y   T   P   G   T   I   N   I   T   W
CTG GAA GAT GGA CAA GTG ATG GAC GTG GAC CTG AGC ACC GCC AGC ACC ACA CAG GAA GGC   < 1020
 L   E   D   G   Q   V   M   D   V   D   L   S   T   A   S   T   T   Q   E   G
GAG CTG GCC TCT ACC CAG AGC GAG CTG ACA CTG AGC CAG AAG CAC TGG CTG AGC GAC CGG   < 1080
 E   L   A   S   T   Q   S   E   L   T   L   S   Q   K   H   W   L   S   D   R
ACC TAC ACC TGT CAA GTG ACC TAC CAG GGC CAC ACC TTC GAG GAC AGC ACC AAG AAG TGC   < 1140
 T   Y   T   C   Q   V   T   Y   Q   G   H   T   F   E   D   S   T   K   K   C
GCC GAC AGC AAC GGG GGA GGA TCT GGC GGA GGT ACC GGA TCC GAA TTC GCG GCC GCC CAC   < 1200
 A   D   S   N   G   G   G   S   G   G   G   T   G   S   E   F   A   A   A   H
CAT CAT CAC CAT CAC TAA
 H   H   H   H   H   *
```

Fig. 24

```
BHD2-scTRAIL
ATG GAG ACA GAC ACA CTC CTG CTA TGG GTA CTG CTG CTC TGG GTT CCA GGT TCC ACC GGT   < 60
 M   E   T   D   T   L   L   L   W   V   L   L   L   W   V   P   G   S   T   G
GAC TAC AAA GAC GAT GAC GAT AAA GGC GGT GGC GGA TCA GCG GCC CAG CCG GCC GAT TTC   < 120
 D   Y   K   D   D   D   D   K   G   G   G   G   S   A   A   Q   P   A   D   F
ACC CCC CCC ACA GTG AAG ATC CTC CAG AGC AGC TGT GAC GGC GGA GGC CAC TTC CCA CCT   < 180
 T   P   P   T   V   K   I   L   Q   S   S   C   D   G   G   G   H   F   P   P
ACC ATC CAG CTG CTG TGT CTG GTG TCC GGC TAC ACC CCC GGC ACC ATC AAC ATC ACC TGG   < 240
 T   I   Q   L   L   C   L   V   S   G   Y   T   P   G   T   I   N   I   T   W
CTG GAA GAT GGA CAA GTG ATG GAC GTG GAC CTG AGC ACC GCC AGC ACC ACA CAG GAA GGC   < 300
 L   E   D   G   Q   V   M   D   V   D   L   S   T   A   S   T   T   Q   E   G
GAG CTG GCC TCT ACC CAG AGC GAG CTG ACA CTG AGC CAG AAG CAC TGG CTG AGC GAC CGG   < 360
 E   L   A   S   T   Q   S   E   L   T   L   S   Q   K   H   W   L   S   D   R
ACC TAC ACC TGT CAA GTG ACC TAC CAG GGC CAC ACC TTC GAG GAC AGC ACC AAG AAG TGC   < 420
 T   Y   T   C   Q   V   T   Y   Q   G   H   T   F   E   D   S   T   K   K   C
GCC GAC AGC AAC GGG GGA AGC GGC GGT GAA TTC ACG CGT GGC ACC AGC GAG GAA ACC ATT   < 480
 A   D   S   N   G   G   S   G   G   E   F   T   R   G   T   S   E   E   T   I
AGC ACC GTC CAG GAA AAG CAG CAG AAC ATC AGC CCC CTG GTC CGG GAG AGA GGC CCC CAG   < 540
 S   T   V   Q   E   K   Q   Q   N   I   S   P   L   V   R   E   R   G   P   Q
AGA GTC GCC GCC CAC ATC ACC GGC ACC CGG GGC AGA AGC AAC ACC CTG AGC AGC CCC AAC   < 600
 R   V   A   A   H   I   T   G   T   R   G   R   S   N   T   L   S   S   P   N
AGC AAG AAC GAG AAG GCC CTG GGC CGG AAG ATC AAC AGC TGG GAG AGC AGC AGA AGC GGC   < 660
 S   K   N   E   K   A   L   G   R   K   I   N   S   W   E   S   S   R   S   G
CAC AGC TTT CTG AGC AAC CTG CAC CTG CGG AAC GGC GAG CTG GTC ATC CAC GAG AAG GGC   < 720
 H   S   F   L   S   N   L   H   L   R   N   G   E   L   V   I   H   E   K   G
TTC TAC TAC ATC TAC AGC CAG ACC TAC TTC AGA TTC CAA GAA GAG ATC AAA GAG AAC ACC   < 780
 F   Y   Y   I   Y   S   Q   T   Y   F   R   F   Q   E   E   I   K   E   N   T
AAG AAC GAC AAG CAG ATG GTG CAG TAC ATC TAC AAG TAC ACC AGC TAC CCC GAC CCC ATC   < 840
 K   N   D   K   Q   M   V   Q   Y   I   Y   K   Y   T   S   Y   P   D   P   I
CTG CTG ATG AAG TCC GCC CGG AAC AGC TGC TGG TCC AAG GAC GCC GAG TAC GGC CTG TAC   < 900
 L   L   M   K   S   A   R   N   S   C   W   S   K   D   A   E   Y   G   L   Y
AGC ATC TAC CAG GGC GGC ATC TTC GAG CTG AAA GAG AAC GAC CGG ATC TTC GTG AGC GTG   < 960
 S   I   Y   Q   G   G   I   F   E   L   K   E   N   D   R   I   F   V   S   V
ACC AAC GAG CAC CTG ATC GAC ATG GAC CAC GAG GCC AGC TTT TTC GGC GCA TTC CTG GTC   < 1020
 T   N   E   H   L   I   D   M   D   H   E   A   S   F   F   G   A   F   L   V
GGC GGA GGG GGA TCC GGC GGA GGA AGC ACC TCC GAA GAG ACT ATC TCT ACA GTC CAG GAA   < 1080
 G   G   G   G   S   G   G   G   S   T   S   E   E   T   I   S   T   V   Q   E
AAA CAG CAG AAT ATC TCC CCT CTC GTG CGG GAG CGG GGA CCT CAG CGG GTG GCC GCC CAT   < 1140
 K   Q   Q   N   I   S   P   L   V   R   E   R   G   P   Q   R   V   A   A   H
ATT ACA GGC ACA AGA GGC CGG TCC AAC ACC CTG TCC TCC CCC AAC TCT AAG AAT GAA AAG   < 1200
 I   T   G   T   R   G   R   S   N   T   L   S   S   P   N   S   K   N   E   K
GCC CTC GGG AGA AAG ATC AAC TCC TGG GAG TCC AGC CGC TCC GGC CAC TCC TTT CTG TCC   < 1260
 A   L   G   R   K   I   N   S   W   E   S   S   R   S   G   H   S   F   L   S
AAT CTG CAC CTG AGA AAT GGG GAG CTG GTC ATT CAC GAA AAG GGG TTT TAC TAT ATC TAC   < 1320
 N   L   H   L   R   N   G   E   L   V   I   H   E   K   G   F   Y   Y   I   Y
TCT CAG ACA TAC TTT AGG TTT CAG GAA GAA ATT AAA GAA AAT ACA AAG AAT GAT AAA CAG   < 1380
 S   Q   T   Y   F   R   F   Q   E   E   I   K   E   N   T   K   N   D   K   Q
ATG GTC CAG TAT ATC TAT AAA TAC ACT TCC TAC CCT GAT CCT ATT CTG CTG ATG AAA AGC   < 1440
 M   V   Q   Y   I   Y   K   Y   T   S   Y   P   D   P   I   L   L   M   K   S
GCC AGA AAC AGC TGT TGG AGC AAG GAT GCC GAA TAT GGG CTC TAC TCT ATC TAC CAG GGG   < 1500
 A   R   N   S   C   W   S   K   D   A   E   Y   G   L   Y   S   I   Y   Q   G
GGG ATT TTT GAA CTT AAG GAG AAT GAC AGA ATC TTT GTG TCT GTG ACA AAT GAG CAT CTG   < 1560
 G   I   F   E   L   K   E   N   D   R   I   F   V   S   V   T   N   E   H   L
ATT GAT ATG GAT CAC GAA GCC TCA TTC TTT GGA GCC TTT CTT GTG GGA GGG GGC GGA TCT   < 1620
 I   D   M   D   H   E   A   S   F   F   G   A   F   L   V   G   G   G   G   S
GGT GGC GGA TCC ACC TCT GAG GAA ACA ATA TCC ACC GTC CAG GAG AAG CAA CAA AAC ATT   < 1680
 G   G   G   S   T   S   E   E   T   I   S   T   V   Q   E   K   Q   Q   N   I
TCC CCC CTC GTG CGC GAA CGG GGC CCA CAG AGG GTC GCC GCT CAC ATT ACA GGG ACC AGG   < 1740
 S   P   L   V   R   E   R   G   P   Q   R   V   A   A   H   I   T   G   T   R
GGC CGC AGC AAT ACC CTG TCC AGC CCC AAC TCC AAA AAT GAG AAA GCG CTG GGC CGG AAG   < 1800
 G   R   S   N   T   L   S   S   P   N   S   K   N   E   K   A   L   G   R   K
ATT AAT TCC TGG GAA AGC TCC AGA AGC GGG CAC TCC TTC TCA GCA ATC TGC ATC TGC CGC   < 1860
 I   N   S   W   E   S   S   R   S   G   H   S   F   L   S   N   L   H   L   R
AAC GGG GAA CTC GTG ATT CAT GAG AAG GGA TTC TAT TAT ATC TAT TCC CAG ACA TAC TTC   < 1920
 N   G   E   L   V   I   H   E   K   G   F   Y   Y   I   Y   S   Q   T   Y   F
CGC TTC CAA GAG GAA ATT AAA GAG AAC ACT AAA AAC GAT AAA CAA ATG GTT CAA TAC ATC   < 1980
 R   F   Q   E   E   I   K   E   N   T   K   N   D   K   Q   M   V   Q   Y   I
TAC AAA TAT ACC TCT TAC CCA GAT CCC ATC CTC CTC ATG AAG AGT GCC AGA AAC TCC TGC   < 2040
 Y   K   Y   T   S   Y   P   D   P   I   L   L   M   K   S   A   R   N   S   C
TGG TCT AAG GAT GCC GAA TAC GGA TTG TAC TCC ATC TAT CAA GGG GGA ATC TTT GAG TTG   < 2100
 W   S   K   D   A   E   Y   G   L   Y   S   I   Y   Q   G   G   I   F   E   L
AAA GAA AAT GAT CGC ATT TTC GTG TCC GTC ACG AAT GAG CAC CTC ATA GAC ATG GAT CAT   < 2160
 K   E   N   D   R   I   F   V   S   V   T   N   E   H   L   I   D   M   D   H
GAA GCG AGT TTC TTC GGG GCT TTC CTC GTG GGT TGA
 E   A   S   F   F   G   A   F   L   V   G   *
```

Fig. 25

Fig. 28
a) scFv-L3 | VH |-GGCGSGGGGSGGSA-| VL |
b) 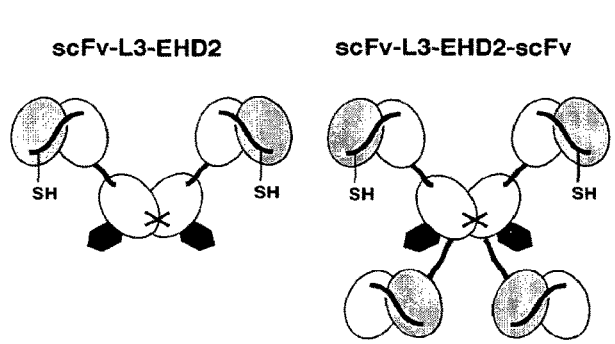
c) 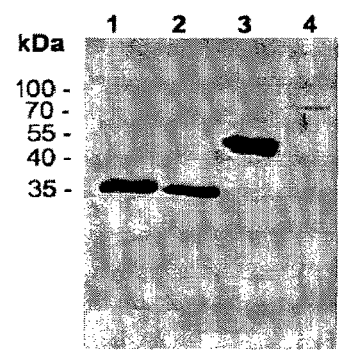

Fig. 29
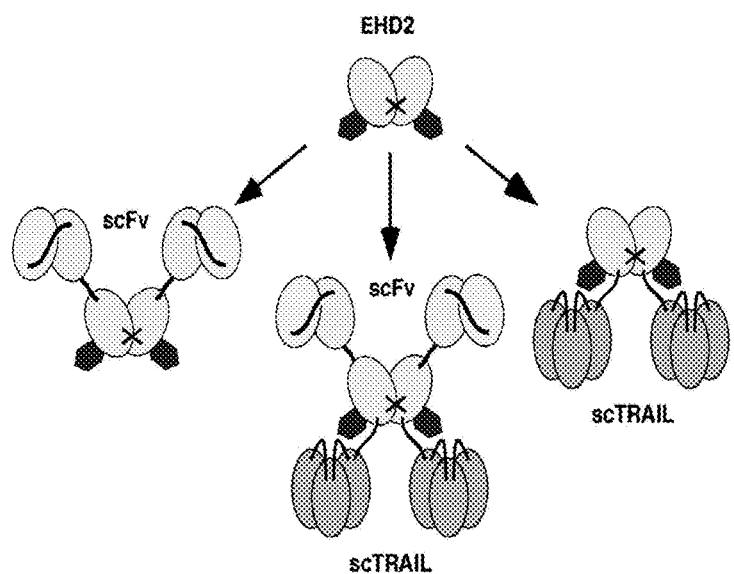
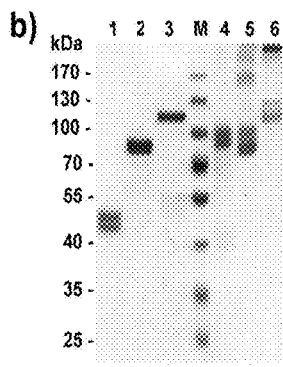
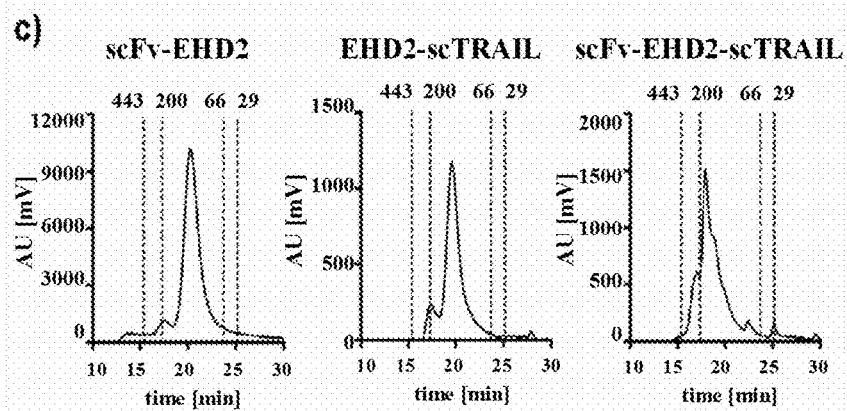
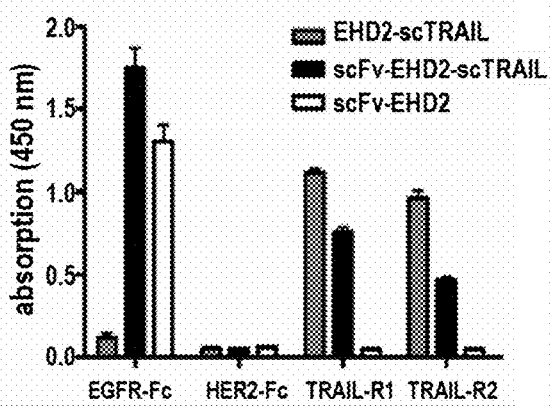
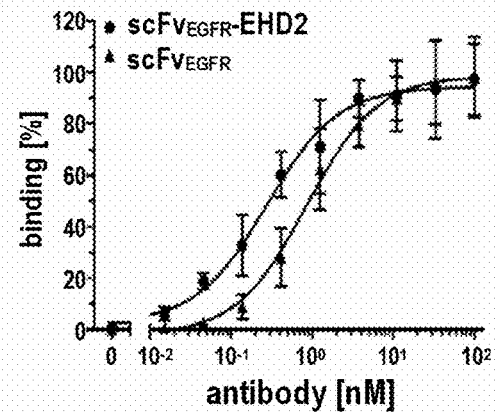

Fig. 37

```
Anti-CEA scFv-EHD2
ATG GAG ACA GAC ACA CTC CTG CTA TGG GTA CTG CTG CTC TGG GTT CCA GGT TCC ACT GGT    < 60
 M   E   T   D   T   L   L   L   W   V   L   L   L   W   V   P   G   S   T   G
GAC GCG GCC Cag cCG GCC ATG GCC CAG GTG AAA CTG CAG CAG TCT GGG GCA GAA CTT GTG    < 120
 D   A   A   Q   P   A   M   A   Q   V   K   L   Q   Q   S   G   A   E   L   V
AGG TCA GGG ACC TCA GTC AAG TTG TCC TGC ACA GCT TCT GGC TTC AAC ATT AAA GAC TCC    < 180
 R   S   G   T   S   V   K   L   S   C   T   A   S   G   F   N   I   K   D   S
TAT ATG CAC TGG TTG AGG CAG GGG CCT GAA CAG GGC CTG GAG TGG ATT GGA TGG ATT GAT    < 240
 Y   M   H   W   L   R   Q   G   P   E   Q   G   L   E   W   I   G   W   I   D
CCT GAG AAT GGT GAT ACT GAA TAT GCC CCG AAG TTC CAG GGC AAG GCC ACT TTT ACT ACA    < 300
 P   E   N   G   D   T   E   Y   A   P   K   F   Q   G   K   A   T   F   T   T
GAC ACA TCC TCC AAC ACA GCC TAC CTG CAG CTC AGC AGC CTG ACA TCT GAG GAC ACT GCC    < 360
 D   T   S   S   N   T   A   Y   L   Q   L   S   S   L   T   S   E   D   T   A
GTC TAT TAT TGT AAT GAG GGG ACT CCG ACT GGG CCG TAC TAC TTT GAC TAC TGG GGC CAA    < 420
 V   Y   Y   C   N   E   G   T   P   T   G   P   Y   Y   F   D   Y   W   G   Q
GGG ACC ACG GTC ACC GTC TCC TCA GGT GGA GGC GGT TCA GGG GGA GGT GGA TCC GGT GGA    < 480
 G   T   T   V   T   V   S   S   G   G   G   G   S   G   G   G   G   S   G   G
GGC GGT TCA GAC ATC GAG CTC ACC CAG TCT CCA GCA ATC ATG TCT GCA TCT CCA GGG GAG    < 540
 G   G   S   D   I   E   L   T   Q   S   P   A   I   M   S   A   S   P   G   E
AAA GTC ACC ATA ACC TGC AGT GCC AGC TCA AGT GTA AGT TAC ATG CAC TGG TTC CAG CAG    < 600
 K   V   T   I   T   C   S   A   S   S   S   V   S   Y   M   H   W   F   Q   Q
AAG CCA GGC ACT TCT CCC AAA CTC TGG ATT TAT AGC ACA TCC AAC CTG GCT TCT GGA GTC    < 660
 K   P   G   T   S   P   K   L   W   I   Y   S   T   S   N   L   A   S   G   V
CCT GCT CGC TTC AGT GGC AGT GGA TCT GGG ACC TCT TAC TCT CTC ACA ATC AGC CGA ATG    < 720
 P   A   R   F   S   G   S   G   S   G   T   S   Y   S   L   T   I   S   R   M
GAG GCT GAA GAT GCT GCC ACT TAT TAC TGC CAG CAA AGG AGT AGT TAC CCA CTC ACG TTC    < 780
 E   A   E   D   A   A   T   Y   Y   C   Q   Q   R   S   S   Y   P   L   T   F
GGT GCT GGC ACC AAG CTG GAG CTG AAA CGG GGA agc tTA GGC GGC TCT GGC GGC GAT TTC    < 840
 G   A   G   T   K   L   E   L   K   R   G   S   L   G   G   S   G   G   D   F
ACC CCC CCC ACA GTG AAG ATC CTC CAG AGC AGC TGT GAC GGC GGA GGC CAC TTC CCA CCT    < 900
 T   P   P   T   V   K   I   L   Q   S   S   C   D   G   G   G   H   F   P   P
ACC ATC CAG CTG CTG TGT CTG GTG TCC GGC TAC ACC CCC GGC ACC ATC AAC ATC ACC TGG    < 960
 T   I   Q   L   L   C   L   V   S   G   Y   T   P   G   T   I   N   I   T   W
CTG GAA GAT GGA CAA GTG ATG GAC GTG GAC CTG AGC ACC GCC AGC ACC ACA CAG GAA GGC    < 1020
 L   E   D   G   Q   V   M   D   V   D   L   S   T   A   S   T   T   Q   E   G
GAG CTG GCC TCT ACC CAG AGC GAG CTG ACA CTG AGC CAG AAG CAC TGG CTG AGC GAC CGG    < 1080
 E   L   A   S   T   Q   S   E   L   T   L   S   Q   K   H   W   L   S   D   R
ACC TAC ACC TGT CAA GTG ACC TAC CAG GGC CAC ACC TTC GAG GAC AGC ACC AAG AAG TGC    < 1140
 T   Y   T   C   Q   V   T   Y   Q   G   H   T   F   E   D   S   T   K   K   C
GCC GAC AGC AAC GGG GGA GGA TCT GGC GGA GGT ACC GGA TCC GAA TTC GCG GCC GCC CAC    < 1200
 A   D   S   N   G   G   G   S   G   G   G   T   G   S   E   F   A   A   A   H
CAT CAT CAC CAT CAC TAA
 H   H   H   H   H   *
```

Fig. 38

```
Anti-HER2 scFv-EHD2
ATG GAG ACA GAC ACA CTC CTG CTA TGG GTA CTG CTG CTC TGG GTT CCA GGT TCC Acc ggT    < 60
 M   E   T   D   T   L   L   L   W   V   L   L   L   W   V   P   G   S   T   G
GAA GTC CAG CTC GTC GAA AGT GGC GGT GGA CTT GTG CAG CCT GGC GGT TCC CTC AGA CTG    < 120
 E   V   Q   L   V   E   S   G   G   G   L   V   Q   P   G   G   S   L   R   L
TCC TGT GCC GCG TCA GGC TTC AAC ATC AAG GAC ACG TAC ATC CAC TGG GTG AGG CAA GCT    < 180
 S   C   A   A   S   G   F   N   I   K   D   T   Y   I   H   W   V   R   Q   A
CCT GGA AAG GGC TTG GAG TGG GTC GCT AGG ATC TAC CCG ACG AAC GGC TAC ACC AGG TAC    < 240
 P   G   K   G   L   E   W   V   A   R   I   Y   P   T   N   G   Y   T   R   Y
GCT GAC TCA GTG AAG GGA AGG TTC ACG ATC AGT GCA GAC ACC AGC AAG AAC ACC GCA TAC    < 300
 A   D   S   V   K   G   R   F   T   I   S   A   D   T   S   K   N   T   A   Y
CTC CAA ATG AAC TCC CTG AGA GCC GAG GAC ACC GCC GTG TAC TAC TGC TCT CGT TGG GGT    < 360
 L   Q   M   N   S   L   R   A   E   D   T   A   V   Y   Y   C   S   R   W   G
GGA GAT GGC TTC TAC GCT ATG GAC TAC TGG GGT CAA GGC ACA CTG GTG ACC GTG TCC AGT    < 420
 G   D   G   F   Y   A   M   D   Y   W   G   Q   G   T   L   V   T   V   S   S
GGT GGC GGA GGC AGT GGC GGA GGT GGC TCA GGA GGC GGA Gga tcC GAC ATC CAG ATG ACC    < 480
 G   G   G   G   S   G   G   G   G   S   G   G   G   S   D   I   Q   M   T
CAG TCA CCC TCA AGC CTC AGT GCC AGC GTC GGA GAT AGA GTG ACC ATA ACG TGC CGA GCT    < 540
 Q   S   P   S   S   L   S   A   S   V   G   D   R   V   T   I   T   C   R   A
TCT CAG GAT GTG AAC ACG GCA GTG GCT TGG TAT CAG CAA AAG CCT GGG AAA GCC CCA AAG    < 600
 S   Q   D   V   N   T   A   V   A   W   Y   Q   Q   K   P   G   K   A   P   K
CTG CTC ATC TAC TCC GCA TCC TTC CTG TAT AGC GGA GTT CCA TCT AGG TTC TCA GGC TCT    < 660
 L   L   I   Y   S   A   S   F   L   Y   S   G   V   P   S   R   F   S   G   S
AGG TCT GGG ACC GAC TTC ACG CTG ACG ATC TCC TCC CTG CAA CCT GAG GAC TTC GCC ACG    < 720
 R   S   G   T   D   F   T   L   T   I   S   S   L   Q   P   E   D   F   A   T
TAC TAC TGC CAG CAG CAC TAC ACG ACT CCT CCA ACC TTC GGT CAG GGA ACG AAG GTC GAG    < 780
 Y   Y   C   Q   Q   H   Y   T   T   P   P   T   F   G   Q   G   T   K   V   E
ATC AAG CGT GCg gcc GCC GGG GGA AGC GGC GGT GAT TTC ACC CCC CCC ACA GTG AAG ATC    < 840
 I   K   R   A   A   A   G   S   G   G   D   F   T   P   P   T   V   K   I
CTC CAG AGC AGC TGT GAC GGC GGA GGC CAC TTC CCA CCT ACC ATC CAG CTG CTG TGT CTG    < 900
 L   Q   S   S   C   D   G   G   G   H   F   P   P   T   I   Q   L   L   C   L
GTG TCC GGC TAC ACC CCC GGC ACC ATC AAC ATC ACC TGG CTG GAA GAT GGA CAA GTG ATG    < 960
 V   S   G   Y   T   P   G   T   I   N   I   T   W   L   E   D   G   Q   V   M
GAC GTG GAC CTG AGC ACC GCC AGC ACC ACA CAG GAA GGC GAG CTG GCC TCT ACC CAG AGC    < 1020
 D   V   D   L   S   T   A   S   T   T   Q   E   G   E   L   A   S   T   Q   S
GAG CTG ACA CTG AGC CAG AAG CAC TGG CTG AGC GAC CGG ACC TAC ACC TGT CAA GTG ACC    < 1080
 E   L   T   L   S   Q   K   H   W   L   S   D   R   T   Y   T   C   Q   V   T
TAC CAG GGC CAC ACC TTC GAG GAC AGC ACC AAG AAG TGC GCC GAC AGC AAC GGA GGT TCA    < 1140
 Y   Q   G   H   T   F   E   D   S   T   K   K   C   A   D   S   N   G   G   S
GGG GGC GCC TCG AGC CAC CAT CAT CAC CAT CAC TAA
 G   G   A   S   S   H   H   H   H   H   *
```

Fig. 39

```
Anti-HER3 scFv-EHD2
ATG GAG ACA GAC ACA CTC CTG CTA TGG GTA CTG CTG CTC TGG GTT CCA GGT TCC Acc ggT    < 60
 M   E   T   D   T   L   L   L   W   V   L   L   L   W   V   P   G   S   T   G
GAA GTG CAG CTG CTG GAA AGC GGA GGC GGC CTG GTG CAG CCT GGC GGC TCT CTG AGA CTG    < 120
 E   V   Q   L   L   E   S   G   G   G   L   V   Q   P   G   G   S   L   R   L
AGC TGT GCC GCC AGC GGC TTC ACC TTC AGC CAC TAC GTG ATG GCC TGG GTC CGA CAG GCC    < 180
 S   C   A   A   S   G   F   T   F   S   H   Y   V   M   A   W   V   R   Q   A
CCT GGC AAG GGA CTG GAA TGG GTG TCC AGC ATC AGC AGC AGC GGC GGC TGG ACC CTG TAC    < 240
 P   G   K   G   L   E   W   V   S   S   I   S   S   S   G   G   W   T   L   Y
GCC GAT AGC GTG AAG GGC CGG TTT ACC ATC AGC CGG GAC AAC AGC AAG AAC ACC CTG TAC    < 300
 A   D   S   V   K   G   R   F   T   I   S   R   D   N   S   K   N   T   L   Y
CTG CAG ATG AAC AGC CTG CGG GCC GAG GAC ACC GCC GTG TAC TAC TGC ACC AGA GGC CTG    < 360
 L   Q   M   N   S   L   R   A   E   D   T   A   V   Y   Y   C   T   R   G   L
AAG ATG GCC ACC ATC TTC GAC TAC TGG GGG CAG GGC ACC CTG GTC ACA GTC TCG AGT GGC    < 420
 K   M   A   T   I   F   D   Y   W   G   Q   G   T   L   V   T   V   S   S   G
GGG GGA GGA TCT GGG GGA GGT GGA AGT GGC GGC GGT GGA TCC CAG TCT GCC CTG ACA CAG    < 480
 G   G   G   S   G   G   G   G   S   G   G   G   G   S   Q   S   A   L   T   Q
CCT GCC AGC GTG TCC GGC AGC CCT GGC CAG AGC ATC ACA ATC AGC TGC ACC GGC ACC AGC    < 540
 P   A   S   V   S   G   S   P   G   Q   S   I   T   I   S   C   T   G   T   S
AGC GAC GTG GGC AGC TAC AAC GTG GTG TCC TGG TAT CAG CAG CAC CCC GGC AAG GCC CCC    < 600
 S   D   V   G   S   Y   N   V   V   S   W   Y   Q   Q   H   P   G   K   A   P
AAG CTG ATC ATC TAC GAG GTG TCC CAG CGG CCC AGC GGC GTG TCC AAC AGA TTC AGC GGC    < 660
 K   L   I   I   Y   E   V   S   Q   R   P   S   G   V   S   N   R   F   S   G
AGC AAG AGC GGC AAC ACC GCC AGC CTG ACC ATC AGC GGG CTG CAG ACC GAG GAC GAG GCC    < 720
 S   K   S   G   N   T   A   S   L   T   I   S   G   L   Q   T   E   D   E   A
GAC TAC TAC TGC TCC AGC TAC GCC GGC AGC AGC ATC TTC GTG ATC TTC GGA GGT GGC ACC    < 780
 D   Y   Y   C   S   S   Y   A   G   S   S   I   F   V   I   F   G   G   G   T
AAA GTG ACC GTG CTG GCg gcc GCC GGG GGA AGC GGC GGT GAT TTC ACC CCC CCC ACA GTG    < 840
 K   V   T   V   L   A   A   A   G   G   S   G   G   D   F   T   P   P   T   V
AAG ATC CTC CAG AGC AGC TGT GAC GGC GGA GGC CAC TTC CCA CCT ACC ATC CAG CTG CTG    < 900
 K   I   L   Q   S   S   C   D   G   G   G   H   F   P   P   T   I   Q   L   L
TGT CTG GTG TCC GGC TAC ACC CCC GGC ACC ATC AAC ATC ACC TGG CTG GAA GAT GGA CAA    < 960
 C   L   V   S   G   Y   T   P   G   T   I   N   I   T   W   L   E   D   G   Q
GTG ATG GAC GTG GAC CTG AGC ACC GCC AGC ACC ACA CAG GAA GGC GAG CTG GCC TCT ACC    < 1020
 V   M   D   V   D   L   S   T   A   S   T   T   Q   E   G   E   L   A   S   T
CAG AGC GAG CTG ACA CTG AGC CAG AAG CAC TGG CTG AGC GAC CGG ACC TAC ACC TGT CAA    < 1080
 Q   S   E   L   T   L   S   Q   K   H   W   L   S   D   R   T   Y   T   C   Q
GTG ACC TAC CAG GGC CAC ACC TTC GAG GAC AGC ACC AAG AAG TGC GCC GAC AGC AAC GGA    < 1140
 V   T   Y   Q   G   H   T   F   E   D   S   T   K   K   C   A   D   S   N   G
GGT TCA GGG GGC GCC TCG AGC CAC CAT CAT CAC CAT CAC TAA
 G   S   G   G   A   S   S   H   H   H   H   H   H   *
```

Fig. 40

```
Anti-CEAxCD3 scDb-EHD2
ATG GAG ACA GAC ACA CTC CTG CTA TGG GTA CTG CTG CTC TGG GTT CCA GGT TCC ACT GGT   < 60
 M   E   T   D   T   L   L   L   W   V   L   L   L   W   V   P   G   S   T   G
GAC GCG GCC Cag cCG GCC ATG GCC CAG GTG AAA CTG CAG CAG TCT GGG GCA GAA CTT GTG   < 120
 D   A   A   Q   P   A   M   A   Q   V   K   L   Q   Q   S   G   A   E   L   V
AGG TCA GGG ACC TCA GTC AAG TTG TCC TGC ACA GCT TCT GGC TTC AAC ATT AAA GAC TCC   < 180
 R   S   G   T   S   V   K   L   S   C   T   A   S   G   F   N   I   K   D   S
TAT ATG CAC TGG TTG AGG CAG GGG CCT GAA CAG GGC CTG GAG TGG ATT GGA TGG ATT GAT   < 240
 Y   M   H   W   L   R   Q   G   P   E   Q   G   L   E   W   I   G   W   I   D
CCT GAG AAT GGT GAT ACT GAA TAT GCC CCG AAG TTC CAG GGC AAG GCC ACT TTT ACT ACA   < 300
 P   E   N   G   D   T   E   Y   A   P   K   F   Q   G   K   A   T   F   T   T
GAC ACA TCC TCC AAC ACA GCC TAC CTG CAG CTC AGC AGC CTG ACA TCT GAG GAC ACT GCC   < 360
 D   T   S   S   N   T   A   Y   L   Q   L   S   S   L   T   S   E   D   T   A
GTC TAT TAT TGT AAT GAG GGG ACT CCG ACT GGG CCG TAC TAC TTT GAC TAC TGG GGC CAA   < 420
 V   Y   Y   C   N   E   G   T   P   T   G   P   Y   Y   F   D   Y   W   G   Q
GGG ACC ACG GTC ACC GTC TCC TCA GGC GGT GGC GGA TCG GAT ATC CAG ATG ACC CAG TCC   < 480
 G   T   T   V   T   V   S   S   G   G   G   G   S   D   I   Q   M   T   Q   S
CCG AGT TCC CTG TCC GCC TCT GTG GGC GAT AGA GTC ACC ATC ACC TGT CGT GCC AGT CAG   < 540
 P   S   S   L   S   A   S   V   G   D   R   V   T   I   T   C   R   A   S   Q
GAC ATC CGT AAT TAT CTG AAC TGG TAT CAA CAG AAA CCA GGA AAA GCT CCG AAA CTA CTG   < 600
 D   I   R   N   Y   L   N   W   Y   Q   Q   K   P   G   K   A   P   K   L   L
ATT TAC TAT ACC TCC CGC CTG GAG TCT GGA GTC CCT TCT CGC TTC TCT GGT TCT GGT TCT   < 660
 I   Y   Y   T   S   R   L   E   S   G   V   P   S   R   F   S   G   S   G   S
GGG ACG GAT TAC ACT CTC ACC ATC AGC AGT CTG CAA CCG GAG GAC TTC GCA ACC TAT TAC   < 720
 G   T   D   Y   T   L   T   I   S   S   L   Q   P   E   D   F   A   T   Y   Y
TGT CAG CAA GGT AAT ACT CTG CCG TGG ACG TTC GGA CAG GGC ACC AAG GTG GAG ATC AAA   < 780
 C   Q   Q   G   N   T   L   P   W   T   F   G   Q   G   T   K   V   E   I   K
CGT GGA GGC GGT GGC AGC GGT GGG CGC GCC TCG GGC GGA GGT GGC TCA GAG GTT CAG CTG   < 840
 R   G   G   G   G   S   G   G   R   A   S   G   G   G   G   S   E   V   Q   L
GTG GAG TCT GGC GGT GGC CTG GTG CAG CCA GGG GGG TCA CTC CGT TTG TCC TGT GCA GCT   < 900
 V   E   S   G   G   G   L   V   Q   P   G   G   S   L   R   L   S   C   A   A
TCT GGC TAC TCC TTT ACC GGC TAC ACT ATG AAC TGG GTG CGT CAG GCC CCA GGT AAG GGC   < 960
 S   G   Y   S   F   T   G   Y   T   M   N   W   V   R   Q   A   P   G   K   G
CTG GAA TGG GTT GCA CTG ATT AAT CCT TAT AAA GGT GTT TCC ACC TAT AAC CAG AAA TTC   < 1020
 L   E   W   V   A   L   I   N   P   Y   K   G   V   S   T   Y   N   Q   K   F
AAG GAT CGT TTC ACG ATA TCC GTA GAT AAA TCC AAA AAC ACA GCC TAC CTG CAA ATG AAC   < 1080
 K   D   R   F   T   I   S   V   D   K   S   K   N   T   A   Y   L   Q   M   N
AGC CTG CGT GCT GAG GAC ACT GCA GTC TAT TAT TGT GCT AGA AGC GGA TAC TAC GGC GAT   < 1140
 S   L   R   A   E   D   T   A   V   Y   Y   C   A   R   S   G   Y   Y   G   D
AGC GAC TGG TAT TTT GAC GTC TGG GGT CAA GGA ACC CTA GTC ACC GTC TCC TCG GGA GGC   < 1200
 S   D   W   Y   F   D   V   W   G   Q   G   T   L   V   T   V   S   S   G   G
GGG GGT TCG GAC ATC GAG CTC ACC CAG TCT CCA GCA ATC ATG TCT GCA TCT CCA GGG GAG   < 1260
 G   G   S   D   I   E   L   T   Q   S   P   A   I   M   S   A   S   P   G   E
AAA GTC ACC ATA ACC TGC AGT GCC AGC TCA AGT GTA AGT TAC ATG CAC TGG TTC CAG CAG   < 1320
 K   V   T   I   T   C   S   A   S   S   S   V   S   Y   M   H   W   F   Q   Q
AAG CCA GGC ACT TCT CCC AAA CTC TGG ATT TAT AGC ACA TCC AAC CTG GCT TCT GGA GTC   < 1380
 K   P   G   T   S   P   K   L   W   I   Y   S   T   S   N   L   A   S   G   V
CCT GCT CGC TTC AGT GGC AGT GGA TCT GGG ACC TCT TAC TCT CTC ACA ATC AGC CGA ATG   < 1440
 P   A   R   F   S   G   S   G   S   G   T   S   Y   S   L   T   I   S   R   M
GAG GCT GAA GAT GCT GCC ACT TAT TAC TGC CAG CAA AGG AGT AGT TAC CCA CTC ACG TTC   < 1500
 E   A   E   D   A   A   T   Y   Y   C   Q   Q   R   S   S   Y   P   L   T   F
GGT GCT GGC ACC AAG CTG GAG CTG AAA CGG GGA agc tTA GGC GGC TCT GGC GGC GAT TTC   < 1560
 G   A   G   T   K   L   E   L   K   R   G   S   L   G   G   S   G   G   D   F
ACC CCC CCC ACA GTG AAG ATC CTC CAG AGC AGC TGT GAC GGC GGA GGC CAC TTC CCA CCT   < 1620
 T   P   P   T   V   K   I   L   Q   S   S   C   D   G   G   G   H   F   P   P
ACC ATC CAG CTG CTG TGT CTG GTG TCC GGC TAC ACC CCC GGC ACC ATC AAC ATC ACC TGG   < 1680
 T   I   Q   L   L   C   L   V   S   G   Y   T   P   G   T   I   N   I   T   W
CTG GAA GAT GGA CAA GTG ATG GAC GTG GAC CTG AGC ACC GCC AGC ACC ACA CAG GAA GGC   < 1740
 L   E   D   G   Q   V   M   D   V   D   L   S   T   A   S   T   T   Q   E   G
GAG CTG GCC TCT ACC CAG AGC GAG CTG ACA CTG AGC CAG AAG CAC TGG CTG AGC GAC CGG   < 1800
 E   L   A   S   T   Q   S   E   L   T   L   S   Q   K   H   W   L   S   D   R
ACC TAC ACC TGT CAA GTG ACC TAC CAG GGC CAC ACC TTC GAG GAC AGC ACC AAG AAG TGC   < 1860
 T   Y   T   C   Q   V   T   Y   Q   G   H   T   F   E   D   S   T   K   K   C
GCC GAC AGC AAC GGG GGA GGA TCT GGC GGA GGT ACC GGA TCC GAA TTC GCG GCC GCC CAC   < 1920
 A   D   S   N   G   G   G   S   G   G   G   T   G   S   E   F   A   A   A   H
CAT CAT CAC CAT CAC TAA
 H   H   H   H   H   *
```

Fig. 41

```
Anti-EGFR scFv-L3-EHD2
ATG GAG ACA GAC ACA CTC CTG CTA TGG GTA CTG CTG CTC TGG GTT CCA GGT TCC Acc ggT   < 60
 M   E   T   D   T   L   L   L   W   V   L   L   L   W   V   P   G   S   T   G
CAG GTG CAG CTG AAG CAG TCT GGA GCT GAA CTG GTG AAA CCC GGG GCA TCA GTG AAG CTG   < 120
 Q   V   Q   L   K   Q   S   G   A   E   L   V   K   P   G   A   S   V   K   L
TCC TGC AAG ACT TCT GGC TAC ACC TTC ACT GAA AAT ATT ATA CAC TGG GTA AAG CAG AGG   < 180
 S   C   K   T   S   G   Y   T   F   T   E   N   I   I   H   W   V   K   Q   R
TCT GGG CAG GGT CTT GAG TGG ATT GGG TGG TTT CAC CCT GGA AGT GGT AGT ATA AAG TAC   < 240
 S   G   Q   G   L   E   W   I   G   W   F   H   P   G   S   G   S   I   K   Y
AAT GAG AAA TTC AAG GAC AAG GCC ACA TTG ACT GCG GAC AAA TCC TCC AGC ACA GTC TAT   < 300
 N   E   K   F   K   D   K   A   T   L   T   A   D   K   S   S   S   T   V   Y
ATG GAG CTT AGT AGA TTG ACA TCT GAA GAC TCT GCG GTC TAT TTC TGT GCA AGA CAC GGA   < 360
 M   E   L   S   R   L   T   S   E   D   S   A   V   Y   F   C   A   R   H   G
GGA ACT GGG CGA GGA GCT ATG GAC TAC TGG GGT CAA GGA ACC TCA GTC ACC GTC TCG AGT   < 420
 G   T   G   R   G   A   M   D   Y   W   G   Q   G   T   S   V   T   V   S   S
GGT GGA TGC GGT TCA GGC GGA GGT GGC TCT GGC GGT AGT GCA CAA ATT CTG ATG ACC CAG   < 480
 G   G   C   G   S   G   G   G   G   S   G   G   S   A   Q   I   L   M   T   Q
TCT CCT GCT TCC TCA GTT GTA TCT CTG GGG CAG AGG GCC ACC ATC TCA TGC AGG GCC AGC   < 540
 S   P   A   S   S   V   V   S   L   G   Q   R   A   T   I   S   C   R   A   S
AAA AGT GTC AGT ACA TCT GCC TAT AGT TAT ATG CAC TGG TAC CAA CAG AAA CCA GGA CAG   < 600
 K   S   V   S   T   S   A   Y   S   Y   M   H   W   Y   Q   Q   K   P   G   Q
CCA CCC AAA CTC CTC ATC TAT CTT GCA TCC AAC CTA GAA TCT GGG GTC CCT CCC AGG TTC   < 660
 P   P   K   L   L   I   Y   L   A   S   N   L   E   S   G   V   P   P   R   F
AGT GGC AGT GGG TCT GGG ACA GAC TTC ACC CTC AAC ATC CAC CCT GTG GAG GAG GAG GAT   < 720
 S   G   S   G   S   G   T   D   F   T   L   N   I   H   P   V   E   E   E   D
GCT GCA ACC TAT TAC TGT CAG CAC AGT AGG GAG CTT CCG TAC ACG TTC GGA GGG GGG ACC   < 780
 A   A   T   Y   Y   C   Q   H   S   R   E   L   P   Y   T   F   G   G   G   T
AAG CTG GAA ATA AAA CGG GCg gcc GCC GGG GGA AGC GGC GGT GAT TTC ACC CCC CCC ACA   < 840
 K   L   E   I   K   R   A   A   A   G   G   S   G   G   D   F   T   P   P   T
GTG AAG ATC CTC CAG AGC AGC TGT GAC GGC GGA GGC CAC TTC CCA CCT ACC ATC CAG CTG   < 900
 V   K   I   L   Q   S   S   C   D   G   G   G   H   F   P   P   T   I   Q   L
CTG TGT CTG GTG TCC GGC TAC ACC CCC GGC ACC ATC AAC ATC ACC TGG CTG GAA GAT GGA   < 960
 L   C   L   V   S   G   Y   T   P   G   T   I   N   I   T   W   L   E   D   G
CAA GTG ATG GAC GTG GAC CTG AGC ACC GCC AGC ACC ACA CAG GAA GGC GAG CTG GCC TCT   < 1020
 Q   V   M   D   V   D   L   S   T   A   S   T   T   Q   E   G   E   L   A   S
ACC CAG AGC GAG CTG ACA CTG AGC CAG AAG CAC TGG CTG AGC GAC CGG ACC TAC ACC TGT   < 1080
 T   Q   S   E   L   T   L   S   Q   K   H   W   L   S   D   R   T   Y   T   C
CAA GTG ACC TAC CAG GGC CAC ACC TTC GAG GAC AGC ACC AAG AAG TGC GCC GAC AGC AAC   < 1140
 Q   V   T   Y   Q   G   H   T   F   E   D   S   T   K   K   C   A   D   S   N
GGA GGT TCA GGG GGC GCC TCG AGC CAC CAT CAT CAC CAT CAC TAA < 1200
 G   G   S   G   G   A   S   S   H   H   H   H   H   H   *
```

Fig. 42

```
Anti-EGFR scFv-L3-EHD2-scFv
ATG GAG ACA GAC ACA CTC CTG CTA TGG GTA CTG CTG CTC TGG GTT CCA GGT TCC ACC GGT      < 60
 M   E   T   D   T   L   L   L   W   V   L   L   L   W   V   P   G   S   T   G
CAG GTG CAG CTG AAG CAG TCT GGA GCT GAA CTG GTG AAA CCC GGG GCA TCA GTG AAG CTG      < 120
 Q   V   Q   L   K   Q   S   G   A   E   L   V   K   P   G   A   S   V   K   L
TCC TGC AAG ACT TCT GGC TAC ACC TTC ACT GAA AAT ATT ATA CAC TGG GTA AAG CAG AGG      < 180
 S   C   K   T   S   G   Y   T   F   T   E   N   I   I   H   W   V   K   Q   R
TCT GGG CAG GGT CTT GAG TGG ATT GGG TGG TTT CAC CCT GGA AGT GGT AGT ATA AAG TAC      < 240
 S   G   Q   G   L   E   W   I   G   W   F   H   P   G   S   G   S   I   K   Y
AAT GAG AAA TTC AAG GAC AAG GCC ACA TTG ACT GCG GAC AAA TCC TCC AGC ACA GTC TAT      < 300
 N   E   K   F   K   D   K   A   T   L   T   A   D   K   S   S   S   T   V   Y
ATG GAG CTT AGT AGA TTG ACA TCT GAA GAC TCT GCG GTC TAT TTC TGT GCA AGA CAC GGA      < 360
 M   E   L   S   R   L   T   S   E   D   S   A   V   Y   F   C   A   R   H   G
GGA ACT GGG CGA GGA GCT ATG GAC TAC TGG GGT CAA GGA ACC TCA GTC ACC GTC TCG AGT      < 420
 G   T   G   R   G   A   M   D   Y   W   G   Q   G   T   S   V   T   V   S   S
GGT GGA TGC GGT TCA GGC GGA GGT GGC TCT GGC GGT AGT GCA CAA ATT CTG ATG ACC CAG      < 480
 G   G   C   G   S   G   G   G   G   S   G   G   S   A   Q   I   L   M   T   Q
TCT CCT GCT TCC TCA GTT GTA TCT CTG GGG CAG AGG GCC ACC ATC TCA TGC AGG GCC AGC      < 540
 S   P   A   S   S   V   V   S   L   G   Q   R   A   T   I   S   C   R   A   S
AAA AGT GTC AGT ACA TCT GCC TAT AGT TAT ATG CAC TGG TAC CAA CAG AAA CCA GGA CAG      < 600
 K   S   V   S   T   S   A   Y   S   Y   M   H   W   Y   Q   Q   K   P   G   Q
CCA CCC AAA CTC CTC ATC TAT CTT GCA TCC AAC CTA GAA TCT GGG GTC CCT CCC AGG TTC      < 660
 P   P   K   L   L   I   Y   L   A   S   N   L   E   S   G   V   P   P   R   F
AGT GGC AGT GGG TCT GGG ACA GAC TTC ACC CTC AAC ATC CAC CCT GTG GAG GAG GAG GAT      < 720
 S   G   S   G   S   G   T   D   F   T   L   N   I   H   P   V   E   E   E   D
GCT GCA ACC TAT TAC TGT CAG CAC AGT AGG GAG CTT CCG TAC ACG TTC GGA GGG GGG ACC      < 780
 A   A   T   Y   Y   C   Q   H   S   R   E   L   P   Y   T   F   G   G   G   T
AAG CTG GAA ATA AAA CGG GCG GCC GCC GGG GGA AGC GGC GGT GAT TTC ACC CCC CCC ACA      < 840
 K   L   E   I   K   R   A   A   A   G   G   S   G   G   D   F   T   P   P   T
GTG AAG ATC CTC CAG AGC AGC TGT GAC GGC GGA GGC CAC TTC CCA CCT ACC ATC CAG CTG      < 900
 V   K   I   L   Q   S   S   C   D   G   G   G   H   F   P   P   T   I   Q   L
CTG TGT CTG GTG TCC GGC TAC ACC CCC GGC ACC ATC AAC ATC ACC TGG CTG GAA GAT GGA      < 960
 L   C   L   V   S   G   Y   T   P   G   T   I   N   I   T   W   L   E   D   G
CAA GTG ATG GAC GTG GAC CTG AGC ACC GCC AGC ACC ACA CAG GAA GGC GAG CTG GCC TCT      < 1020
 Q   V   M   D   V   D   L   S   T   A   S   T   T   Q   E   G   E   L   A   S
ACC CAG AGC GAG CTG ACA CTG AGC CAG AAG CAC TGG CTG AGC GAC CGG ACC TAC ACC TGT      < 1080
 T   Q   S   E   L   T   L   S   Q   K   H   W   L   S   D   R   T   Y   T   C
CAA GTG ACC TAC CAG GGC CAC ACC TTC GAG GAC AGC ACC AAG AAG TGC GCC GAC AGC AAC      < 1140
 Q   V   T   Y   Q   G   H   T   F   E   D   S   T   K   K   C   A   D   S   N
GGA GGT TCA GGG GGC GCC TCG AGC GAA TTC CAG GTG CAG CTG AAG CAG TCT GGA GCT GAA      < 1200
 G   G   S   G   G   A   S   S   E   F   Q   V   Q   L   K   Q   S   G   A   E
CTG GTG AAA CCC GGG GCA TCA GTG AAG CTG TCC TGC AAG ACT TCT GGC TAC ACC TTC ACT      < 1260
 L   V   K   P   G   A   S   V   K   L   S   C   K   T   S   G   Y   T   F   T
GAA AAT ATT ATA CAC TGG GTA AAG CAG AGG TCT GGG CAG GGT CTT GAG TGG ATT GGG TGG      < 1320
 E   N   I   I   H   W   V   K   Q   R   S   G   Q   G   L   E   W   I   G   W
TTT CAC CCT GGA AGT GGT AGT ATA AAG TAC AAT GAG AAA TTC AAG GAC AAG GCC ACA TTG      < 1380
 F   H   P   G   S   G   S   I   K   Y   N   E   K   F   K   D   K   A   T   L
ACT GCG GAC AAA TCC TCC AGC ACA GTC TAT ATG GAG CTT AGT AGA TTG ACA TCT GAA GAC      < 1440
 T   A   D   K   S   S   S   T   V   Y   M   E   L   S   R   L   T   S   E   D
TCT GCG GTC TAT TTC TGT GCA AGA CAC GGA GGA ACT GGG CGA GGA GCT ATG GAC TAC TGG      < 1500
 S   A   V   Y   F   C   A   R   H   G   G   T   G   R   G   A   M   D   Y   W
GGT CAA GGA ACC TCA GTC ACC GTC TCG AGT GGT GGA GGC GGT TCA GGC GGA GGT GGC TCT      < 1560
 G   Q   G   T   S   V   T   V   S   S   G   G   G   G   S   G   G   G   G   S
GGC GGT AGT GCA CAA ATT CTG ATG ACC CAG TCT CCT GCT TCC TCA GTT GTA TCT CTG GGG      < 1620
 G   G   S   A   Q   I   L   M   T   Q   S   P   A   S   S   V   V   S   L   G
CAG AGG GCC ACC ATC TCA TGC AGG GCC AGC AAA AGT GTC AGT ACA TCT GCC TAT AGT TAT      < 1680
 Q   R   A   T   I   S   C   R   A   S   K   S   V   S   T   S   A   Y   S   Y
ATG CAC TGG TAC CAA CAG AAA CCA GGA CAG CCA CCC AAA CTC CTC ATC TAT CTT GCA TCC      < 1740
 M   H   W   Y   Q   Q   K   P   G   Q   P   P   K   L   L   I   Y   L   A   S
AAC CTA GAA TCT GGG GTC CCT CCC AGG TTC AGT GGC AGT GGG TCT GGG ACA GAC TTC ACC      < 1800
 N   L   E   S   G   V   P   P   R   F   S   G   S   G   S   G   T   D   F   T
CTC AAC ATC CAC CCT GTG GAG GAG GAG GAT GCT GCA ACC TAT TAC TGT CAG CAC AGT AGG      < 1860
 L   N   I   H   P   V   E   E   E   D   A   A   T   Y   Y   C   Q   H   S   R
GAG CTT CCG TAC ACG TTC GGA GGG GGG ACC AAG CTG GAA ATA AAA CGG GCG GCC GCC CAC      < 1920
 E   L   P   Y   T   F   G   G   G   T   K   L   E   I   K   R   A   A   A   H
CAT CAT CAC CAT CAC TAA
 H   H   H   H   H   *
```

Fig. 43

```
MHD2-scTNF_R2
ATG GAG ACA GAC ACA CTC CTG CTA TGG GTA CTG CTG CTC TGG GTT CCA GGT TCC ACC GGT   < 60
 M   E   T   D   T   L   L   L   W   V   L   L   L   W   V   P   G   S   T   G
GAC GCG GCC CAG CCG GCC GGA GGC GGT GCG GCC GCA CAC CAT CAT CAC CAT CAC GGA GGT   < 120
 D   A   A   Q   P   A   G   G   G   A   A   A   H   H   H   H   H   H   G   G
ACC GGC GGG GGA GGT TCA GGC GGA AAG CTT GGA GGC TCT GGC GGA GCC GAG CTG CCC CCT   < 180
 T   G   G   G   G   S   G   G   K   L   G   G   S   G   G   A   E   L   P   P
AAG GTG TCC GTG TTC GTG CCC CCC AGG GAC GGC TTC TTC GGC AAC CCC AGA AAG AGC AAG   < 240
 K   V   S   V   F   V   P   P   R   D   G   F   F   G   N   P   R   K   S   K
CTG ATC TGC CAG GCC ACC GGC TTC AGC CCC AGA CAG ATC CAG GTG TCC TGG CTG CGC GAG   < 300
 L   I   C   Q   A   T   G   F   S   P   R   Q   I   Q   V   S   W   L   R   E
GGC AAA CAG GTC GGA AGC GGC GTG ACC ACC GAC CAG GTG CAG GCC GAG GCC AAA GAG AGC   < 360
 G   K   Q   V   G   S   G   V   T   T   D   Q   V   Q   A   E   A   K   E   S
GGC CCC ACC ACC TAC AAA GTG ACC AGC ACC CTG ACC ATC AAA GAG TCC GAC TGG CTG GGC   < 420
 G   P   T   T   Y   K   V   T   S   T   L   T   I   K   E   S   D   W   L   G
CAG AGC ATG TTC ACC TGT CGG GTG GAC CAC CGG GGC CTG ACC TTC CAG CAG AAC GCC AGC   < 480
 Q   S   M   F   T   C   R   V   D   H   R   G   L   T   F   Q   Q   N   A   S
TCT ATG TGC GTG CCC GAC GGC GGA GGG TCC GGC GGA GGT ACC GGA TCC GAA TTC CTC GCC   < 540
 S   M   C   V   P   D   G   G   G   S   G   G   T   G   S   E   F   L   A
AGC AGC CGG ACC CCT AGC GAT AAG CCC GTG GCC CAC GTG GTG GCC AAT CCT CAG GCC GAG   < 600
 S   S   R   T   P   S   D   K   P   V   A   H   V   V   A   N   P   Q   A   E
GGC CAG CTG CAG TGG CTG AAC AGA CGG GCC AAC GCC CTG CTG GCC AAC GGC GTG GAG CTG   < 660
 G   Q   L   Q   W   L   N   R   R   A   N   A   L   L   A   N   G   V   E   L
CGG GAC AAC CAG CTG GTC GTG CCC AGC GAG GGC CTG TAC CTG ATC TAC AGC CAG GTG CTG   < 720
 R   D   N   Q   L   V   V   P   S   E   G   L   Y   L   I   Y   S   Q   V   L
TTC AAG GGC CAG GGC TGC CCT TCT ACC CAC GTG CTG CTG ACC CAC ACC ATC AGC CGG ATC   < 780
 F   K   G   Q   G   C   P   S   T   H   V   L   L   T   H   T   I   S   R   I
GCC GTG AGC TAC CAG ACC AAA GTG AAC CTG CTG TCC GCC ATC AAG AGC CCC TGC CAG AGA   < 840
 A   V   S   Y   Q   T   K   V   N   L   L   S   A   I   K   S   P   C   Q   R
GAG ACA CCT GAG GGC GCC GAG GCC AAG CCT TGG TAC GAG CCC ATC TAC CTG GGC GGC GTG   < 900
 E   T   P   E   G   A   E   A   K   P   W   Y   E   P   I   Y   L   G   G   V
TTC CAG CTG GAA AAG GGC GAC CGG CTG TCC GCC GAG ATC AAC CGG CCC GAC TAC CTG AAC   < 960
 F   Q   L   E   K   G   D   R   L   S   A   E   I   N   R   P   D   Y   L   N
TTC CGG GAG AGC GGC CAG GTG TAC TTC GGC ATC ATA GCG CTG GGC GGA GGG GGC AGC AGC   < 1020
 F   R   E   S   G   Q   V   Y   F   G   I   I   A   L   G   G   G   S   S
AGC AGA ACC CCC TCC GAC AAG CCT GTG GCT CAT GTG GTG GCT AAC CCC CAG GCT GAA GGA   < 1080
 S   R   T   P   S   D   K   P   V   A   H   V   V   A   N   P   Q   A   E   G
CAG CTG CAG TGG CTG AAT CGG AGA GCT AAT GCT CTG CTG GCT AAT GGG GTG GAA CTG AGA   < 1140
 Q   L   Q   W   L   N   R   R   A   N   A   L   L   A   N   G   V   E   L   R
GAT AAT CAG CTG GTC GTG CCT TCT GAG GGG CTG TAT CTG ATC TAT TCT CAG GTG CTG TTT   < 1200
 D   N   Q   L   V   V   P   S   E   G   L   Y   L   I   Y   S   Q   V   L   F
AAA GGA CAG GGG TGT CCC AGC ACA CAT GTG CTG CTG ACA CAT ACA ATC TCC AGA ATC GCC   < 1260
 K   G   Q   G   C   P   S   T   H   V   L   L   T   H   T   I   S   R   I   A
GTG TCT TAT CAG ACA AAA GTG AAT CTG CTG AGT GCC ATC AAG TCC CCC TGT CAG CGG GAA   < 1320
 V   S   Y   Q   T   K   V   N   L   L   S   A   I   K   S   P   C   Q   R   E
ACC CCT GAA GGG GCC GAA GCT AAA CCT TGG TAT GAA CCT ATC TAT CTG GGG GGA GTG TTT   < 1380
 T   P   E   G   A   E   A   K   P   W   Y   E   P   I   Y   L   G   G   V   F
CAG CTG GAA AAA GGG GAC AGA CTG AGC GCC GAG ATT AAC AGA CCT GAT TAC CTG AAT TTC   < 1440
 Q   L   E   K   G   D   R   L   S   A   E   I   N   R   P   D   Y   L   N   F
AGA GAA TCC GGG CAG GTG TAC TTT GGG ATT ATC GCC CTG GGA GGG GGC GGA TCC AGC TCC   < 1500
 R   E   S   G   Q   V   Y   F   G   I   I   A   L   G   G   G   S   S
AGA ACC CCC AGT GAC AAA CCA GTG GCC CAT GTG GTG GCC AAC CCA CAG GCT GAG GGG CAG   < 1560
 R   T   P   S   D   K   P   V   A   H   V   V   A   N   P   Q   A   E   G   Q
CTG CAG TGG CTG AAC CGC AGA GCC AAT GCC CTG CTG GCC AAT GGC GTG GAA CTG CGC GAC   < 1620
 L   Q   W   L   N   R   R   A   N   A   L   L   A   N   G   V   E   L   R   D
AAT CAG CTG GTC GTG CCA TCC GAA GGA CTG TAC CTG ATC TAC TCA CAG GTG CTG TTT AAG   < 1680
 N   Q   L   V   V   P   S   E   G   L   Y   L   I   Y   S   Q   V   L   F   K
GGG CAG GGA TGC CCC TCC ACT CAT GTG CTG CTG ACT CAC ACT ATC TCT CGG ATT GCT GTG   < 1740
 G   Q   G   C   P   S   T   H   V   L   L   T   H   T   I   S   R   I   A   V
TCC TAC CAG ACT AAA GTG AAT CTG CTG TCT GCT ATT AAG TCT CCT TGC CAG CGC GAG ACT   < 1800
 S   Y   Q   T   K   V   N   L   L   S   A   I   K   S   P   C   Q   R   E   T
CCA GAG GGG GCT GAA GCC AAG CCC TGG TAT GAG CCA ATC TAT CTG GGA GGG GTG TTC CAG   < 1860
 P   E   G   A   E   A   K   P   W   Y   E   P   I   Y   L   G   G   V   F   Q
CTG GAA AAG GGG GAT CGC CTG AGC GCC GAA ATC AAT AGA CCA GAC TAT CTG AAC TTT CGC   < 1920
 L   E   K   G   D   R   L   S   A   E   I   N   R   P   D   Y   L   N   F   R
GAG TCT GGA CAG GTG TAC TTT GGA ATC ATT GCT CTG TGA
 E   S   G   Q   V   Y   F   G   I   I   A   L   *
```

Fig. 44

```
EHD2-scTNF_R2-L16aa
ATG GAG ACA GAC ACA CTC CTG CTA TGG GTA CTG CTG CTC TGG GTT CCA GGT TCC ACC GGT    < 60
 M   E   T   D   T   L   L   L   W   V   L   L   L   W   V   P   G   S   T   G
GAC GCG GCC CAG CCG GCC GGA GGC GGT GCG GCC GCA CAC CAT CAT CAC CAT CAC GGA GGT    < 120
 D   A   A   Q   P   A   G   G   G   A   A   A   H   H   H   H   H   H   G   G
ACC GGC GGG GGA GGT TCA GGC GGA AAG CTT GGC GGC TCT GGC GGC GAT TTC ACC CCC CCC    < 180
 T   G   G   G   G   S   G   G   K   L   G   G   S   G   G   D   F   T   P   P
ACA GTG AAG ATC CTC CAG AGC AGC TGT GAC GGC GGA GGC CAC TTC CCA CCT ACC ATC CAG    < 240
 T   V   K   I   L   Q   S   S   C   D   G   G   G   H   F   P   P   T   I   Q
CTG CTG TGT CTG GTG TCC GGC TAC ACC CCC GGC ACC ATC AAC ATC ACC TGG CTG GAA GAT    < 300
 L   L   C   L   V   S   G   Y   T   P   G   T   I   N   I   T   W   L   E   D
GGA CAA GTG ATG GAC GTG GAC CTG AGC ACC GCC AGC ACC ACA CAG GAA GGC GAG CTG GCC    < 360
 G   Q   V   M   D   V   D   L   S   T   A   S   T   T   Q   E   G   E   L   A
TCT ACC CAG AGC GAG CTG ACA CTG AGC CAG AAG CAC TGG CTG AGC GAC CGG ACC TAC ACC    < 420
 S   T   Q   S   E   L   T   L   S   Q   K   H   W   L   S   D   R   T   Y   T
TGT CAA GTG ACC TAC CAG GGC CAC ACC TTC GAG GAC AGC ACC AAG AAG TGC GCC GAC AGC    < 480
 C   Q   V   T   Y   Q   G   H   T   F   E   D   S   T   K   K   C   A   D   S
AAC GGG GGA GGA TCT GGC GGA GGT ACC GGA TCC GAA TTC CTC GCC AGC AGC CGG ACC CCT    < 540
 N   G   G   G   S   G   G   G   T   G   S   E   F   L   A   S   S   R   T   P
AGC GAT AAG CCC GTG GCC CAC GTG GTG GCC AAT CCT CAG GCC GAG GGC CAG CTG CAG TGG    < 600
 S   D   K   P   V   A   H   V   V   A   N   P   Q   A   E   G   Q   L   Q   W
CTG AAC AGA CGG GCC AAC GCC CTG CTG GCC AAC GGC GTG GAG CTG CGG GAC AAC CAG CTG    < 660
 L   N   R   R   A   N   A   L   L   A   N   G   V   E   L   R   D   N   Q   L
GTC GTG CCC AGC GAG GGC CTG TAC CTG ATC TAC AGC CAG GTG CTG TTC AAG GGC CAG GGC    < 720
 V   V   P   S   E   G   L   Y   L   I   Y   S   Q   V   L   F   K   G   Q   G
TGC CCT TCT ACC CAC GTG CTG CTG ACC CAC ACC ATC AGC CGG ATC GCC GTG AGC TAC CAG    < 780
 C   P   S   T   H   V   L   L   T   H   T   I   S   R   I   A   V   S   Y   Q
ACC AAA GTG AAC CTG CTG TCC GCC ATC AAG AGC CCC TGC CAG AGA GAG ACA CCT GAG GGC    < 840
 T   K   V   N   L   L   S   A   I   K   S   P   C   Q   R   E   T   P   E   G
GCC GAG GCC AAG CCT TGG TAC GAG CCC ATC TAC CTG GGC GTG TTC CAG CTG GAA AAG    < 900
 A   E   A   K   P   W   Y   E   P   I   Y   L   G   V   F   Q   L   E   K
GGC GAC CGG CTG TCC GCC GAG ATC AAC CGG CCC GAC TAC CTG AAC TTC CGG GAG AGC GGC    < 960
 G   D   R   L   S   A   E   I   N   R   P   D   Y   L   N   F   R   E   S   G
CAG GTG TAC TTC GGC ATC ATA GCG CTG GGC GGA GGG GGC AGC AGC AGC AGA ACC CCC TCC    < 1020
 Q   V   Y   F   G   I   I   A   L   G   G   G   G   S   S   S   R   T   P   S
GAC AAG CCT GTG GCT CAT GTG GTG GCT AAC CCC CAG GCT GAA GGA CAG CTG CAG TGG CTG    < 1080
 D   K   P   V   A   H   V   V   A   N   P   Q   A   E   G   Q   L   Q   W   L
AAT CGG AGA GCT AAT GCT CTG CTG GCT AAT GGG GTG GAA CTG AGA GAT AAT CAG CTG GTC    < 1140
 N   R   R   A   N   A   L   L   A   N   G   V   E   L   R   D   N   Q   L   V
GTG CCT TCT GAG GGG CTG TAT CTG ATC TAT TCT CAG GTG CTG TTT AAA GGA CAG GGG TGT    < 1200
 V   P   S   E   G   L   Y   L   I   Y   S   Q   V   L   F   K   G   Q   G   C
CCC AGC ACA CAT GTG CTG CTG ACA CAT ACA ATC TCC AGA ATC GCC GTG TCT TAT CAG ACA    < 1260
 P   S   T   H   V   L   L   T   H   T   I   S   R   I   A   V   S   Y   Q   T
AAA GTG AAT CTG CTG AGT GCC ATC AAG TCC CCT TGT CAG CGG GAA ACC CCT GAA GGG GCC    < 1320
 K   V   N   L   L   S   A   I   K   S   P   C   Q   R   E   T   P   E   G   A
GAA GCT AAA CCT TGG TAT GAA CCT ATC TAT CTG GGG GGA GTG TTT CAG CTG GAA AAA GGG    < 1380
 E   A   K   P   W   Y   E   P   I   Y   L   G   G   V   F   Q   L   E   K   G
GAC AGA CTG AGC GCC GAG ATT AAC AGA CCT GAT TAC CTG AAT TTC AGA GAA TCC GGG CAG    < 1440
 D   R   L   S   A   E   I   N   R   P   D   Y   L   N   F   R   E   S   G   Q
GTG TAC TTT GGG ATT ATC GCC CTG GGA GGG GGC GGA TCC AGC TCC AGA ACC CCC AGT GAC    < 1500
 V   Y   F   G   I   I   A   L   G   G   G   G   S   S   S   R   T   P   S   D
AAA CCA GTG GCC CAT GTG GTG GCC AAC CCA CAG GCT GAG GGG CAG CTG CAG TGG CTG AAC    < 1560
 K   P   V   A   H   V   V   A   N   P   Q   A   E   G   Q   L   Q   W   L   N
CGC AGA GCC AAT GCC CTG CTG GCC AAT GGC GTG GAA CTG CGC GAC AAT CAG CTG GTC GTG    < 1620
 R   R   A   N   A   L   L   A   N   G   V   E   L   R   D   N   Q   L   V   V
CCA TCC GAA GGA CTG TAC CTG ATC TAC TCA CAG GTG CTG TTT AAG GGG CAG GGA TGC CCC    < 1680
 P   S   E   G   L   Y   L   I   Y   S   Q   V   L   F   K   G   Q   G   C   P
TCC ACT CAT GTG CTG CTG ACT CAC ACT ATC TCT CGG ATT GCT GTG TCC TAC ACT AAA    < 1740
 S   T   H   V   L   L   T   H   T   I   S   R   I   A   V   S   Y   Q   T   K
GTG AAT CTG CTG TCT GCT ATT AAG TCT CCT TGC CAG CGC GAG ACT CCA GAG GGG GCT GAA    < 1800
 V   N   L   L   S   A   I   K   S   P   C   Q   R   E   T   P   E   G   A   E
GCC AAG CCC TGG TAT GAG CCA ATC TAT CTG GGA GGG GTG TTC CAG CTG GAA AAG GGG GAT    < 1860
 A   K   P   W   Y   E   P   I   Y   L   G   G   V   F   Q   L   E   K   G   D
CGC CTG AGC GCC GAA ATC AAT AGA CCA GAC TAT CTG AAC TTT CGC GAG TCT GGA CAG GTG    < 1920
 R   L   S   A   E   I   N   R   P   D   Y   L   N   F   R   E   S   G   Q   V
TAC TTT GGA ATC ATT GCT CTG TGA
 Y   F   G   I   I   A   L   *
```

Fig. 45

```
EHD2-scTNF_R2-L28aa
ATG GAG ACA GAC ACA CTC CTG CTA TGG GTA CTG CTG CTC TGG GTT CCA GGT TCC ACC GGT   < 60
 M   E   T   D   T   L   L   L   W   V   L   L   L   W   V   P   G   S   T   G
GAC GCG GCC CAG CCG GCC GGA GGC GGT GCG GCC GCA CAC CAT CAT CAC CAT CAC GGA GGT   < 120
 D   A   A   Q   P   A   G   G   G   A   A   A   H   H   H   H   H   H   G   G
ACC GGC GGG GGA GGT TCA GGC GGA AAG CTT GGC GGC TCT GGC GGC GAT TTC ACC CCC CCC   < 180
 T   G   G   G   G   S   G   G   K   L   G   G   S   G   G   D   F   T   P   P
ACA GTG AAG ATC CTC CAG AGC AGC TGT GAC GGC GGA GGC CAC TTC CCA CCT ACC ATC CAG   < 240
 T   V   K   I   L   Q   S   S   C   D   G   G   G   H   F   P   P   T   I   Q
CTG CTG TGT CTG GTG TCC GGC TAC ACC CCC GGC ACC ATC AAC ATC ACC TGG CTG GAA GAT   < 300
 L   L   C   L   V   S   G   Y   T   P   G   T   I   N   I   T   W   L   E   D
GGA CAA GTG ATG GAC GTG GAC CTG AGC ACC GCC AGC ACC ACA GAG GAA GGC GAG CTG GCC   < 360
 G   Q   V   M   D   V   D   L   S   T   A   S   T   T   Q   E   G   E   L   A
TCT ACC CAG AGC GAG CTG ACA CTG AGC CAG AAG CAC TGG CTG AGC GAC CGG ACC TAC ACC   < 420
 S   T   Q   S   E   L   T   L   S   Q   K   H   W   L   S   D   R   T   Y   T
TGT CAA GTG ACC TAC CAG GGC CAC ACC TTC GAG GAC AGC ACC AAG AAG TGC GCC GAC AGC   < 480
 C   Q   V   T   Y   Q   G   H   T   F   E   D   S   T   K   K   C   A   D   S
AAC GGG GGA GGA TCT GGG GGA GGA TCT GGG GGA GGA TCT GGG GGA GGA TCT GGC GGA GGT   < 540
 N   G   G   G   S   G   G   G   S   G   G   G   S   G   G   G   S   G   G   G
TCT GGG GGA TCC GAA TTC CTC GCC AGC AGC CGG ACC CCT AGC GAT AAG CCC GTG GCC CAC   < 600
 S   G   G   S   E   F   L   A   S   S   R   T   P   S   D   K   P   V   A   H
GTG GTG GCC AAT CCT CAG GCC GAG GGC CAG CTG CAG TGG CTG AAC AGA CGG GCC AAC GCC   < 660
 V   V   A   N   P   Q   A   E   G   Q   L   Q   W   L   N   R   R   A   N   A
CTG CTG GCC AAC GGC GTG GAG CTG CGG GAC AAC CAG CTG GTC GTG CCC AGC GAG GGC CTG   < 720
 L   L   A   N   G   V   E   L   R   D   N   Q   L   V   V   P   S   E   G   L
TAC CTG ATC TAC AGC CAG GTG CTG TTC AAG GGC CAG GGC TGC CCT TCT ACC CAC GTG CTG   < 780
 Y   L   I   Y   S   Q   V   L   F   K   G   Q   G   C   P   S   T   H   V   L
CTG ACC CAC ACC ATC AGC CGG ATC GCC GTG AGC TAC CAG ACC AAA GTG AAC CTG CTG TCC   < 840
 L   T   H   T   I   S   R   I   A   V   S   Y   Q   T   K   V   N   L   L   S
GCC ATC AAG AGC CCC TGC CAG AGA GAG ACA CCT GAG GGC GCC GAG GCC AAG CCT TGG TAC   < 900
 A   I   K   S   P   C   Q   R   E   T   P   E   G   A   E   A   K   P   W   Y
GAG CCC ATC TAC CTG GGC GGC GTG TTC CAG CTG GAA AAG GGC GAC CGG CTG TCC GCC GAG   < 960
 E   P   I   Y   L   G   G   V   F   Q   L   E   K   G   D   R   L   S   A   E
ATC AAC CGG CCC GAC TAC CTG AAC TTC CGG GAG AGC GGC CAG GTG TAC TTC GGC ATC ATA   < 1020
 I   N   R   P   D   Y   L   N   F   R   E   S   G   Q   V   Y   F   G   I   I
GCG CTG GGC GGA GGG GGC AGC AGC AGC AGA ACC CCC TCC GAC AAG CCT GTG GCT CAT GTG   < 1080
 A   L   G   G   G   G   S   S   S   R   T   P   S   D   K   P   V   A   H   V
GTG GCT AAC CCC CAG GCT GAA GGA CAG CTG CAG TGG CTG AAT CGG AGA GCT AAT GCT CTG   < 1140
 V   A   N   P   Q   A   E   G   Q   L   Q   W   L   N   R   R   A   N   A   L
CTG GCT AAT GGG GTG GAA CTG AGA GAT AAT CAG CTG GTC GTG CCT TCT GAG GGG CTG TAT   < 1200
 L   A   N   G   V   E   L   R   D   N   Q   L   V   V   P   S   E   G   L   Y
CTG ATC TAT TCT CAG GTG CTG TTT AAA GGA CAG GGG TGT CCC AGC ACA CAT GTG CTG CTG   < 1260
 L   I   Y   S   Q   V   L   F   K   G   Q   G   C   P   S   T   H   V   L   L
ACA CAT ACA ATC TCC AGA ATC GCC GTG TCT TAT CAG ACA AAA GTG AAT CTG CTG AGT GCC   < 1320
 T   H   T   I   S   R   I   A   V   S   Y   Q   T   K   V   N   L   L   S   A
ATC AAG TCC CCC TGT CAG CGG GAA ACC CCT GAA GGG GCC GAA GCT AAA CCT TGG TAT GAA   < 1380
 I   K   S   P   C   Q   R   E   T   P   E   G   A   E   A   K   P   W   Y   E
CCT ATC TAT CTG GGG GGA GTG TTT CAG CTG GAA AAA GGG GAC AGA CTG AGC GCC GAG ATT   < 1440
 P   I   Y   L   G   G   V   F   Q   L   E   K   G   D   R   L   S   A   E   I
AAC AGA CCT GAT TAC CTG AAT TTC AGA GAA TCC GGG CAG GTG TAC TTT GGG ATT ATC GCC   < 1500
 N   R   P   D   Y   L   N   F   R   E   S   G   Q   V   Y   F   G   I   I   A
CTG GGA GGG GGC GGA TCC AGC TCC AGA ACC CCC AGT GAC AAA CCA GTG GCC CAT GTG GTG   < 1560
 L   G   G   G   G   S   S   S   R   T   P   S   D   K   P   V   A   H   V   V
GCC AAC CCA CAG GCT GAG GGG CAG CTG CAG TGG CTG AAC CGC AGA GCC AAT GCC CTG CTG   < 1620
 A   N   P   Q   A   E   G   Q   L   Q   W   L   N   R   R   A   N   A   L   L
GCC AAT GGC GTG GAA CTG CGC GAC AAT CAG CTG GTC GTG CCA TCC GAA GGA CTG TAC CTG   < 1680
 A   N   G   V   E   L   R   D   N   Q   L   V   V   P   S   E   G   L   Y   L
ATC TAC TCA CAG GTG CTG TTT AAG GGG CAG GGA TGC CCC TCC ACT CAT GTG CTG CTG ACT   < 1740
 I   Y   S   Q   V   L   F   K   G   Q   G   C   P   S   T   H   V   L   L   T
CAC ACT ATC TCT CGG ATT GCT GTG TCC TAC CAG ACT AAA GTG AAT CTG CTG TCT GCT ATT   < 1800
 H   T   I   S   R   I   A   V   S   Y   Q   T   K   V   N   L   L   S   A   I
AAG TCT CCT TGC CAG CGC GAG ACT CCA GAG GGG GCT GAA GCC AAG CCC TGG TAT GAG CCA   < 1860
 K   S   P   C   Q   R   E   T   P   E   G   A   E   A   K   P   W   Y   E   P
ATC TAT CTG GGA GGG GTG TTC CAG CTG GAA AAG GGG GAT CGC CTG AGC GCC GAA ATC AAT   < 1920
 I   Y   L   G   G   V   F   Q   L   E   K   G   D   R   L   S   A   E   I   N
AGA CCA GAC TAT CTG AAC TTT CGC GAG TCT GGA CAG GTG TAC TTT GGA ATC ATT GCT CTG   < 1980
 R   P   D   Y   L   N   F   R   E   S   G   Q   V   Y   F   G   I   I   A   L
TGA
 *
```

IgM AND IgE HEAVY CHAIN DOMAIN 2 AS COVALENTLY LINKED HOMODIMERIZATION MODULES FOR THE GENERATION OF FUSION PROTEINS WITH DUAL SPECIFICITY

This application is a continuing application of U.S. application Ser. No. 15/645,892, filed Jul. 10, 2017 (now U.S. Pat. No. 10,875,928), which was a continuing application of U.S. application Ser. No. 14/391,930, filed Oct. 10, 2014, which was a U.S. National Phase of International Application No. PCT/EP2013/001126, filed Apr. 16, 2013, and claims priority to International Application No. PCT/EP2012/056938, filed Apr. 16, 2012, the disclosures of each of which are hereby incorporated by reference in their entireties.

REFERENCE TO AN ELECTRONIC SEQUENCE LISTING

The instant application contains an electronic Sequence Listing text file in ASCII format that has been submitted electronically and is hereby incorporated by reference in its entirety. The Sequence Listing text file was created on Dec. 20, 2016, is named "14-1690-PCTUSCON_SubstituteSequenceListing_ST25.txt" and is 228 kilobytes in size.

The present invention provides polypeptides comprising a heavy chain domain 2 (HD2) from IgM or IgE and at least one pharmaceutically active moiety, complexes thereof and their use for therapy and prophylaxis.

BACKGROUND

Fusion of therapeutic proteins such as antibodies, cytokines and growth factors to homodimerization modules generates bivalent molecules generally displaying improved efficacy due to increased valency but also improved pharmacokinetic properties (Deyev & Lebedenkov, 2008; Cuesta et al., 2010; Kontermann, 2010). Furthermore, combining two different effector molecules allows for the generation of molecules with dual specificity. Such multivalent molecules can be applied for dual targeting approaches using bispecific antibodies or using bifunctional molecules composed of an effector molecule and an antibody moiety (Müller & Kontermann, 2010; Schrama et al., 2006; Deckert, 2009). Various homo-dimerization and multimerization modules have been established including the Fc region as well as $C_H3$ and Cκ domains of immunoglobulins (Jazayeri & Carroll, 2008; Hu et al., 1996; Giersberg et al., 2011) but also other protein domains and peptides, for example derived from streptavidin, p53, uteroglobin, tenascin and collagen (Ventura et al., 2009; Dübel et al., 1995; Pack & Plückthun, 1992; Rheinnecker et al., 1996; Wüest et al., 2002; Fan et al., 2008). However, many of these modules are either non-human and, thus can induce an immune response. Furthermore, many of these modules are not covalently connected by disulfide bonds, thus have a reduced stability, and might be difficult to be produced. Finally, some of these multimerization domains, e.g. the Fc region of IgG, trigger undesired ADCC (antibody dependent cell-mediated cytotoxicity) or CDC (complement-dependent cytotoxicity) effector functions causing unwanted side effects.

To overcome these disadvantages in the prior art present inventors investigated into the usage of alternative multimerization modules. Surprisingly, it was found that the IgM $C_H2$ domain (MHD2) and the IgE $C_H2$ domain (EHD2) which replace the hinge region connecting two heavy chains in other Ig molecules, allow for the production of stable dimers due to the formation of disulfide bonds between two MHD2 or between two EHD2. Because of the central location of the MHD2 and EHD2 within the heavy chain of IgM or IgE, respectively, containing further heavy chain sequences at both ends, both domains were found to be ideally suited for the generation of dimeric fusion proteins composed of proteins fused to the N- and/or C-terminus of either HD2. Thus, the usage of the MHD2 or EHD2 domain allows for the generation of multivalent and bifunctional molecules held together by the covalently linked dimerization domains MHD2 or EHD2. Such dimers proved to be particularly stable whilst retaining their flexibility. Furthermore, no ADCC or CDC effector function is associated with their usages as dimerization module. Because they are derived from natural plasma proteins, they are easy to produce at high yields. Natural occurring N-glycosylation of these domains further improve stability and solubility under physiological conditions.

SUMMARY OF THE INVENTION

In a first aspect the present invention provides a polypeptide comprising a heavy chain domain 2 (HD2) from IgM or IgE and at least one pharmaceutically active moiety, under the proviso that the pharmaceutically active moiety is not a Fab or Fc fragment from IgM or IgE.

In a second aspect the present invention provides a nucleic acid molecule comprising a sequence encoding the polypeptide of the first aspect.

In a third aspect the present invention provides a vector comprising the nucleic acid molecule of the second aspect.

In a fourth aspect the present invention provides a complex comprising at least two polypeptides of the first aspect.

In a fifth aspect the present invention provides a cell comprising the polypeptide of the first aspect, the nucleic acid molecule of the second aspect, the vector of the third aspect, or the complex of the fourth aspect.

In a sixth aspect the present invention provides a composition comprising the polypeptide of the first aspect, the nucleic acid molecule of the second aspect, the vector of the third aspect, the complex of the fourth aspect, or the cell of the fifth aspect.

In a seventh aspect, the present invention provides the polypeptide of the first aspect, the nucleic acid molecule of the second aspect, the vector of the third aspect, the complex of the fourth aspect, or the cell of the fifth aspect for use as a medicament.

FIGURES

Figure 1:
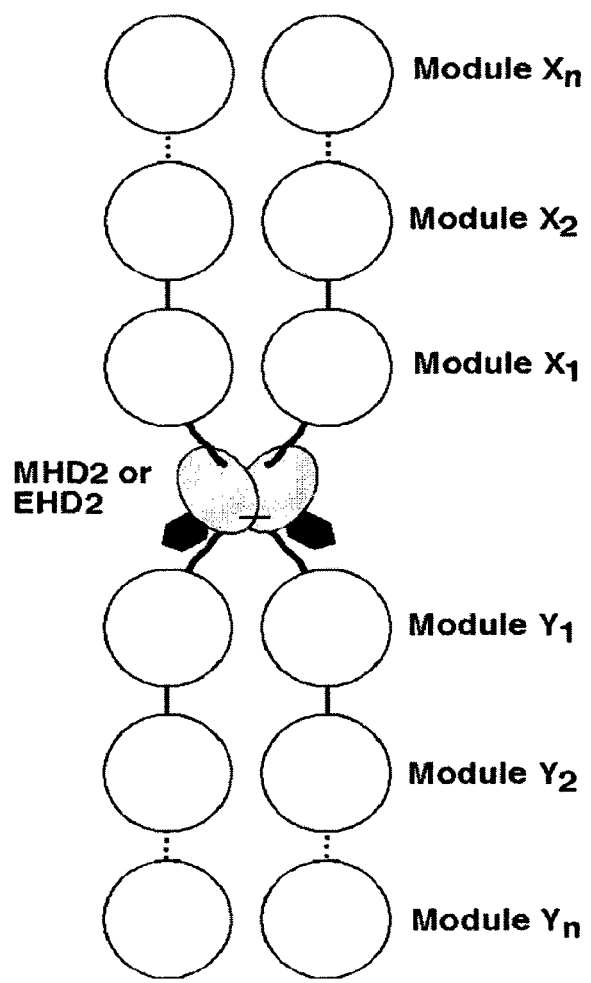

FIG. 1: The IgM heavy chain domain 2 (MHD2) and IgE heavy chain domain 2 (EHD2) is used as covalently linked homodimerization module. Further modules can be fused to either the N- or C-terminus, or to both ends. Each of the modules $X_1, X_2, \ldots X_m$, as well as $Y_1, Y_2, \ldots Y_n$, can be identical or different. Numbers of fused modules is between 1 to n and does not have to be identical between N- and C-terminal fusion.

FIG. 2: Sequence analysis of the human MHD2 (SEQ ID NO:01) and EHD2 (SEQ ID NO:02) as well as alignment of the two sequences. Inter- and intradomain cysteine bonds as well as potential N-glycosylation sites (NIT, NAS) are marked.

FIG. 3: a) Assembly of bivalent or tetravalent scFv-MHD2 fusion proteins. Bivalent, monospecific scFv-MHD2 fusion proteins are generated by fusing a scFv either to the N-terminus or the C-terminus of the MHD2, respectively. Tetravalent, bispecific scFv-MHD2 fusion proteins are generated by fusing a scFv directed against antigen A to the N-terminus of the MHD2 and another scFv directed against antigen B to the C-terminus of the MHD2. b) Schematic arrangement of the variable domains of the scFvs and the MHD2. For secretion into the cell culture supernatant the fusion proteins contain an N-terminal leader sequence (L). For purification and detection the fusion proteins contain further a C-terminal hexahistidyl-tag (His6). c) SDS-PAGE analysis of the purified MHD2 fusion proteins directed against EGFR or HER2, or both antigens. Proteins were analyzed under reducing (1-3) or non-reducing (4-6) conditions (1 and 3, scFv$_{EGFR}$-MHD2; 2 and 5, MHD2-scFv$_{HER2}$; 3 and 6, scFv$_{EGFR}$-MHD2-scFv$_{HER2}$). The gel was stained with Coomassie brilliant blue G250. Dimeric assembly of the fusion proteins is indicated by the upper band visible under non-reducing conditions corresponding to disulfide-bond linked dimers.

FIG. 4: Bioactivity of scFv-MHD2 fusion proteins. a) Binding of the antibody-MHD2 fusion proteins to immobilized receptor-Fc fusion proteins in ELISA. The three scFv-MHD2 fusion proteins showed binding to the respective EGFR- and or HER2-Fc fusion proteins. No binding was seen with an HER3-Fc fusion protein included as negative control. b) Binding of the scFv-MHD2 fusion proteins to various cell lines as indicated analyzed by flow cytometry. Bound proteins were detected with a FITC-labelled anti-His-tag antibody.

FIG. 5: a) Assembly of the MHD2-scTNF, scFv-MHD2-scTNF, and scFv-MHD2 fusion proteins. Bivalent MHD2-scTNF fusion proteins are generated by fusing scTNF to the C-terminus of the MHD2. The scFv-MHD2-scTNF fusion proteins are generated by fusing a scFv to the N-terminus of the MHD2 and scTNF to the C-terminus of the MHD2. b) Schematic arrangement of the variable domains of the scFvs, the MHD2 and the scTNF in the fusion proteins. For secretion into the cell culture supernatant the fusion proteins contain an N-terminal leader sequence (L). For purification and detection the fusion proteins contain further a C-terminal hexahistidyl-tag (His6). c) SDS-PAGE analysis of the purified fusion proteins under reducing (1-4) or non-reducing (5-8) conditions (1 and 5, scTNF; 2 and 6, scFv$_{EGFR}$-MHD2; 3 and 7, MHD2-scTNF; 4 and 8, scFv$_{EGFR}$-MHD2-scTNF). The gel was stained with Coomassie brilliant blue G250. Dimeric assembly of the fusion proteins is indicated by the upper band visible under non-reducing conditions corresponding to disulfide-bond linked dimers (lanes 6-8). c) Size exclusion chromatography (SEC) of scTNF. d) SEC of MHD2-scTNF. e) SEC of scFv$_{EGFR}$-MHD2-scTNF. This analysis further demonstrates dimeric assembly of the fusion proteins. f) Determination of the melting point of scFv$_{EGFR}$-MHD2-scTNF by dynamic light scattering.

FIG. 6: a) Binding of the scFv$_{EGFR}$-MHD2-scTNF, MHD2-scTNF and scFv$_{EGFR}$-MHD2 to an EGFR-Fc fusion protein in ELISA. HER2-Fc and HER3-Fc were included as negative controls. An anti-human Fc antibody was used as coating control. b) Binding of the scFv$_{EGFR}$-MHD2-scTNF fusion protein to different cells lines (A431, NCI-H460) in the presence or absence of monoclonal antibodies (anti-EGFR cetuximab, anti-HER trastuzumab) analyzed by flow cytometry (grey, cells alone, bold line; cells incubated with scFv$_{EGFR}$-MHD2-scTNF; thin line, cells incubated with scFv$_{EGFR}$-MHD2-scTNF and excess amounts of cetuximab or trastuzumab). c) Effect of the fusion proteins on killing of MEF-TNFR1 cells. d) Effect of the fusion proteins on killing of MEF-TNFR2 cells. Here, only the dimeric MHD2-scTNF fusion protein is capable of triggering TNFR2-mediated cell killing. e) IL-8 release from HT1080 cells induced by increasing concentrations of scFv$_{EGFR}$-MHD2-scTNF, MHD2-scTNF, and scTNF (n=4, +/−SD). scFv$_{EGFR}$-MHD was included as negative control. f) Inhibition of scFv$_{EGFR}$-MHD2-scTNF (20 pM) induced IL-8 secretion by excess amounts of anti-EGFR antibody Cetuximab (660 nM). No effects were seen for IL-8 release induced by MHD2-scTNF and scTNF, respectively. Trastuzumab (anti-HER2) was included as negative control.

FIG. 7: a) Assembly of the MHD2-scTRAIL and scFv-MHD2-scTRAIL fusion proteins. Bivalent MHD2-scTRAIL fusion proteins are generated by fusing scTRAIL to the C-terminus of the MHD2. The scFv-MHD2-scTRAIL fusion proteins are generated by fusing a scFv to the N-terminus of the MHD2 and scTRAIL to the C-terminus of the MHD2. b) Schematic arrangement of the variable domains of the scFvs, the MHD2 and the scTRAIL in the fusion proteins. For secretion into the cell culture supernatant the fusion proteins contain an N-terminal leader sequence (L). For purification and detection the fusion proteins contain further an N-terminal FLAG-tag (FLAG-tag). c) SDS-PAGE analysis of the purified fusion proteins under reducing (1-4) or non-reducing (5-8) conditions (1 and 4, scTRAIL; 2 and 5, MHD2-scTRAIL; 3 and 6, scFv$_{EGFR}$-MHD2-scTRAIL). The gel was stained with Coomassie brilliant blue G250. Dimeric assembly of the fusion proteins is indicated by the upper band visible under non-reducing conditions corresponding to disulfide-bond linked dimers (lanes 4-6).

Figure 8:
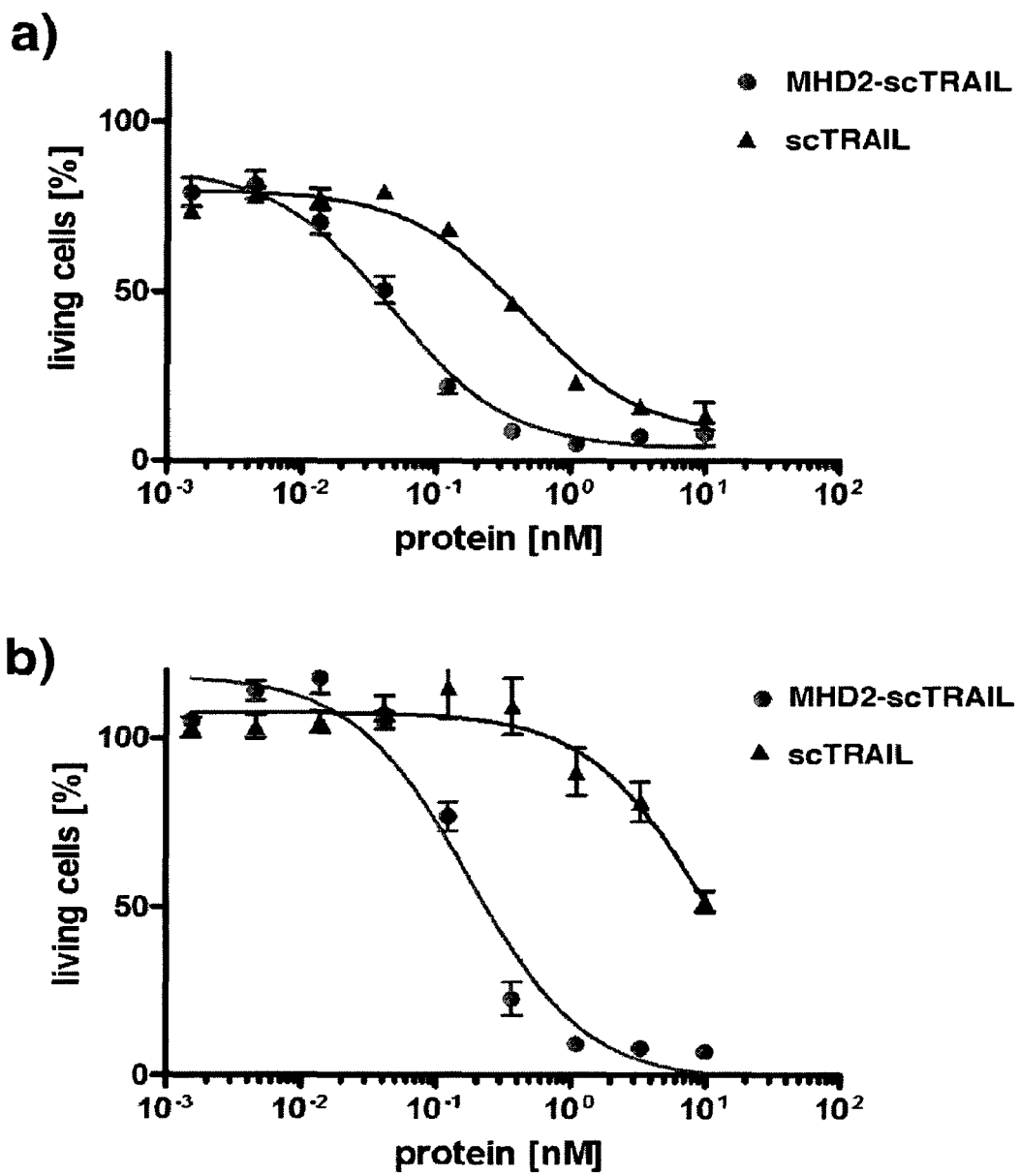

FIG. 8: Cytotoxic activity of scTRAIL and MHD2-scTRAIL on NCI-H460 (a) and Colo205 (b) cells in the presence of 250 ng/ml bortezomib. Cells were incubated for 24 h with the proteins and cytotoxicity was determined by crystal violet staining of remaining cells. MHD2-scTRAIL showed a 10- to 50-fold increased cytotoxic activity compared to scTRAIL.

FIG. 9: a) Assembly of the EHD2-scTRAIL, scFv-EHD2-scTRAIL, and scFv-EHD2 fusion proteins. Bivalent scFv-EHD2 fusion proteins are generated by fusing an scFv directed against EGFR to the N-terminus of the EHD2. Bivalent EHD2-scTRAIL fusion proteins are generated by fusing scTRAIL to the C-terminus of the EHD2. The scFv-EHD2-scTRAIL fusion proteins are generated by fusing a scFv to the N-terminus of the EHD2 and scTRAIL to the C-terminus of the EHD2. b) Schematic arrangement of the variable domains of the scFvs, the EHD2 and the scTRAIL in the fusion proteins. For secretion into the cell culture supernatant the fusion proteins contain an N-terminal leader sequence (L). For purification and detection the fusion proteins contain further an N-terminal FLAG-tag (FLAG-tag). c) Immunoblot analysis of cell culture supernatant of HEK293 cells transiently transfected with an expression plasmid for scFv-EHD2 under non-reducing (1) or reducing (2) conditions. The fusion protein was detected with an anti-FLAG-tag antibody or anti-His-tag antibody. Dimeric assembly of the fusion protein is indicated by the upper band visible under non-reducing conditions corresponding to disulfide-bond linked dimers (lanes 1). d) Immunoblot analysis of cell culture supernatant of HEK293 cells transiently transfected with an expression plasmid for EHD2-scTRAIL under non-reducing (1) or reducing (2) conditions. The fusion protein was detected with an anti-FLAG-tag antibody. Dimeric assembly of the fusion protein is indicated by the upper band visible under non-reducing conditions corresponding to disulfide-bond linked dimers (lanes 1). e)

Immunoblot analysis of cell culture supernatant of HEK293 cells transiently transfected with an expression plasmid for scFv-EHD2-scTRAIL under non-reducing (1) or reducing (2) conditions. The fusion protein was detected with an anti-FLAG-tag antibody. Dimeric assembly of the fusion protein is indicated by the upper band visible under non-reducing conditions corresponding to disulfide-bond linked dimers (lanes 1).

Figure 10:
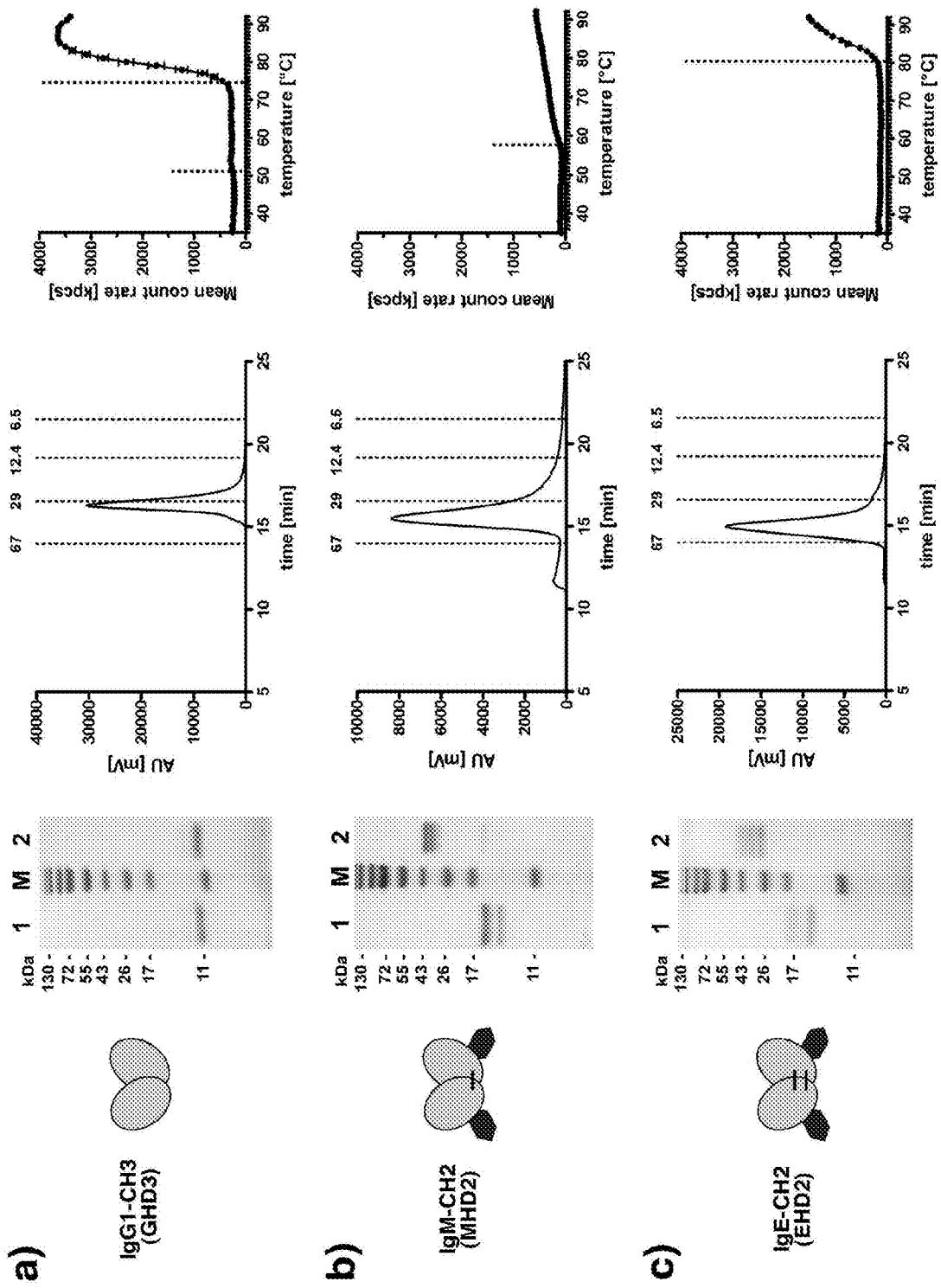

FIG. 10: Comparison of recombinant CH3 domain of human IgG1 (GHD3) (a), the human MHD2 domain (b) and the human EHD2 domain (c). SDS-PAGE analysis of the purified protein was performed under reducing (1) and non-reducing (2) conditions. Gels were stained with Coomassie brilliant blue G250. Dimeric assembly and linkage by disulfide-bonds was demonstrated for MHD2 and EHD2. Heterogeneity regarding N-glycosylation was also observed for MHD2 and EHD2 indicated by 2 to 3 bands under reducing and non-reducing conditions, respectively. Size-exclusion chromatography confirmed dimeric assembly of the domains, with the two N-glycosylated domains (MHD2, EHD2) migrating with an apparent size which is larger than that of the GHD3 domain. Determination of melting points by dynamic light scattering revealed for CH3 of IgG1 a first melting point at around 50° C. (probably due to domain dissociation) and a second major melting point at 75° C. (probably due to complete denaturation), while no sharp increase of signals but a gradual increase starting at around 56° C. was observed for MHD2, indicating that the protein is rather stable up to a temperature of 92° C. For EHD2, a single thermal melting point of approximately 80-82° C. was determined.

FIG. 11: Nucleic acid (SEQ ID NO:37) and amino acid (SEQ ID NO:03) sequence of anti-HER2 scFvs (4D5). The leader peptide is underlined.

FIG. 12: Nucleic acid (SEQ ID NO:38) and amino acid (SEQ ID NO:04) sequence of anti-EGFR scFvs (hu225). The leader peptide is underlined.

FIG. 13: Nucleic acid (SEQ ID NO:39) and amino acid (SEQ ID NO:05) sequence of scTNF. Linkers connecting the individual TRAIL monomers are underlined.

FIG. 14: Nucleic acid (SEQ ID NO:40) and amino acid (SEQ ID NO:06) sequence of scTRAIL. Linkers connecting the individual TRAIL monomers are underlined.

FIG. 15: Nucleic acid (SEQ ID NO:41) and amino acid (SEQ ID NO:07) sequence of $scFv_{EGFR-MHD2}$. The MHD2 is shown in grey. Leader peptide and linkers connecting the individual domains are underlined.

FIG. 16: Nucleic acid (SEQ ID NO:42) and amino acid (SEQ ID NO:08) sequence of $MHD2-scF_{vHER2}$. The MHD2 is shown in grey. Leader peptide and linkers connecting the individual domains are underlined.

Figure 17:
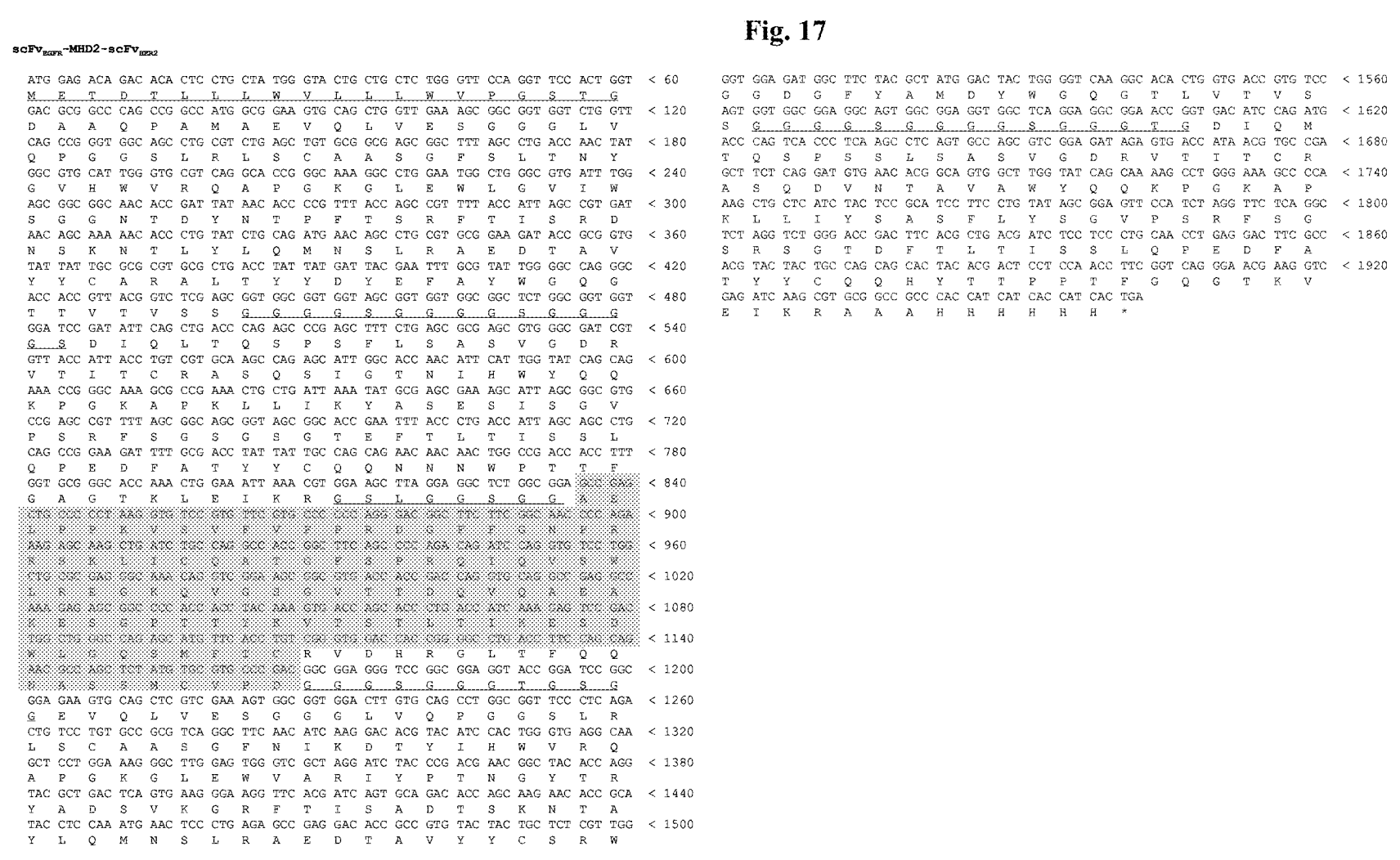

FIG. 17: Nucleic acid (SEQ ID NO:43) and amino acid (SEQ ID NO:09) sequence of $scFv_{EGFR-MHD2}$-$scFv_{HER2}$. The MHD2 is shown in grey. Leader peptide and linkers connecting the individual domains are underlined.

FIG. 18: Nucleic acid (SEQ ID NO:44) and amino acid (SEQ ID NO:10) sequence of MHD2-scTNF. The MHD2 is shown in grey. Leader peptide and linkers connecting the individual domains are underlined.

Figure 19:
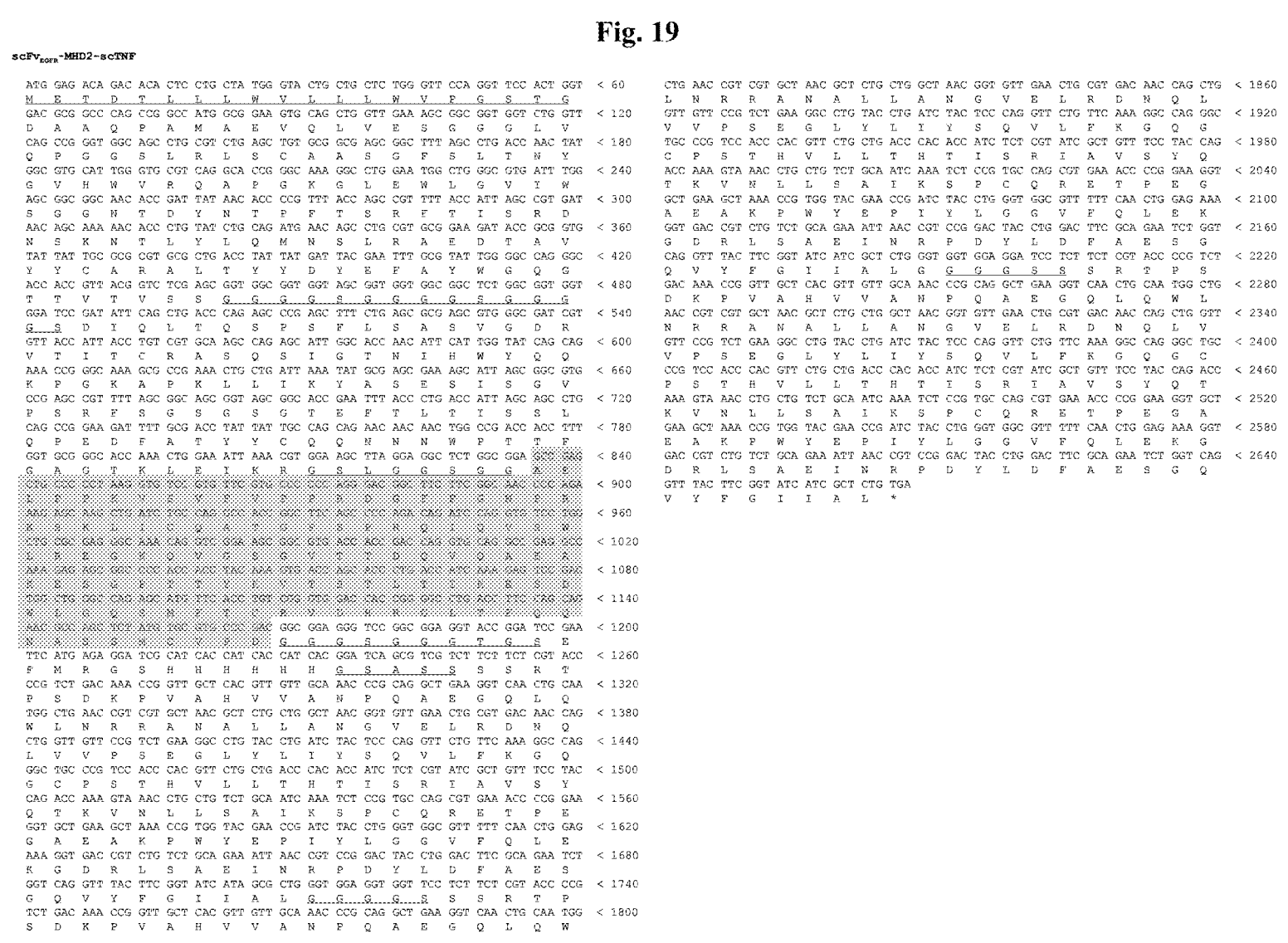

FIG. 19: Nucleic acid (SEQ ID NO:45) and amino acid (SEQ ID NO:11) sequence of $scFv_{EGFR-MHD2}$-ScTNF. The MHD2 is shown in grey. Leader peptide and linkers connecting the individual domains are underlined.

FIG. 20: Nucleic acid (SEQ ID NO:46) and amino acid (SEQ ID NO:12) sequence of MHD2-scTRAIL. The MHD2 is shown in grey. Leader peptide and Linkers connecting the individual domains are underlined.

Figure 21:
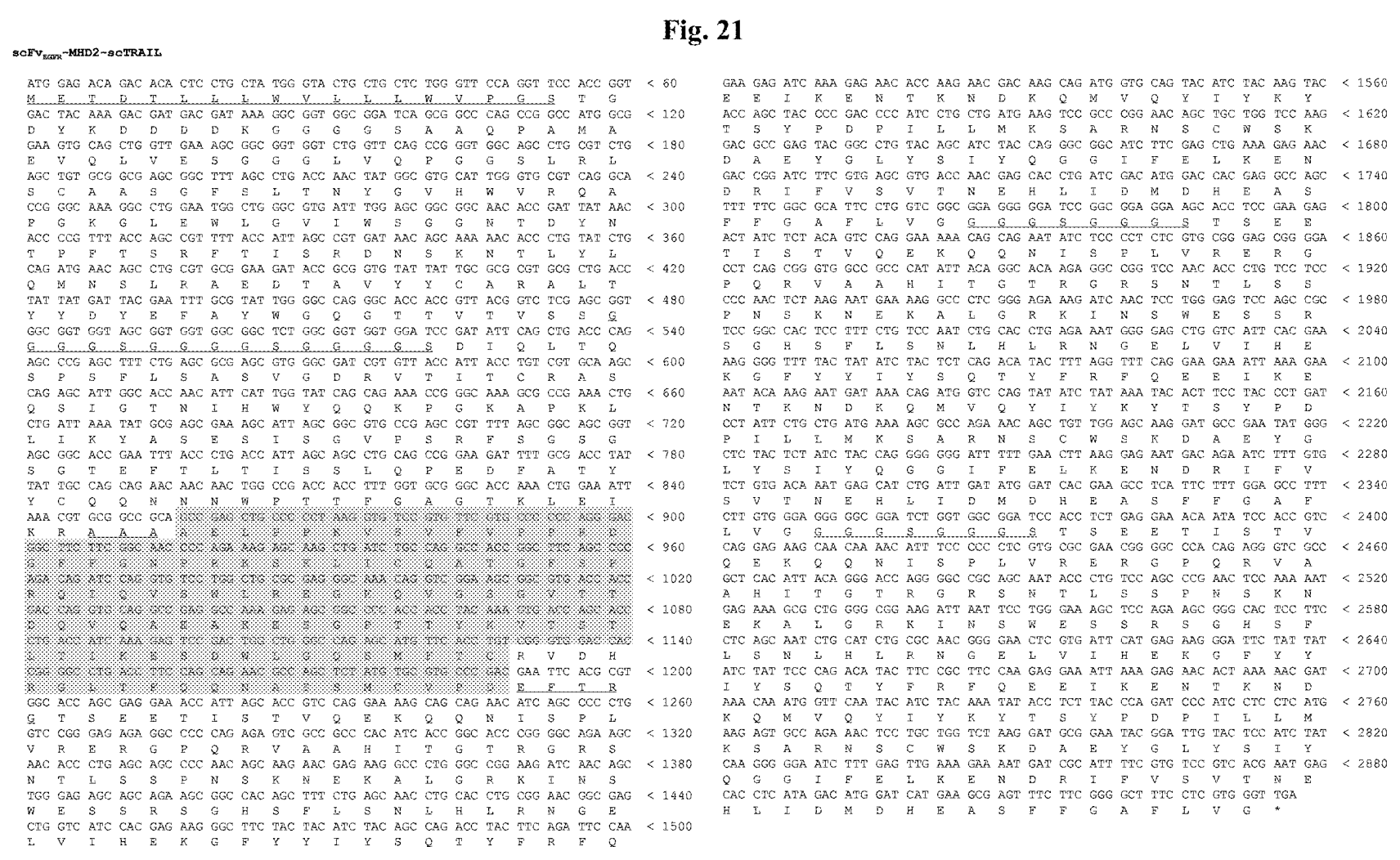

FIG. 21: Nucleic acid (SEQ ID NO:47) and amino acid (SEQ ID NO:13) sequence of $scFv_{EGFR-MHD2}$-scTRAIL. The MHD2 is shown in grey. Leader peptide and linkers connecting the individual domains are underlined.

Figure 22:
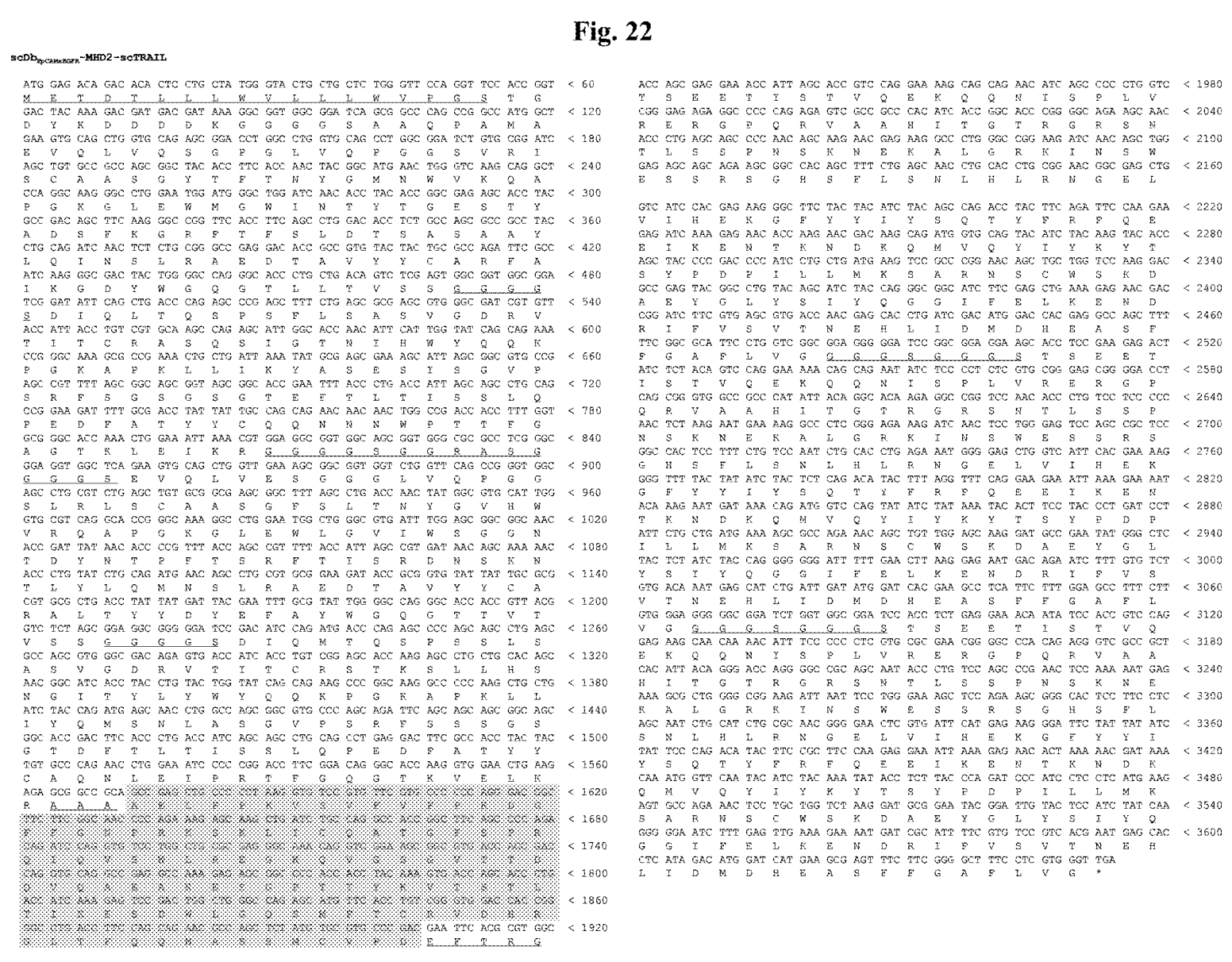

FIG. 22: Nucleic acid (SEQ ID NO:48) and amino acid (SEQ ID NO:14) sequence of $scDb_{EpCAMxEGFR-MHD2}$-scTRAIL. The MHD2 is shown in grey. Leader peptide and Linkers connecting the individual domains are underlined.

FIG. 23: Nucleic acid (SEQ ID NO:49) and amino acid (SEQ ID NO:15) sequence of $scFv_{EGFR-EHD2}$. The EHD2 is shown in grey. Leader peptide and Linkers connecting the individual domains are underlined.

FIG. 24: Nucleic acid (SEQ ID NO:50) and amino acid (SEQ ID NO:16) sequence of EHD2-scTRAIL. The MHD2 is shown in grey. Leader peptide and Linkers connecting the individual domains are underlined.

Figure 25:
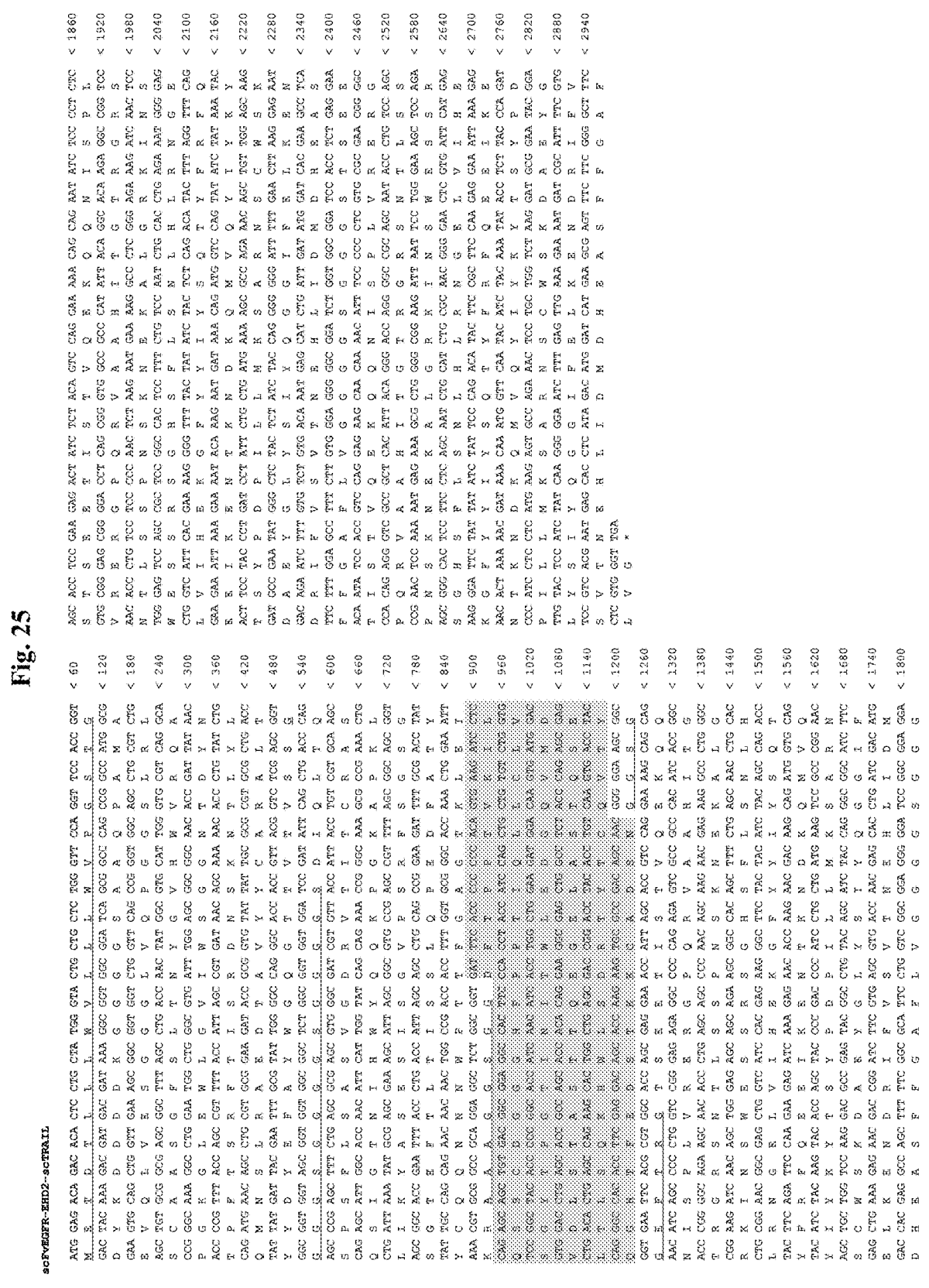

FIG. 25: Nucleic acid (SEQ ID NO:51) and amino acid (SEQ ID NO:17) sequence of $scFv_{EGFR-EHD2}$-scTRAIL. The MHD2 is shown in grey. Leader peptide and linkers connecting the individual domains are underlined.

Figure 26:
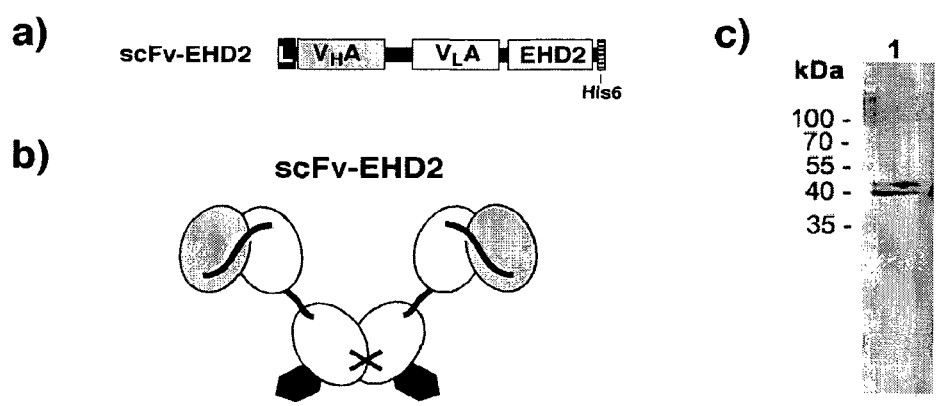

FIG. 26: a) Schematic arrangement of scFv-EHD2 fusion proteins (L=leader peptide; His6=hexahistidyl tag). b) Schematic structure of scFv-EHD2 fusion proteins (the EHD2 domains are shown in white). c) Immunoblotting experiment showing the expression of anti-HER3 scFv-EHD2 fusion protein (lane 1). Proteins were separated on a 12% SDS-PAGE under reducing conditions and detected with a HRP-conjugated anti-His-tag antibody. The fusion protein has the expected size of approximately 40 to 45 kDa. The detected double band indicates glycosylated and non-glycosylated proteins.

Figure 27:
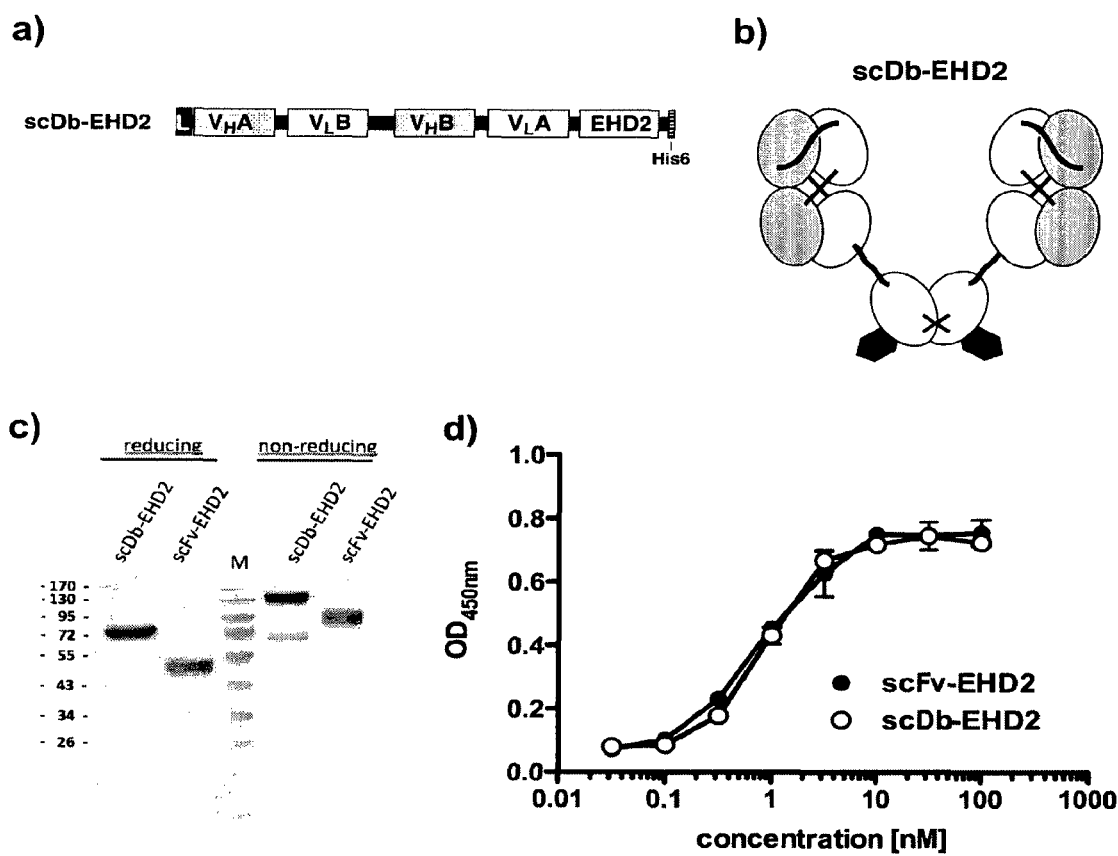

FIG. 27: a) Schematic arrangement of bispecific scDb-EHD2 fusion protein (L=leader peptide; His6=hexahistidyl tag). b) Schematic structure of a scDb-EHD2 fusion protein (the EHD2 domains are shown in white). c) SDS-PAGE of purified fusion proteins under reducing or nonreducing conditions. Gel was stained with Coomassie. d) ELISA of binding of scFv-EHD2 and scDb-EHD2 to immobilized CEA (3 µg/ml). Bound antibodies were detected with an HRP-conjugated anti-His-tag antibody.

FIG. 28: a) Schematic composition of the scFv-L3 fragment used to generate scFv-L3-EHD2 fusion proteins with the cysteine as position 3 of the linker sequence (SEQ ID NO:52). b) Schematic structure of scFv-L3-EHD2 and scFv-L3-EHD2-scFv fusion proteins (the EHD2 domains are shown in white). c) Immunoblotting experiment showing the expression of anti-FAP scFv-L3 (lane 1), a diabody Db-Cys (lane 2), an scFv-L3-EHD2 (lane 3), and an scFv-L3-EHD3-scFv in the supernatant of transiently transfected HEK293 cells. Proteins were separated on a 12% SDS-PAGE under reducing conditions and detected with a HRP-conjugated anti-His-tag antibody. All proteins have the expected size.

FIG. 29: a) Schematic illustration of the various EHD2 fusion proteins. b) SDS-PAGE analysis of the purified fusion proteins under reducing (lanes 1-3) or non-reducing (lanes 4-6) conditions (scFv-EHD2, lanes 1, 4; EHD2-scTRAIL, lanes 2, 5; scFv-EHD2-scTRAIL, lanes 3, 6). c) SEC analysis of the purified fusion proteins. d) ELISA for binding of the fusion proteins to EGFR and TRAIL receptors 1 and 2 using recombinant receptor-Fc fusion proteins. HER2-Fc was included as negative control. e) Titration of scFv-EHD2 and scFv directed against EGFR in ELISA for binding to immobilized EGFR.

Figure 30:
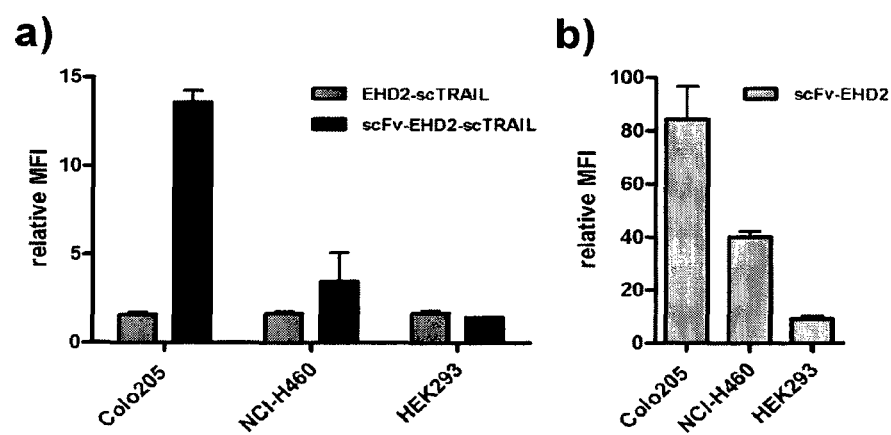

FIG. 30: Binding of EHD2 fusions proteins to EGFR-expressing cell lines analyzed by flow cytometry. a) Binding of EHD2-scTRAIL and scFv-EHD2-scTRAIL to Colo205, NCI-H460 and HEK293 using an anti-FLAG-tag antibody for detection. b) Binding of scFv-EHD2 to Colo205, NCI-H460 and HEK293 using an anti-His-tag antibody for detection.

Figure 31:
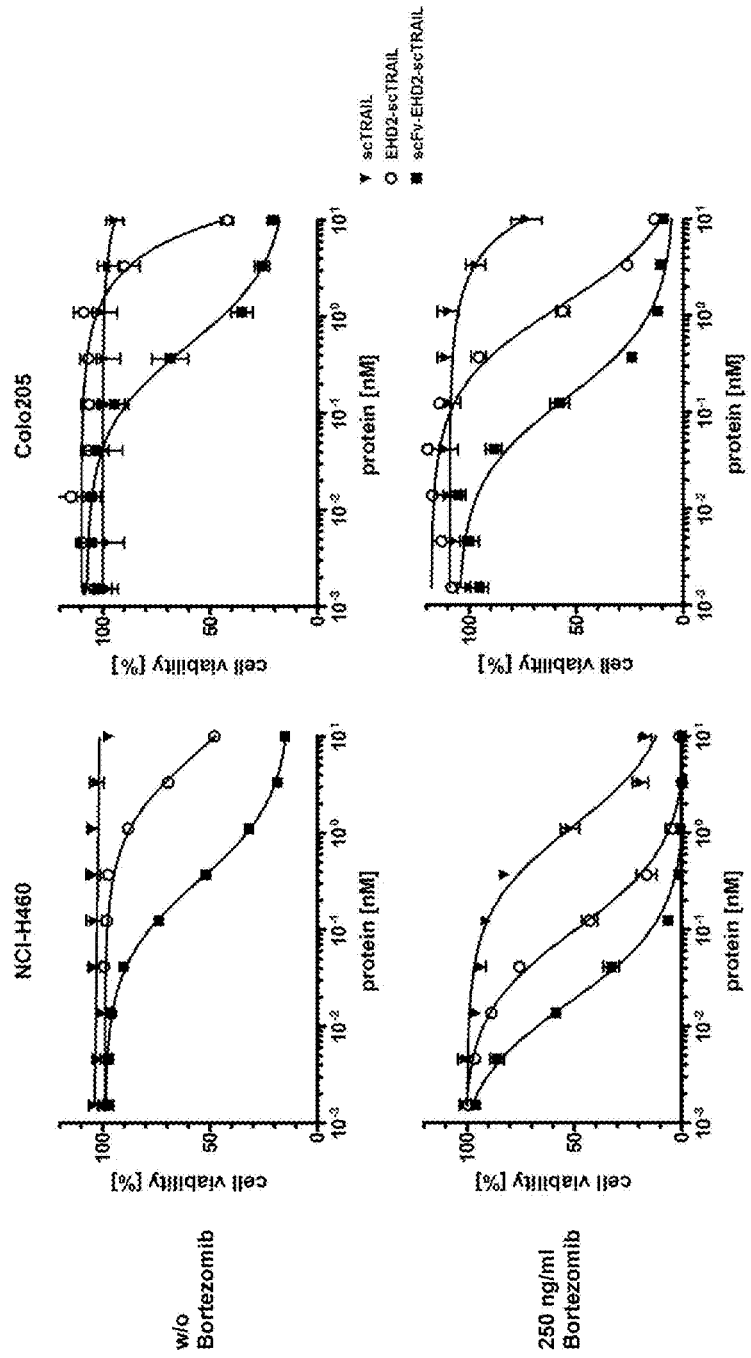

FIG. 31: In vitro cytotoxicity of EHD2-scTRAIL and scFv-EHD2-scTRAIL in comparison to scTRAIL. Cytotoxicity was analyzed with two cell lines (NCI-H460, Colo205) in the absence or presence of bortezomib (250 ng/ml). Cells were incubated for 16 h with the fusion proteins and viable cells were determined by crystal violet staining.

Figure 32:
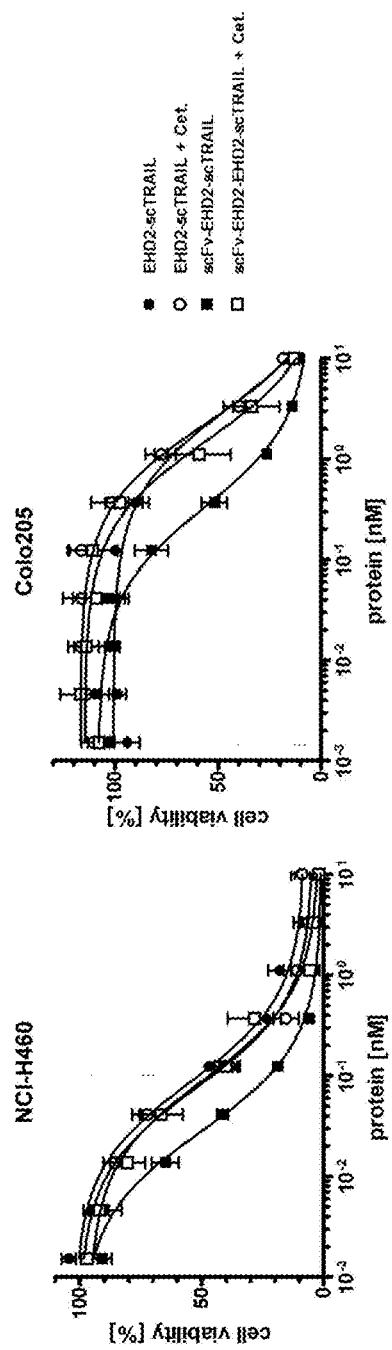

FIG. 32: In vitro cytotoxicity of EHD2-scTRAIL and scFv-EHD2-scTRAIL in the absence or presence of cetuximab. Cytotoxicity was analyzed with two cell lines (NCI-H460, Colo205) in presence of bortezomib (250 ng/ml) with or without an 100-fold molar excess of cetuximab (Cet.), which blocks binding of the anti-EGFR scFv to cells. Cells were incubated for 16 h with the fusion proteins and viable cells were determined by crystal violet staining.

Figure 33:
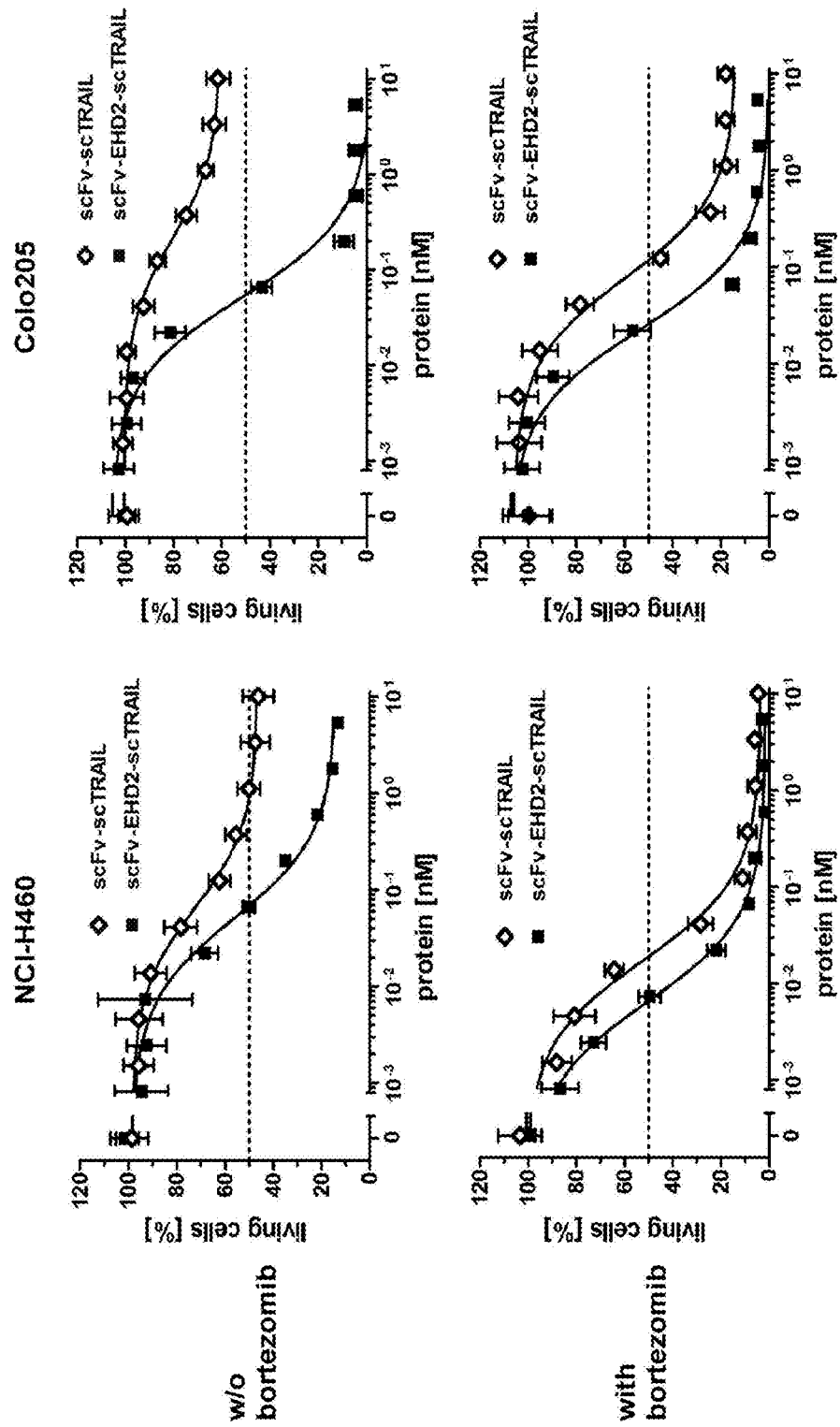

FIG. 33: In vitro cytotoxicity of scFv-EHD2-scTRAIL in comparison to scFv-scTRAIL. Cytotoxicity was analyzed with two cell lines (NCI-H460, Colo205) in the absence or presence of bortezomib (250 ng/ml). Cells were incubated for 16 h with the fusion proteins and viable cells were determined by crystal violet staining.

Figure 34:
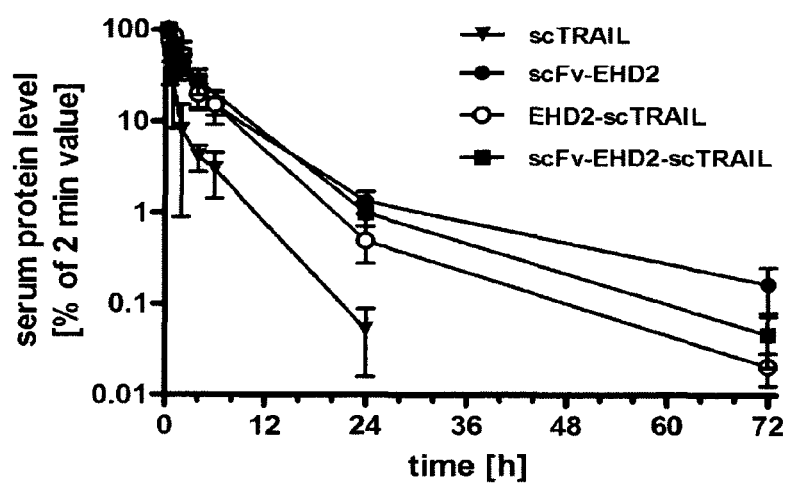

FIG. 34: Pharmacokinetics of EHD2 fusion proteins in mice. scTRAIL and the EHD2 fusion proteins (25 µg per animal) were injected i.v. into CD1 mice (n=3) and serum concentrations were determined by ELISA.

Figure 35:
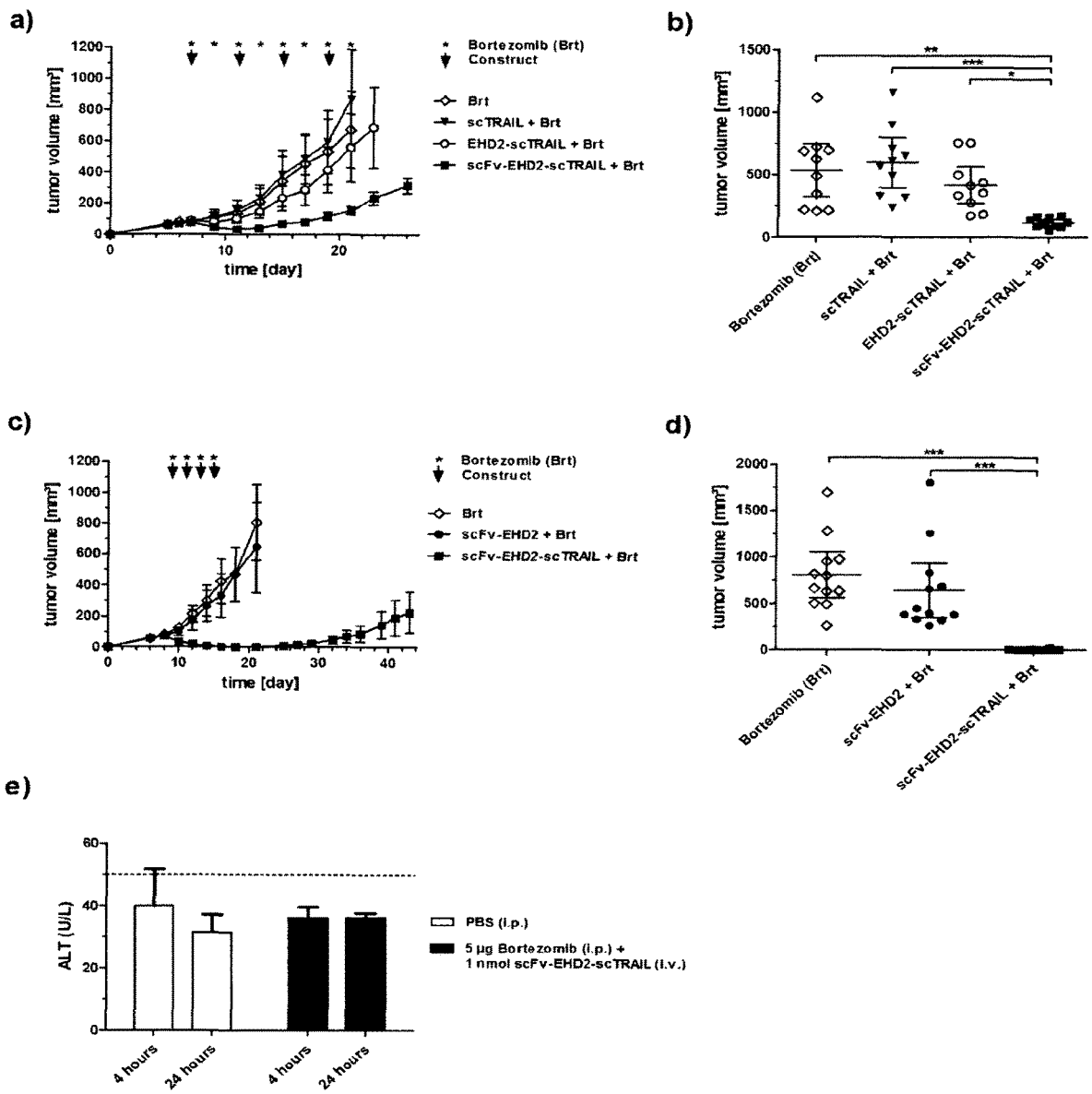

FIG. 35: a) In vivo antitumor activity of EHD2-scTRAIL and scFv-EHD2-scTRAIL in comparison to scTRAIL. NMRI nude mice bearing s.c. Colo205 xenograft tumors received four i.v. injections of the proteins (0.35 nmol of the fusion proteins and 0.7 nmol of scTRAIL) every four days as well as eight i.p. injection of bortezomib (Brt, 5 µg/injection) every second day. a) tumor growth. b) Tumor volumes at day 13. c) In vivo antitumor activity of scFv-EHD2-scTRAIL in comparison with scFv-EHD2 and bortezomib treatment. NMRI nude mice bearing s.c. Colo205 xenograft tumors received four i.v. injections of the proteins (1 nmol of the fusion proteins) as well as four i.p. injection of bortezomib (Brt, 5 µg/injection) every second day. b) Tumor volumes at day 21. e) An ALT-assay was performed 4 or 24 hours after injection of scFv-EHD2-scTRAIL (1 nmol, i.v.) together with bortezomib (5 µg, i.p.) into CD1 mice. No statistically significant differences were observed in comparison to a PBS control. All values were below the threshold of 50 U/L.

Figure 36:
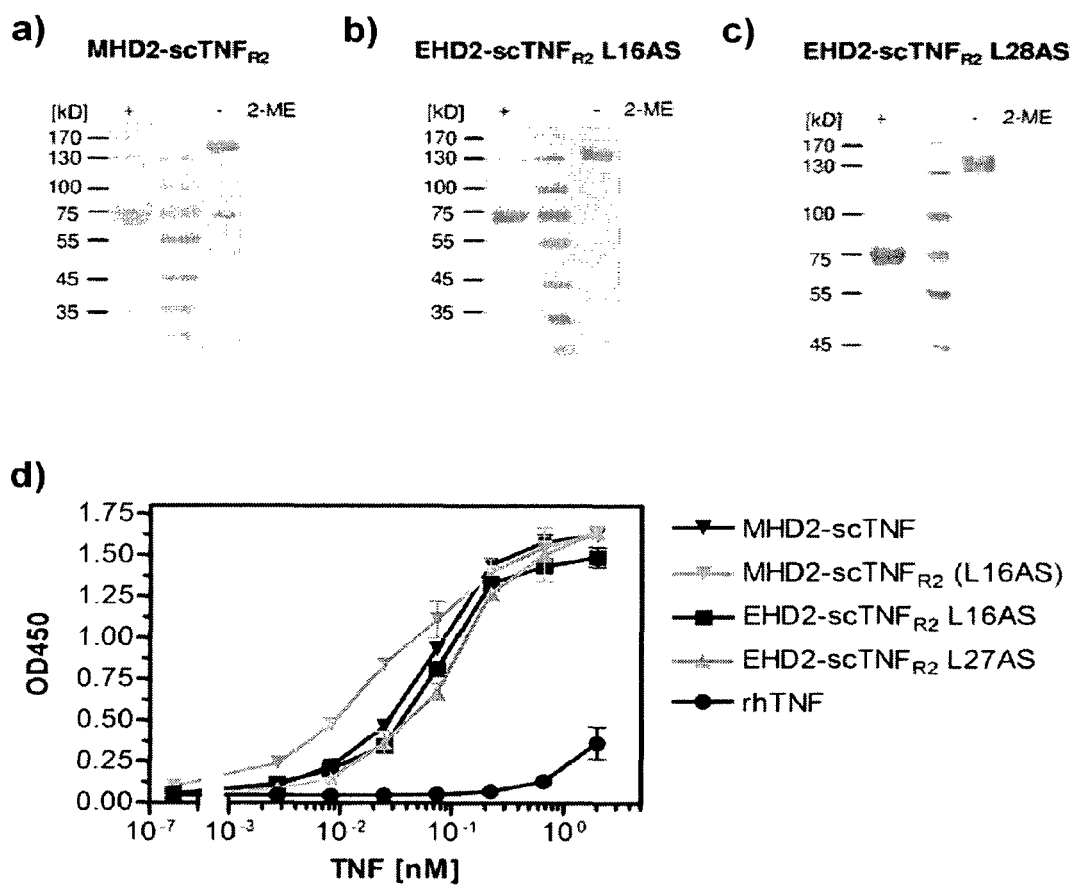

FIG. 36: a-c) Purified TNF variants (a: MHD2-scTNF$_{R2}$, b: EHD2-scTNF$_{R2}$ with a 16 aa linker between EHD2 and scTNFR2 as well as c: EHD2-scTNF$_{R2}$ with a 28 aa linker between EHD2 and scTNFR2) were analyzed by 8% SDS-PAGE under reducing (+2-ME) or non-reducing (−2-ME) conditions and stained with Coomassie. d) Binding studies with TNFR2-Fc fusion protein. Plates were coated with 1 µg/ml TNFR2-Fc fusion protein (Enbrel). TNF fusion proteins were incubated for 1 h at RT and bound TNF fusion proteins were detected using HRP-conjugated anti-TNF antibodies and TMB substrate (n=2).

FIG. 37: Nucleic acid (SEQ ID NO:53) and amino acid (SEQ ID NO:54) sequence of Anti-CEA scFv-EHD2.

FIG. 38: Nucleic acid (SEQ ID NO:55) and amino acid (SEQ ID NO:56) sequence of Anti-HER2 scFv-EHD2.

FIG. 39: Nucleic acid (SEQ ID NO:57) and amino acid (SEQ ID NO:58) sequence of Anti-HER3 scFv-EHD2.

FIG. 40: Nucleic acid (SEQ ID NO:59) and amino acid (SEQ ID NO:60) sequence of Anti-CEAxCD3 scDb-EHD2.

FIG. 41: Nucleic acid (SEQ ID NO:61) and amino acid (SEQ ID NO:62) sequence of Anti-EGFR scFv-L3-EHD2.

FIG. 42: Nucleic acid (SEQ ID NO:63) and amino acid (SEQ ID NO:64) sequence of Anti-EGFR scFv-L3-EHD2-scFv.

FIG. 43: Nucleic acid (SEQ ID NO:65) and amino acid (SEQ ID NO:66) sequence of MHD2-scTNF$_{R2}$.

FIG. 44: Nucleic acid (SEQ ID NO:67) and amino acid (SEQ ID NO:68) sequence of EHD2-scTNF$_{R2-L16aa}$.

FIG. 45: Nucleic acid (SEQ ID NO:69) and amino acid (SEQ ID NO:70) sequence of EHD2-scTNF$_{R2-L28aa}$.

DETAILED DESCRIPTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety. Nothing herein is to be construed as an admission that the invention is not entitled to antedate such disclosure by virtue of prior invention.

Definitions

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The terms "protein" and "polypeptide" are used interchangeably herein and refer to any peptide-bond-linked chain of amino acids, regardless of length or post-translational modification. Proteins usable in the present invention (including protein derivatives, protein variants, protein fragments, protein segments, protein epitopes and protein domains) can be further modified by chemical modification. This means such a chemically modified polypeptide comprises other chemical groups than the 20 naturally occurring amino acids. Examples of such other chemical groups include without limitation glycosylated amino acids and phosphorylated amino acids. Chemical modifications of a polypeptide may provide advantageous properties as compared to the parent polypeptide, e.g. one or more of enhanced stability, increased biological half-life, or increased water solubility.

The terms "polynucleotide" and "nucleic acid" are used interchangeably herein and are understood as a polymeric or oligomeric macromolecule made from nucleotide monomers. Nucleotide monomers are composed of a nucleobase, a five-carbon sugar (such as but not limited to ribose or 2'-deoxyribose), and one to three phosphate groups. Typically, a polynucleotide is formed through phosphodiester bonds between the individual nucleotide monomers. The nucleic acids, can e.g. be synthesized chemically, e.g. in accordance with the phosphotriester method (see, for example, Uhlmann & Peyman (1990) Chemical Reviews 90:543-584).

As used herein, the term "variant" is to be understood as a polynucleotide or protein which differs in comparison to the polynucleotide or protein from which it is derived by one or more changes in its length or sequence. The polypeptide or polynucleotide from which a protein or nucleic acid variant is derived is also known as the parent or parental polypeptide or polynucleotide. "Dimerizing variants" as referred to herein are variants of a parental dimerization domain which differ from said parental dimerization domain by one or more changes in its length or sequence as detailed above. The term "variant" or "dimerizing variants" comprises "fragments" or "derivatives" of the parent molecule. Typically, "fragments" are smaller in length or size than the parent molecule, whilst "derivatives" exhibit one or more differences in their sequence in comparison to the parent molecule. Also encompassed are modified molecules such as but not limited to post-translationally modified proteins (e.g. glycosylated, biotinylated, phosphorylated, ubiquitinated, palmitoylated, or proteolytically cleaved proteins) and modified nucleic acids such as methylated DNA. Also mixtures of different molecules such as but not limited to RNA-DNA hybrids, are encompassed by the term "variant" or "dimerizing variants". Typically, a variant or dimerizing variants is constructed artificially, preferably by gene-technological means whilst the parent polypeptide or polynucleotide is a wild-type protein or polynucleotide. However, also naturally occurring variants are to be understood to be encompassed by the term "variant" or "dimerizing variants" as used herein. Further, the variants or dimerizing variants usable in the present invention may also be derived from homologs, orthologs, or paralogs of the parent molecule or from artificially constructed variant, provided that the variant or dimerizing variants exhibits at least one biological activity of the parent molecule, i.e. is functionally active.

The changes in the nucleotide or amino acid sequence may be nucleotide or amino acid exchanges, insertions, deletions, 5'- or 3' truncations, N- or C-terminal truncations, or any combination of these changes, which may occur at one or several sites. In preferred embodiments, a variant usable in the present invention exhibits a total number of up to 150 (up to 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, or 150) changes in the nucleotide or amino acid sequence (i.e. exchanges, insertions, deletions, and/or truncations). Amino acid exchanges may be conservative and/or non-conservative. Typical substitutions are among the aliphatic amino acids, among the amino acids having aliphatic hydroxyl side chain, among the amino acids having acidic residues, among the amide derivatives, among the amino acids with basic residues, or the amino acids having aromatic residues. Typical semi-conservative and conservative substitutions are:

| Amino acid | Conservative substitution | Semi-conservative |
|---|---|---|
| A | G; S; T | N; V; C |
| C | A; V; L | M; I; F; G |
| D | E; N; Q | A; S; T; K; R; H |
| E | D; Q; N | A; S; T; K; R; H |
| F | W; Y; L; M; H | I; V; A |
| G | A | S; N; T; D; E; N; Q |
| H | Y; F; K; R | L; M; A |
| I | V; L; M; A | F; Y; W; G |
| K | R; H | D; E; N; Q; S; T; A |
| L | M; I; V; A | F; Y; W; H; C |
| M | L; I; V; A | F; Y; W; C; |
| N | Q | D; E; S; T; A; G; K; R |
| P | V; I | L; A; M; W; Y; S; T; C; F |
| Q | N | D; E; A; S; T; L; M; K; R |
| R | K; H | N; Q; S; T; D; E; A |
| S | A; T; G; N | D; E; R; K |
| T | A; S; G; N; V | D; E; R; K; I |
| V | A; L; I | M; T; C; N |
| W | F; Y; H | L; M; I; V; C |
| Y | F; W; H | L; M; I; V; C |

Changing from A, F, H, I, L, M, P, V, W or Y to C is semi-conservative if the new cysteine remains as a free thiol. Furthermore, the skilled person will appreciate that glycines at sterically demanding positions should not be substituted and that P should not be introduced into parts of the protein which have an alpha-helical or a beta-sheet structure.

Alternatively or additionally, a "variant" or "dimerizing variant" as used herein, can be characterized by a certain degree of sequence identity to the parent polypeptide or parent polynucleotide from which it is derived. More precisely, a protein variant in the context of the present invention exhibits at least 70% sequence identity to its parent polypeptide. A polynucleotide variant in the context of the present invention exhibits at least 70% sequence identity to its parent polynucleotide. Preferably, the sequence identity of protein variants is over a continuous stretch of 20, 30, 40, 45, 50, 60, 70, 80, 90, 100 or more amino acids. Preferably, the sequence identity of polynucleotide variants is over a continuous stretch of 60, 90, 120, 135, 150, 180, 210, 240, 270, 300 or more nucleotides.

The term "at least 70% sequence identity" is used throughout the specification with regard to polypeptide and polynucleotide sequence comparisons. This expression preferably refers to a sequence identity of at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to the respective reference polypeptide or to the respective reference polynucleotide.

In case where two sequences are compared and the reference sequence is not specified in comparison to which the sequence identity percentage is to be calculated, the sequence identity is to be calculated with reference to the longer of the two sequences to be compared, if not specifically indicated otherwise. If the reference sequence is indicated, the sequence identity is determined on the basis of the full length of the reference sequence indicated by SEQ ID, if not specifically indicated otherwise. For example, a peptide sequence consisting of 90 amino acids compared to the amino acid sequence of a human MHD2 domain may exhibit a maximum sequence identity percentage of 81.08% (90/111) while a sequence with a length of 78 amino acids may exhibit a maximum sequence identity percentage of 70.03% (78/111). The similarity of nucleotide and amino acid sequences, i.e. the percentage of sequence identity, can be determined via sequence alignments. Such alignments can be carried out with several art-known algorithms, preferably with the mathematical algorithm of Karlin and Altschul (Karlin & Altschul (1993) Proc. Natl. Acad. Sci. USA 90:5873-5877), with hmmalign (HMMER package, hmmer-.wustl.edu/) or with the CLUSTAL algorithm (Thompson et al. (1994) Nucleic Acids Res. 22:4673-4680) available e.g. on www.ebi.ac.uk/Tools/clustalw/ or on www.ebi.ac.uk/Tools/clustalw2/index.html or on npsa-pbil.ibcp.fr/cgi-bin/npsa_automat.pl?page=/NPSA/npsa_clustalw.html. Preferred parameters used are the default parameters as they are set on www.ebi.ac.uk/Tools/clustalw/or www.ebi.ac.uk/Tools/clustalw2/index.html. The grade of sequence identity (sequence matching) may be calculated using e.g. BLAST, BLAT or BlastZ (or BlastX). A similar algorithm is incorporated into the BLASTN and BLASTP programs of Altschul et al. (1990) J. Mol. Biol. 215:403-410. BLAST polynucleotide searches are performed with the BLASTN program, score=100, word length=12. BLAST protein searches are performed with the BLASTP program, score=50, word length=3. To obtain gapped alignments for comparative purposes, Gapped BLAST is utilized as described in Altschul et al. (1997) Nucleic Acids Res. 25:3389-3402. When utilizing BLAST and Gapped BLAST programs, the default parameters of the respective programs are used. Sequence matching analysis may be supplemented by established homology mapping techniques like Shuffle-LAGAN (Brudno M. (2003b) Bioinformatics 19 Suppl 1:154-162) or Markov random fields. When percentages of sequence identity are referred to in the present application, these percentages are calculated in relation to the full length of the longer sequence, if not specifically indicated otherwise.

"Hybridization" can also be used as a measure of sequence identity or homology between two nucleic acid sequences. Hybridization conditions are known to those skilled in the art and can be found, for example, in Current Protocols in Molecular Biology, John Wiley & Sons, N. Y., 6.3.1-6.3.6, 1991. "Moderate hybridization conditions" are defined as equivalent to hybridization in 2× sodium chloride/sodium citrate (SSC) at 30° C., followed by a wash in 1×SSC, 0.1% SDS at 50° C. "Highly stringent conditions" are defined as equivalent to hybridization in 6× sodium chloride/sodium citrate (SSC) at 45° C., followed by a wash in 0.2×SSC, 0.1% SDS at 65° C.

The term "immunoglobulin (Ig)" as used herein refers to immunity conferring glycoproteins of the immunoglobulin superfamily. "Surface immunoglobulins" are attached to the membrane of effector cells by their transmembrane region and encompass molecules such as but not limited to B-cell receptors, T-cell receptors, class I and II major histocompatibility complex (MHC) proteins, beta-2 microglobulin (β2M), CD3, CD4 and CD8. Typically, the term "antibody" as used herein refers to secreted immunoglobulins which lack the transmembrane region and can thus, be released into the bloodstream and body cavities. Human antibodies are grouped into different isotypes based on the heavy chain they possess. There are five types of human Ig heavy chains denoted by the Greek letters: α, δ, ε, γ, and μ. The type of heavy chain present defines the class of antibody, i.e. these chains are found in IgA, IgD, IgE, IgG, and IgM antibodies, respectively, each performing different roles, and directing the appropriate immune response against different types of antigens. Distinct heavy chains differ in size and composition; α and γ comprise approximately 450 amino acids, while μ and ε have approximately 550 amino acids (Janeway et al. (2001) Immunobiology, Garland Science). IgA is found in mucosal areas, such as the gut, respiratory tract and urogenital tract, as well as in saliva, tears, and breast milk and prevents colonization by pathogens (Underdown & Schiff (1986) Annu. Rev. Immunol. 4:389-417). IgD mainly functions as an antigen receptor on B cells that have not been exposed to antigens and is involved in activating basophils and mast cells to produce antimicrobial factors (Geisberger et al. (2006) Immunology 118:429-437; Chen et al. (2009) Nat. Immunol. 10:889-898). IgE is involved in allergic reactions via its binding to allergens triggering the release of histamine from mast cells and basophils. IgE is also involved in protecting against parasitic worms (Pier et al. (2004) Immunology, Infection, and Immunity, ASM Press). IgG provides the majority of antibody-based immunity against invading pathogens and is the only antibody isotype capable of crossing the placenta to give passive immunity to fetus (Pier et al. (2004) Immunology, Infection, and Immunity, ASM Press). In humans there are four different IgG subclasses (IgG1, 2, 3, and 4), named in order of their abundance in serum with IgG1 being the most abundant (~66%), followed by IgG2 (~23%), IgG3 (~7%) and IgG (~4%). The biological profile of the different IgG classes is determined by the structure of the respective hinge region. IgM is expressed on the surface of B cells in a monomeric form and in a secreted pentameric form with very high avidity. IgM is involved in eliminating pathogens in the early stages of B cell mediated (humoral) immunity before sufficient IgG is produced (Geisberger et al. (2006) Immunology 118:429-437).

Antibodies are not only found as monomers but are also known to form dimers of two Ig units (e.g. IgA), tetramers of four Ig units (e.g. IgM of teleost fish), or pentamers of five Ig units (e.g. mammalian IgM). Antibodies are typically made of four polypeptide chains comprising two identical heavy chains and identical two light chains which are connected via disulfide bonds and resemble a "Y"-shaped macro-molecule. Each of the chains comprises a number of immunoglobulin domains out of which some are constant domains and others are variable domains. Immunoglobulin domains consist of a 2-layer sandwich of between 7 and 9 antiparallel β-strands arranged in two β-sheets. Typically, the "heavy chain" of an antibody comprises four Ig domains with three of them being constant ($C_H$ domains: $C_H1$, $C_H2$, $C_H3$) domains and one of the being a variable domain ($V_H$), with the exception of IgM and IgE which contain one variable (VH) and four constant regions ($C_H1$, $C_H2$, $C_H3$, $C_H4$). The additional domain ($C_H2$: Cμ2, Cε2) in the heavy chains of IgM and IgE molecules connects the two heavy chains instead of the hinge region contained in other Ig molecules (Perkins et al., 1991; Beavil et al., 1995; Wan et al., 2002). The "light chain" typically comprises one constant Ig domain ($C_L$) and one variable Ig domain ($V_L$). Exemplified, the human IgM heavy chain is composed of four Ig domains linked from N- to C-terminus in the order $V_H$-$C_H1$-$C_H2$-$C_H3$-$C_H4$ (also referred to as $V_H$-Cμ1-Cμ2-Cμ3-Cμ4), whereas the human IgM light chain is composed of two immunoglobulin domains linked from N- to C-terminus in the order $V_L$-$C_L$, being either of the kappa or lambda type (Vκ-Cκ or Vλ-Cλ).

Exemplified, the constant chain of human IgM comprises 452 amino acids. Throughout the present specification and claims, the numbering of the amino acid positions in an immunoglobulin are that of the "EU index" as in Kabat, E. A., Wu, T. T., Perry, H. M., Gottesman, K. S., and Foeller, C., (1991) Sequences of proteins of immunological interest, 5th ed. U.S. Department of Health and Human Service, National Institutes of Health, Bethesda, MD. The "EU index as in Kabat" refers to the residue numbering of the human IgM EU antibody. Accordingly, $C_H$ domains in the context of IgM are as follows: "$C_H1$" refers to amino acid positions 118-215 according to the EU index as in Kabat; "$C_H2$" refers to amino acid positions 231-340 according to the EU index as in Kabat; "$C_H3$" refers to amino acid positions 341-446 according to the EU index as in Kabat. "$C_H4$" refers to amino acid positions 447-558 according to the OU index as in Kabat.

Whilst in human IgA, IgG, and IgD molecules two heavy chains are connected via their hinge region, IgE and IgM antibodies do not comprise such hinge region. Instead, IgE and IgM antibodies possess an additional Ig domain, their $C_H2$ domain, which functions as dimerization domain between two heavy chains. In contrast to rather flexible and linear hinge regions of other antibodies, the $C_H2$ domain of IgE and IgM are composed of two beta sheets stabilized by an intradomain disulfide bond forming a c-type immunoglobulin fold (Bork et al., 1994; Wan et al., 2002). Furthermore, the MHD2 and EHD2 domains contain one N-glycosylation site.

The "human IgE heavy chain domain 2" ("EHD2") consists of 106 amino acid residues. The domain contains an intradomain disulfide bond formed between Cys261 and Cys321 (EU numbering as in Kabat). Typically, two EHD2 domains are covalently linked by two interdomain disulfide bonds between Cys247 and Cys337. The EHD2 contains an N-glycosylation site at Asn275 (FIG. 2).

The amino acid sequence of human EHD2 is provided in SEQ ID NO: 2.

The "IgM heavy chain domain 2" ("MHD2") consists of 111 amino acid residues (12.2 kDa) forming a homodimer covalently held together by a disulfide bond formed between cysteine residue 337 of two domains (Davis et al., 1989; Davis & Shulman, 1989). The domain is further stabilized by an intradomain disulfide bond formed between Cys261 and Cys321. Typically, two MHD2 domains are covalently linked by an interdomain disulfide bond between Cys337. The MHD2 contains an N-glycosylation site at Asn333 (FIG. 2).

The amino acid sequence of human MHD2 is provided in SEQ ID NO: 1.

The human MHD2 and EHD2 have approximately 25% sequence identity (FIG. 2).

Papain digestion of antibodies produces two identical antigen binding fragments, called "Fab fragments" (also referred to as "Fab portion" or "Fab region") each with a single antigen binding site, and a residual "Fc fragment" (also referred to as "Fc portion" or "Fc region") whose name reflects its ability to crystallize readily. The crystal structure of the human IgG Fc region has been determined (Deisenhofer (1981) Biochemistry 20:2361-2370). In IgG, IgA and IgD isotypes, the Fc region is composed of two identical protein fragments, derived from the $C_H2$ and $C_H3$ domains of the antibody's two heavy chains; in IgM and IgE isotypes, the Fc regions contain three heavy chain constant domains ($C_H2$-4) in each polypeptide chain. In addition, smaller immunoglobulin molecules exist naturally or have been constructed artificially. The term "Fab' fragment" refers to a Fab fragment additionally comprising the hinge region of an Ig molecule whilst "F(ab')$_2$ fragments" are understood to comprise two Fab' fragments being either chemically linked or connected via a disulfide bond. Whilst "single domain antibodies (sdAb)" (Desmyter et al. (1996) Nat. Structure Biol. 3:803-811) and "Nanobodies" only comprise a single $V_H$ domain, "single chain Fv (scFv)" fragments comprise the heavy chain variable domain joined via a short linker peptide to the light chain variable domain (Huston et al. (1988) Proc. Natl. Acad. Sci. USA 85, 5879-5883). Divalent single-chain variable fragments (di-scFvs) can be engineered by linking two scFvs (scFvA-scFvB). This can be done by producing a single peptide chain with two $V_H$ and two $V_L$ regions, yielding "tandem scFvs" ($V_HA-V_LA-V_HB-V_LB$). Another possibility is the creation of scFvs with linkers that are too short for the two variable regions to fold together, forcing scFvs to dimerize. Usually linkers with a length of 5 residues are used to generate these dimers. This type is known as "diabodies". Still shorter linkers (one or two amino acids) between a $V_H$ and $V_L$ domain lead to the formation of monospecific trimers, so-called "triabodies" or "tribodies". Bispecific diabodies are formed by expressing to chains with the arrangement $V_HA-V_LB$ and $V_HB-V_LA$ or $V_LA-V_HB$ and $V_LB-V_HA$, respectively. Single-chain diabodies (scDb) comprise a $V_HA-V_LB$ and a $V_HB-V_LA$ fragment which are linked by a linker peptide (P) of 12-20 amino acids, preferably 14 amino acids, ($V_HA-V_LB-P-V_HB-V_LA$). "Bispecific T-cell engagers (BiTEs)" are fusion proteins consisting of two scFvs of different antibodies wherein one of the scFvs binds to T cells via the CD3 receptor, and the other to a tumor cell via a tumor specific molecule (Kufer et al. (2004) Trends Biotechnol. 22:238-244). Dual affinity retargeting molecules ("DART") molecules) are diabodies additionally stabilized through a C-terminal disulfide bridge.

The term "pharmaceutically active moiety" as used herein, is understood to refer to a part or moiety of a macromolecule or complex, i.e. a polypeptide, polynucleotide or complex thereof, which mediates a pharmaceutical effect including but not limited to prophylactic, therapeutic, and/or diagnostic effects.

As used herein, "prevent", "preventing", "prevention", or "prophylaxis" of a disease or disorder means preventing that such disease or disorder occurs in a patient. Accordingly, a moiety having a prophylactic effect prevents the onset of a disease or disorder in a patient.

As used herein, "treat", "treating", "treatment" or "therapy" of a disease or disorder means accomplishing one or more of the following: (a) reducing the severity of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in an individual that has previously had the disorder(s); and (e) limiting or preventing recurrence of symptoms in individuals that were previously symptomatic for the disorder(s). Accordingly, a moiety having a therapeutic effect treats the symptoms of a disease or disorder by accomplishing one or more of above named effects (a)-(e).

The terms "identify", "identifying", "identification" or "diagnosis" of a disease or disorder are used herein to refer to the determination of the nature and the cause of a disease or disorder. Accordingly, a moiety having a diagnostic effect allows for the determination of the nature and the cause of a disease or disorder.

"Symptoms" of a disease or disorder are implication of the disease or disorder noticeable by the tissue, organ or organism having such disease or disorder and include but are not limited to pain, weakness, tenderness, strain, stiffness, and spasm of the tissue, an organ or an individual as well as the presence, absence, increase, decrease, of specific indicators such as biomarkers or molecular markers. The term "disease" and "disorder" as used herein, refer to an abnormal condition, especially an abnormal medical condition such as an illness or injury, wherein a tissue, an organ or an individual is not able to efficiently fulfil its function anymore. Typically, but not necessarily, a disease or disorder is associated with specific symptoms or signs indicating the presence of such disease or disorder. Diseases or disorders include but are not limited to autoimmune diseases, allergic diseases, cancer type diseases, cutaneous conditions, endocrine diseases, blood diseases and disorders, eye diseases and disorders, genetic disorders, inflammatory diseases, infectious diseases, intestinal diseases, neurological disorders, and mental illness. Exemplified, autoimmune diseases include but are not limited to Diabetes mellitus type 1, rheumatoid arthritis, psoriasis, Crohns Disease, autoimmune cardiomyopathy, autoimmune hepatitis, Hashimoto's thyroiditis, and Sjogern's syndrome. Exemplified, allergic diseases include but are not limited to allergic rhinitis, asthma, atopic eczema, anaphylaxis, insect venom allergies, drug allergies, and food allergies. Exemplified, cancer type diseases include but are not limited to Basal cell carcinoma, Bladder cancer, Bone cancer, Brain tumor, Breast cancer, Burkitt lymphoma, Cervical cancer, Colon Cancer, Cutaneous T-cell lymphoma, Esophageal cancer, Retinoblastoma, Gastric (Stomach) cancer, Gastrointestinal stromal tumor, Glioma, Hodgkin lymphoma, Kaposi sarcoma, Leukemias, Lymphomas, Melanoma, Oropharyngeal cancer, Ovarian cancer, Pancreatic cancer, Pleuropulmonary blastoma, Prostate cancer, Throat cancer, Thyroid cancer, and Urethral cancer. Exemplified, cutaneous conditions include but are not limited to Acne, Dermatitis, Eczema, conditions of the skin appendages, conditions of the subcutaneous fat, disturbances of pigmentation, epidermal nevi, epidermal neoplasms, epidermal cysts, erythemas, frostbites genodermatoses, mucinoses, neurocutaneous conditions (e.g. Wiskott-Aldrich syndrome), and psoriasis. Exemplified, endocrine diseases include but are not limited to Diabetes mellitus type 1 and type 2, Osteoporosis, and Cushing's disease. Exemplified, blood diseases and disorders include but are not limited to coagulopathies (hemophilia A, hemophila B, etc.), fibrinolytic disorders, complement deficiencies, immunoglobulin deficiencies, and anemia. Exemplified, genetic disorders include but are not limited to color blindness, cystic fibrosis, Down syndrome, Sickle-cell disease, and Turner syndrome. Exemplified, inflammatory diseases include but are not limited to rheumatoid arthritis, Crohn's disease, ulcerative colitis, ankylosing spondylitis, atheriosclerosis, osteoarthrisis, and asthma. Exemplified, infectious diseases include but are not limited to infections diseases caused by viruses, bacteria, worms, prions or other pathogens or parasites such as African sleeping sickness, AIDS, HIV infection, Anthrax, Borreliosis, Calicivirus infection (Norovirus and Sapovirus), Chickenpox, Chlamydia infection, Cholera, Clostridium infection, Colorado tick fever (CTF), common cold, Creutzfeldt-Jakob disease, Dengue fever (DEN-1, DEN-2, DEN-3 and DEN-4), Ebola, Enterovirus infection, infections with Human herpesvirus 6 (HHV-6) and Human herpesvirus 7 (HHV-7), Gonorrhea, Streptoccocal infections (group A and B), Hand, foot and mouth disease (HFMD), *Helicobacter pylori* infection, Hepatitis (A, B, C, and D), Herpes infection, Papillomavirus infection, Parainfluenza virus infection, Influenza, Lassa fever, Marburg fever, Measles, Meningitis, Mumps, Pasteurellosis, Pediculus infection, Plague, Pneumococcal infection, Respiratory syncytial virus infection, Rotavirus infection, Rubella virus infection, Salmonella food poisoning and infection, SARS, Scabies infections, Schistosomiasis, Smallpox, Staphylococcal food poisoning and infection, Syphilis, Tetanus, Trichophyton infection, Tuberculosis, Typhus, Venezuelan equine encephalitis, and Yellow fever. Exemplified, intestinal diseases include but are not limited to Gastroenteritis, Ileus, Ileitis, Colitis, Appendicitis, Coeliac disease, Irritable bowel syndrome, Diverticular disease, Diarrhea, Polyp, and Ulcerative colitis. Exemplified, neurological disorders include but are not limited to Amyotrophic Lateral Sclerosis (ALS), Alzheimer's disease, Brain damage, Creutzfeldt-Jakob disease, Cushing's syndrome, Dyslexia, Encephalitis, Epilepsy, Headache, Huntington's disease, Migraine, Multiple sclerosis, Parkinson's disease, Polio, Rabies, Schizophrenia, and Stroke. Exemplified, mental illness include but are not limited to Acute stress disorder, attention-deficit hyperactivity disorder (ADHD), Autistic disorder, Borderline personality disorder, Bulimia nervosa, Burn Out, Schizophrenia, Depression, Cognitive disorder, Communication disorder, Eating disorder, Kleptomania, Learning disorders, Male erectile disorder, Melancholia, Obsessive-compulsive disorder (OCD), Paranoia Pathological gambling, Posttraumatic stress disorder (PTSD), Psychotic disorder, Hypersomnia, Insomnia, and Tourette's syndrome.

A "pharmaceutically active moiety" typically comprises a biological and/or chemical pharmaceutical, e.g. ligands, effector molecules, half-life extension modules and imaging molecules. The term "ligand" refers to a chemical or biological substance that forms a complex with another molecule to fulfil a specific biological function. Ligands include but are not limited to substrates, inhibitors, and activators, such as antigen-binding molecules, scaffold proteins, natural ligands, ligand-binding receptor fragments, and apatamers. The term "effector molecule" typically refers to small molecules, peptides or polypeptides that bind to a protein and thereby alter the activity of that protein. They include but are not limited to cytokines, chemokines, immuno(co)-stimulatory molecules, immunosuppressive molecules, death ligands, apoptosis-inducing proteins, kinases, prodrug-converting enzymes, RNases, agonistic antibody or antibody fragment, antagonistic antibody or antibody fragment, toxins, growth factors, hormone, coagulation factor, fibrinolytic protein, peptides mimicking these, and fragments, fusion proteins or derivatives thereof. "Half-life extension modules" prolong the half-life, e.g. the "plasma half-life" or the "serum half-life", of a chemical or biological substance. Imaging molecules are those binding to specific target molecules thereby, allowing the visualization of the location of that molecule.

"Chemical pharmaceuticals" are typically understood to refer to chemical compounds synthesized artificially which are effective in the prevention, treatment or diagnosis of disorders or diseases.

"Biologicals" are typically understood to refer to medical drugs produced using biotechnological means and are used for prophylactic, therapeutic, and/or in vivo diagnostic purposes. Biologicals include but are not limited to peptides, polypeptides, proteins and nucleic acids (e.g. DNA, RNA, or hybrids thereof). Approved therapeutic biologicals include but are not limited to hormones (e.g. insulin, hGH, FSH, Glucagon-like peptide 1, parathyroid hormone, calcitonin, lutropin, glucagon), growth factors (e.g. erythropoietin, G-CSF/GM-CSF, IGF-1), interferons (e.g. IFN-α, IFN-β, IFN-γ), interleukins (e.g. IL-2, IL-11, IL-1Ra), coagulation factors (e.g. factor VIII, factor IX, factor VIIa, thrombin), thrombolytics and anti-coagulants (e.g. t-PA, hirudin, activated protein C), enzymes (e.g. α-glucosidase, glucocerebrosidase, iduronate-2-sulfatase, galactosidase, urate oxidase, DNase), antigen-binding molecule such as antibodies and antibody fragments (e.g. IgG, Fab), and fusion proteins thereof (e.g. TNFR2-Fc, TMP-Fc, CTLA-4-Fc, IL-1R-Fc, LFA-3-Fc, IL-2-DT).

A "peptide linker" in the context of the present invention refers to an amino acid sequence which sterically separates two parts or moieties of a complex, e.g. two peptides or proteins. Typically such linker consists of between 1 and 100 amino acids having a minimum length of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acids, and a maximum length of at least 100, 95, 90, 85, 80, 75, 70, 65, 60, 55, 50, 45, 40, 35, 34, 33, 32, 31, 30, 29, 28, 27, 26, 25, 24, 23, 22, 21, 20, 19, 18, 17, 16, or 15 amino acids or less. The indicated preferred minimum and maximum lengths of the peptide linker according to the present invention may be combined, if such a combination makes mathematically sense, e.g. such linker may consist of 1-15, or 12-40, or 25-75, or 1-100 amino acids. Peptide linkers may also provide flexibility among the two moieties that are linked together. Such flexibility is generally increased if the amino acids are small. Accordingly, flexible peptide linkers comprise an increased content of small amino acids, in particular of glycines and/or alanines, and/or hydrophilic amino acids such as serines, threonines, asparagines and glutamines. Preferably, more than 20%, 30%, 40%, 50%, 60% or more of the amino acids of the peptide linker are small amino acids.

The term "cleavage site" as used herein refers to an amino acid sequence or nucleotide sequence wherein this sequence directs the division of a complex or a macromolecule (e.g. a nucleic acid or a protein), e.g. because it is recognized by a cleaving enzyme, and/or can be divided. Typically, a polypeptide chain is cleaved by hydrolysis of one or more peptide bonds that link the amino acids and a polynucleotide chain is cleaved by hydrolysis of one or more of the phosphodiester bond between the nucleotides. Cleavage of peptide- or phosphodiester-bonds may originate from chemical or enzymatic cleavage. Enzymatic cleavage refers to such cleavage being attained by proteolytic enzymes including but not limited to restriction endonuclease (e.g. type I, type II, type II, type IV or artificial restriction enzymes) and endo- or exo-peptidases or -proteases (e.g. serine-proteases, cysteine-proteases, metallo-proteases, threonine proteases, aspartate proteases, glutamic acid proteases). Typically, enzymatic cleavage occurs due to self-cleavage or is affected by an independent proteolytic enzyme. Enzymatic cleavage of a protein or polypeptide can happen either co- or post-translational. Accordingly, the term "endopeptidase cleavage site" used herein, refers to a cleavage cite within the amino acid or nucleotide sequence where this sequence is cleaved or is cleavable by an endopeptidase (e.g. trypsin, pepsin, elastase, thrombin, collagenase, furin, thermolysin, endopeptidase V8, cathepsins).

The term "self-cleavage site" as used herein refers to a cleavage site within the amino acid sequence where this sequence is cleaved or is cleavable without such cleavage involving any additional molecule. It is understood that cleavage sites typically comprise several amino acids. Thus, the cleavage site may also serve the purpose of a peptide linker, i.e. sterically separating two peptides or proteins.

As used herein, the term "vector" refers to a protein or a polynucleotide or a mixture thereof which is capable of being introduced or of introducing the proteins and/or nucleic acid comprised therein into a cell. In the context of the present invention it is preferred that the genes of interest encoded by the introduced polynucleotide are expressed within the cell upon introduction of the vector or vectors. Examples of suitable vectors include but are not limited to plasmids, cosmids, phages, viruses or artificial chromosomes.

The term "complex" as used herein, refers to a whole that comprehends a number of individual components, parts or moieties which are in close proximity to each other and fulfil a common or interrelated function. The individual moieties of a complex may be of the same or of differing nature, i.e. they may be composed of the same, a similar or of differing chemical entities such as but not limited to nucleotides, amino acids, nucleic acids, peptides, polypeptides, proteins, carbohydrates, and/or lipids. Exemplified, a complex may comprise a number of associated proteins, or a mixture of one or more proteins and one or more nucleic acids or a mixture of one or more proteins and one or more lipids and/or carbohydrates. It is understood that any other combination of identical, similar or differing chemical entities is also encompassed. The individual moieties of a complex may or may not be interconnected. Typically, the individual parts of a complex are connected via covalent or non-covalent bonds.

The term "multimerization" as used herein refers to the formation of a macromolecular complex of two or more molecules, e.g. proteins or nucleic acids, (i.e. two, three, four, five or more molecules), whilst the term "dimerization" as used herein refers specifically to the formation of a macromolecular complex of two molecules, e.g. proteins or nucleic acids. A homodimer is formed by two identical molecules (so-called "homodimerization"), whilst a heterodimer is formed by two different macromolecules (so-called "heterodimerization"). Typically, in a "dimer", the two macromolecules are bound via non-covalent or covalent bonds, e.g. disulfide-bonds (R—S—S—R). In the context of the present invention, the MHD2 or the EHD2 may serve as a "dimerization tool" in that homodimers are formed between two MHD2 domains or between two EHD2 domains via disulfide-bonds between the two Cys337 of the two MHD2 domains or between the two Cys247 and Cys337 of the two EHD2 domains (Cys247 of one domain pairs with Cys337 of the other domain), respectively. Because of the central location of the MHD2 or EHD2 within the heavy chain of the IgM or IgE molecule, further modules can be fused to either the N- and/or the C-Terminus of these HD2 domains. These modules may comprise one or more pharmaceutically active moieties as defined above and/or below. Accordingly, the MHD2 and EHD2 are used as covalently linked "homodimerization module" allowing for the generation of multivalent and bifunctional molecules held together by the covalently linked dimerization domains.

The term "modular system" as used herein refers to a system subdivided into smaller parts ("modules") that can be independently created and then used in different systems to drive multiple functionalities. Typically, the individual modules are isolated, self-contained functional elements which are functionally partitioning into discrete scalable, reusable modules. In the context of the present invention, the term "modules" refers in particular to self-sufficient parts or separable component of a macromolecule, e.g. polynucleotide or polypeptide, or a complex. Typically, a module can evolve, function, and/or exist independently of the rest of the macromolecule or complex and consists of one or several domains with each of them being a three-dimensional structure being stably and independently folded. Such module typically forms an independent functional unit within the macromolecule or complex.

The terms "pharmaceutical", "medicament" and "drug" are used interchangeably herein, referring to a substance and/or a combination of substances being used for the identification, prevention or treatment of a disease or disorder.

The terms "preparation" and "composition" are intended to include the formulation of the active compound with encapsulating material as a carrier providing a capsule in which the active component with or without other carriers, is surrounded by a carrier, which is thus in association with the active compound.

"Pharmaceutically acceptable" means approved by a regulatory agency of the Federal or a state government or listed in the U.S. Pharmacopeia or other generally recognized pharmacopeia for use in animals, and more particularly in humans.

The term "active ingredient" refers to the substance in a pharmaceutical composition or formulation that is biologically active, i.e. that provides pharmaceutical value. A pharmaceutical composition may comprise one or more active ingredients which may act in conjunction with or independently of each other. The active ingredient can be formulated as neutral or salt forms. Pharmaceutically acceptable salts include those formed with free amino groups such as but not limited to those derived from hydrochloric, phosphoric, acetic, oxalic, tartaric acids, etc., and those formed with free carboxyl groups such as but not limited to those derived from sodium, potassium, ammonium, calcium, ferric hydroxides, isopropylamine, triethylamine, 2-ethylamino ethanol, histidine, procaine, and the like.

The term "carrier", as used herein, refers to a pharmacologically inactive substance such as but not limited to a diluent, excipient, surfactants, stabilizers, physiological buffer solutions or vehicles with which the therapeutically active ingredient is administered. Such pharmaceutical carriers can be liquid or solid. Liquid carrier include but are not limited to sterile liquids, such as saline solutions in water and oils, including but not limited to those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. A saline solution is a preferred carrier when the pharmaceutical composition is administered intravenously. Examples of suitable pharmaceutical carriers are described in "Remington's Pharmaceutical Sciences" by E. W. Martin.

Suitable pharmaceutical "excipients" include starch, glucose, lactose, sucrose, gelatine, malt, rice, flour, chalk, silica gel, sodium stearate, glycerol monostearate, talc, sodium chloride, dried skim milk, glycerol, propylene, glycol, water, ethanol and the like.

"Surfactants" include anionic, cationic, and non-ionic surfactants such as but not limited to sodium deoxycholate, sodium dodecylsulfate, Triton X-100, and polysorbates such as polysorbate 20, polysorbate 40, polysorbate 60, polysorbate 65 and polysorbate 80.

"Stabilizers" include but are not limited to mannitol, sucrose, trehalose, albumin, as well as protease and/or nuclease antagonists.

"Physiological buffer solution" include but are not limited to sodium chloride solution, demineralized water, as well as suitable organic or inorganic buffer solutions such as but not limited to phosphate buffer, citrate buffer, tris buffer (tris (hydroxymethyl)aminomethane), HEPES buffer ([4 (2 hydroxyethyl)piperazino]ethanesulphonic acid) or MOPS buffer (3 morpholino-1 propanesulphonic acid). The choice of the respective buffer in general depends on the desired buffer molarity. Phosphate buffer are suitable, for example, for injection and infusion solutions.

The term "adjuvant" refers to agents that augment, stimulate, activate, potentiate, or modulate the immune response to the active ingredient of the composition at either the cellular or humoral level, e.g. immunologic adjuvants stimulate the response of the immune system to the actual antigen, but have no immunological effect themselves. Examples of such adjuvants include but are not limited to inorganic adjuvants (e.g. inorganic metal salts such as aluminium phosphate or aluminium hydroxide), organic adjuvants (e.g. saponins or squalene), oil-based adjuvants (e.g. Freund's complete adjuvant and Freund's incomplete adjuvant), cytokines (e.g. IL-1β, IL-2, IL-7, IL-12, IL-18, GM-CFS, and INF-γ) particulate adjuvants (e.g. immuno-stimulatory complexes (ISCOMS), liposomes, or biodegradable microspheres), virosomes, bacterial adjuvants (e.g. monophosphoryl lipid A, or muramyl peptides), synthetic adjuvants (e.g. non-ionic block copolymers, muramyl peptide analogues, or synthetic lipid A), or synthetic polynucleotides adjuvants (e.g. polyarginine or polylysine).

An "effective amount" or "therapeutically effective amount" is an amount of a therapeutic agent sufficient to achieve the intended purpose. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art.

EMBODIMENTS

In a first aspect the present invention provides a polypeptide comprising a heavy chain domain 2 (HD2) from IgM or IgE and at least one pharmaceutically active moiety. The pharmaceutically active moiety is envisaged not to be a Fab or Fc fragment from IgM or IgE or a part thereof, i.e. the invention does not comprise naturally occurring IgM or IgE.

In preferred embodiments such polypeptide does not comprise one or more of the heavy chain constant domains $C_H1$, $C_H3$ and/or $C_H4$ of the IgM or IgE isotypes, i.e. the polypeptide does not comprise $C_H1$, $C_H3$, $C_H4$, $C_H1$ and $C_H3$, $C_H1$ and $C_H4$, $C_H3$ and $C_H4$, or $C_H1$, $C_H3$ and $C_H4$.

It is particularly preferred that said polypeptide comprises only the heavy chain domain 2 $C_H2$ (HD2) of IgE or IgM. Preferably, no additional part(s) of IgE or IgM are comprised. Accordingly, it is envisaged that said polypeptide comprises the HD2 domain of IgE or IgM as sole domain of IgE or IgM.

Preferably such polypeptide resembles a peptide-bond-linked chain of amino acids which may optionally be chemically modified, e.g. may comprise glycosylated amino acids and/or phosphorylated amino acids and/or may be PEGylated, HESylated, and/or polysialiated. In preferred embodiments the HD2 from IgM or IgE comprises one or more cysteine residues. It is particularly preferred that the HD2 of IgM (MHD2) comprises at least three cysteine residues, preferably two cysteine residues forming an intradomain disulfide bond and the third one allowing for the formation of interdomain disulfide bonds. In preferred embodiments these disulfide bonds improve the intradomain and/or interdomain stability of the MHD2. Preferably, these cysteine residues are located at positions 261, 321 and 337 of the MHD2 (EU numbering as in Kabat). In further embodiments, it is preferred that the HD2 of IgE (EHD2) comprises at least four cysteine residues, preferably two cysteine residues forming an intradomain disulfide bond and two cysteine residues allowing for the formation of interdomain disulfide bonds. In preferred embodiments these disulfide bonds improve the intradomain and/or interdomain stability of the EHD2. Preferably, these cysteine residues are located at positions 261 and 321, and at position 247 and 337, respectively, of the EHD2 (EU numbering as in Kabat).

In preferred embodiments, the HD2 domain comprises an amino acid sequence according to SEQ ID NO: 1 or SEQ ID NO: 2 or dimerizing variants thereof.

Preferably, the MHD2 comprises the amino acid sequence:

```
AELPPKVSVFVPPRDGFFGNPRKSKLICQATGFSPRQIQVSWLREGKQ

VGSGVTTDQVQAEAKESGPTTYKVTSTLTIKESDWLGQSMFTCRVDHR

GLTFQQNASSMCVPD as given in SEQ ID NO: 1 or variants thereof.
```

Preferably, the EHD2 comprises the amino acid sequence:

```
DFTPPTVKILQSSCDGGGHFPPTIQLLCLVSGYTPGTINITWLEDGQVM

DVDLSTASTTQEGELASTQSELTLSQKHWLSDRTYTCQVTYQGHTFEDS

TKKCADSN as given in SEQ ID NO: 2 or dimerizing variants thereof.
```

In preferred embodiments a dimerizing variant has at least 70% sequence identity to the MHD2 or EHD2 of SEQ ID NO: 1 or SEQ ID NO: 2, respectively. It is particularly preferred that a variant has at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the MHD2 or EHD2 of SEQ ID NO: 1 or SEQ ID NO: 2, respectively. In particularly preferred embodiments a variant has at least 80%, at least 90% or at least 95% sequence identity to the MHD2 or EHD2 of SEQ ID NO: 1 or SEQ ID NO: 2, respectively. It is preferred that said dimerizing variants exhibits at least one biological activity of the parent MHD2 or EHD2, i.e. is functionally active. It is particularly preferred that said dimerizing variant remains functionally active by being able to dimerize with a second MHD2 or EHD2 or dimerizing variant thereof.

In preferred embodiments, said dimerizing variants may exhibit amino acid exchanges, preferably conservative and/or non-conservative amino acid exchanges, amino acid deletions and/or amino acid additions. Preferably, these amino acid exchanges, deletions and/or additions are in regions of the sequence which are less or not conserved in orthologous or paralogous sequences. Preferably, conserved and/or highly conserved regions in the sequence are not altered. It is particularly preferred that the cysteine residues in MHD2 and EHD2, respectively, are maintained.

In an IgM or IgE molecule the HD2 occupies a central position within the heavy chain with further heavy chain sequences being connected at the C- and N-terminal ends of the HD2 domain. These connected heavy chain sequences do not influence, alter, or inhibit the ability of the HD2 to fulfil its function to dimerize. Accordingly, it is envisaged that further modules may be fused to the N- and/or C-Terminus of either HD2 domain without influencing, altering or inhibiting the ability of the HD2 to dimerize. Thus, both domains are suitable as anchor points in a modular system comprising further individual or a plurality of functionally distinct modules, such as but not limited to chemical and biological molecules (e.g. small chemical entities, peptides, proteins, protein domains, protein fragments, nucleic acids, or hybrids thereof). Preferably, said modules exhibit a size, surface charge, and function such as not to influence, alter or inhibit the function of the HD2 in dimerization. Modules which would interfere with the function of the HD2 may be fused via linker peptide to minimize and/or abolish the interfering effect. In preferred embodiments modules fused to the C- and/or N-Terminus of the HD2 of IgM or IgE comprise at least one pharmaceutically active moiety. Thus, in preferred embodiments at least one pharmaceutically active moiety is connected to the N- and/or C-Terminus of the HD2.

The number of fused modules, preferably comprising at least one pharmaceutically active moiety, may be 1 or more, i.e. 1, 2, 3, 4, 5, 6, 7, 8, 9, 10 or more, at the N- and/or C-Terminus of the HD2. It is understood by the skilled person that the number of fused modules is primarily limited by the desired function of the resulting polypeptide as well as by functional or sterical limitations due to size or surface charge of the resulting polypeptide. Typically such resulting polypeptide is up to 1000 kDa in size, i.e. 5, 10, 20, 30, 40, 50, 100, 150, 200, 250, 300, 350, 400, 450, 500, 550, 600, 650, 700, 750, 800, 850, 900, 950 or 1000 kDa, but may even be bigger if suitable in the respective context.

In further embodiments, at least two modules, preferably comprising at least two pharmaceutically active moieties, are connected to either or both of the N- and/or C-Terminus of the HD2 of IgM or IgE. Each X and Y module, respectively, may be identical or different modules, preferably identical or different pharmaceutically active moieties. Thus, it is envisaged that $X_m$ modules are connected to the N-Terminus of the MHD2 or EHD2 domain and $Y_n$ modules are connected to the C-Terminus of the MHD2 or EHD2 domain, wherein m is preferably between 0 and 10, i.e. 0, 1, 2, 3, 4, 5, 6, 7, 8, 9 or 10, and n is preferably between 0 and 10, i.e. 0, 1, 2, 3, 4, 5, 6, 7, 8, 9 or 10, with the proviso that at least one of m and n is 1 or more. M and n may be identical or different.

Accordingly, such polypeptide may have one of the following structures: $X_m$-MHD2-$Y_n$, more preferably $X_1$-MHD2, MHD2-$Y_1$, $X_1$-$X_2$-MHD2, MHD2-$Y_1$-$Y_2$, MHD2-$Y_1$-$[Y]_{n-1}$, $X_1$-MHD2-$Y_1$, $X_1$-$X_2$-MHD2-$Y_1$-$Y_2$, $X_1$-$[X]_{m-1}$-MHD2-$Y_1$-$[Y]_{n-1}$, $X_1$-MHD2-$Y_1$-$Y_2$, $X_1$-MHD2-$Y_1$-$[Y]_{n-1}$, $X_1$-$X_2$-MHD2-$Y_1$, or $X_1$-$[X]_{m-1}$-MHD2-$Y_1$; $X_m$-EHD2-$Y_n$, more preferably $X_1$-EHD2, EHD2-$Y_1$, $X_1$-$X_2$-EHD2, $X_1$-$[X]_{m-1}$-EHD2, EHD2-$Y_1$-$Y_2$, EHD2-$Y_1$-$[Y]_{n-1}$, $X_1$-EHD2-$Y_1$, $X_1$-$X_2$-EHD2-$Y_1$-$Y_2$, $X_1$-$[X]_{m-1}$-EHD2-$Y_1$-$[Y]_{n-1}$, $X_1$-EHD2-$Y_1$-$Y_2$, $X_1$-EHD2-$Y_1$-$[Y]_{n-1}$, $X_1$-$X_2$-EHD2-$Y_1$, or $X_1$-$[X]_{m-1}$-EHD2-$Y_1$ wherein m is preferably between 0 and 10, i.e. 0, 1, 2, 3, 4, 5, 6, 7, 8, 9 or 10, and n is preferably between 0 and 10, i.e. 0, 1, 2, 3, 4, 5, 6, 7, 8, 9 or 10, with the proviso that at least one of m and n is 1 or more. M and n may be identical or different. Particularly preferred combinations of m and n are the following: m=1 and n=0; m=0 and n=1, m=1 and n=1; m=1 and n=2; m=1 and n=3; m=1 and n=4; m=1 and n=5; m=1 and n=6; m=1 and n=7; m=1 and n=8; m=1 and n=9; m=1 and n=10; m=2 and n=1; m=2 and n=2; m=2 and n=3; m=2 and n=4; m=2 and n=5; m=2 and n=6; m=2 and n=7; m=2 and n=8; m=2 and n=9; m=2 and n=10; m=3 and n=1; m=3 and n=2; m=3 and n=3; m=3 and n=4; m=3 and n=5; m=3 and n=6; m=3 and n=7; m=3 and n=8; m=3 and n=9; m=3 and n=10; m=4 and n=1; m=4 and n=2; m=4 and n=3; m=4 and n=4; m=4 and n=5; m=4 and n=6; m=4 and n=7; m=4 and n=8; m=4 and n=9; m=4 and n=10; m=5 and n=1; m=5 and n=2; m=5 and n=3; m=5 and n=4; m=5 and n=5; m=5 and n=6; m=5 and n=7; m=5 and n=8; m=5 and n=9; m=5 and n=10; m=6 and n=1; m=6 and n=2; m=6 and n=3; m=6 and n=4; m=6 and n=5; m=6 and n=6; m=6 and n=7; m=6 and n=8; m=6 and n=9; m=6 and n=10; m=7 and n=1; m=7 and n=2; m=7 and n=3; m=7 and n=4; m=7 and n=5; m=7 and n=6; m=7 and n=7; m=7 and n=8; m=7 and n=9; m=7 and n=10; m=8 and n=1; m=8 and n=2; m=8 and n=3; m=8 and n=4; m=8 and n=5; =8 and n=6; m=8 and n=7; m=8 and n=8; m=8 and n=9; m=8 and n=10; m=9 and n=1; m=9 and n=2; m=9 and n=3; m=9 and n=4; m=9 and n=5; m=9 and n=6; m=9 and n=7; m=9 and n=8; m=9 and n=9; m=9 and n=10; m=10 and n=1; m=10 and n=2; m=10 and n=3; m=10 and n=4; m=10 and n=5; m=10 and n=6; m=10 and n=7; m=10 and n=8; m=10 and n=9; m=10 and n=10.

The module, preferably the pharmaceutically active moiety, may be connected directly to the MHD2 or EHD2 or may be connected indirectly via one or more linkers (L). In embodiments wherein more than one module is connected to the HD2 domain, the individual modules may be connected directly to each other or may be connected indirectly via one or more linkers (L). Modules that interfere with the dimerization of MHD2 and EHD2, respectively, or with the function of a further connected module, are preferably connected indirectly via a linker. Similarly, it is preferred to use an indirect connection through a linker, if the dimerization of MHD2 and EHD2 interferes with the pharmaceutical activity of the pharmaceutically active moiety. Thus, in preferred embodiments at least one pharmaceutically active moiety is connected to the HD2 directly or indirectly via one or more linkers.

Preferably, the one or more linkers comprise peptide linkers which sterically separate the connected module, preferably the pharmaceutically active moiety, from the HD2 domain. In embodiments wherein more than one module, preferably pharmaceutically active moieties, is connected to the HD2 domain, linkers comprise peptide linkers which sterically separate the connected modules from the HD2 domain, and peptide linkers which sterically separate different connected module from one another.

Preferably, peptide linkers have a length between 5 and 40 amino acids (i.e. 1, 2, 3, 4, 5, 6, 7, 8, 9, 10, 11, 12, 13, 14, 15, 16, 17, 18, 19, 20, 21, 22, 23, 24, 25, 26, 27, 28, 29 30, 31, 32, 33, 34 35, 36, 37, 38, 39, 40 amino acids), more preferably between 5 and 20 amino acids (i.e. 1, 2, 3, 4, 5, 6, 7, 8, 9, 10, 11, 12, 13, 14, 15, 16, 17, 18, 19, 20 amino acids), most preferably 8 to 15 amino acids (i.e. 8, 9, 10, 11, 12, 13, 14, 15 amino acids). Linkers of suitable length allowing for the sterical separation of fused modules from the HD2 domain or from further connected modules can be selected by the skilled person using routine methodology well-known in the art (Arai et al., 2001; George & Heringa et al., 2003; Wriggers et al., 2005; Tanaka et al., 2005).

Particularly preferred are flexible peptide linkers. Flexible linkers are composed of amino acids without bulky side chains that impede rotation or bending of the amino acid chain. Flexible linkers preferably comprise G, S, T, and A residues. Preferably at least 50% of the amino acids of the flexible linker peptide consists of amino acids selected from the group consisting of G, S, T, and A. More preferably at least 60%, 70%, 80%, 90%, 95% or 100% of the amino acids of the linker consists of amino acids selected from the group consisting of G, S, T, and A.

A large number of peptide linkers, suitable to sterically separate the HD2 domain from the module, preferably the pharmaceutically active moiety, are described in the art (Robinson & Sauer, 1998; Völkel et al., 2001; Kavoosi et al., 2007; Watanabe et al., 2011). Preferred peptide linkers include but are not limited to linker peptide 1: GGGGS (SEQ ID NO: 18), linker peptide 2: GGGGSGGGGS (SEQ ID NO: 19), linker peptide 3: GGGGSGGGGSGGGGS (SEQ ID NO: 20), linker peptide 4: GSLGGSGG (SEQ ID NO: 21), linker peptide 5: GGGSGGGT (SEQ ID NO: 22), linker peptide 6: GGGSGGGTGS (SEQ ID NO: 23), linker peptide 7: GGGSGGGTGSGG (SEQ ID NO: 24), linker peptide 8: GGGSGGGS (SEQ ID NO: 25), linker peptide 9: EFTRG (SEQ ID NO: 26), and linker peptide 10: AAA (SEQ ID NO: 27), or multimers, derivatives and fragments thereof.

In further preferred embodiments the one or more linkers comprise one or more cleavage sites, i.e. one or more sequence areas wherein the linker sequence may be chemically or enzymatically cleaved by division of one or more peptide-bonds. It is preferred that the cleavage site allows for the release of the pharmaceutically active moiety once the intended destination is reached. Enzymatic cleavage may be attained by proteolytic enzymes including but not limited to restriction endonuclease (e.g. type I, type II, type II, type IV or artificial restriction enzymes) and endo- or exo-peptidases or -proteases (e.g. serine-proteases, cysteine-proteases, metallo-proteases, threonine proteases, aspartate proteases, glutamic acid proteases). In particularly preferred embodiments the one or more cleavage sites comprise one or more endopeptidase cleavage sites, i.e. wherein the sequence is cleaved or is cleavable by an endopeptidase such as but not limited to trypsin, pepsin, elastase, thrombin, collagenase, furin, thermolysin, endopeptidase V8, and/or cathepsins.

It is envisaged that depending on how many modules are attached to the HD2 peptide linkers may be positioned between the C- and/or N-Terminus of the HD2 domain as well as between the different modules. In embodiments wherein more than one linker is present between different modules and/or the HD2 domain, these linkers may be identical or differ from each other. Accordingly, such polypeptide may have one of the following structures:

$X_1$-L-MHD2, $X_1$-$X_2$-L-MHD2, $X_1$-L-$X_2$-L-MHD2, $X_1$-L-$X_2$-MHD2, $X_1$-$[X]_{m-1}$-L-MHD2, $X_1$-L-$[X]_{m-1}$-L-MHD2, $X_1$-L-$[X]_{m-1}$-MHD2, $Y_1$-L-MHD2, $Y_1$-$Y_2$-L-MHD2, $Y_1$-L-$Y_2$-L-MHD2, $Y_1$-L-$Y_2$-MHD2, $Y_1$-$[Y]_{n-1}$-L-MHD2, $Y_1$-L-$[Y]_{n-1}$-L-MHD2, $Y_1$-L-$[Y]_{n-1}$-MHD2, $X_1$-L-MHD2-L-$Y_1$, $X_1$-MHD2-L-$Y_1$, $X_1$-L-MHD2-L-$Y_1$, $X_1$-$X_2$-L-MHD2-L-$Y_1$-$Y_2$, $X_1$-$X_2$-MHD2-L-$Y_1$-$Y_2$, $X_1$-$X_2$-L-MHD2-$Y_1$-$Y_2$, $X_1$-L-$X_2$-L-MHD2-L-$Y_1$-L-$Y_2$, $X_1$-$X_2$-L-MHD2-L-$Y_1$-L-$Y_2$, $X_1$-L-$X_2$-L-MHD2-L-$Y_1$-L-$Y_2$, $X_1$-L-$X_2$-L-MHD2-$Y_1$-L-$Y_2$, $X_1$-L-$X_2$-L-MHD2-$Y_1$-$Y_2$, $X_1$-L-$X_2$-MHD2-$Y_1$-L-$Y_2$, $X_1$-$X_2$-MHD2-L-$Y_1$-L-$Y_2$, $X_1$-L-$X_2$-L-MHD2-$Y_1$-L-$Y_2$, $X_1$-$[X]_{n-1}$-L-MHD2-L-$Y_1$-$[Y]_{n-1}$, $X_1$-$[X]_{m-1}$-MHD2-L-$Y_1$-$[Y]_{n-1}$, $X_1$-$[X]_{m-1}$-L-MHD2-$Y_1$-$[Y]_{n-1}$, $X_1$-L-$[X]_{m-1}$-L-MHD2-L-$Y_1$-L-$[Y]_{n-1}$, $X_1$-$[X]_{m-1}$-L-MHD2-L-$Y_1$-L-$[Y]_{n-1}$ $X_1$-L-$[X]_{m-1}$-MHD2-L-$Y_1$-L-$[Y]_{n-1}$, $X_1$-L-$X_2$-L-MHD2-$Y_1$-L-$[Y]_{n-1}$, $X_1$-L-$[X]_{m-1}$-L-MHD2-L-$Y_1$-$[Y]_{n-1}$, $X_1$-L-$[X]_{m-1}$-MHD2-$Y_1$-L-$[Y]_{n-1}$, $X_1$-$[X]_{m-1}$-MHD2-L-$Y_1$-L-$[Y]_{n-1}$, or $X_1$-L-$[X]_{m-1}$-L-MHD2-$Y_1$-$[Y]_{m-1}$;

$X_1$-L-EHD2, $X_1$-$X_2$-L-EHD2, $X_1$-L-$X_2$-L-EHD2, $X_1$-L-$X_2$-EHD2, $X_1$-$[X]_{m-1}$-L-EHD2, $X_1$-L-$[X]_{m-1}$-L-EHD2, $X_1$-L-$[X]_{m-1}$-EHD2, $Y_1$-L-EHD2, $Y_1$-$Y_2$-L-EHD2, $Y_1$-L-$Y_2$-L-EHD2, $Y_1$-L-$Y_2$-EHD2, $Y_1$-$[Y]_{n-1}$-L-EHD2, $Y_1$-L-$[Y]_{n-1}$-L-EHD2, $Y_1$-L-$[Y]_{n-1}$-EHD2, $X_1$-L-EHD2-L-$Y_1$, $X_1$-EHD2-L-$Y_1$, $X_1$-L-EHD2-L-$Y_1$, $X_1$-$X_2$-L-EHD2-L-$Y_1$-$Y_2$, $X_1$-$X_2$-EHD2-L-$Y_1$-$Y_2$, $X_1$-$X_2$-L-EHD2-$Y_1$-$Y_2$, $X_1$-L-$X_2$-L-EHD2-L-$Y_1$-L-$Y_2$, $X_1$-$X_2$-L-EHD2-L-$Y_1$-L-$Y_2$, $X_1$-L-$X_2$-L-EHD2-L-$Y_1$-L-$Y_2$, $X_1$-L-$X_2$-L-EHD2-$Y_1$-L-$Y_2$, $X_1$-L-$X_2$-EHD2-$Y_1$-L-$Y_2$, $X_1$-L-$X_2$-L-EHD2-L-$Y_1$-$Y_2$, $X_1$-L-$X_2$-EHD2-$Y_1$-L-$Y_2$, $X_1$-$X_2$-EHD2-L-$Y_1$-L-$Y_2$, $X_1$-L-$X_2$-L-EHD2-$Y_1$-$Y_2$, $X_1$-$[X]_{m-1}$-L-EHD2-L-$Y_1$-$[Y]_{n-1}$, $X_1$-$[X]_{m-1}$-L-EHD2-L-$Y_1$-$[Y]_{n-1}$, $X_1$-$[X]_{m-1}$-L-EHD2-$Y_1$-$[Y]_{n-1}$, $X_1$-L-$[X]_{m-1}$-L-EHD2-L-$Y_1$-L-$[Y]_{n-1}$, $X_1$-$[X]_{m-1}$-L-EHD2-L-$Y_1$-L-$[Y]_{n-1}$, $X_1$-L-$[X]_{m-1}$-L-EHD2-L-$Y_1$-L-$[Y]_{n-1}$, $X_1$-L-$X_2$-L-EHD2-$Y_1$-L-$[Y]_{n-1}$, $X_1$-L-$[X]_{m-1}$-L-EHD2-L-$Y_1$-$[Y]_{n-1}$, $X_1$-L-$[X]_{m-1}$-EHD2-$Y_1$-L-$[Y]_{n-1}$, $X_1$-$[X]_{m-1}$-EHD2-L-$Y_1$-L-$[Y]_{n-1}$, or $X_1$-L-$[X]_{m-1}$-L-EHD2-$Y_1$-$[Y]_{n-1}$. m and n have in each case the above indicated preferred and particularly preferred meanings.

In preferred embodiments the at least one pharmaceutically active moiety is a chemical pharmaceutical or a biological. In embodiments wherein the at least one pharmaceutically active moiety is a biological it is preferred that such biological is a peptide, polypeptide, protein and/or nucleic acid (e.g. DNA, RNA, or hybrids thereof). In particularly preferred embodiments such biological is selected from the group consisting of hormones (e.g. insulin, hGH, FSH, Glucagon-like peptide 1, parathyroid hormone, calcitonin, lutropin, glucagon); growth factors (e.g. erythropoietin, thrombopoetin, G-CSF/GM-CSF, IGF-1); cytokines (e.g. TNF, TRAIL, TGF-β) such as interferons (e.g. IFN-α, IFN-β, IFN-γ) and interleukins (e.g. IL-2, IL-11, IL-1Ra); coagulation factors (e.g. factor VIII, factor IX, factor VIIa, thrombin); thrombolytics and anti-coagulants (e.g. t-PA, hirudin, activated protein C); enzymes (e.g. α-glucosidase, glucocerebrosidase, iduronate-2-sulfatase, galactosidase, urate oxidase, DNase); antigen-binding molecule such as antibodies and antibody fragments (e.g. IgG, Fab, Fc); and fusion proteins thereof (e.g. TNFR2-Fc, TMP-Fc, CTLA-4-Fc, IL-1R-Fc, LFA-3-Fc, IL-2-DT).

In further preferred embodiments, the at least one pharmaceutically active moiety is selected from the group consisting of ligands, effector molecules, half-life extension modules, and imaging molecules. Preferably, ligands are any chemical or biological substance that forms a complex with another molecule to fulfil a specific biological function such as substrates, inhibitors, and activators. More preferably, ligands include but are not limited to antigen-binding molecules, scaffold proteins, natural ligands (e.g. EGF, VEGF, PDGF, FGF, EPO, TPO, TGF-β, TNF, TRAIL), ligand-binding receptor fragments (e.g. TNFR1, TNFR2, VEGFR, CTLA-4, LFA-3, BR3, CD95R, IL-1R, FGFR1), and apatamers (e.g. anti-Thrombin, anti-FIXa, anti-C3b, anti-VEGF, anti-CD40L).

Preferably, scaffold proteins are regulators of key signalling pathways including but not limited to KSR, MEKK1, BCL-10, MAPK, AHNAK-1, HOMER, Pellino, NLRP, DLG1, Spinophilin, Plant FLU regulatory protein.

Preferably, the antigen-binding molecule is selected from the group consisting of an antibody fragment, a Fab fragment (excluding those from IgM or IgE), a Fab' fragment (excluding those from IgM or IgE), a heavy chain antibody, a single-domain antibody (sdAb), variable domain of a heavy chain antibody, VHH, Nanobodies, a single-chain variable fragment (scFv), a tandem scFv, a bispecific T-cell engager (BITEs), a diabody, a single-chain diabody, a DART molecule, a triple body, a nanoantibody, an alternative scaffold protein (e.g. DARPins, Anticalins, Affibody molecules, Microbodies, Monobodies, Fynomers, Adnetins, Tetranectins, Kunitz domains, Affilins, Avimers), and a fusion protein thereof. It is preferred that the antigen-binding molecule binds to an antigen that is pharmaceutically relevant, i.e. which is suitable to prevent, diagnose and/or treat a disease or the symptoms of a disease or disorder. In preferred embodiment the disease is a cancer type disease. Preferably, the antigen-binding molecule recognises a tumor-associated antigen such as but not limited to EGFR, HER2, HER3, HER4, carcinoembryonic antigen (CEA), alphafetoprotein (AFP), CA-125, epithelial tumor antigen (ETA), tyrosinase, melanoma-associated antigen (MAGE), and abnormal products of ras and p53, estrogen receptors, 5-alpha-reductase, prostaglandin-endoperoxide synthase 2, VEGFRs, integrin receptor family, fibroblast activation protein, galectin, EpCAM, CEA, CD44, CD44v, CD2, CD5, CD7, CD19, CD20, CD21, CD22, CD24, CD25, CD30, CD33, CD38, CD40, CD52, CD56, CD71, CD72, CD73, CD105, CD117, CD123, claudins, c-Met, PDGFR, IGF1-R, HMW-MAA, TAG-72, GD2, GD3, GM2, folate receptor, Le$^y$, MUC-1, MUC-2, PSMA, PSCA and uPAR. In preferred embodiments the antigen-binding molecule is envisaged not to be a Fab or Fc fragment from IgM or IgE.

In particularly preferred embodiments the antigen-binding molecule is a scFv, preferably an anti-HER2 scFv or an anti-EGFR scFv, more preferably according to SEQ ID NO: 3 or 4, or variants thereof.

In preferred embodiments, effector molecules, i.e. small molecules, peptides or polypeptides that bind to a protein and thereby alter the activity of that protein, include but are not limited to cytokines, chemokines, immuno(co)-stimulatory molecules, immunosuppressive molecules, death ligands, apoptosis-inducing proteins, enzymes (e.g. kinases) prodrug-converting enzymes, RNases, agonistic antibody or antibody fragment, antagonistic antibody or antibody fragment, toxins, growth factors, hormone, coagulation factor, fibrinolytic protein, peptides mimicking these, and fragments, fusion proteins or derivatives thereof.

In preferred embodiments, cytokines are interleukins and/or interferons. Interleukins (IL) include but are not limited to Interleukin-1, Interleukin-2, Interleukin-3, Interleukin-4, Interleukin-5, Interleukin-6, Interleukin-7, Interleukin-8, Interleukin-9, Interleukin-10, Interleukin-11, Interleukin 12, Interleukin-13, Interleukin-14, Interleukin-15, Interleukin-16, Interleukin-17, Interleukin-18, Interleukin-19, Interleukin-20, Interleukin-21, Interleukin-22, Interleukin-23, Interleukin-24, Interleukin-25, Interleukin-26 Interleukin-27, Interleukin-28, Interleukin-29, Interleukin-30, Interleukin-31, Interleukin-32, Interleukin-33, Interleukin-34 and Interleukin-35. Interferons (IFN) include but are not limited to interferon type I (e.g. IFN-α, IFN-β and IFN-ω), interferon type II (e.g. IFN-γ), and interferon type III. In particular included are interferon A1, interferon A2, interferon A4, interferon A5, interferon A6, interferon A7, interferon A8, interferon A10, interferon A13, interferon A14, interferon A16, interferon A17, interferon A21, interferon B1, TNF, TRAIL, and FasL.

In preferred embodiments chemokines include but are not limited to CC chemokines, CXC chemokines, C chemokines, and CX3C chemokines. In particular chemokine include but are not limited to CCL1, CCL2, CCL3, CCL4, CCL5, CCL6, CCL7, CCL8, CCL9/CCL10, CCL11, CCL12, CCL13, CCL14, CCL15, CCL16, CCL17, CCL18, CCL19, CCL20, CCL21, CCL22, CCL23, CCL24, CCL25, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCL17, XCL1, XCL2, and CX3CL1.

In preferred embodiments, immuno-(co)stimulatory proteins include but are not limited to B7.1, B7.2, 4-1BBL, LIGHT, ICOSL, GITRL, CD40L, OX40L, and CD70.

Immuno-suppressive proteins preferably include but are not limited to IL1-Ra, IL-10, CTLA-4, PD-L1, and PD-L2, and toxins preferably include but are not limited to *Pseudomonas* exotoxin A, Diphtheria toxin and ricin.

In preferred embodiments apoptosis-inducing proteins include but are not limited to Bid, Bik, Puma, and Bim, and proapoptotic cytokines (death ligands) such as but not limited to TNF, scTNF, TRAIL, scTRAIL, and FasL.

In preferred embodiments enzymes include but are not limited to oxidoreductases, transferases, hydrolases, lyases, isomerases, ligases. Kinases include but are not limited to AGC kinases such as PKA, PKC and PKG, CaM kinases such as calcium/calmodulin-dependent protein kinases and serine/threonine protein kinases (e.g. DAPK2), CK1 such as the casein kinase 1 group, CMGC such as CDK, MAPK, GSK3 and CLK kinases, STE such as homologs of yeast Sterile 7, Sterile 11, and Sterile 20 kinases, tyrosine kinases (TK), the tyrosine-kinase like group of kinases (TKL), receptor-associated tyrosine kinases, MAP kinases, and histidine kinases.

Pro-drug-converting enzymes include but are not limited to esterases such as but not limited to acetylesterase, thiolester hydrolases, phosphoric monoester hydrolases, phosphoric diester hydrolases, triphosphoric monoester hydrolases, sulfuric ester hydrolases (sulfatases), diphosphoric monoester hydrolases, and phosphoric triester hydrolases; phosphatases such as but not limited to tyrosine-specific phosphatases, serine/threonine specific phosphatases, dual specificity phosphatases, histidine phosphatase, and lipid phosphatase; and reductases such as but not limited to 5-alpha reductase, dihydrofolate reductase, HMG-CoA reductase, methemoglobin reductase, ribonucleotide reductase, thioredoxin reductase, E. coli nitroreductase, methylenetetrahydrofolate reductase, and carboxypeptidase G2, cytosine deaminase, nitroreductase, thymidine kinase.

RNAses include endoribonucleases such as but are not limited to RNase A, RNase H, RNase I, RNase III, RNase L, RNase P, RNase PhyM, RNase T1, RNase T2, RNase U2, RNase V1, and RNase V, and exoribonucleases such as but not limited to Polynucleotide Phosphorylase (PNPase), RNase PH, RNase II, RNase R, RNase D, RNase T, Oligoribonuclease Exoribonuclease I, and Exoribonuclease II.

Agonistic antibodies or antibody fragments include those that cause an action in a tissue, organ or individual such as but not limited to receptor-signalling, gene expression, protein synthesis, and protein degradation, e.g. directed against TRAIL receptors, anti-glucocorticoid-induced tumor necrosis factor family receptor (GITR), and CD40. Typically, Agonistic antibody or antibody fragment act by binding to the active site or to allosteric sites of a receptor molecule thereby, triggering a specific reaction.

Antagonistic antibodies or antibody fragments include those blocking the action of an agonist. Typically, antagonistic antibodies or antibody fragments act by binding to the active site or to allosteric sites of a receptor molecule, or interact with unique binding sites not normally involved in the regulation of the activity of the receptor, e.g. anti-CTLA-4, anti-TNFR1, anti-VEGFR, anti-PDGFR, anti-EGFR, anti-Her2. Typically, an antagonistic antibody or antibody fragment competes with the agonist at structurally-defined binding sites or alters the binding site of the agonist in a manner that the agonist is not able to cause the action it would normally cause due to its binding.

In preferred embodiments growth factors include but are not limited to Adrenomedullin (AM), Angiopoietin (Ang), Autocrine motility factor, Bone morphogenetic proteins (BMPs), Brain-derived neurotrophic factor (BDNF), Epidermal growth factor (EGF), Erythropoietin (EPO), Fibroblast growth factor (FGF), Glial cell line-derived neurotrophic factor (GDNF), Granulocyte colony-stimulating factor (G-CSF), Granulocyte macrophage colony-stimulating factor (GM-CSF), Growth differentiation factor-9 (GDF9), Hepatocyte growth factor (HGF), Hepatoma-derived growth factor (HDGF), Insulin-like growth factor (IGF), Migration-stimulating factor Myostatin (GDF-8), Nerve growth factor (NGF) and other neurotrophins, Platelet-derived growth factor (PDGF), Thrombopoietin (TPO), Transforming growth factor alpha (TGF-α), Transforming growth factor beta (TGF-β), Vascular endothelial growth factor (VEGF), Wnt Signaling Pathway, and placental growth factor (P1GF).

In preferred embodiments, coagulation factors include but are not limited to Thrombin, Factor V, Factor VII, Factor VIII, Factor IX, Factor X, Factor XI, Factor XII and Factor XIII, and active fragments thereof.

In preferred embodiments fibrinolytic proteins include but are not limited to plasmin, urokinase, plasminogen, α2-antiplasmin, tissue-plasminogen activator (t-PA), and plasminogen activator inhibitor-1 (PAI-1).

In particularly preferred embodiments, the cytokine is the tumor-necrosis factor (TNF), more preferably according to SEQ ID NO: 5 or variants thereof. In further preferred embodiments the cytokine is the TNF-relative apoptosis-inducing factor (TRAIL), more preferably according to SEQ ID NO: 6 or variants thereof.

Mimicking peptides and proteins include peptides and proteins which mimic activities of other peptides or proteins, in particular of peptides or proteins named herein above or below, such as but not limited to thrombopoietin-mimetic peptides, erythropoietin-mimetic peptides.

In further embodiments, half-life extension modules are chemical or biological substances that alter the half-life, e.g. the "plasma half-life" or the "serum half-life", of the polypeptide of the present invention. Preferably, the half-life extension module is selected from the group consisting of immunoglobulin binding domains (IgBD), albumin, albumin-binding domains (ABD), peptides, small molecules, fatty acids, antibody fragments, single-domain antibodies, VHH, scaffold proteins, and natural ligands exhibiting affinity for a long-circulating plasma protein, either of which are optionally PEGylated, HESylated, Polysialylated, N-glycosylated, O-glycosylated, or PEG-mimicking polypeptides. Preferably, an IgBD may bind to any of the domains of an Ig molecule, i.e. to the variable domains VH or VL and/or to the constant domains CH1, CH2, CH3 CH4 and/or CL of an Ig molecule. IGBDs include but are not limited to domains derived from protein A (SpA) of *Staphylococcus aureus*, streptococcal protein G (SpG), protein L (PpL) from *Peptostreptococcus magnus*, protein Eib from *Escherichia coli*, protein Sbi from *Staphylococcus*, and streptococcal proteins MAG, MIG, H, M and ZAG.

In further embodiments, imaging molecules are those binding to specific target molecules thereby, allowing the visualization of the location of that molecule. Preferably, the imaging molecule is selected from the group consisting of bioluminescent reagents, chemiluminescent reagents, fluorescent imaging reagents, photosensitizers, chelating reagents, and radioactive moieties.

Imaging molecule include bioluminescent, chemiluminescent and fluorescent imaging reagent such as but not limited to luciferase from Renilla reniformis and/or Metridia Longa, peroxalate, polymethines (e.g. cyanine dyes such as Cy3, Cy5, Cy5.5, Cy7) squaraine derivatives, phthalocyanine, porphhyrin derivatives, and BODIPY analogous (BODIPY FL, BODIPY R6G, BODIPY TR, BODIPY TMR, BODIPY 581/591, BODIPY 630/650, BODIPY 650/665), as well as fluorescent proteins such as but not limited to GFP, EGPF, CFP, BFP, YFP, DsRED (Chudakov et al. (2010) Physiol. Rev. 90:1103-1163).

Chelating reagents are capable of binding at least one metal ion, such as but not limited to calcium, magnesium, iron, aluminium, zinc, copper, arsenic, lead, thallium, and mercury ions, by chelation. Such chelating reagents may comprise ethylenediamine tetraacetic acid (EDTA), ethylenediamine tetraacetic acid (calcium disodium versante) (CaNa2-EDTA), dimercaprol (BAL), dimercaptosuccinic acid (DMSA), dimercapto-propane sulfonate (DMPS), ferritin, deferoxamine and deferasirox, deferiprone (1,2-dimethyl-3-hydroxyl-4-pyridinone), DOTA, DTPA, DADT, DADS, DO3A, N2S2MAMA, Triamidethiol, phosphonates, organic gadolinium complexes, penicillamine, and antibiotic drugs of the tetracycline family.

In preferred embodiments the radioactive moiety comprises a radionuclide. The radioactive moiety may be an isotope of F, Br, Mn, Co, Ga, As, Zr, P, C, S, H, I, In, Lu, Cu, Rh, Bi, At, Y, Re, Ac, Tc, or Hg atom. The radioactive moiety labels polypeptide of the present invention radioactively allowing for its detection, e.g in the human body, rendering it not only useful for diagnostic approaches (radioimmunodetection: RAID) but also suitable in therapeutic applications (radioimmunotherapy: RAIT).

Photosensitizers are chemical compounds capable of light emission or formation of free radicals and singlet oxigen after being excited by light of a specific wavelength. Photosensitizers are used e.g. for photodynamic therapy. In preferred embodiments photosensitizers include but are not limited to compounds of the porphyrin family, texaphyrin family, the chlorin family and the phthalocyanine family, in particular including HpD, ALA, M-ALA, Vertiporfin, Lutexaphyrin, Temoporfin, Talaporfin, HPPH, Phthalocyanine, and Napthalocyanine.

In particularly preferred embodiments the polypeptide comprises an MHD2 domain to which C-Terminus a scFv$_{EGFR}$ is fused and/or to which N-Terminus a scFv$_{HER2}$ is fused. In further preferred embodiments a scTRAIL or a scTNF is fused to the C- and/or N-Terminus of the MHD2 domain. In particularly preferred embodiments, scFv$_{EGFR}$ is fused to the N-terminus of MHD2 and scFv$_{HER2}$ is fused to the C-Terminus of MHD2. In further preferred embodiments scFv$_{EGFR}$ is fused to the N-terminus of MHD2 and scTNF is fused to the C-Terminus of MHD2. In further preferred embodiments scFv$_{EGFR}$ is fused to the N-terminus of MHD2 and scTRAIL is fused to the C-Terminus of MHD2. In further preferred embodiments scDb$_{EpCAMxEGFR}$ is fused to the N-terminus of MHD2 and scTRAIL is fused to the C-Terminus of MHD2. Highly preferred are polypeptides according to SEQ ID NO: 7, 8, 9, 10, 11, 12, 13, or 14.

In particularly preferred embodiments the polypeptide comprises an EHD2 domain to which C-Terminus a scFv$_{EGFR}$ is fused and/or to which N-Terminus a scFV$_{HER2}$ is fused. In further preferred embodiments a scTRAIL or a scTNF is fused to the C- and/or N-Terminus of the EHD2 domain. In particularly preferred embodiments, scFv$_{EGFR}$ is fused to the N-terminus of EHD2 and scFv$_{HER2}$ is fused to the C-Terminus of EHD2. In further preferred embodiments scFv$_{EGFR}$ is fused to the N-terminus of EHD2 and scTNF is fused to the C-Terminus of EHD2. In further preferred embodiments scFv$_{EGFR}$ is fused to the N-terminus of EHD2 and scTRAIL is fused to the C-Terminus of EHD2. In further preferred embodiments scDb$_{EpCAMxEGFR}$ is fused to the N-terminus of EHD2 and scTRAIL is fused to the C-Terminus of EHD2. Highly preferred are polypeptides according to SEQ ID NO: 15, 16, or 17.

In a second aspect, the present invention provides a nucleic acid molecule comprising a sequence encoding the polypeptide of the first aspect of the present invention. Preferably, such nucleic acid molecule comprises a DNA and/or RNA molecule.

In a third aspect the present invention provides a vector comprising the polynucleotide of the second aspect of the present invention. It is understood that suitable vectors include but are not limited to plasmids, cosmids, phages, viruses and/or artificial chromosomes.

In a fourth aspect the present invention provides a complex comprising at least two polypeptides of the first aspect of the present invention. In preferred embodiments the at least two polypeptides are connected via their HD2 domains, preferably via covalent or non-covalent bonds. It is particularly preferred that the covalent bond is a disulfide bond which is preferably formed between two cysteine residues, each residing within the HD2 domain of the respective polypeptide. The at least two polypeptides forming the complex may comprise the same or different HD2 domains. It is particularly preferred that the at least two polypeptides forming the complex comprise the same HD2, i.e. the at least two polypeptides forming a complex comprise an MHD2 or the at least two polypeptides forming a complex comprise an EHD2.

The at least two polypeptides may be identical or different with regard to the modules fused to the N- and/or C-Terminus of the HD2 domain or with regard to the linker peptides connecting the HD2 domains and the fused modules, i.e. they may comprise identical or differing modules, preferably pharmaceutically active moieties, attached to their HD2 domain and may comprise different peptide linkers connecting different modules, as described in detail above. Thus, in preferred embodiments the complex comprises at least two polypeptides of the following structure, wherein the at least two polypeptides are identical or different:

$X_1$-HD2, HD2-$Y_1$, $X_1$-$X_2$-HD2, $X_1$-$[X]_{m-1}$-HD2, HD2-$Y_1$-$Y_2$, HD2-$Y_1$-$[Y]_{n-1}$, $X_1$-HD2-$Y_1$, $X_1$-$X_2$-HD2-$Y_1$-$Y_2$, $X_1$-$[X]_{m-1}$-HD2-$Y_1$-$[Y]_{n-1}$, $X_1$-HD2-$Y_1$-$Y_2$, $X_1$-HD2-$Y_1$-$Y_n$, $X_1$-$X_2$-HD2-$Y_1$, $X_1$-$[X]_{m-1}$-HD2-$Y_1$, $X_1$-L-HD2, $X_1$-$X_2$-L-HD2, $X_1$-L-$X_2$-L-HD2, $X_1$-L-$X_2$-HD2, $X_1$-$[X]_{m-1}$-L-HD2, $X_1$-L-$[X]_{m-1}$-L-HD2, $X_1$-L-$[X]_{m-1}$-HD2, $Y_1$-L-HD2, $Y_1$-$Y_2$-L-HD2, $Y_1$-L-$Y_2$-L-HD2, $Y_1$-L-$Y_2$-HD2, $Y_1$-$[Y]_{n-1}$-L-HD2, $Y_1$-L-$[Y]_{n-1}$-L-HD2, $Y_1$-L-$[Y]_{n-1}$-HD2, $X_1$-L-HD2-L-$Y_1$, $X_1$-HD2-L-$Y_1$, $X_1$-L-HD2-$Y_1$, $X_1$-$X_2$-L-HD2-L-$Y_1$-$Y_2$, $X_1$-$X_2$-HD2-L-$Y_1$-$Y_2$, $X_1$-$X_2$-L-HD2-$Y_1$-$Y_2$, $X_1$-L-$X_2$-L-HD2-L-$Y_1$-L-$Y_2$, $X_1$-$X_2$-L-HD2-L-$Y_1$-L-$Y_2$, $X_1$-L-$X_2$-HD2-L-$Y_1$-L-$Y_2$, $X_1$-L-$X_2$-L-HD2-$Y_1$-L-$Y_2$, $X_1$-L-$X_2$-L-HD2-L-$Y_1$-$Y_2$, $X_1$-L-$X_2$-HD2-$Y_1$-L-$Y_2$, $X_1$-$X_2$-HD2-L-$Y_1$-$Y_2$, $X_1$-L-$X_2$-L-HD2-$Y_1$-$Y_2$, $X_1$-$[X]_{m-1}$-L-HD2-L-$Y_1$-$[Y]_{n-1}$, $X_1$-$[X]_{m-1}$-L-HD2-$Y_1$-$[Y]_{n-1}$, $X_1$-$[X]_{m-1}$-L-HD2-$Y_1$-$[Y]_{n-1}$, $X_1$-L-$[X]_{m-1}$-HD2-L-$Y_1$-L-$[Y]_{n-1}$, $X_1$-$[X]_{m-1}$-L-HD2-L-$Y_1$-L-$[Y]_{n-1}$, $X_1$-L-$[X]_{m-1}$-HD2-L-$Y_1$-L-$[Y]_{n-1}$, $X_1$-L-$X_2$-HD2-$Y_1$-L-$[Y]_{n-1}$, $X_1$-L-$[X]_{m-1}$-HD2-L-$Y_1$-$[Y]_{n-1}$, $X_1$-L-$[X]_{m-1}$-HD2-$Y_1$-L-$[Y]_{n-1}$, or $X_1$-L-$[X]_{m-1}$-HD2-$Y_1$-$[Y]_{n-1}$. m and n have in each case the above indicated preferred and particularly preferred meanings.

In particularly preferred embodiments, complexes are formed between two polypeptides each of which comprises an MHD2 domain to which C-Terminus a scFv$_{EGFR}$ is fused and/or to which N-Terminus a scFV$_{HER2}$ is fused; an MHD2 domain to which C- and/or N-Terminus a scTRAIL or a scTNF is fused; an MHD2 to which N-Terminus a scFv$_{EGFR}$ is fused and to which C-Terminus a cFv$_{HER2}$ is fused, an MHD2 domain to which N-terminus scFv$_{EGFR}$ is fused and to which C-Terminus scTNF is fused; an MHD2 to which N-terminus scFv$_{EGFR}$ is fused and to which C-Terminus scTRAIL; and an MHD2 to which N-terminus scDb$_{EpCAMxEGFR}$ is fused and to which C-Terminus scTRAIL. Highly preferred are complexes formed between two polypeptides according to SEQ ID NO: 7, 8, 9, 10, 11, 12, 13, or 14.

In particularly preferred embodiments, complexes are formed between two polypeptides each of which comprises an EHD2 domain to which C-Terminus a scFv$_{EGFR}$ is fused and/or to which N-Terminus a scFV$_{HER2}$ is fused; an EHD2 domain to which C- and/or N-Terminus a scTRAIL or a scTNF is fused; an EHD2 to which N-Terminus a scFv$_{EGFR}$ is fused and to which C-Terminus a scFv$_{HER2}$ is fused, an EHD2 domain to which N-terminus scFv$_{EGFR}$ is fused and to which C-Terminus scTNF is fused; an EHD2 to which N-terminus scFv$_{EGFR}$ is fused and to which C-Terminus scTRAIL; and an EHD2 to which N-terminus scDb$_{EpCAMx-EGFR}$ is fused and to which C-Terminus scTRAIL. Highly preferred are complexes formed between two polypeptides according to SEQ ID NO: 15, 16, or 17.

In a fifth aspect the present invention provides a cell comprising the polypeptide of the first aspect, the nucleic acid molecule of the second aspect, the vector of the third aspect, or the complex of the fourth aspect. It is understood that such cell includes but is not limited to prokaryotic (e.g. a bacterial cell) or eukaryotic cells (e.g. a fungal, plant or animal cell).

In a sixth aspect the present invention provides a composition comprising the polypeptide of the first aspect, the nucleic acid molecule of the second aspect, the vector of the third aspect, the complex of the fourth aspect, or the cell of the fifth aspect and a pharmaceutical acceptable carrier and/or excipient. Preferably, such composition is a pharmaceutical composition.

In preferred embodiments the pharmaceutical composition further comprises a pharmaceutically acceptable carrier and/or excipient and optionally one or more additional active substances. Preferably, the composition of the fifth aspect contains a therapeutically effective amount of the compound, preferably in purified form, together with a suitable amount of carrier and/or excipient so as to provide the form for proper administration to the patient. The formulation should suit the mode of administration.

The pharmaceutical compositions can take the form of solutions, suspensions, emulsion, tablets, pills, capsules, powders, sustained-release formulations and the like. The pharmaceutical composition can be formulated as a suppository, with traditional binders and carriers such as triglycerides.

For preparing pharmaceutical compositions of the present invention, pharmaceutically acceptable carriers can be either solid or liquid. Solid form compositions include powders, tablets, pills, capsules, lozenges, cachets, suppositories, and dispersible granules. A solid excipient can be one or more substances, which may also act as diluents, flavoring agents, binders, preservatives, tablet disintegrating agents, or an encapsulating material. In powders, the excipient is preferably a finely divided solid, which is in a mixture with the finely divided inhibitor of the present invention. In tablets, the active ingredient is mixed with the carrier having the necessary binding properties in suitable proportions and compacted in the shape and size desired. Suitable excipients are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. For preparing suppositories, a low melting wax, such as a mixture of fatty acid glycerides or cocoa butter, is first melted and the active component is dispersed homogeneously therein, as by stirring. The molten homogeneous mixture is then poured into convenient sized moulds, allowed to cool, and thereby to solidify. Tablets, powders, capsules, pills, cachets, and lozenges can be used as solid dosage forms suitable for oral administration.

Liquid form compositions include solutions, suspensions, and emulsions, for example, water, saline solutions, aqueous dextrose, glycerol solutions or water/propylene glycol solutions. For parenteral injections (e.g. intravenous, intraarterial, intraosseous infusion, intramuscular, subcutaneous, intraperitoneal, intradermal, and intrathecal injections), liquid preparations can be formulated in solution in, e.g. aqueous polyethylene glycol solution. A saline solution is a preferred carrier when the pharmaceutical composition is administered intravenously.

Preferably, the pharmaceutical composition is in unit dosage form. In such form the composition may be subdivided into unit doses containing appropriate quantities of the active component. The unit dosage form can be a packaged composition, the package containing discrete quantities of the composition, such as packaged tablets, capsules, and powders in vials or ampoules. Also, the unit dosage form can be a capsule, an injection vial, a tablet, a cachet, or a lozenge itself, or it can be the appropriate number of any of these in packaged form.

The composition, if desired, can also contain minor amounts of wetting or emulsifying agents, or pH buffering agents.

Furthermore, such pharmaceutical composition may also comprise other pharmacologically active substance such as but not limited to adjuvants and/or additional active ingredients. Adjuvants in the context of the present invention include but are not limited to inorganic adjuvants, organic adjuvants, oil-based adjuvants, cytokines, particulate adjuvants, virosomes, bacterial adjuvants, synthetic adjuvants, or synthetic polynucleotides adjuvants.

In a seventh aspect, the present invention provides the polypeptide of the first aspect, the nucleic acid molecule of the second aspect, the vector of the third aspect, the complex of the fourth aspect, or the cell of the fifth aspect as described in detail above for use as a medicament. In preferred embodiments the complex is for use in medicine, i.e. for use in the prophylaxis, treatment or diagnosis of a disorder or disease such as but not limited to autoimmune diseases, allergic diseases, cancer type diseases, cutaneous conditions, endocrine diseases, eye diseases and disorders, genetic disorders, infectious diseases, intestinal diseases, neurological disorders, and mental illness. Exemplified, autoimmune diseases include but are not limited to Diabetes mellitus type 1, rheumatoid arthritis, psoriasis, Crohns Disease, autoimmune cardiomyopathy, autoimmune hepatitis, Hashimoto's thyroiditis, and Sjogern's syndrome. Exemplified, allergic diseases include but are not limited to allergic rhinitis, asthma, atopic eczema, anaphylaxis, insect venom allergies, drug allergies, and food allergies. Exemplified, cancer type diseases include but are not limited to Basal cell carcinoma, Bladder cancer, Bone cancer, Brain tumor, Breast cancer, Burkitt lymphoma, Cervical cancer, Colon Cancer, Cutaneous T-cell lymphoma, Esophageal cancer, Retinoblastoma, Gastric (Stomach) cancer, Gastrointestinal stromal tumor, Glioma, Hodgkin lymphoma, Kaposi sarcoma, Leukemias, Lymphomas, Melanoma, Oropharyngeal cancer, Ovarian cancer, Pancreatic cancer, Pleuropulmonary blastoma, Prostate cancer, Throat cancer, Thyroid cancer, and Urethral cancer. Exemplified, cutaneous conditions include but are not limited to Acne, Dermatitis, Eczema, conditions of the skin appendages, conditions of the subcutaneous fat, disturbances of pigmentation, epidermal nevi, epidermal neoplasms, epidermal cysts, erythemas, frostbites genodermatoses, mucinoses, neurocutaneous conditions (e.g. Wiskott-Aldrich syndrome), and psoriasis. Exemplified, endocrine diseases include but are not limited to Diabetes mellitus type 1 and type 2, Osteoporosis, and Cushing's disease. Exemplified, genetic disorders include but are not limited to color blindness, cystic fibrosis, Down syndrome, Sickle-cell disease, and Turner syndrome. Exemplified, infectious diseases include but are not limited to infections diseases caused by viruses, bacteria, worms, prions or other pathogens or parasites such as African sleeping sickness, AIDS, HIV infection, Anthrax, Borreliosis, Calicivirus infection (Norovirus and Sapovirus), Chickenpox, Chlamydia infection, Cholera, Clostridium infection, Colorado tick fever (CTF), common cold, Creutzfeldt-Jakob disease, Dengue fever (DEN-1, DEN-2, DEN-3 and DEN-4), Ebola, Enterovirus infection, infections with Human herpesvirus 6 (HHV-6) and Human herpesvirus 7 (HHV-7), Gonorrhea, Streptoccocal infections (group A and B), Hand, foot and mouth disease (HFMD), *Helicobacter pylori* infection, Hepatitis (A, B, C, and D), Herpes infection, Papillomavirus infection, Parainfluenza virus infection, Influenza, Lassa fever, Marburg fever, Measles, Meningitis, Mumps, Pasteurellosis, Pediculus infection, Plague, Pneumococcal infection, Respiratory syncytial virus infection, Rotavirus infection, Rubella virus infection, Salmonella food poisoning and infection, SARS, Scabies infections, Schistosomiasis, Smallpox, Staphylococcal food poisoning and infection, Syphilis, Tetanus, Trichophyton infection, Tuberculosis, Typhus, Venezuelan equine encephalitis, and Yellow fever. Exemplified, intestinal diseases include but are not limited to Gastroenteritis, Ileus, Ileitis, Colitis, Appendicitis, Coeliac disease, Irritable bowel syndrome, Diverticular disease, Diarrhea, Polyp, and Ulcerative colitis. Exemplified, neurological disorders include but are not limited to Amyotrophic Lateral Sclerosis (ALS), Alzheimer's disease, Brain damage, Creutzfeldt-Jakob disease, Cushing's syndrome, Dyslexia, Encephalitis, Epilepsy, Headache, Huntington's disease, Migraine, Multiple sclerosis, Parkinson's disease, Polio, Rabies, Schizophrenia, and Stroke. Exemplified, mental illness include but are not limited to Acute stress disorder, attention-deficit hyperactivity disorder (ADHD), Autistic disorder, Borderline personality disorder, Bulimia nervosa, Burn Out, Schizophrenia, Depression, Cognitive disorder, Communication disorder, Eating disorder, Kleptomania, Learning disorders, Male erectile disorder, Melancholia, Obsessive-compulsive disorder (OCD), Paranoia Pathological gambling, Posttraumatic stress disorder (PTSD), Psychotic disorder, Hypersomnia, Insomnia, and Tourette's syndrome.

The following examples are merely illustrative of the present invention and should not be construed to limit the scope of the invention as indicated by the appended claims in any way.

EXAMPLES

Example 1: Production of scFv-MHD2 Fusion Proteins

A humanized anti-EGFR scFv (hu225) was generated from the antibody C225 (Goldstein et al., 1995) by CDR grafting. The anti-HER2 scFv 4D5 was reproduced from published sequences (Carter et al., 1992). Both scFvs as well as the sequence of the human IgM heavy chain domain 2 (MHD2) were condon-optimized for expression in human cells and synthesized by Geneart, now a Life Technologies subsidiary (Darmstadt, Germany), adding appropriate cloning sites. Two bivalent antibody-MHD2 fusion proteins were generated fusing either a humanized anti-EGFR scFv to the N-terminus of the MHD2 (scFvEGFR-MHD2; scFvA-MHD2) or an anti-HER2 scFv to the C-terminus of the MHD2 (MHD2-scFvHER2; MHD2-scFvB), respectively. In addition, a tetravalent, bispecific fusion protein was produced fusing scFvA to the N-terminus and scFvB to the C-terminus of the MHD2 (scFvEGFR-MHD2-scFvHER2; scFvA-MHD2-scFvB) (FIG. 3a, b). All constructs were cloned into the eukaryotic expression vector pSecTagA and produced in stably transfected HEK293 cells with yields in the range of 1.5 to 2.5 mg/L supernatant. SDS-PAGE analysis revealed under reducing conditions the expected molecular masses of the monomeric polypeptide chains (approximately 50 kDa for monospecific MHD2 fusion proteins and 75 kDa for bispecific MHD2 fusion protein) taking into account the presence of one potential N-glycosylation site in the MHD2 (see FIG. 3c). Under nonreducing conditions all constructs showed a band corresponding to dimeric molecules, although a second band with the size of monomers were observed. For the monospecific MHD2 fusion proteins, approximately 80-90% of the molecules were present as disulfide-linked dimers, while for the bispecific MHD2 fusion protein approximately 50% were disulfide-linked.

Example 2: Bioactivity of scFv-MHD2 Fusion Proteins

Selectivity of the antibody-MHD2 fusion proteins was analyzed by ELISA using Fc fusion proteins of the extracellular region of EGFR, HER2, and HER3, respectively (FIG. 4a). $scFv_{EGFR}$-MHD2 showed a specific binding to EGFR and MHD2-$scFv_{HER2}$ to HER2, while the $scFv_{EGFR}$-MHD2-$scFv_{HER2}$ fusion protein showed binding to both receptors. No binding was observed for the HER3-Fc fusion protein, included as negative control. Furthermore, the antibody-MHD2 fusion proteins were analyzed by flow cytometry for binding to different tumor cell lines expressing various amounts of EGFR and HER2 (FIG. 4b). The EGFR-expressing cell line A431 showed strong binding of $scFv_{EGFR}$-MHD2 and $scFv_{EGFR}$-MHD2-$scFv_{HER2}$, while no or only marginal binding was detected for MHD2-$scFv_{HER2}$ (FIG. 4b). In contrast, the HER2-positive cell line SKBR3 showed strong binding of MHD2-$scFv_{HER2}$ and $scFv_{EGFR}$-MHD2-$scFv_{HER2}$ and only weak binding of $scFv_{EGFR}$-MHD2 (FIG. 4b). The lung carcinoma cell line NCI-H460, expressing low amounts of EGFR and HER2, showed weak binding of $scFv_{EGFR}$-MHD2 and MHD2-$scFv_{HER2}$ but an increased binding of $scFv_{EGFR}$-MHD2-$scFv_{HER2}$ (FIG. 4b). Similar results were observed for the colon carcinoma cell line Colo205 (FIG. 4b). Except for SKBR3, an increased binding was observed for the bispecific MHD2 fusion protein compared with the two monospecific MHD2 fusion proteins.

Example 3: Production MHD2-scTNF Fusion Proteins

An antibody-TNF MHD2 fusion protein was generated fusing the anti-EGFR scFv to the N-terminus of the MHD2 and a single-chain TNF derivative (scTNF; Krippner-Heidenreich et al., 2008) to the C-terminus of the MHD2 (scFv-MHD2-scTNF). Furthermore, a bivalent cytokine-MHD2 molecule was generated lacking the scFv (MHD2- scTNF) (FIG. 5a, b). The two constructs were produced in HEK293 cells with yields of 5 to 12 mg/L supernatant. SDS-PAGE showed under reducing conditions single bands corresponding to the molecular mass of the monomeric polypeptides (70 kDa for MHD2-scTNF and 100 kDa for scFv-MHD2-scTNF). Dimeric assembly was seen under non-reducing conditions with approximately 40% of the MHD2-scTNF and approximately 95% of the scFv-MHD2-scTNF present as dimers (FIG. 5c). Dimeric assembly was confirmed by size exclusion chromatography (SEC) (FIG. 5d-f). ScTNF included for comparison eluted at a major peak with an apparent molecular mass of approximately 50 kDa. The MHD2-scTNF molecule revealed a major peak of approximately 200 kDa and the scFv-MHD2-scTNF showed a major peak corresponding to approximately 300 kDa. Melting points were also determined for scFv-MHD2-scTNF indicated a major melting point, at approximately 77° C. (FIG. 5g).

Example 4: Bioactivity of the MHD2-scTNF Fusion Proteins

In ELISA, the scFv-MHD2-scTNF fusion protein showed specific binding to an EGFR-Fc fusion protein, while no binding was observed for MHD2-scTNF (FIG. 6a). Binding to EGFR was further confirmed by flow cytometry with EGFR-expressing cells lines A431 and HT1080 (FIG. 6b). Binding of scFv-MHD2-scTNF to both cell lines could be blocked by pre-incubation with cetuximab. No or only marginal effects were observed with trastuzumab (anti-HER2).

Next, the fusion proteins were tested for triggering cell death on mouse embryonic fibroblasts (MEF) stably transfected to express either the extracellular region of human TNFR1 (MEF-TNFR1) or TNFR2 (MEF-TNFR2) fused to the transmembrane and cytoplasmic region of Fas (Krippner-Heidenreich et al., 2002). These cell lines allow to discriminate between the action of soluble TNF and membrane-bound TNF (mTNF), with mTNF or multimeric TNF required to active MEF-TNFR2. A titration of scTNF, MHD2-TNF and scFv-MHD2 showed a strong cytotoxic activity of scTNF and MHD2-scTNF on MEF-TNFR1, while on MEF-TNFR2 cell killing was only induced by the dimeric MHD2-scTNF construct (FIG. 6c, d). ScFv-MHD2 was inactive on both cell lines.

Bioactivity of the scTNF fusion proteins was further analyzed by measuring the TNF-mediated secretion of IL-8 from HT1080 cells. ScTNF as well as the MHD2-scTNF fusion protein induced secretion of IL-8 in a concentration-dependent manner with EC50 values of around 1-10 nM (FIG. 6e). A strongly increased stimulatory activity was observed with scFv-MHD2-scTNF, with an optimum at around 10 pM. At higher concentrations, the IL-8 release declined to approximately 25% of the highest values. The scFv-MHD2 fusion protein lacking the scTNF moiety, included as negative control, showed no stimulatory activity. IL-8 secretion induced by scFv-MHD2-scTNF was almost complete blocked to the level induced by the untargeted MHD2-scTNF fusion protein and scTNF with excess amounts of Cetuximab (660 nM) directed against the same epitope, while Trastuzumab had no effect. Both antibodies did not affect IL-8 secretion induced by MHD2-scTNF and scTNF, respectively (FIG. 6f).

Example 5: Production of MHD2-scTRAIL Fusion Proteins

A bivalent MHD2-scTRAIL molecule was generated fusing a single-chain derivative of TRAIL (scTRAIL; Schneider et al., 2010) to the C-terminus of the MHD2 domain (FIG. 7a, b). Furthermore, an antibody-MHD2-scTRAIL fusion protein was generated fusing the anti-EGFR scFv to the N-terminus of the MHD2 and a single-chain TRAIL derivative to the C-terminus of the MHD2 (scFv-MHD2-scTRAIL). The constructs were produced in HEK293 cells with yields of 0.3 to 0.5 mg/L supernatant. SDS-PAGE showed under reducing conditions single bands corresponding to the molecular mass of the monomeric polypeptides (100 kDa for MHD2-scTRAIL and 115 kDa for scFv-MHD2-scTRAIL). Dimeric assembly was seen under non-reducing conditions for MHD2-scTRAIL and scFv-MHD2-scTRAIL (FIG. 7c).

Example 6: Bioactivity of MHD2-scTRAIL Fusion Proteins

Bioactivity of the scTRAIL fusion proteins was further analyzed in cytotoxicity assays using the EGFR-expressing cell lines NCI-H460 (a) and Colo205 (b). To sensitize these cells for TRAIL-induced apoptosis, bortezomib, which is a clinically approved proteasome inhibitor, was added at a concentration of 250 ng/ml. ScTRAIL as well as the MHD2-scTRAIL fusion protein induced killing of these cell lines in a concentration-dependent manner (FIG. 8a, b). The $EC_{50}$ values for scTRAIL were 450 pM on NCI-H460 cells and 9.8 nM on Colo205 cells. The MHD2-scTRAIL fusion protein showed a markedly increased cytotoxic potential with $EC_{50}$ values of 47 pM on NCI-H460 cells and 180 pM on Colo205 cells, corresponding to a 9.6- and 54-fold increased bioactivity, depending on the cell line used.

Example 7: Production of EHD2-scTRAIL Fusion Proteins

A bivalent scFv-EHD2 was generated fusing an scFv directed against EGFR to the N-terminus of the EHD2 domain. A bivalent EHD2-scTRAIL molecule was generated fusing a single-chain derivative of TRAIL (scTRAIL) to the C-terminus of the EHD2 domain. Furthermore, an scFv-EHD2-scTRAIL fusion protein was generated fusing the anti-EGFR scFv to the N-terminus of the EHD2 and a single-chain TRAIL derivative to the C-terminus of the EHD2 (scFv-EHD2-scTNF) (FIG. 9a, b). DNA encoding the fusion proteins were cloned into mammalian expression vector pSecTag and produced in transiently transfected HEK293 cells. Secretion of soluble scFv-EHD2 (FIG. 9c), EHD2-scTRAIL (FIG. 9d) and scFv-EHD2-scTRAIL (FIG. 9e) into the cell culture supernatant was confirmed by immunoblotting (FIG. 9c-e). Under reducing conditions, single bands corresponding to the monomeric polypeptides were detected (lanes 2), while under non-reducing conditions (lane 1) dimeric molecules (upper band) were identified corresponding to disulfide-linked dimers.

Example 8: Comparison of MHD2 and EHD2 with IgG1-CH3

The individual MHD2, EHD2 as well as the CH3 domain from human IgG1 heavy chain were produced from stably transfected HEK293 and purified by IMAC. In SDS-PAGE, the CH3 (GHD3) domain showed under reducing (FIG. 10a, lane 1) as well as non-reducing conditions (FIG. 10a, lane 2) a single band corresponding to the monomeric polypeptide, confirming that the domains are not covalently linked. Size-exclusion chromatography confirmed dimeric assembly of the domains. By dynamic light scattering, a first melting point at around 50° C. (probably due to domain dissociation) and a second major melting point at 75° C. (probably due to complete denaturation) was observed. In SDS-PAGE, the CH2 domain of IgM (MHD2) showed under reducing (FIG. 10c, lane 1) bands corresponding to the monomeric polypeptide, while under non-reducing conditions (FIG. 10b, lane 2) bands corresponding to dimeric molecules were detected, confirming that the domains are covalently linked. This analysis also demonstrated partial N-glycosylation apparent by two bands under reducing conditions, which was confirmed by deglycosylation with PNGaseF (not shown). Size exclusion chromatography further confirmed dimeric assembly of the domains. By dynamic light scattering, no clear transition was observed but a continuous increase of aggregate formation starting at approximately 56° C. was found, presumably caused by the heterogeneity of the preparation, also indicating that the domain is rather stable even at high temperatures. In SDS-PAGE, the CH2 domain of IgE (EHD2) showed under reducing conditions (FIG. 10c, lane 1) bands corresponding to the monomeric polypeptide, while under non-reducing conditions (FIG. 10c, lane 2) bands corresponding to dimeric molecules were detected, confirming that the domains are also covalently linked. Similar to MHD2, this analysis also demonstrated partial N-glycosylation apparent by two bands under reducing conditions. Size exclusion chromatography further confirmed dimeric assembly of the domains. By dynamic light scattering, a single thermal melting point of approximately 80-82° C. was determined.

Example 9: scFv-EHD2 Fusion Proteins

Various scFv-EHD2 fusion proteins were generated by fusing scFvs directed against CEA, HER2, or HER3 to the N-terminus of the EHD2 (FIG. 26). All constructs were cloned into mammalian expression vector pSecTagA and produced in transiently or stably transfected HEK293 cells. The anti-HER3 scFv-EHD2 fusion protein could be detected by immunoblotting with an anti-His-tag antibody in the supernatant of transiently transfected cells (FIG. 26c). Anti-CEA scFv-EHD2 was purified from the cell culture supernatant by immobilized metal affinity chromatography. SDS-PAGE analysis of purified anti-CEA scFv-EHD2 confirmed dimeric assembly of the fusion protein (see FIG. 27c). ELISA with immobilized CEA further confirmed correct assembly of the antigen binding sites (FIG. 27d).

Example 10: A Bispecific scDb-EHD2 Fusion Proteins for T Cell Retargeting

A bispecific single-chain diabody (scDb)-EHD2 fusion protein was generated by fusing a scDb directed against CEA and human CD3 to the N-terminus of the EHD2 (FIG. 27a, b). The construct was cloned into mammalian expression vector pSecTagA and produced in stably transfected HEK293 cells. Protein was purified from the cell culture supernatant by immobilized metal affinity chromatography. For comparison we included an scFv-EHD2 fusion protein directed against CEA (see example 9). The proteins migrated in SDS-PAGE under reducing conditions with a molecular mass of 80 kDa (scDb-EHD2) and 45 kDa (scFv-EHD2), respectively, corresponding in size to the single polypeptide. Under non-reducing conditions, the proteins migrated with an apparent molecular mass corresponding to dimeric molecules, demonstrating disulfide bond formation. Both proteins showed similar binding to immobilized CEA in ELISA (FIG. 27d), confirming functionality of the antigen-binding sites.

Example 11: Bivalent scFv-Cys-EHD2 and Tetravalent scFv-Cys-EHD2-scFv Fusion Proteins for Chemical Coupling Antibodies can be used as carriers of molecules for diagnosis and therapy, e.g. drugs, toxins, and imaging reagents. In order to facilitate conjugation of these molecules, thiol groups can be introduced into the antibody molecule, e.g. by introducing one or more cysteine residues into the protein sequence, ideally at positions which do not interfere with antigen binding. We have recently described modified scFv molecules (Messerschmidt et al., 2008, Bioconjug. Chem. 19, 362-369) containing an additional cysteine residue either at the C-terminus of an scFv molecule or at the linker sequence connecting the VH and VL domains. Using an anti-FAP scFv (scFv-L3) containing a cysteine residue at position 3 of the 14 residue long linker (GGCGSGGGGSGGSA), a bivalent scFv-Cys-EHD2 was generated by fusing the scFv-L3 to the N-terminus of the EHD2 (FIG. 28). In addition, a tetravalent scFv-L3-EHD2-scFv fusion protein was generated by fusing an unmodified anti-FAP scFv to the C-terminus of the EHD2 domain (FIG. 28). The encoding DNA sequence was cloned into mammalian expression vector pSecTagA and stably transfected into HEK293 cells. The expressed protein was detected in the supernatant using anti-His-tag antibodies, demonstrating production and secretion of the full-length polypeptides in mammalian cells (FIG. 28c).

Example 12: EHD2-scTRAIL Fusion Proteins Targeting EGFR-Expressing Tumor Cells

Various fusion proteins were generated fusing an anti-EGFR scFv to the N-terminus (scFv-EHD2), a single-chain derivative of TRAIL (scTRAIL) to the C-terminus (EHD2-scTRAIL), or the scFv to the N-terminus and scTRAIL to the C-terminus of EHD2 (scFv-EHD2-scTRAIL) (FIG. 29a). All fusion proteins were produced in stably transfected HEK293 cells and purified by affinity chromatography with yields of 7.9 mg/L supernatant for the hexahistidyl-tagged scFv-EHD2, and 2.8 and 7.9 mg/L supernatant for the FLAG-tagged EHD2-scTRAIL and scFv-EHD2-scTRAIL fusion proteins, respectively. SDS-PAGE analysis confirmed purity and integrity of the fusion proteins as well as formation of disulfide-linked dimers, although only a fraction of the EHD2-scTRAIL and the scFv-EHD2-scTRAIL molecules showed covalent linkage (FIG. 29b). Nevertheless, correct assembly into dimeric molecules was demonstrated by SEC, indicating the presence of dimeric molecules even in the absence of interchain disulfide bonds (FIG. 29c). N-glycosylation of the EHD2 was confirmed by deglycosylation of the scFv-EHD2 fusion protein with PNGase F. After deglycosylation, only a single band was detected in SDS-PAGE under non-reducing conditions, corresponding in size to the faster migrating band seen for the untreated fusion protein (not shown). Functionality of the fusion proteins was shown by ELISA (FIG. 29d, e). Here, scFv-EHD2 and scFv-EHD2-scTRAIL bound to immobilized EGFR-Fc fusion protein, while no binding was seen for EHD2-scTRAIL. None of the fusion proteins was capable of binding to HER2-Fc included as negative control. Furthermore, EHD2-scTRAIL and scFv-EHD2-scTRAIL showed also binding to recombinant TRAIL-R1 and TRAIL-R2 in ELISA (FIG. 29d). A titration of the bivalent scFv-EHD2 in comparison with monovalent anti-EGFR scFv in ELISA demonstrated increased binding of the bivalent fusion protein (FIG. 29e). Furthermore, scFv-EHD2 and scFv-EHD2-scTRAIL showed binding to cell lines (Colo205, NCI-H460) expressing EGFR, while only marginal binding was observed for HEK293 cells lacking significant expression of EGFR (FIG. 30a, b). Only weak binding was observed for EHD2-scTRAIL to these cell lines, indicating a rather low expression of TRAIL receptors. This was confirmed by flow cytometry analysis of the cell lines with monoclonal antibodies directed against TRAIL receptors 1 to 4.

Example 13: An Anti-EGFR scFv-EHD2-scTRAIL Fusion Protein Shows Potent Tumor Cell Killing In Vitro The cytotoxic activity of the fusion proteins were determined on NCI-H460 and Colo205 cells incubated with the fusion proteins for 1 day in the absence or presence of the proteasome inhibitor bortezomib (Velcade), which is known to sensitize tumor cells for TRAIL action (FIG. 31). In the absence of bortezomib, scTRAIL did not induce cell death over the analyzed concentration range (1 pM-10 nM). In contrast, EHD2-scTRAIL caused cell death with an $IC_{50}$ of 7.2 nM (NCI-H460) and 10 nM (Colo205), respectively (Table 1). Compared with EHD2-scTRAIL, cytotoxic activity was further increased approximately 20-fold for the scFv-EHD2-scTRAIL fusion protein, supporting the contribution of targeted delivery. Cytotoxicity was improved for all proteins in the presence of 250 mg/ml bortezomib. Again EHD2-scTRAIL was more potent than scTRAIL and strongest effects were observed for scFv-EHD2-scTRAIL (Table 1). The scFv-EHD2 fusion protein showed no cytotoxic activity over the analyzed concentration range (not shown). To investigate the contribution of scFv-mediated targeting to cytotoxicity, experiments were repeated in the absence or presence of excess amounts of cetuximab, recognizing the same epitope as scFv hu225. Cytotoxic activity of scFv-EHD2-scTRAIL in the presence of cetuximab was reduced to that observed for EHD2-scTRAIL, while cetuximab had no effects on the cytotoxicity of EHD2-scTRAIL (FIG. 32; Table 1). Furthermore, we compared the cytotoxicity on NCI-460 and Colo205 cells of bivalent scFv-EHD2-sc-TRAIL with that of a monovalent scFv-scTRAIL fusion protein (FIG. 33). A strongly increased cytotoxic activity was observed for the dimeric scFv-EHD2-scTRAIL fusion protein for both cell lines and in the absence or presence of bortezomib. In the absence of bortezomib, scFv-scTRAIL reached approximately 50- to 60% of cell killing at the highest concentration of the fusion protein. In contrast, the scFv-EHD2-scTRAIL fusion protein mediated potent killing of both cell lines. In the presence of bortezomib, the cytotoxic activity of the scFv-EHD2-scTRAIL was increased approximately 3- to 4-fold compared with scFv-scTRAIL (FIG. 33).

TABLE 1

In vitro cytotoxicity

| construct | Bortezomib | Cetuximab | $IC_{50}$ (nM) NCI-H460 | Colo205 |
|---|---|---|---|---|
| scTRAIL | − | − | >10 | >10 |
|  | + | − | 1.16 | >10 |
| EHD2-scTRAIL | − | − | 7.2 | 10 |
|  | + | − | 0.10 | 1.28 |
|  | + | + | 0.09 | 2.39 |
| scFv-EHD2-scTRAIL | − | − | 0.32 | 0.50 |
|  | + | − | 0.02 | 0.14 |
|  | + | + | 0.15 | 1.43 |
| scFv-EHD2 | + | − | − | − |

Example 14: Pharmacokinetics of EHD2-scTRAIL Fusion Proteins

Pharmacokinetic properties of the fusion proteins were determined in CD1 mice receiving a single i.v. injection of 25 µg protein (FIG. 34). All three EHD2 fusion proteins exhibited a prolonged circulation time compared with scTRAIL. Terminal half-lives were increased from 3.3 h for scTRAIL to 7.4 to 10.8 h for the EHD2 fusion proteins resulting also in a 3- to 4-fold increased $AUC_{0-24h}$ (Table 2). Differences of the terminal half-life and AUC between scTRAIL and the various fusion proteins were all statistically significant (p<0.05), while the AUC of the EHD2 fusion proteins were statistically not significantly different from each other (p>0.05).

TABLE 2

Pharmacokinetic properties of EHD2 fusion proteins

| construct | $M_r$ (kDa) | $S_r$ (nm) | $t_{1/2}b$ (h) | $AUC_{0-24h}$ (%h) |
|---|---|---|---|---|
| scTRAIL | 67.5 | 3.3<sup>#</sup> | 3.3 ± 0.3 | 114 ± 42 |
| scFv-EHD2 | 82.8 | 4.4 | 10.8 ± 0.7 | 356 ± 76 |
| EHD2-scTRAIL | 164.6 | 4.6 | 7.4 ± 0.4 | 400 ± 123 |
| scFv-EHD2-scTRAIL | 218.6 | 5.1 | 8.0 ± 1.4 | 483 ± 166 |

The molecular masses were calculated for the dimeric molecules

Example 15: An Anti-EGFR scFv-EHD2-scTRAIL Fusion Protein Shows Potent Antitumor Activity The scTRAIL fusion proteins were then tested in nude mice bearing subcutaneous Colo205 tumors for their antitumor activity. Mice received four i.v. injections of scTRAIL, EHD2-scTRAIL or scFv-EHD2-scTRAIL, respectively, over 16 days. Doses of 0.7 nmol scTRAIL and 0.35 nmol EHD2-scTRAIL and scFv-EHD2-scTRAIL were used, thus mice received equimolar doses in respect to scTRAIL. All mice, including a control group, received furthermore bortezomib (i.p.) every second day over a period of 14 days (FIG. 35a). Bortezomib at this dose does not induce any antitumor effects in this xenograft tumor model. A statistically significant reduction of tumor growth was observed for scFv-EHD2-scTRAIL, while EHD2-sc-TRAIL showed only a minor effect on tumor growth (FIG. 35b). At the applied doses, scTRAIL had no effect compared with the bortezomib control group. In a further experiment we compared the antitumor activity of the scFv-EHD2-scTRAIL fusion protein at a dose of 1 nmol with that of a scFv-EHD2 fusion protein lacking the scTRAIL moiety (FIG. 35c, d). Mice received four i.v. injections of the fusion proteins every second day. As before, bortezomib was included (5 µg/i.p. injection). A strong anti-tumor activity was seen for the scFv-EHD2-scTRAIL fusion protein, while scFv-EHD2 had no effect compared with bortezomib treatment alone (FIG. 35d). Finally, a possible liver toxicity of the scFv-EHD2-scTRAIL fusion protein was analyzed in the presence of bortezomib after a single injection. No increase in ALT was found 4 or 24 hours after treatment and values were similar to PBS-treated mice (FIG. 35e).

Example 16: TNFR2-Selective MHD2- and EHD2-scTNF$_{R2}$ Fusion Proteins

Tumor necrosis factor (TNF) exerts its biological functions via two distinct receptors. Whereas the TNF receptor (TNFR) 1 mainly mediates inflammatory responses, the TNFR2 is involved in tissue protection and regeneration. In particular, it has been demonstrated that TNFR2 can protect neurons against excitotoxic insults in vitro and promotes neuronal survival as well as oligodendrocyte regeneration after ischemic and neurotoxic insults, respectively. Accordingly, TNF variants selectively activating TNFR2 could potentially be useful as therapeutic regimen in a variety of diseases. Soluble recombinant TNF is a strong mediator of inflammation, predominantly through TNFR1 activation, as soluble TNF is not sufficient to activate TNFR2. In contrast, the membrane-bound form of TNF (memTNF) fully activates both TNFRs. Therefore, TNFR2-specific therapeutics need to comply with two basic requirements: mimicry of memTNF and, in order to avoid dose limiting severe inflammatory responses, and receptor selectivity. TNFR2 selectivity was ensured by introducing known TNFR discriminating mutations in the TNF molecule (D143N/A145R). The TNFR2-selective mutant was used in the single-chain TNF format (scTNF$_{R2}$), consisting of three TNF monomers connected by short peptide linkers. Multimerization was achieved by fusion of the scTNF$_{R2}$ to either MHD2 (MHD2-scTNF$_{R2}$) or EHD2 (EHD2-scTNF$_{R2}$), respectively. All proteins were produced in stably transfected HEK293 cells and purified by IMAC from the cell culture supernatant. SDS-PAGE analysis demonstrated dimeric assembly of the fusion proteins (FIG. 36a-c). The MHD2-scTNF$_{R2}$ and EHD2-scTNF$_{R2}$ fusion proteins showed selective binding to TNFR2-Fc fusion proteins in ELISA while recombinant human TNF (rhTNF) included in this study showed only weak binding to TNFR2-Fc, demonstrating an increased binding activity of the bivalent MHD2- and EHD2 fusion proteins.

```
Sequence Listing-Free Text Information
Amino acid sequence of human MHD2:
                                     SEQ ID NO: 1
AELPPKVSVFVPPRDGFFGNPRKSKLICQATGFSPRQIQVSWLREGK

QVGSGVTTDQVQAEAKESGPTTYKVTSTLTIKESDWLGQSMFTCRVD

HRGLTFQQNASSMCVPD

Amino acid sequence of human EHD2:
                                     SEQ ID NO: 2
DFTPPTVKILQSSCDGGGHFPPTIQLLCLVSGYTPGTINITWLEDGQ

VMDVDLSTASTTQEGELASTQSELTLSQKHWLSDRTYTCQVTYQGHT

FEDSTKKCADSN

SEQ ID NO: 3
Amino acid sequence of anti-HER2 scFvs (4D5)

SEQ ID NO: 4
Amino acid sequence of anti-EGFR scFvs (hu225)

SEQ ID NO: 5
Amino acid sequence of scTNF

SEQ ID NO: 6
Amino acid sequence of scTRAIL

SEQ ID NO: 7
Amino acid sequence of scFv$_{EGFR}$-MHD2

SEQ ID NO: 8
Amino acid sequence of MHD2-scFv$_{HER2}$

SEQ ID NO: 9
Amino acid sequence of scFv$_{EGFR}$-MHD2-scFv$_{HER2}$

SEQ ID NO: 10
Amino acid sequence of MHD2-scTNF

SEQ ID NO: 11
Amino acid sequence of scFv$_{EGFR}$-MHD2-scTNF

SEQ ID NO: 12
Amino acid sequence of MHD2-scTRAIL

SEQ ID NO: 13
Amino acid sequence of scFv$_{EGFR}$-MHD2-scTRAIL

SEQ ID NO: 14
Amino acid sequence of scDb$_{EpCAMxEGFR}$-MHD2-scTRAIL

SEQ ID NO: 15
Amino acid sequence of scFv$_{EGFR}$-EHD2

SEQ ID NO: 16
Amino acid sequence of EHD2-scTRAIL

SEQ ID NO: 17
Amino acid sequence of scFv$_{EGFR}$-EHD2-scTRAIL linker peptide 1:
                                     SEQ ID NO: 18
GGGGS linker peptide 2:
                                     SEQ ID NO: 19
GGGGSGGGGS linker peptide 3:
                                     SEQ ID NO: 20
GGGGSGGGGSGGGGS linker peptide 4:
                                     SEQ ID NO: 21
GSLGGSGG linker peptide 5:
                                     SEQ ID NO: 22
GGGSGGGT linker peptide 6:
                                     SEQ ID NO: 23
GGGSGGGTGS linker peptide 7:
                                     SEQ ID NO: 24
GGGSGGGTGSGG linker peptide 8:
                                     SEQ ID NO: 25
GGGSGGGS linker peptide 9:
                                     SEQ ID NO: 26
EFTRG linker peptide 10:
                                     SEQ ID NO: 27
AAA
```

-continued

Amino acid sequence of Anti-CEA scFv-EHD2  SEQ ID NO: 28

Amino acid sequence of Anti-HER2 scFv-EHD2  SEQ ID NO: 29

Amino acid sequence of Anti-HER3 scFv-EHD2  SEQ ID NO: 30

Amino acid sequence of Anti-CEAxCD3 scDb-EHD2  SEQ ID NO: 31

Amino acid sequence of Anti-EGFR scFv-L3-EHD2  SEQ ID NO: 32

Amino acid sequence of Anti-EGFR scFv-L3-EHD2-scFv  SEQ ID NO: 33

Amino acid sequence of MHD2-scTNF$_{R2}$  SEQ ID NO: 34

Amino acid sequence of EHD2-scTNF$_{R2}$-L16aa  SEQ ID NO: 35

Amino acid sequence of EHD2-scTNF$_{R2}$-L28aa  SEQ ID NO: 36

LIST OF REFERENCES

1. Arai, R., Ueda, H., Kitayama, A., Kamiya, N, & Nagamune, T. (2001); Design of linkers which effectively separate domains of a bifunctional fusion protein. Protein Engineering. 14, 8, 529-532.
2. Carter, P., Presta, L., Gorman, C. M., Ridgway, J. B. B., Henner, D., Wong, W. L. T., Rowland, A. M., Kotts, C., Carver, M. E. & Shepard, H. M. (1992) Humanization of an anti-p185$^{HER2}$ antibody for human cancer therapy. Proc. Natl. Acad. Sci. USA 89, 4285-4289.
3. Cuesta, A. M., Sainz-Pastor, N., Bonet, J., Oliva, B. & Alvarez-Vallina, L. (2010) Multivalent antibodies: when design surpasses evolution. Trends Biotechnol. 28, 355-362.
4. Deckert, P. M. (2009) Current constructs and targets in clinical development for antibody-based cancer therapy. Curr. Drug Targets 10, 158-175.
5. Deyev, S. M. & Lebedenko, E. N. (2008) Multivalency: the hallmark of antibodies used for optimization of tumor targeting by design. BioEssays 30, 904-918.
6. Dübel, S., Breitling, F., Kontermann, R., Schmidt, T., Skerra, A. & Little, M. (1995) Bifunctional and multimeric complexes of streptavidin fused to single chain antibodies (scFv). J. Immunol. Methods 178, 201-209.
7. George, R. A., & Heringa, J. (2003), An analysis of protein domain linkers: their classification and role in protein folding. Protein Engineering. 15, 11, 871-879.
8. Goldstein, N. I., Prewett, M., Zuklys, K., Rockwell, P. & Mendelsohn, J. (1995) Biological efficacy of a chimeric antibody to the epidermal growth factor receptor in a human tumor xenograft model. Clin. Cancer Res. 1, 1311-1318.
9. Hu, S. Z., Shively, L., Rautibschek, A., Sherman, M., Williams, L. E., Wong, J. Y. C., Shively, J. E. & Wu, A. M. (1996) Minibody: a novel engineered anti-carcinoembryonic antigen antibody fragment (single-chain Fv-C$_H$3) which exhibits rapid, high-level targeting of xenografts. Cancer Res. 56, 3055-3061.
10. Jazayeri, J. A. & Carroll, G. J. (2008) Fc-based cytokines: Prospects for engineering superior therapeutics. Biodrugs 22, 11-26.
11. Kavoosi, M., Creagh, A. L., Kilburn, D. G., & Haynes, C. A. (2007) Strategy for Selecting and Characterizing Linker Peptides for CBM9-Tagged Fusion Proteins Expressed in *Escherichia coli*. Biotechnology and Bioengineering, 98, 3, 599-610.
12. Kontermann, R. E. (2010) Alternative antibody formats. Curr. Opin. Mol. Ther. 12, 176-183.
13. Krippner-Heidenreich, A., Tübing, F., Bryde, S., Willi, S., Zimmermann, G. & Scheurich, P. (2002) Control of receptor-induced signaling complex formation by the kinetics of ligand/receptor interaction. J. Biol. Chem. 277, 4415544163.
14. Krippner-Heidenreich, A., Grunwald, I., Zimmermann, G., Kühnle, M., Gerspach, J., Sterns, T., Shnyder, S. D., Gill, J. H., Mannel, D. N., Pfizenmaier, K. & Scheurich, P. (2008) Single-chain TNF, a TNF derivative with enhanced stability and antitumor activity. J. Immunol. 180, 8176-8183.
15. Mülner, D. & Kontermann, R. E. (2010) Bispecific antibodies for cancer immunotherapy: current perspectives. BioDrugs 24, 89-98.
16. Pack, P. & Plückthun, A. (1992) Miniantibodies: use of amphipathic helices to produce functional, flexibly linked dimeric FV fragments with high avidity in *Escherichia coli*. Biochemistry 31, 1579-1584.
17. Rheinnecker, M., Hardt, C., Ilag, L. L., Kufer, P., Gruber, R., Hoess, A., Lupas, A., Rottenberg, C., PlUckthun, A. & Pack, P. (1996) Multivalent antibody fragments with high functional affinity for a tumor-associated carbohydrate antigen. J. Immunol. 157, 2989-2997.
18. Robinson, C. R., & Sauer, R. T. (1998) Optimizing the stability of single-chain proteins by linker length and composition mutagenesis. PNAS USA, 95, 5929-5934.
19. Schrama, D., Reisfeld, R. A. & Becker, J. C. (2006) Antibody targeted drugs as cancer therapeutics. Nat. Rev. Drug Discov. 5, 147-159.
20. Tanaka, T., Yokoyama, S., & Kuroda, Y. (2005) Improvement of Domain Linker Prediction by Incorporating Loop-Length-Dependent Characteristics. Biopolymers (Peptide Science), 84, 161-168.
21. Ventura, E., Sassi, F., Fossati, s., Parodi, A., Blalock W., Balza, E., Castellani, P., Borsi, L., Camemolla, B. & Zardi, L. (2009) Use of uteroglobin for the engineering of polyvalent, polyspecific fusion proteins. J. Biol. Chem. 284, 26646-26654.
22. Völkel T., Korn, T., Bach, M., Müller, R., & Kontermann, R. E. (2001) Optimized linker sequences for the expression of monomeric and dimeric bispecific single-chain diabodies. Protein Engineering, 14, 10, 815-823.
23. Watanabe, H., Kanazaki, K., Nakanishi, T., Shiotsuka, H., Hatakeyama, S., Kaieda, M., Imamura, T., Umetsu, M., & Kumagai, I. (2011) Biomimetic Engineering of Modular Bispecific Antibodies for Biomolecule Immobilization. ACS Langmuir, 27, 9656-9661.
24. Wriggers W., Chakravarty, S., Jennings, P. A., (2005) Control of Protein Functional Dynamics by Peptide Linkers. Biopolymers (Peptide Science), 80, 736-746.

The invention claimed is:

1. A polypeptide comprising a heavy chain domain 2 (HD2) from IgM and at least one pharmaceutically active moiety, under the proviso that the pharmaceutically active moiety is not a Fab or Fc fragment from IgM or IgE, wherein the HD2 domain from IgM comprises an amino acid sequence having at least 99% identity to the amino acid sequence of SEQ ID NO: 1 or a dimerizing variant thereof; wherein the polypeptide does not comprise heavy chain constant domain CH3 of IgM; and wherein the pharmaceutically active moiety is an antibody or antigen binding fragment thereof, a ligand, a cytokine, a receptor, or a tumor marker.

2. The polypeptide of claim 1, wherein at least one pharmaceutically active moiety is connected to the N- and/or C-Terminus of the HD2.

3. The polypeptide of claim 1, wherein at least one pharmaceutically active moiety is connected to the HD2 directly or indirectly via one or more linkers.

4. The polypeptide of claim 3, wherein the one or more linkers comprise peptide linkers.

5. The polypeptide of claim 4, wherein the peptide linkers comprise one or more cleavage sites.

6. The polypeptide of claim 1, wherein at least two identical or at least two different pharmaceutically active moieties are connected to the HD2.

7. The polypeptide of claim 1, wherein the ligand is selected from the group consisting of an antigen-binding molecule, a scaffold protein, a ligand-binding receptor fragment, and an aptamer.

8. The polypeptide of claim 7, wherein the antigen-binding molecule is selected from the group consisting of an antibody fragment, a Fab fragment, a Fab' fragment, a heavy chain antibody, a single-domain antibody (sdAb), a variable domain of a heavy chain antibody, a VHH, a Nanobody, a single-chain variable fragment (scFv), a tandem scFv, a bispecific T-cell engager, a diabody, a single-chain diabody, a triple body, a nanoantibody, a scaffold protein, and a fusion protein thereof.

9. The polypeptide of claim 1, wherein the antibody or antigen binding fragment is an anti-HER2 or an anti-EGFR scFv.

10. The polypeptide of claim 1, wherein the cytokine is the tumor-necrosis factor (TNF).

11. The polypeptide of claim 1, wherein the cytokine is the TNF-relative apoptosis-inducing factor (TRAIL).

12. The polypeptide of claim 1, which further comprises a half-life extension module, selected from the group consisting of an immunoglobulin binding domain (IgBD), albumin, an albumin-binding domain (ABD), a fatty acid, a single-domain antibody, a VHH, a scaffold protein, and a ligand exhibiting affinity for a long-circulating plasma protein.

13. The polypeptide of claim 1, which further comprises an imaging molecule, selected from the group consisting of a bioluminescent reagent, a chemiluminescent reagent, a fluorescent imaging reagent, a photosensitizer, a chelating reagent, and a radioactive moiety.

14. A complex comprising at least two polypeptides according to claim 1.

15. The complex of claim 14, wherein the at least two polypeptides are connected via their HD2 domains.

16. The complex of claim 14, wherein the at least two polypeptides are connected via covalent or non-covalent bonds.

17. The complex of claim 16, wherein the at least two polypeptides are connected via a covalent bond and the covalent bond is a disulfide bond.

18. The complex of claim 14, wherein the at least two polypeptides are identical or different.

19. A composition comprising the polypeptide of claim 1 and a pharmaceutically acceptable carrier.

20. The composition of claim 19, which further comprises a pharmaceutically acceptable excipient.

21. The polypeptide of claim 1, wherein the HD2 domain from IgM consists of the amino acid sequence according to SEQ ID NO: 1.

22. The polypeptide of claim 1, wherein the polypeptide does not comprise heavy chain constant domain CH1 of IgM.

23. The polypeptide of claim 1, wherein the polypeptide does not comprise heavy chain constant domain CH4 of IgM.

24. The polypeptide of claim 1, wherein the polypeptide does not comprise heavy chain constant domain CH1 and CH4 of IgM.

25. The polypeptide of claim 12, wherein the half-life extension module is PEGylated, HESylated, polysialylated, N-glycosylated, or O-glycosylated.

* * * * *

SEQUENCE LISTING

<160> NUMBER OF SEQ ID NOS: 70

<210> SEQ ID NO 1
<211> LENGTH: 111
<212> TYPE: PRT
<213> ORGANISM: Homo sapiens

<400> SEQUENCE: 1

Ala Glu Leu Pro Pro Lys Val Ser Val Phe Val Pro Pro Arg Asp Gly
1               5                   10                  15

Phe Phe Gly Asn Pro Arg Lys Ser Lys Leu Ile Cys Gln Ala Thr Gly
            20                  25                  30

Phe Ser Pro Arg Gln Ile Gln Val Ser Trp Leu Arg Glu Gly Lys Gln
        35                  40                  45

Val Gly Ser Gly Val Thr Thr Asp Gln Val Gln Ala Glu Ala Lys Glu
    50                  55                  60

Ser Gly Pro Thr Thr Tyr Lys Val Thr Ser Thr Leu Thr Ile Lys Glu
65                  70                  75                  80

Ser Asp Trp Leu Gly Gln Ser Met Phe Thr Cys Arg Val Asp His Arg
                85                  90                  95

Gly Leu Thr Phe Gln Gln Asn Ala Ser Ser Met Cys Val Pro Asp
            100                 105                 110

<210> SEQ ID NO 2
<211> LENGTH: 106
<212> TYPE: PRT
<213> ORGANISM: Homo sapiens

<400> SEQUENCE: 2

Asp Phe Thr Pro Pro Thr Val Lys Ile Leu Gln Ser Ser Cys Asp Gly
1               5                   10                  15

Gly Gly His Phe Pro Pro Thr Ile Gln Leu Leu Cys Leu Val Ser Gly
            20                  25                  30

Tyr Thr Pro Gly Thr Ile Asn Ile Thr Trp Leu Glu Asp Gly Gln Val
        35                  40                  45

Met Asp Val Asp Leu Ser Thr Ala Ser Thr Thr Gln Glu Gly Glu Leu
    50                  55                  60

Ala Ser Thr Gln Ser Glu Leu Thr Leu Ser Gln Lys His Trp Leu Ser
65                  70                  75                  80

Asp Arg Thr Tyr Thr Cys Gln Val Thr Tyr Gln Gly His Thr Phe Glu
                85                  90                  95

Asp Ser Thr Lys Lys Cys Ala Asp Ser Asn
            100                 105

<210> SEQ ID NO 3
<211> LENGTH: 265
<212> TYPE: PRT
<213> ORGANISM: Homo sapiens

<400> SEQUENCE: 3

Met Lys Tyr Leu Leu Pro Thr Ala Ala Ala Gly Leu Leu Leu Leu Ala
1               5                   10                  15

Ala Gln Pro Ala Met Ala Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Asn Ile Lys Asp Thr Tyr Ile His Trp Val Arg Gln Ala Pro Gly
    50                  55                  60

Lys Gly Leu Glu Trp Val Ala Arg Ile Tyr Pro Thr Asn Gly Tyr Thr
65                  70                  75                  80

Arg Tyr Ala Asp Ser Val Lys Gly Arg Phe Thr Ile Ser Ala Asp Thr
                85                  90                  95

Ser Lys Asn Thr Ala Tyr Leu Gln Met Asn Ser Leu Arg Ala Glu Asp
            100                 105                 110

Thr Ala Val Tyr Tyr Cys Ser Arg Trp Gly Gly Asp Gly Phe Tyr Ala
        115                 120                 125

Met Asp Tyr Trp Gly Gln Gly Thr Leu Val Thr Val Ser Ser Gly Gly
    130                 135                 140

Gly Gly Ser Gly Gly Gly Ser Gly Gly Thr Gly Asp Ile Gln
145                 150                 155                 160

Met Thr Gln Ser Pro Ser Ser Leu Ser Ala Ser Val Gly Asp Arg Val
                165                 170                 175

Thr Ile Thr Cys Arg Ala Ser Gln Asp Val Asn Thr Ala Val Ala Trp
            180                 185                 190

Tyr Gln Gln Lys Pro Gly Lys Ala Pro Lys Leu Leu Ile Tyr Ser Ala
        195                 200                 205

Ser Phe Leu Tyr Ser Gly Val Pro Ser Arg Phe Ser Gly Ser Arg Ser
    210                 215                 220

Gly Thr Asp Phe Thr Leu Thr Ile Ser Ser Leu Gln Pro Glu Asp Phe
225                 230                 235                 240

Ala Thr Tyr Tyr Cys Gln Gln His Tyr Thr Thr Pro Pro Thr Phe Gly
                245                 250                 255

Gln Gly Thr Lys Val Glu Ile Lys Arg
            260                 265

<210> SEQ ID NO 4
<211> LENGTH: 264
<212> TYPE: PRT
<213> ORGANISM: Homo sapiens

<400> SEQUENCE: 4

Met Lys Tyr Leu Leu Pro Thr Ala Ala Ala Gly Leu Leu Leu Leu Ala
1               5                   10                  15

Ala Gln Pro Ala Met Ala Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Ser Leu Thr Asn Tyr Gly Val His Trp Val Arg Gln Ala Pro Gly
    50                  55                  60

Lys Gly Leu Glu Trp Leu Gly Val Ile Trp Ser Gly Gly Asn Thr Asp
65                  70                  75                  80

Tyr Asn Thr Pro Phe Thr Ser Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Ala Leu Thr Tyr Tyr Asp Tyr Glu Phe
        115                 120                 125

Ala Tyr Trp Gly Gln Gly Thr Thr Val Thr Val Ser Ser Gly Gly Gly
    130                 135                 140

Gly Ser Gly Gly Gly Gly Ser Gly Gly Gly Gly Ser Asp Ile Gln Leu
145                 150                 155                 160

Thr Gln Ser Pro Ser Phe Leu Ser Ala Ser Val Gly Asp Arg Val Thr

```
            165                 170                 175
Ile Thr Cys Arg Ala Ser Gln Ser Ile Gly Thr Asn Ile His Trp Tyr
        180                 185                 190

Gln Gln Lys Pro Gly Lys Ala Pro Lys Leu Leu Ile Lys Tyr Ala Ser
        195                 200                 205

Glu Ser Ile Ser Gly Val Pro Ser Arg Phe Ser Gly Ser Gly Ser Gly
        210                 215                 220

Thr Glu Phe Thr Leu Thr Ile Ser Ser Leu Gln Pro Glu Asp Phe Ala
225                 230                 235                 240

Thr Tyr Tyr Cys Gln Gln Asn Asn Asn Trp Pro Thr Thr Phe Gly Ala
                245                 250                 255

Gly Thr Lys Leu Glu Ile Lys Arg
            260

<210> SEQ ID NO 5
<211> LENGTH: 472
<212> TYPE: PRT
<213> ORGANISM: Artificial Sequence
<220> FEATURE:
<223> OTHER INFORMATION: scTNF

<400> SEQUENCE: 5

Ser Ser Arg Thr Pro Ser Asp Lys Pro Val Ala His Val Val Ala Asn
1               5                   10                  15

Pro Gln Ala Glu Gly Gln Leu Gln Trp Leu Asn Arg Arg Ala Asn Ala
            20                  25                  30

Leu Leu Ala Asn Gly Val Glu Leu Arg Asp Asn Gln Leu Val Val Pro
        35                  40                  45

Ser Glu Gly Leu Tyr Leu Ile Tyr Ser Gln Val Leu Phe Lys Gly Gln
    50                  55                  60

Gly Cys Pro Ser Thr His Val Leu Leu Thr His Thr Ile Ser Arg Ile
65                  70                  75                  80

Ala Val Ser Tyr Gln Thr Lys Val Asn Leu Leu Ser Ala Ile Lys Ser
                85                  90                  95

Pro Cys Gln Arg Glu Thr Pro Glu Gly Ala Glu Ala Lys Pro Trp Tyr
            100                 105                 110

Glu Pro Ile Tyr Leu Gly Gly Val Phe Gln Leu Glu Lys Gly Asp Arg
        115                 120                 125

Leu Ser Ala Glu Ile Asn Arg Pro Asp Tyr Leu Asp Phe Ala Glu Ser
    130                 135                 140

Gly Gln Val Tyr Phe Gly Ile Ile Ala Leu Gly Gly Gly Gly Ser Ser
145                 150                 155                 160

Ser Arg Thr Pro Ser Asp Lys Pro Val Ala His Val Val Ala Asn Pro
                165                 170                 175

Gln Ala Glu Gly Gln Leu Gln Trp Leu Asn Arg Arg Ala Asn Ala Leu
            180                 185                 190

Leu Ala Asn Gly Val Glu Leu Arg Asp Asn Gln Leu Val Val Pro Ser
        195                 200                 205

Glu Gly Leu Tyr Leu Ile Tyr Ser Gln Val Leu Phe Lys Gly Gln Gly
    210                 215                 220

Cys Pro Ser Thr His Val Leu Leu Thr His Thr Ile Ser Arg Ile Ala
225                 230                 235                 240

Val Ser Tyr Gln Thr Lys Val Asn Leu Leu Ser Ala Ile Lys Ser Pro
                245                 250                 255

Cys Gln Arg Glu Thr Pro Glu Gly Ala Glu Ala Lys Pro Trp Tyr Glu
```

```
                    260                 265                 270
Pro Ile Tyr Leu Gly Gly Val Phe Gln Leu Glu Lys Gly Asp Arg Leu
            275                 280                 285

Ser Ala Glu Ile Asn Arg Pro Asp Tyr Leu Asp Phe Ala Glu Ser Gly
        290                 295                 300

Gln Val Tyr Phe Gly Ile Ile Ala Leu Gly Gly Gly Ser Ser Ser
305                 310                 315                 320

Arg Thr Pro Ser Asp Lys Pro Val Ala His Val Val Ala Asn Pro Gln
                325                 330                 335

Ala Glu Gly Gln Leu Gln Trp Leu Asn Arg Arg Ala Asn Ala Leu Leu
            340                 345                 350

Ala Asn Gly Val Glu Leu Arg Asp Asn Gln Leu Val Val Pro Ser Glu
        355                 360                 365

Gly Leu Tyr Leu Ile Tyr Ser Gln Val Leu Phe Lys Gly Gln Gly Cys
    370                 375                 380

Pro Ser Thr His Val Leu Leu Thr His Thr Ile Ser Arg Ile Ala Val
385                 390                 395                 400

Ser Tyr Gln Thr Lys Val Asn Leu Leu Ser Ala Ile Lys Ser Pro Cys
                405                 410                 415

Gln Arg Glu Thr Pro Glu Gly Ala Glu Ala Lys Pro Trp Tyr Glu Pro
            420                 425                 430

Ile Tyr Leu Gly Gly Val Phe Gln Leu Glu Lys Gly Asp Arg Leu Ser
        435                 440                 445

Ala Glu Ile Asn Arg Pro Asp Tyr Leu Asp Phe Ala Glu Ser Gly Gln
    450                 455                 460

Val Tyr Phe Gly Ile Ile Ala Leu
465                 470
```

<210> SEQ ID NO 6
<211> LENGTH: 580
<212> TYPE: PRT
<213> ORGANISM: Artificial Sequence
<220> FEATURE:
<223> OTHER INFORMATION: scTRAIL

<400> SEQUENCE: 6

```
Thr Arg Gly Thr Ser Glu Glu Thr Ile Ser Thr Val Gln Glu Lys Gln
1               5                   10                  15

Gln Asn Ile Ser Pro Leu Val Arg Glu Arg Gly Pro Gln Arg Val Ala
            20                  25                  30

Ala His Ile Thr Gly Thr Arg Gly Arg Ser Asn Thr Leu Ser Ser Pro
        35                  40                  45

Asn Ser Lys Asn Glu Lys Ala Leu Gly Arg Lys Ile Asn Ser Trp Glu
    50                  55                  60

Ser Ser Arg Ser Gly His Ser Phe Leu Ser Asn Leu His Leu Arg Asn
65                  70                  75                  80

Gly Glu Leu Val Ile His Glu Lys Gly Phe Tyr Tyr Ile Tyr Ser Gln
                85                  90                  95

Thr Tyr Phe Arg Phe Gln Glu Glu Ile Lys Glu Asn Thr Lys Asn Asp
            100                 105                 110

Lys Gln Met Val Gln Tyr Ile Tyr Lys Tyr Thr Ser Tyr Pro Asp Pro
        115                 120                 125

Ile Leu Leu Met Lys Ser Ala Arg Asn Ser Cys Trp Ser Lys Asp Ala
    130                 135                 140

Glu Tyr Gly Leu Tyr Ser Ile Tyr Gln Gly Gly Ile Phe Glu Leu Lys
```

```
145                 150                 155                 160
Glu Asn Asp Arg Ile Phe Val Ser Val Thr Asn Glu His Leu Ile Asp
            165                 170                 175
Met Asp His Glu Ala Ser Phe Phe Gly Ala Phe Leu Val Gly Gly Gly
            180                 185                 190
Gly Ser Gly Gly Gly Ser Thr Ser Glu Glu Thr Ile Ser Thr Val Gln
            195                 200                 205
Glu Lys Gln Gln Asn Ile Ser Pro Leu Val Arg Glu Arg Gly Pro Gln
210                 215                 220
Arg Val Ala Ala His Ile Thr Gly Thr Arg Gly Arg Ser Asn Thr Leu
225                 230                 235                 240
Ser Ser Pro Asn Ser Lys Asn Glu Lys Ala Leu Gly Arg Lys Ile Asn
            245                 250                 255
Ser Trp Glu Ser Ser Arg Ser Gly His Ser Phe Leu Ser Asn Leu His
            260                 265                 270
Leu Arg Asn Gly Glu Leu Val Ile His Glu Lys Gly Phe Tyr Tyr Ile
            275                 280                 285
Tyr Ser Gln Thr Tyr Phe Arg Phe Gln Glu Glu Ile Lys Glu Asn Thr
            290                 295                 300
Lys Asn Asp Lys Gln Met Val Gln Tyr Ile Tyr Lys Tyr Thr Ser Tyr
305                 310                 315                 320
Pro Asp Pro Ile Leu Leu Met Lys Ser Ala Arg Asn Ser Cys Trp Ser
            325                 330                 335
Lys Asp Ala Glu Tyr Gly Leu Tyr Ser Ile Tyr Gln Gly Gly Ile Phe
            340                 345                 350
Glu Leu Lys Glu Asn Asp Arg Ile Phe Val Ser Val Thr Asn Glu His
            355                 360                 365
Leu Ile Asp Met Asp His Glu Ala Ser Phe Phe Gly Ala Phe Leu Val
            370                 375                 380
Gly Gly Gly Gly Ser Gly Gly Gly Ser Thr Ser Glu Glu Thr Ile Ser
385                 390                 395                 400
Thr Val Gln Glu Lys Gln Gln Asn Ile Ser Pro Leu Val Arg Glu Arg
            405                 410                 415
Gly Pro Gln Arg Val Ala Ala His Ile Thr Gly Thr Arg Gly Arg Ser
            420                 425                 430
Asn Thr Leu Ser Ser Pro Asn Ser Lys Asn Glu Lys Ala Leu Gly Arg
            435                 440                 445
Lys Ile Asn Ser Trp Glu Ser Ser Arg Ser Gly His Ser Phe Leu Ser
            450                 455                 460
Asn Leu His Leu Arg Asn Gly Glu Leu Val Ile His Glu Lys Gly Phe
465                 470                 475                 480
Tyr Tyr Ile Tyr Ser Gln Thr Tyr Phe Arg Phe Gln Glu Glu Ile Lys
            485                 490                 495
Glu Asn Thr Lys Asn Asp Lys Gln Met Val Gln Tyr Ile Tyr Lys Tyr
            500                 505                 510
Thr Ser Tyr Pro Asp Pro Ile Leu Leu Met Lys Ser Ala Arg Asn Ser
            515                 520                 525
Cys Trp Ser Lys Asp Ala Glu Tyr Gly Leu Tyr Ser Ile Tyr Gln Gly
            530                 535                 540
Gly Ile Phe Glu Leu Lys Glu Asn Asp Arg Ile Phe Val Ser Val Thr
545                 550                 555                 560
Asn Glu His Leu Ile Asp Met Asp His Glu Ala Ser Phe Phe Gly Ala
            565                 570                 575
```

Phe Leu Val Gly
            580

<210> SEQ ID NO 7
<211> LENGTH: 410
<212> TYPE: PRT
<213> ORGANISM: Artificial Sequence
<220> FEATURE:
<223> OTHER INFORMATION: scFvEGFR-MHD2

<400> SEQUENCE: 7

Met Glu Thr Asp Thr Leu Leu Leu Trp Val Leu Leu Trp Val Pro
1               5                   10                  15

Gly Ser Thr Gly Asp Ala Ala Gln Pro Ala Met Ala Glu Val Gln Leu
            20                  25                  30

Val Glu Ser Gly Gly Gly Leu Val Gln Pro Gly Gly Ser Leu Arg Leu
        35                  40                  45

Ser Cys Ala Ala Ser Gly Phe Ser Leu Thr Asn Tyr Gly Val His Trp
50                  55                  60

Val Arg Gln Ala Pro Gly Lys Gly Leu Glu Trp Leu Gly Val Ile Trp
65                  70                  75                  80

Ser Gly Gly Asn Thr Asp Tyr Asn Thr Pro Phe Thr Ser Arg Phe Thr
                85                  90                  95

Ile Ser Arg Asp Asn Ser Lys Asn Thr Leu Tyr Leu Gln Met Asn Ser
            100                 105                 110

Leu Arg Ala Glu Asp Thr Ala Val Tyr Tyr Cys Ala Arg Ala Leu Thr
        115                 120                 125

Tyr Tyr Asp Tyr Glu Phe Ala Tyr Trp Gly Gln Gly Thr Thr Val Thr
130                 135                 140

Val Ser Ser Gly Gly Gly Gly Ser Gly Gly Gly Gly Ser Gly Gly Gly
145                 150                 155                 160

Gly Ser Asp Ile Gln Leu Thr Gln Ser Pro Ser Phe Leu Ser Ala Ser
                165                 170                 175

Val Gly Asp Arg Val Thr Ile Thr Cys Arg Ala Ser Gln Ser Ile Gly
            180                 185                 190

Thr Asn Ile His Trp Tyr Gln Gln Lys Pro Gly Lys Ala Pro Lys Leu
        195                 200                 205

Leu Ile Lys Tyr Ala Ser Glu Ser Ile Ser Gly Val Pro Ser Arg Phe
210                 215                 220

Ser Gly Ser Gly Ser Gly Thr Glu Phe Thr Leu Thr Ile Ser Ser Leu
225                 230                 235                 240

Gln Pro Glu Asp Phe Ala Thr Tyr Tyr Cys Gln Gln Asn Asn Asn Trp
                245                 250                 255

Pro Thr Thr Phe Gly Ala Gly Thr Lys Leu Glu Ile Lys Arg Gly Ser
            260                 265                 270

Leu Gly Gly Ser Gly Gly Ala Glu Leu Pro Pro Lys Val Ser Val Phe
        275                 280                 285

Val Pro Pro Arg Asp Gly Phe Phe Gly Asn Pro Arg Lys Ser Lys Leu
290                 295                 300

Ile Cys Gln Ala Thr Gly Phe Ser Pro Arg Gln Ile Gln Val Ser Trp
305                 310                 315                 320

Leu Arg Glu Gly Lys Gln Val Gly Ser Gly Val Thr Thr Asp Gln Val
                325                 330                 335

Gln Ala Glu Ala Lys Glu Ser Gly Pro Thr Thr Tyr Lys Val Thr Ser
            340                 345                 350

```
Thr Leu Thr Ile Lys Glu Ser Asp Trp Leu Gly Gln Ser Met Phe Thr
        355                 360                 365

Cys Arg Val Asp His Arg Gly Leu Thr Phe Gln Gln Asn Ala Ser Ser
        370                 375                 380

Met Cys Val Pro Asp Gly Gly Ser Gly Gly Gly Thr Gly Ser Glu
385                 390                 395                 400

Phe Ala Ala Ala His His His His His
                405                 410

<210> SEQ ID NO 8
<211> LENGTH: 413
<212> TYPE: PRT
<213> ORGANISM: Artificial Sequence
<220> FEATURE:
<223> OTHER INFORMATION: MHD2-scFvHER2

<400> SEQUENCE: 8

Met Glu Thr Asp Thr Leu Leu Leu Trp Val Leu Leu Leu Trp Val Pro
1               5                   10                  15

Gly Ser Thr Gly Asp Ala Ala Gln Pro Ala Ser Ala Gly Ala Gly Ser
            20                  25                  30

Leu Gly Gly Ser Gly Gly Ala Glu Leu Pro Pro Lys Val Ser Val Phe
        35                  40                  45

Val Pro Pro Arg Asp Gly Phe Phe Gly Asn Pro Arg Lys Ser Lys Leu
50                  55                  60

Ile Cys Gln Ala Thr Gly Phe Ser Pro Arg Gln Ile Gln Val Ser Trp
65                  70                  75                  80

Leu Arg Glu Gly Lys Gln Val Gly Ser Gly Val Thr Thr Asp Gln Val
                85                  90                  95

Gln Ala Glu Ala Lys Glu Ser Gly Pro Thr Thr Tyr Lys Val Thr Ser
            100                 105                 110

Thr Leu Thr Ile Lys Glu Ser Asp Trp Leu Gly Gln Ser Met Phe Thr
        115                 120                 125

Cys Arg Val Asp His Arg Gly Leu Thr Phe Gln Gln Asn Ala Ser Ser
    130                 135                 140

Met Cys Val Pro Asp Gly Gly Ser Gly Gly Gly Thr Gly Ser Gly
145                 150                 155                 160

Gly Glu Val Gln Leu Val Glu Ser Gly Gly Gly Leu Val Gln Pro Gly
                165                 170                 175

Gly Ser Leu Arg Leu Ser Cys Ala Ala Ser Gly Phe Asn Ile Lys Asp
            180                 185                 190

Thr Tyr Ile His Trp Val Arg Gln Ala Pro Gly Lys Gly Leu Glu Trp
        195                 200                 205

Val Ala Arg Ile Tyr Pro Thr Asn Gly Tyr Thr Arg Tyr Ala Asp Ser
    210                 215                 220

Val Lys Gly Arg Phe Thr Ile Ser Ala Asp Thr Ser Lys Asn Thr Ala
225                 230                 235                 240

Tyr Leu Gln Met Asn Ser Leu Arg Ala Glu Asp Thr Ala Val Tyr Tyr
                245                 250                 255

Cys Ser Arg Trp Gly Gly Asp Gly Phe Tyr Ala Met Asp Tyr Trp Gly
            260                 265                 270

Gln Gly Thr Leu Val Thr Val Ser Ser Gly Gly Gly Gly Ser Gly Gly
        275                 280                 285

Gly Gly Ser Gly Gly Gly Thr Gly Asp Ile Gln Met Thr Gln Ser Pro
    290                 295                 300
```

```
Ser Ser Leu Ser Ala Ser Val Gly Asp Arg Val Thr Ile Thr Cys Arg
305                 310                 315                 320

Ala Ser Gln Asp Val Asn Thr Ala Val Ala Trp Tyr Gln Gln Lys Pro
                325                 330                 335

Gly Lys Ala Pro Lys Leu Leu Ile Tyr Ser Ala Ser Phe Leu Tyr Ser
            340                 345                 350

Gly Val Pro Ser Arg Phe Ser Gly Ser Arg Ser Gly Thr Asp Phe Thr
        355                 360                 365

Leu Thr Ile Ser Ser Leu Gln Pro Glu Asp Phe Ala Thr Tyr Tyr Cys
    370                 375                 380

Gln Gln His Tyr Thr Thr Pro Pro Thr Phe Gly Gln Gly Thr Lys Val
385                 390                 395                 400

Glu Ile Lys Arg Ala Ala Ala His His His His His His
                405                 410

<210> SEQ ID NO 9
<211> LENGTH: 653
<212> TYPE: PRT
<213> ORGANISM: Artificial Sequence
<220> FEATURE:
<223> OTHER INFORMATION: scFvEGFR-MHD2-scFvHER2

<400> SEQUENCE: 9

Met Glu Thr Asp Thr Leu Leu Leu Trp Val Leu Leu Leu Trp Val Pro
1               5                   10                  15

Gly Ser Thr Gly Asp Ala Ala Gln Pro Ala Met Ala Glu Val Gln Leu
            20                  25                  30

Val Glu Ser Gly Gly Gly Leu Val Gln Pro Gly Gly Ser Leu Arg Leu
        35                  40                  45

Ser Cys Ala Ala Ser Gly Phe Ser Leu Thr Asn Tyr Gly Val His Trp
    50                  55                  60

Val Arg Gln Ala Pro Gly Lys Gly Leu Glu Trp Leu Gly Val Ile Trp
65                  70                  75                  80

Ser Gly Gly Asn Thr Asp Tyr Asn Thr Pro Phe Thr Ser Arg Phe Thr
                85                  90                  95

Ile Ser Arg Asp Asn Ser Lys Asn Thr Leu Tyr Leu Gln Met Asn Ser
                100                 105                 110

Leu Arg Ala Glu Asp Thr Ala Val Tyr Tyr Cys Ala Arg Ala Leu Thr
            115                 120                 125

Tyr Tyr Asp Tyr Glu Phe Ala Tyr Trp Gly Gln Gly Thr Thr Val Thr
        130                 135                 140

Val Ser Ser Gly Gly Gly Gly Ser Gly Gly Gly Gly Ser Gly Gly Gly
145                 150                 155                 160

Gly Ser Asp Ile Gln Leu Thr Gln Ser Pro Ser Phe Leu Ser Ala Ser
                165                 170                 175

Val Gly Asp Arg Val Thr Ile Thr Cys Arg Ala Ser Gln Ser Ile Gly
            180                 185                 190

Thr Asn Ile His Trp Tyr Gln Gln Lys Pro Gly Lys Ala Pro Lys Leu
        195                 200                 205

Leu Ile Lys Tyr Ala Ser Glu Ser Ile Ser Gly Val Pro Ser Arg Phe
    210                 215                 220

Ser Gly Ser Gly Ser Gly Thr Glu Phe Thr Leu Thr Ile Ser Ser Leu
225                 230                 235                 240

Gln Pro Glu Asp Phe Ala Thr Tyr Tyr Cys Gln Gln Asn Asn Asn Trp
                245                 250                 255
```

```
Pro Thr Thr Phe Gly Ala Gly Thr Lys Leu Glu Ile Lys Arg Gly Ser
            260                 265                 270

Leu Gly Gly Ser Gly Gly Ala Glu Leu Pro Pro Lys Val Ser Val Phe
        275                 280                 285

Val Pro Pro Arg Asp Gly Phe Phe Gly Asn Pro Arg Lys Ser Lys Leu
    290                 295                 300

Ile Cys Gln Ala Thr Gly Phe Ser Pro Arg Gln Ile Gln Val Ser Trp
305                 310                 315                 320

Leu Arg Glu Gly Lys Gln Val Gly Ser Gly Val Thr Thr Asp Gln Val
                325                 330                 335

Gln Ala Glu Ala Lys Glu Ser Gly Pro Thr Thr Tyr Lys Val Thr Ser
            340                 345                 350

Thr Leu Thr Ile Lys Glu Ser Asp Trp Leu Gly Gln Ser Met Phe Thr
        355                 360                 365

Cys Arg Val Asp His Arg Gly Leu Thr Phe Gln Gln Asn Ala Ser Ser
    370                 375                 380

Met Cys Val Pro Asp Gly Gly Ser Gly Gly Thr Gly Ser Gly
385                 390                 395                 400

Gly Glu Val Gln Leu Val Glu Ser Gly Gly Leu Val Gln Pro Gly
                405                 410                 415

Gly Ser Leu Arg Leu Ser Cys Ala Ala Ser Gly Phe Asn Ile Lys Asp
                420                 425                 430

Thr Tyr Ile His Trp Val Arg Gln Ala Pro Gly Lys Gly Leu Glu Trp
            435                 440                 445

Val Ala Arg Ile Tyr Pro Thr Asn Gly Tyr Thr Arg Tyr Ala Asp Ser
450                 455                 460

Val Lys Gly Arg Phe Thr Ile Ser Ala Asp Thr Ser Lys Asn Thr Ala
465                 470                 475                 480

Tyr Leu Gln Met Asn Ser Leu Arg Ala Glu Asp Thr Ala Val Tyr Tyr
                485                 490                 495

Cys Ser Arg Trp Gly Gly Asp Gly Phe Tyr Ala Met Asp Tyr Trp Gly
            500                 505                 510

Gln Gly Thr Leu Val Thr Val Ser Ser Gly Gly Gly Ser Gly Gly
        515                 520                 525

Gly Gly Ser Gly Gly Gly Thr Gly Asp Ile Gln Met Thr Gln Ser Pro
        530                 535                 540

Ser Ser Leu Ser Ala Ser Val Gly Asp Arg Val Thr Ile Thr Cys Arg
545                 550                 555                 560

Ala Ser Gln Asp Val Asn Thr Ala Val Ala Trp Tyr Gln Gln Lys Pro
                565                 570                 575

Gly Lys Ala Pro Lys Leu Leu Ile Tyr Ser Ala Ser Phe Leu Tyr Ser
            580                 585                 590

Gly Val Pro Ser Arg Phe Ser Gly Ser Arg Ser Gly Thr Asp Phe Thr
        595                 600                 605

Leu Thr Ile Ser Ser Leu Gln Pro Glu Asp Phe Ala Thr Tyr Tyr Cys
    610                 615                 620

Gln Gln His Tyr Thr Thr Pro Pro Thr Phe Gly Gln Gly Thr Lys Val
625                 630                 635                 640

Glu Ile Lys Arg Ala Ala Ala His His His His His
                645                 650

<210> SEQ ID NO 10
<211> LENGTH: 648
```

<212> TYPE: PRT
<213> ORGANISM: Artificial Sequence
<220> FEATURE:
<223> OTHER INFORMATION: MHD2-scTNF

<400> SEQUENCE: 10

```
Met Glu Thr Asp Thr Leu Leu Leu Trp Val Leu Leu Leu Trp Val Pro
1               5                   10                  15

Gly Ser Thr Gly Asp Ala Ala Gln Pro Ala Ser Ala Gly Ala Gly Ser
            20                  25                  30

Leu Gly Gly Ser Gly Gly Ala Glu Leu Pro Pro Lys Val Ser Val Phe
        35                  40                  45

Val Pro Pro Arg Asp Gly Phe Phe Gly Asn Pro Arg Lys Ser Lys Leu
    50                  55                  60

Ile Cys Gln Ala Thr Gly Phe Ser Pro Arg Gln Ile Gln Val Ser Trp
65                  70                  75                  80

Leu Arg Glu Gly Lys Gln Val Gly Ser Gly Val Thr Thr Asp Gln Val
                85                  90                  95

Gln Ala Glu Ala Lys Glu Ser Gly Pro Thr Thr Tyr Lys Val Thr Ser
            100                 105                 110

Thr Leu Thr Ile Lys Glu Ser Asp Trp Leu Gly Gln Ser Met Phe Thr
        115                 120                 125

Cys Arg Val Asp His Arg Gly Leu Thr Phe Gln Gln Asn Ala Ser Ser
    130                 135                 140

Met Cys Val Pro Asp Gly Gly Ser Gly Gly Thr Gly Ser Glu
145                 150                 155                 160

Phe Met Arg Gly Ser His His His His His His Gly Ser Ala Ser Ser
                165                 170                 175

Ser Ser Arg Thr Pro Ser Asp Lys Pro Val Ala His Val Val Ala Asn
            180                 185                 190

Pro Gln Ala Glu Gly Gln Leu Gln Trp Leu Asn Arg Arg Ala Asn Ala
        195                 200                 205

Leu Leu Ala Asn Gly Val Glu Leu Arg Asp Asn Gln Leu Val Val Pro
    210                 215                 220

Ser Glu Gly Leu Tyr Leu Ile Tyr Ser Gln Val Leu Phe Lys Gly Gln
225                 230                 235                 240

Gly Cys Pro Ser Thr His Val Leu Leu Thr His Thr Ile Ser Arg Ile
                245                 250                 255

Ala Val Ser Tyr Gln Thr Lys Val Asn Leu Leu Ser Ala Ile Lys Ser
            260                 265                 270

Pro Cys Gln Arg Glu Thr Pro Glu Gly Ala Glu Ala Lys Pro Trp Tyr
        275                 280                 285

Glu Pro Ile Tyr Leu Gly Gly Val Phe Gln Leu Glu Lys Gly Asp Arg
    290                 295                 300

Leu Ser Ala Glu Ile Asn Arg Pro Asp Tyr Leu Asp Phe Ala Glu Ser
305                 310                 315                 320

Gly Gln Val Tyr Phe Gly Ile Ile Ala Leu Gly Gly Gly Ser Ser
                325                 330                 335

Ser Arg Thr Pro Ser Asp Lys Pro Val Ala His Val Val Ala Asn Pro
            340                 345                 350

Gln Ala Glu Gly Gln Leu Gln Trp Leu Asn Arg Arg Ala Asn Ala Leu
        355                 360                 365

Leu Ala Asn Gly Val Glu Leu Arg Asp Asn Gln Leu Val Val Pro Ser
    370                 375                 380
```

Glu Gly Leu Tyr Leu Ile Tyr Ser Gln Val Leu Phe Lys Gly Gln Gly
385                 390                 395                 400

Cys Pro Ser Thr His Val Leu Leu Thr His Thr Ile Ser Arg Ile Ala
                405                 410                 415

Val Ser Tyr Gln Thr Lys Val Asn Leu Leu Ser Ala Ile Lys Ser Pro
            420                 425                 430

Cys Gln Arg Glu Thr Pro Glu Gly Ala Glu Ala Lys Pro Trp Tyr Glu
        435                 440                 445

Pro Ile Tyr Leu Gly Gly Val Phe Gln Leu Glu Lys Gly Asp Arg Leu
    450                 455                 460

Ser Ala Glu Ile Asn Arg Pro Asp Tyr Leu Asp Phe Ala Glu Ser Gly
465                 470                 475                 480

Gln Val Tyr Phe Gly Ile Ile Ala Leu Gly Gly Gly Ser Ser Ser Ser
                485                 490                 495

Arg Thr Pro Ser Asp Lys Pro Val Ala His Val Val Ala Asn Pro Gln
            500                 505                 510

Ala Glu Gly Gln Leu Gln Trp Leu Asn Arg Arg Ala Asn Ala Leu Leu
        515                 520                 525

Ala Asn Gly Val Glu Leu Arg Asp Asn Gln Leu Val Val Pro Ser Glu
530                 535                 540

Gly Leu Tyr Leu Ile Tyr Ser Gln Val Leu Phe Lys Gly Gln Gly Cys
545                 550                 555                 560

Pro Ser Thr His Val Leu Leu Thr His Thr Ile Ser Arg Ile Ala Val
                565                 570                 575

Ser Tyr Gln Thr Lys Val Asn Leu Leu Ser Ala Ile Lys Ser Pro Cys
            580                 585                 590

Gln Arg Glu Thr Pro Glu Gly Ala Glu Ala Lys Pro Trp Tyr Glu Pro
        595                 600                 605

Ile Tyr Leu Gly Gly Val Phe Gln Leu Glu Lys Gly Asp Arg Leu Ser
    610                 615                 620

Ala Glu Ile Asn Arg Pro Asp Tyr Leu Asp Phe Ala Glu Ser Gly Gln
625                 630                 635                 640

Val Tyr Phe Gly Ile Ile Ala Leu
                645

<210> SEQ ID NO 11
<211> LENGTH: 888
<212> TYPE: PRT
<213> ORGANISM: Artificial Sequence
<220> FEATURE:
<223> OTHER INFORMATION: scFvEGFR-MHD2-scTNF

<400> SEQUENCE: 11

Met Glu Thr Asp Thr Leu Leu Leu Trp Val Leu Leu Leu Trp Val Pro
1               5                   10                  15

Gly Ser Thr Gly Asp Ala Ala Gln Pro Ala Met Ala Glu Val Gln Leu
            20                  25                  30

Val Glu Ser Gly Gly Gly Leu Val Gln Pro Gly Gly Ser Leu Arg Leu
        35                  40                  45

Ser Cys Ala Ala Ser Gly Phe Ser Leu Thr Asn Tyr Gly Val His Trp
50                  55                  60

Val Arg Gln Ala Pro Gly Lys Gly Leu Glu Trp Leu Gly Val Ile Trp
65                  70                  75                  80

Ser Gly Gly Asn Thr Asp Tyr Asn Thr Pro Phe Thr Ser Arg Phe Thr
                85                  90                  95

-continued

Ile Ser Arg Asp Asn Ser Lys Asn Thr Leu Tyr Leu Gln Met Asn Ser
            100                 105                 110

Leu Arg Ala Glu Asp Thr Ala Val Tyr Cys Ala Arg Ala Leu Thr
    115                 120                 125

Tyr Tyr Asp Tyr Glu Phe Ala Tyr Trp Gly Gln Gly Thr Thr Val Thr
    130                 135                 140

Val Ser Ser Gly Gly Gly Gly Ser Gly Gly Gly Gly Ser Gly Gly Gly
145                 150                 155                 160

Gly Ser Asp Ile Gln Leu Thr Gln Ser Pro Ser Phe Leu Ser Ala Ser
            165                 170                 175

Val Gly Asp Arg Val Thr Ile Thr Cys Arg Ala Ser Gln Ser Ile Gly
            180                 185                 190

Thr Asn Ile His Trp Tyr Gln Gln Lys Pro Gly Lys Ala Pro Lys Leu
            195                 200                 205

Leu Ile Lys Tyr Ala Ser Glu Ser Ile Ser Gly Val Pro Ser Arg Phe
            210                 215                 220

Ser Gly Ser Gly Ser Gly Thr Glu Phe Thr Leu Thr Ile Ser Ser Leu
225                 230                 235                 240

Gln Pro Glu Asp Phe Ala Thr Tyr Tyr Cys Gln Gln Asn Asn Asn Trp
                245                 250                 255

Pro Thr Thr Phe Gly Ala Gly Thr Lys Leu Glu Ile Lys Arg Gly Ser
            260                 265                 270

Leu Gly Gly Ser Gly Gly Ala Glu Leu Pro Pro Lys Val Ser Val Phe
            275                 280                 285

Val Pro Pro Arg Asp Gly Phe Phe Gly Asn Pro Arg Lys Ser Lys Leu
            290                 295                 300

Ile Cys Gln Ala Thr Gly Phe Ser Pro Arg Gln Ile Gln Val Ser Trp
305                 310                 315                 320

Leu Arg Glu Gly Lys Gln Val Gly Ser Gly Val Thr Thr Asp Gln Val
                325                 330                 335

Gln Ala Glu Ala Lys Glu Ser Gly Pro Thr Thr Tyr Lys Val Thr Ser
            340                 345                 350

Thr Leu Thr Ile Lys Glu Ser Asp Trp Leu Gly Gln Ser Met Phe Thr
            355                 360                 365

Cys Arg Val Asp His Arg Gly Leu Thr Phe Gln Gln Asn Ala Ser Ser
            370                 375                 380

Met Cys Val Pro Asp Gly Gly Ser Gly Gly Gly Thr Gly Ser Glu
385                 390                 395                 400

Phe Met Arg Gly Ser His His His His His Gly Ser Ala Ser Ser
                405                 410                 415

Ser Ser Arg Thr Pro Ser Asp Lys Pro Val Ala His Val Val Ala Asn
            420                 425                 430

Pro Gln Ala Glu Gly Gln Leu Gln Trp Leu Asn Arg Arg Ala Asn Ala
            435                 440                 445

Leu Leu Ala Asn Gly Val Glu Leu Arg Asp Asn Gln Leu Val Val Pro
            450                 455                 460

Ser Glu Gly Leu Tyr Leu Ile Tyr Ser Gln Val Leu Phe Lys Gly Gln
465                 470                 475                 480

Gly Cys Pro Ser Thr His Val Leu Leu Thr His Thr Ile Ser Arg Ile
                485                 490                 495

Ala Val Ser Tyr Gln Thr Lys Val Asn Leu Leu Ser Ala Ile Lys Ser
            500                 505                 510

Pro Cys Gln Arg Glu Thr Pro Glu Gly Ala Glu Ala Lys Pro Trp Tyr

```
            515                 520                 525
Glu Pro Ile Tyr Leu Gly Gly Val Phe Gln Leu Glu Lys Gly Asp Arg
530                 535                 540
Leu Ser Ala Glu Ile Asn Arg Pro Asp Tyr Leu Asp Phe Ala Glu Ser
545                 550                 555                 560
Gly Gln Val Tyr Phe Gly Ile Ile Ala Leu Gly Gly Gly Ser Ser
                565                 570                 575
Ser Arg Thr Pro Ser Asp Lys Pro Val Ala His Val Val Ala Asn Pro
                580                 585                 590
Gln Ala Glu Gly Gln Leu Gln Trp Leu Asn Arg Arg Ala Asn Ala Leu
                595                 600                 605
Leu Ala Asn Gly Val Glu Leu Arg Asp Asn Gln Leu Val Val Pro Ser
610                 615                 620
Glu Gly Leu Tyr Leu Ile Tyr Ser Gln Val Leu Phe Lys Gly Gln Gly
625                 630                 635                 640
Cys Pro Ser Thr His Val Leu Leu Thr His Thr Ile Ser Arg Ile Ala
                645                 650                 655
Val Ser Tyr Gln Thr Lys Val Asn Leu Leu Ser Ala Ile Lys Ser Pro
                660                 665                 670
Cys Gln Arg Glu Thr Pro Glu Gly Ala Glu Ala Lys Pro Trp Tyr Glu
                675                 680                 685
Pro Ile Tyr Leu Gly Gly Val Phe Gln Leu Glu Lys Gly Asp Arg Leu
                690                 695                 700
Ser Ala Glu Ile Asn Arg Pro Asp Tyr Leu Asp Phe Ala Glu Ser Gly
705                 710                 715                 720
Gln Val Tyr Phe Gly Ile Ile Ala Leu Gly Gly Gly Ser Ser Ser
                725                 730                 735
Arg Thr Pro Ser Asp Lys Pro Val Ala His Val Val Ala Asn Pro Gln
                740                 745                 750
Ala Glu Gly Gln Leu Gln Trp Leu Asn Arg Arg Ala Asn Ala Leu Leu
                755                 760                 765
Ala Asn Gly Val Glu Leu Arg Asp Asn Gln Leu Val Val Pro Ser Glu
770                 775                 780
Gly Leu Tyr Leu Ile Tyr Ser Gln Val Leu Phe Lys Gly Gln Gly Cys
785                 790                 795                 800
Pro Ser Thr His Val Leu Leu Thr His Thr Ile Ser Arg Ile Ala Val
                805                 810                 815
Ser Tyr Gln Thr Lys Val Asn Leu Leu Ser Ala Ile Lys Ser Pro Cys
                820                 825                 830
Gln Arg Glu Thr Pro Glu Gly Ala Glu Ala Lys Pro Trp Tyr Glu Pro
                835                 840                 845
Ile Tyr Leu Gly Gly Val Phe Gln Leu Glu Lys Gly Asp Arg Leu Ser
                850                 855                 860
Ala Glu Ile Asn Arg Pro Asp Tyr Leu Asp Phe Ala Glu Ser Gly Gln
865                 870                 875                 880
Val Tyr Phe Gly Ile Ile Ala Leu
                885

<210> SEQ ID NO 12
<211> LENGTH: 724
<212> TYPE: PRT
<213> ORGANISM: Artificial Sequence
<220> FEATURE:
<223> OTHER INFORMATION: MHD2-scTRAIL
```

```
<400> SEQUENCE: 12

Met Asp Trp Thr Trp Arg Val Phe Cys Leu Leu Ala Val Ala Pro Gly
1               5                   10                  15

Ala His Ser Leu Asp Asp Tyr Lys Asp Asp Asp Lys Glu Phe Ala
            20                  25                  30

Glu Leu Pro Pro Lys Val Ser Phe Val Pro Arg Asp Gly Phe
        35                  40                  45

Phe Gly Asn Pro Arg Lys Ser Lys Leu Ile Cys Gln Ala Thr Gly Phe
50                  55                  60

Ser Pro Arg Gln Ile Gln Val Ser Trp Leu Arg Glu Gly Lys Gln Val
65                  70                  75                  80

Gly Ser Gly Val Thr Thr Asp Gln Val Gln Ala Glu Ala Lys Glu Ser
                85                  90                  95

Gly Pro Thr Thr Tyr Lys Val Ser Thr Leu Thr Ile Lys Glu Ser
                100                 105                 110

Asp Trp Leu Gly Gln Ser Met Phe Thr Cys Arg Val Asp His Arg Gly
            115                 120                 125

Leu Thr Phe Gln Gln Asn Ala Ser Ser Met Cys Val Pro Asp Glu Phe
130                 135                 140

Thr Arg Gly Thr Ser Glu Glu Thr Ile Ser Thr Val Gln Glu Lys Gln
145                 150                 155                 160

Gln Asn Ile Ser Pro Leu Val Arg Glu Arg Gly Pro Gln Arg Val Ala
                165                 170                 175

Ala His Ile Thr Gly Thr Arg Gly Arg Ser Asn Thr Leu Ser Ser Pro
            180                 185                 190

Asn Ser Lys Asn Glu Lys Ala Leu Gly Arg Lys Ile Asn Ser Trp Glu
            195                 200                 205

Ser Ser Arg Ser Gly His Ser Phe Leu Ser Asn Leu His Leu Arg Asn
210                 215                 220

Gly Glu Leu Val Ile His Glu Lys Gly Phe Tyr Tyr Ile Tyr Ser Gln
225                 230                 235                 240

Thr Tyr Phe Arg Phe Gln Glu Glu Ile Lys Glu Asn Thr Lys Asn Asp
                245                 250                 255

Lys Gln Met Val Gln Tyr Ile Tyr Lys Tyr Thr Ser Tyr Pro Asp Pro
                260                 265                 270

Ile Leu Leu Met Lys Ser Ala Arg Asn Ser Cys Trp Ser Lys Asp Ala
            275                 280                 285

Glu Tyr Gly Leu Tyr Ser Ile Tyr Gln Gly Gly Ile Phe Glu Leu Lys
290                 295                 300

Glu Asn Asp Arg Ile Phe Val Ser Val Thr Asn Glu His Leu Ile Asp
305                 310                 315                 320

Met Asp His Glu Ala Ser Phe Phe Gly Ala Phe Leu Val Gly Gly Gly
                325                 330                 335

Gly Ser Gly Gly Gly Ser Thr Ser Glu Glu Thr Ile Ser Thr Val Gln
                340                 345                 350

Glu Lys Gln Gln Asn Ile Ser Pro Leu Val Arg Glu Arg Gly Pro Gln
            355                 360                 365

Arg Val Ala Ala His Ile Thr Gly Thr Arg Gly Arg Ser Asn Thr Leu
370                 375                 380

Ser Ser Pro Asn Ser Lys Asn Glu Lys Ala Leu Gly Arg Lys Ile Asn
385                 390                 395                 400

Ser Trp Glu Ser Ser Arg Ser Gly His Ser Phe Leu Ser Asn Leu His
                405                 410                 415
```

Leu Arg Asn Gly Glu Leu Val Ile His Glu Lys Gly Phe Tyr Tyr Ile
            420                 425                 430

Tyr Ser Gln Thr Tyr Phe Arg Phe Gln Glu Glu Ile Lys Glu Asn Thr
            435                 440                 445

Lys Asn Asp Lys Gln Met Val Gln Tyr Ile Tyr Lys Tyr Thr Ser Tyr
450                 455                 460

Pro Asp Pro Ile Leu Leu Met Lys Ser Ala Arg Asn Ser Cys Trp Ser
465                 470                 475                 480

Lys Asp Ala Glu Tyr Gly Leu Tyr Ser Ile Tyr Gln Gly Gly Ile Phe
                485                 490                 495

Glu Leu Lys Glu Asn Asp Arg Ile Phe Val Ser Val Thr Asn Glu His
            500                 505                 510

Leu Ile Asp Met Asp His Glu Ala Ser Phe Phe Gly Ala Phe Leu Val
        515                 520                 525

Gly Gly Gly Gly Ser Gly Gly Ser Thr Ser Glu Glu Thr Ile Ser
530                 535                 540

Thr Val Gln Glu Lys Gln Gln Asn Ile Ser Pro Leu Val Arg Glu Arg
545                 550                 555                 560

Gly Pro Gln Arg Val Ala Ala His Ile Thr Gly Thr Arg Gly Arg Ser
                565                 570                 575

Asn Thr Leu Ser Ser Pro Asn Ser Lys Asn Glu Lys Ala Leu Gly Arg
            580                 585                 590

Lys Ile Asn Ser Trp Glu Ser Ser Arg Ser Gly His Ser Phe Leu Ser
        595                 600                 605

Asn Leu His Leu Arg Asn Gly Glu Leu Val Ile His Glu Lys Gly Phe
    610                 615                 620

Tyr Tyr Ile Tyr Ser Gln Thr Tyr Phe Arg Phe Gln Glu Glu Ile Lys
625                 630                 635                 640

Glu Asn Thr Lys Asn Asp Lys Gln Met Val Gln Tyr Ile Tyr Lys Tyr
                645                 650                 655

Thr Ser Tyr Pro Asp Pro Ile Leu Leu Met Lys Ser Ala Arg Asn Ser
            660                 665                 670

Cys Trp Ser Lys Asp Ala Glu Tyr Gly Leu Tyr Ser Ile Tyr Gln Gly
        675                 680                 685

Gly Ile Phe Glu Leu Lys Glu Asn Asp Arg Ile Phe Val Ser Val Thr
    690                 695                 700

Asn Glu His Leu Ile Asp Met Asp His Glu Ala Ser Phe Phe Gly Ala
705                 710                 715                 720

Phe Leu Val Gly

<210> SEQ ID NO 13
<211> LENGTH: 978
<212> TYPE: PRT
<213> ORGANISM: Artificial Sequence
<220> FEATURE:
<223> OTHER INFORMATION: scFvEGFR-MHD2-scTRAIL

<400> SEQUENCE: 13

Met Glu Thr Asp Thr Leu Leu Leu Trp Val Leu Leu Leu Trp Val Pro
1               5                   10                  15

Gly Ser Thr Gly Asp Tyr Lys Asp Asp Asp Lys Gly Gly Gly Gly
                20                  25                  30

Ser Ala Ala Gln Pro Ala Met Ala Glu Val Gln Leu Val Glu Ser Gly
        35                  40                  45

-continued

Gly Gly Leu Val Gln Pro Gly Gly Ser Leu Arg Leu Ser Cys Ala Ala
 50              55                  60

Ser Gly Phe Ser Leu Thr Asn Tyr Gly Val His Trp Val Arg Gln Ala
 65              70                  75                  80

Pro Gly Lys Gly Leu Glu Trp Leu Gly Val Ile Trp Ser Gly Gly Asn
             85                  90                  95

Thr Asp Tyr Asn Thr Pro Phe Thr Ser Arg Phe Thr Ile Ser Arg Asp
            100                 105                 110

Asn Ser Lys Asn Thr Leu Tyr Leu Gln Met Asn Ser Leu Arg Ala Glu
            115                 120                 125

Asp Thr Ala Val Tyr Tyr Cys Ala Arg Ala Leu Thr Tyr Tyr Asp Tyr
130                 135                 140

Glu Phe Ala Tyr Trp Gly Gln Gly Thr Thr Val Thr Val Ser Ser Gly
145                 150                 155                 160

Gly Gly Gly Ser Gly Gly Gly Ser Gly Gly Gly Ser Asp Ile
            165                 170                 175

Gln Leu Thr Gln Ser Pro Ser Phe Leu Ser Ala Ser Val Gly Asp Arg
            180                 185                 190

Val Thr Ile Thr Cys Arg Ala Ser Gln Ser Ile Gly Thr Asn Ile His
            195                 200                 205

Trp Tyr Gln Gln Lys Pro Gly Lys Ala Pro Lys Leu Leu Ile Lys Tyr
210                 215                 220

Ala Ser Glu Ser Ile Ser Gly Val Pro Ser Arg Phe Ser Gly Ser Gly
225                 230                 235                 240

Ser Gly Thr Glu Phe Thr Leu Thr Ile Ser Ser Leu Gln Pro Glu Asp
            245                 250                 255

Phe Ala Thr Tyr Tyr Cys Gln Gln Asn Asn Asn Trp Pro Thr Thr Phe
            260                 265                 270

Gly Ala Gly Thr Lys Leu Glu Ile Lys Arg Ala Ala Ala Glu Leu
            275                 280                 285

Pro Pro Lys Val Ser Val Phe Val Pro Pro Arg Asp Gly Phe Phe Gly
290                 295                 300

Asn Pro Arg Lys Ser Lys Leu Ile Cys Gln Ala Thr Gly Phe Ser Pro
305                 310                 315                 320

Arg Gln Ile Gln Val Ser Trp Leu Arg Glu Gly Lys Gln Val Gly Ser
            325                 330                 335

Gly Val Thr Thr Asp Gln Val Gln Ala Glu Ala Lys Glu Ser Gly Pro
            340                 345                 350

Thr Thr Tyr Lys Val Thr Ser Thr Leu Thr Ile Lys Glu Ser Asp Trp
            355                 360                 365

Leu Gly Gln Ser Met Phe Thr Cys Arg Val Asp His Arg Gly Leu Thr
370                 375                 380

Phe Gln Gln Asn Ala Ser Ser Met Cys Val Pro Asp Glu Phe Thr Arg
385                 390                 395                 400

Gly Thr Ser Glu Glu Thr Ile Ser Thr Val Gln Glu Lys Gln Gln Asn
            405                 410                 415

Ile Ser Pro Leu Val Arg Glu Arg Gly Pro Gln Arg Val Ala Ala His
            420                 425                 430

Ile Thr Gly Thr Arg Gly Arg Ser Asn Thr Leu Ser Ser Pro Asn Ser
            435                 440                 445

Lys Asn Glu Lys Ala Leu Gly Arg Lys Ile Asn Ser Trp Glu Ser Ser
450                 455                 460

Arg Ser Gly His Ser Phe Leu Ser Asn Leu His Leu Arg Asn Gly Glu

```
            465                 470                 475                 480
Leu Val Ile His Glu Lys Gly Phe Tyr Ile Tyr Ser Gln Thr Tyr
                    485                 490                 495

Phe Arg Phe Gln Glu Glu Ile Lys Glu Asn Thr Lys Asn Asp Lys Gln
                500                 505                 510

Met Val Gln Tyr Ile Tyr Lys Tyr Thr Ser Tyr Pro Asp Pro Ile Leu
                515                 520                 525

Leu Met Lys Ser Ala Arg Asn Ser Cys Trp Ser Lys Asp Ala Glu Tyr
            530                 535                 540

Gly Leu Tyr Ser Ile Tyr Gln Gly Gly Ile Phe Glu Leu Lys Glu Asn
545                 550                 555                 560

Asp Arg Ile Phe Val Ser Val Thr Asn Glu His Leu Ile Asp Met Asp
                    565                 570                 575

His Glu Ala Ser Phe Phe Gly Ala Phe Leu Val Gly Gly Gly Ser
                580                 585                 590

Gly Gly Gly Ser Thr Ser Glu Glu Thr Ile Ser Thr Val Gln Glu Lys
            595                 600                 605

Gln Gln Asn Ile Ser Pro Leu Val Arg Glu Arg Gly Pro Gln Arg Val
610                 615                 620

Ala Ala His Ile Thr Gly Thr Arg Gly Arg Ser Asn Thr Leu Ser Ser
625                 630                 635                 640

Pro Asn Ser Lys Asn Glu Lys Ala Leu Gly Arg Lys Ile Asn Ser Trp
                    645                 650                 655

Glu Ser Ser Arg Ser Gly His Ser Phe Leu Ser Asn Leu His Leu Arg
                660                 665                 670

Asn Gly Glu Leu Val Ile His Glu Lys Gly Phe Tyr Ile Tyr Ser
            675                 680                 685

Gln Thr Tyr Phe Arg Phe Gln Glu Glu Ile Lys Glu Asn Thr Lys Asn
            690                 695                 700

Asp Lys Gln Met Val Gln Tyr Ile Tyr Lys Tyr Thr Ser Tyr Pro Asp
705                 710                 715                 720

Pro Ile Leu Leu Met Lys Ser Ala Arg Asn Ser Cys Trp Ser Lys Asp
                    725                 730                 735

Ala Glu Tyr Gly Leu Tyr Ser Ile Tyr Gln Gly Gly Ile Phe Glu Leu
                740                 745                 750

Lys Glu Asn Asp Arg Ile Phe Val Ser Val Thr Asn Glu His Leu Ile
            755                 760                 765

Asp Met Asp His Glu Ala Ser Phe Phe Gly Ala Phe Leu Val Gly Gly
770                 775                 780

Gly Ser Gly Gly Gly Ser Thr Ser Glu Glu Thr Ile Ser Thr Val
785                 790                 795                 800

Gln Glu Lys Gln Gln Asn Ile Ser Pro Leu Val Arg Glu Arg Gly Pro
                    805                 810                 815

Gln Arg Val Ala Ala His Ile Thr Gly Thr Arg Gly Arg Ser Asn Thr
                820                 825                 830

Leu Ser Ser Pro Asn Ser Lys Asn Glu Lys Ala Leu Gly Arg Lys Ile
            835                 840                 845

Asn Ser Trp Glu Ser Ser Arg Ser Gly His Ser Phe Leu Ser Asn Leu
850                 855                 860

His Leu Arg Asn Gly Glu Leu Val Ile His Glu Lys Gly Phe Tyr Tyr
865                 870                 875                 880

Ile Tyr Ser Gln Thr Tyr Phe Arg Phe Gln Glu Glu Ile Lys Glu Asn
                    885                 890                 895
```

```
Thr Lys Asn Asp Lys Gln Met Val Gln Tyr Ile Tyr Lys Tyr Thr Ser
            900                 905                 910

Tyr Pro Asp Pro Ile Leu Leu Met Lys Ser Ala Arg Asn Ser Cys Trp
            915                 920                 925

Ser Lys Asp Ala Glu Tyr Gly Leu Tyr Ser Ile Tyr Gln Gly Gly Ile
            930                 935                 940

Phe Glu Leu Lys Glu Asn Asp Arg Ile Phe Val Ser Val Thr Asn Glu
945                 950                 955                 960

His Leu Ile Asp Met Asp His Glu Ala Ser Phe Phe Gly Ala Phe Leu
                965                 970                 975

Val Gly

<210> SEQ ID NO 14
<211> LENGTH: 1217
<212> TYPE: PRT
<213> ORGANISM: Artificial Sequence
<220> FEATURE:
<223> OTHER INFORMATION: scDbEpCAMxEGFR-MHD2-scTRAIL

<400> SEQUENCE: 14

Met Glu Thr Asp Thr Leu Leu Leu Trp Val Leu Leu Leu Trp Val Pro
1               5                   10                  15

Gly Ser Thr Gly Asp Tyr Lys Asp Asp Asp Lys Gly Gly Gly Gly Gly
            20                  25                  30

Ser Ala Ala Gln Pro Ala Met Ala Glu Val Gln Leu Val Gln Ser Gly
        35                  40                  45

Pro Gly Leu Val Gln Pro Gly Gly Ser Val Arg Ile Ser Cys Ala Ala
50                  55                  60

Ser Gly Tyr Thr Phe Thr Asn Tyr Gly Met Asn Trp Val Lys Gln Ala
65                  70                  75                  80

Pro Gly Lys Gly Leu Glu Trp Met Gly Trp Ile Asn Thr Tyr Thr Gly
                85                  90                  95

Glu Ser Thr Tyr Ala Asp Ser Phe Lys Gly Arg Phe Thr Phe Ser Leu
            100                 105                 110

Asp Thr Ser Ala Ser Ala Ala Tyr Leu Gln Ile Asn Ser Leu Arg Ala
        115                 120                 125

Glu Asp Thr Ala Val Tyr Tyr Cys Ala Arg Phe Ala Ile Lys Gly Asp
    130                 135                 140

Tyr Trp Gly Gln Gly Thr Leu Leu Thr Val Ser Ser Gly Gly Gly Gly
145                 150                 155                 160

Ser Asp Ile Gln Leu Thr Gln Ser Pro Ser Phe Leu Ser Ala Ser Val
                165                 170                 175

Gly Asp Arg Val Thr Ile Thr Cys Arg Ala Ser Gln Ser Ile Gly Thr
            180                 185                 190

Asn Ile His Trp Tyr Gln Gln Lys Pro Gly Lys Ala Pro Lys Leu Leu
        195                 200                 205

Ile Lys Tyr Ala Ser Glu Ser Ile Ser Gly Val Pro Ser Arg Phe Ser
    210                 215                 220

Gly Ser Gly Ser Gly Thr Glu Phe Thr Leu Thr Ile Ser Ser Leu Gln
225                 230                 235                 240

Pro Glu Asp Phe Ala Thr Tyr Tyr Cys Gln Gln Asn Asn Asn Trp Pro
                245                 250                 255

Thr Thr Phe Gly Ala Gly Thr Lys Leu Glu Ile Lys Arg Gly Gly Gly
            260                 265                 270
```

-continued

Gly Ser Gly Gly Arg Ala Ser Gly Gly Gly Ser Glu Val Gln Leu
          275                 280                 285

Val Glu Ser Gly Gly Gly Leu Val Gln Pro Gly Gly Ser Leu Arg Leu
    290                 295                 300

Ser Cys Ala Ala Ser Gly Phe Ser Leu Thr Asn Tyr Gly Val His Trp
305                 310                 315                 320

Val Arg Gln Ala Pro Gly Lys Gly Leu Glu Trp Leu Gly Val Ile Trp
                325                 330                 335

Ser Gly Gly Asn Thr Asp Tyr Asn Pro Phe Thr Ser Arg Phe Thr
            340                 345                 350

Ile Ser Arg Asp Asn Ser Lys Asn Thr Leu Tyr Leu Gln Met Asn Ser
    355                 360                 365

Leu Arg Ala Glu Asp Thr Ala Val Tyr Tyr Cys Ala Arg Ala Leu Thr
    370                 375                 380

Tyr Tyr Asp Tyr Glu Phe Ala Tyr Trp Gly Gln Gly Thr Thr Val Thr
385                 390                 395                 400

Val Ser Ser Gly Gly Gly Gly Ser Asp Ile Gln Met Thr Gln Ser Pro
                405                 410                 415

Ser Ser Leu Ser Ala Ser Val Gly Asp Arg Val Thr Ile Thr Cys Arg
            420                 425                 430

Ser Thr Lys Ser Leu Leu His Ser Asn Gly Ile Thr Tyr Leu Tyr Trp
    435                 440                 445

Tyr Gln Gln Lys Pro Gly Lys Ala Pro Lys Leu Leu Ile Tyr Gln Met
    450                 455                 460

Ser Asn Leu Ala Ser Gly Val Pro Ser Arg Phe Ser Ser Gly Ser
465                 470                 475                 480

Gly Thr Asp Phe Thr Leu Thr Ile Ser Ser Leu Gln Pro Glu Asp Phe
                485                 490                 495

Ala Thr Tyr Tyr Cys Ala Gln Asn Leu Glu Ile Pro Arg Thr Phe Gly
            500                 505                 510

Gln Gly Thr Lys Val Glu Leu Lys Arg Ala Ala Ala Glu Leu Pro
    515                 520                 525

Pro Lys Val Ser Val Phe Val Pro Pro Arg Asp Gly Phe Phe Gly Asn
530                 535                 540

Pro Arg Lys Ser Lys Leu Ile Cys Gln Ala Thr Gly Phe Ser Pro Arg
545                 550                 555                 560

Gln Ile Gln Val Ser Trp Leu Arg Glu Gly Lys Gln Val Gly Ser Gly
                565                 570                 575

Val Thr Thr Asp Gln Val Gln Ala Glu Ala Lys Glu Ser Gly Pro Thr
            580                 585                 590

Thr Tyr Lys Val Thr Ser Thr Leu Thr Ile Lys Glu Ser Asp Trp Leu
    595                 600                 605

Gly Gln Ser Met Phe Thr Cys Arg Val Asp His Arg Gly Leu Thr Phe
    610                 615                 620

Gln Gln Asn Ala Ser Ser Met Cys Val Pro Asp Glu Phe Thr Arg Gly
625                 630                 635                 640

Thr Ser Glu Glu Thr Ile Ser Thr Val Gln Glu Lys Gln Gln Asn Ile
                645                 650                 655

Ser Pro Leu Val Arg Glu Arg Gly Pro Gln Arg Val Ala Ala His Ile
            660                 665                 670

Thr Gly Thr Arg Gly Arg Ser Asn Thr Leu Ser Ser Pro Asn Ser Lys
    675                 680                 685

Asn Glu Lys Ala Leu Gly Arg Lys Ile Asn Ser Trp Glu Ser Ser Arg

-continued

```
            690             695             700
Ser Gly His Ser Phe Leu Ser Asn Leu His Leu Arg Asn Gly Glu Leu
705                 710             715                 720

Val Ile His Glu Lys Gly Phe Tyr Tyr Ile Tyr Ser Gln Thr Tyr Phe
                725             730             735

Arg Phe Gln Glu Glu Ile Lys Glu Asn Thr Lys Asn Asp Lys Gln Met
            740             745             750

Val Gln Tyr Ile Tyr Lys Tyr Thr Ser Tyr Pro Asp Pro Ile Leu Leu
            755             760             765

Met Lys Ser Ala Arg Asn Ser Cys Trp Ser Lys Asp Ala Glu Tyr Gly
            770             775             780

Leu Tyr Ser Ile Tyr Gln Gly Gly Ile Phe Glu Leu Lys Glu Asn Asp
785                 790             795                 800

Arg Ile Phe Val Ser Val Thr Asn Glu His Leu Ile Asp Met Asp His
                805             810             815

Glu Ala Ser Phe Phe Gly Ala Phe Leu Val Gly Gly Gly Ser Gly
            820             825             830

Gly Gly Ser Thr Ser Glu Glu Thr Ile Ser Thr Val Gln Glu Lys Gln
            835             840             845

Gln Asn Ile Ser Pro Leu Val Arg Glu Arg Gly Pro Gln Arg Val Ala
850                 855             860

Ala His Ile Thr Gly Thr Arg Gly Arg Ser Asn Thr Leu Ser Ser Pro
865                 870             875             880

Asn Ser Lys Asn Glu Lys Ala Leu Gly Arg Lys Ile Asn Ser Trp Glu
                885             890             895

Ser Ser Arg Ser Gly His Ser Phe Leu Ser Asn Leu His Leu Arg Asn
                900             905             910

Gly Glu Leu Val Ile His Glu Lys Gly Phe Tyr Tyr Ile Tyr Ser Gln
                915             920             925

Thr Tyr Phe Arg Phe Gln Glu Glu Ile Lys Glu Asn Thr Lys Asn Asp
            930             935             940

Lys Gln Met Val Gln Tyr Ile Tyr Lys Tyr Thr Ser Tyr Pro Asp Pro
945                 950             955             960

Ile Leu Leu Met Lys Ser Ala Arg Asn Ser Cys Trp Ser Lys Asp Ala
                965             970             975

Glu Tyr Gly Leu Tyr Ser Ile Tyr Gln Gly Gly Ile Phe Glu Leu Lys
            980             985             990

Glu Asn Asp Arg Ile Phe Val Ser  Val Thr Asn Glu His  Leu Ile Asp
            995             1000            1005

Met Asp  His Glu Ala Ser Phe  Phe Gly Ala Phe Leu  Val Gly Gly
    1010            1015            1020

Gly Gly  Ser Gly Gly Gly Ser  Thr Ser Glu Glu Thr  Ile Ser Thr
    1025            1030            1035

Val Gln  Glu Lys Gln Gln Asn  Ile Ser Pro Leu Val  Arg Glu Arg
    1040            1045            1050

Gly Pro  Gln Arg Val Ala Ala  His Ile Thr Gly Thr  Arg Gly Arg
    1055            1060            1065

Ser Asn  Thr Leu Ser Ser Pro  Asn Ser Lys Asn Glu  Lys Ala Leu
    1070            1075            1080

Gly Arg  Lys Ile Asn Ser Trp  Glu Ser Ser Arg Ser  Gly His Ser
    1085            1090            1095

Phe Leu  Ser Asn Leu His Leu  Arg Asn Gly Glu Leu  Val Ile His
    1100            1105            1110
```

Glu Lys Gly Phe Tyr Tyr Ile Tyr Ser Gln Thr Tyr Phe Arg Phe
    1115                1120                1125

Gln Glu Glu Ile Lys Glu Asn Thr Lys Asn Asp Lys Gln Met Val
    1130                1135                1140

Gln Tyr Ile Tyr Lys Tyr Thr Ser Tyr Pro Asp Pro Ile Leu Leu
    1145                1150                1155

Met Lys Ser Ala Arg Asn Ser Cys Trp Ser Lys Asp Ala Glu Tyr
    1160                1165                1170

Gly Leu Tyr Ser Ile Tyr Gln Gly Gly Ile Phe Glu Leu Lys Glu
    1175                1180                1185

Asn Asp Arg Ile Phe Val Ser Val Thr Asn Glu His Leu Ile Asp
    1190                1195                1200

Met Asp His Glu Ala Ser Phe Phe Gly Ala Phe Leu Val Gly
    1205                1210                1215

<210> SEQ ID NO 15
<211> LENGTH: 405
<212> TYPE: PRT
<213> ORGANISM: Artificial Sequence
<220> FEATURE:
<223> OTHER INFORMATION: scFvEGFR-EHD2

<400> SEQUENCE: 15

Met Glu Thr Asp Thr Leu Leu Leu Trp Val Leu Leu Leu Trp Val Pro
1               5                   10                  15

Gly Ser Thr Gly Asp Ala Ala Gln Pro Ala Met Ala Glu Val Gln Leu
            20                  25                  30

Val Glu Ser Gly Gly Gly Leu Val Gln Pro Gly Gly Ser Leu Arg Leu
        35                  40                  45

Ser Cys Ala Ala Ser Gly Phe Ser Leu Thr Asn Tyr Gly Val His Trp
    50                  55                  60

Val Arg Gln Ala Pro Gly Lys Gly Leu Glu Trp Leu Gly Val Ile Trp
65                  70                  75                  80

Ser Gly Gly Asn Thr Asp Tyr Asn Thr Pro Phe Thr Ser Arg Phe Thr
                85                  90                  95

Ile Ser Arg Asp Asn Ser Lys Asn Thr Leu Tyr Leu Gln Met Asn Ser
            100                 105                 110

Leu Arg Ala Glu Asp Thr Ala Val Tyr Tyr Cys Ala Arg Ala Leu Thr
        115                 120                 125

Tyr Tyr Asp Tyr Glu Phe Ala Tyr Trp Gly Gln Gly Thr Thr Val Thr
    130                 135                 140

Val Ser Ser Gly Gly Gly Gly Ser Gly Gly Gly Gly Ser Gly Gly Gly
145                 150                 155                 160

Gly Ser Asp Ile Gln Leu Thr Gln Ser Pro Ser Phe Leu Ser Ala Ser
                165                 170                 175

Val Gly Asp Arg Val Thr Ile Thr Cys Arg Ala Ser Gln Ser Ile Gly
            180                 185                 190

Thr Asn Ile His Trp Tyr Gln Gln Lys Pro Gly Lys Ala Pro Lys Leu
        195                 200                 205

Leu Ile Lys Tyr Ala Ser Glu Ser Ile Ser Gly Val Pro Ser Arg Phe
    210                 215                 220

Ser Gly Ser Gly Ser Gly Thr Glu Phe Thr Leu Thr Ile Ser Ser Leu
225                 230                 235                 240

Gln Pro Glu Asp Phe Ala Thr Tyr Tyr Cys Gln Gln Asn Asn Asn Trp
                245                 250                 255

```
Pro Thr Thr Phe Gly Ala Gly Thr Lys Leu Glu Ile Lys Arg Gly Ser
            260                 265                 270

Leu Gly Gly Ser Gly Gly Asp Phe Thr Pro Thr Val Lys Ile Leu
        275                 280                 285

Gln Ser Ser Cys Asp Gly Gly His Phe Pro Pro Thr Ile Gln Leu
    290                 295                 300

Leu Cys Leu Val Ser Gly Tyr Thr Pro Gly Thr Ile Asn Ile Thr Trp
305                 310                 315                 320

Leu Glu Asp Gly Gln Val Met Asp Val Asp Leu Ser Thr Ala Ser Thr
                325                 330                 335

Thr Gln Glu Gly Glu Leu Ala Ser Thr Gln Ser Glu Leu Thr Leu Ser
            340                 345                 350

Gln Lys His Trp Leu Ser Asp Arg Thr Tyr Thr Cys Gln Val Thr Tyr
        355                 360                 365

Gln Gly His Thr Phe Glu Asp Ser Thr Lys Lys Cys Ala Asp Ser Asn
    370                 375                 380

Gly Gly Gly Ser Gly Gly Gly Thr Gly Ser Glu Phe Ala Ala Ala His
385                 390                 395                 400

His His His His His
            405

<210> SEQ ID NO 16
<211> LENGTH: 731
<212> TYPE: PRT
<213> ORGANISM: Artificial Sequence
<220> FEATURE:
<223> OTHER INFORMATION: EHD2-scTRAIL

<400> SEQUENCE: 16

Met Glu Thr Asp Thr Leu Leu Leu Trp Val Leu Leu Leu Trp Val Pro
1               5                   10                  15

Gly Ser Thr Gly Asp Tyr Lys Asp Asp Asp Asp Lys Gly Gly Gly Gly
                20                  25                  30

Ser Ala Ala Gln Pro Ala Asp Phe Thr Pro Thr Val Lys Ile Leu
            35                  40                  45

Gln Ser Ser Cys Asp Gly Gly His Phe Pro Pro Thr Ile Gln Leu
    50                  55                  60

Leu Cys Leu Val Ser Gly Tyr Thr Pro Gly Thr Ile Asn Ile Thr Trp
65                  70                  75                  80

Leu Glu Asp Gly Gln Val Met Asp Val Asp Leu Ser Thr Ala Ser Thr
                85                  90                  95

Thr Gln Glu Gly Glu Leu Ala Ser Thr Gln Ser Glu Leu Thr Leu Ser
            100                 105                 110

Gln Lys His Trp Leu Ser Asp Arg Thr Tyr Thr Cys Gln Val Thr Tyr
        115                 120                 125

Gln Gly His Thr Phe Glu Asp Ser Thr Lys Lys Cys Ala Asp Ser Asn
    130                 135                 140

Gly Gly Ser Gly Gly Glu Phe Thr Arg Gly Thr Ser Glu Glu Thr Ile
145                 150                 155                 160

Ser Thr Val Gln Glu Lys Gln Gln Asn Ile Ser Pro Leu Val Arg Glu
                165                 170                 175

Arg Gly Pro Gln Arg Val Ala Ala His Ile Thr Gly Thr Arg Gly Arg
            180                 185                 190

Ser Asn Thr Leu Ser Ser Pro Asn Ser Lys Asn Glu Lys Ala Leu Gly
        195                 200                 205
```

```
Arg Lys Ile Asn Ser Trp Glu Ser Ser Arg Ser Gly His Ser Phe Leu
    210                 215                 220
Ser Asn Leu His Leu Arg Asn Gly Glu Leu Val Ile His Glu Lys Gly
225                 230                 235                 240
Phe Tyr Tyr Ile Tyr Ser Gln Thr Tyr Phe Arg Phe Gln Glu Glu Ile
                245                 250                 255
Lys Glu Asn Thr Lys Asn Asp Lys Gln Met Val Gln Tyr Ile Tyr Lys
            260                 265                 270
Tyr Thr Ser Tyr Pro Asp Pro Ile Leu Leu Met Lys Ser Ala Arg Asn
        275                 280                 285
Ser Cys Trp Ser Lys Asp Ala Glu Tyr Gly Leu Tyr Ser Ile Tyr Gln
    290                 295                 300
Gly Gly Ile Phe Glu Leu Lys Glu Asn Asp Arg Ile Phe Val Ser Val
305                 310                 315                 320
Thr Asn Glu His Leu Ile Asp Met Asp His Glu Ala Ser Phe Phe Gly
                325                 330                 335
Ala Phe Leu Val Gly Gly Gly Ser Gly Gly Gly Ser Thr Ser Glu
            340                 345                 350
Glu Thr Ile Ser Thr Val Gln Glu Lys Gln Gln Asn Ile Ser Pro Leu
        355                 360                 365
Val Arg Glu Arg Gly Pro Gln Arg Val Ala Ala His Ile Thr Gly Thr
    370                 375                 380
Arg Gly Arg Ser Asn Thr Leu Ser Ser Pro Asn Ser Lys Asn Glu Lys
385                 390                 395                 400
Ala Leu Gly Arg Lys Ile Asn Ser Trp Glu Ser Ser Arg Ser Gly His
                405                 410                 415
Ser Phe Leu Ser Asn Leu His Leu Arg Asn Gly Glu Leu Val Ile His
            420                 425                 430
Glu Lys Gly Phe Tyr Tyr Ile Tyr Ser Gln Thr Tyr Phe Arg Phe Gln
        435                 440                 445
Glu Glu Ile Lys Glu Asn Thr Lys Asn Asp Lys Gln Met Val Gln Tyr
    450                 455                 460
Ile Tyr Lys Tyr Thr Ser Tyr Pro Asp Pro Ile Leu Leu Met Lys Ser
465                 470                 475                 480
Ala Arg Asn Ser Cys Trp Ser Lys Asp Ala Glu Tyr Gly Leu Tyr Ser
                485                 490                 495
Ile Tyr Gln Gly Gly Ile Phe Glu Leu Lys Glu Asn Asp Arg Ile Phe
            500                 505                 510
Val Ser Val Thr Asn Glu His Leu Ile Asp Met Asp His Glu Ala Ser
        515                 520                 525
Phe Phe Gly Ala Phe Leu Val Gly Gly Gly Ser Gly Gly Gly Ser
    530                 535                 540
Thr Ser Glu Glu Thr Ile Ser Thr Val Gln Glu Lys Gln Gln Asn Ile
545                 550                 555                 560
Ser Pro Leu Val Arg Glu Arg Gly Pro Gln Arg Val Ala Ala His Ile
                565                 570                 575
Thr Gly Thr Arg Gly Arg Ser Asn Thr Leu Ser Ser Pro Asn Ser Lys
            580                 585                 590
Asn Glu Lys Ala Leu Gly Arg Lys Ile Asn Ser Trp Glu Ser Ser Arg
        595                 600                 605
Ser Gly His Ser Phe Leu Ser Asn Leu His Leu Arg Asn Gly Glu Leu
    610                 615                 620
```

Val Ile His Glu Lys Gly Phe Tyr Tyr Ile Tyr Ser Gln Thr Tyr Phe
625                 630                 635                 640

Arg Phe Gln Glu Glu Ile Lys Glu Asn Thr Lys Asn Asp Lys Gln Met
        645                 650                 655

Val Gln Tyr Ile Tyr Lys Tyr Thr Ser Tyr Pro Asp Pro Ile Leu Leu
            660                 665                 670

Met Lys Ser Ala Arg Asn Ser Cys Trp Ser Lys Asp Ala Glu Tyr Gly
            675                 680                 685

Leu Tyr Ser Ile Tyr Gln Gly Gly Ile Phe Glu Leu Lys Glu Asn Asp
        690                 695                 700

Arg Ile Phe Val Ser Val Thr Asn Glu His Leu Ile Asp Met Asp His
705                 710                 715                 720

Glu Ala Ser Phe Phe Gly Ala Phe Leu Val Gly
                725                 730

<210> SEQ ID NO 17
<211> LENGTH: 983
<212> TYPE: PRT
<213> ORGANISM: Artificial Sequence
<220> FEATURE:
<223> OTHER INFORMATION: scFvEGFR-EHD2-scTRAIL

<400> SEQUENCE: 17

Met Glu Thr Asp Thr Leu Leu Leu Trp Val Leu Leu Leu Trp Val Pro
1               5                   10                  15

Gly Ser Thr Gly Asp Tyr Lys Asp Asp Asp Lys Gly Gly Gly Gly Gly
                20                  25                  30

Ser Ala Ala Gln Pro Ala Met Ala Glu Val Gln Leu Val Glu Ser Gly
            35                  40                  45

Gly Gly Leu Val Gln Pro Gly Gly Ser Leu Arg Leu Ser Cys Ala Ala
        50                  55                  60

Ser Gly Phe Ser Leu Thr Asn Tyr Gly Val His Trp Val Arg Gln Ala
65                  70                  75                  80

Pro Gly Lys Gly Leu Glu Trp Leu Gly Val Ile Trp Ser Gly Gly Asn
                85                  90                  95

Thr Asp Tyr Asn Thr Pro Phe Thr Ser Arg Phe Thr Ile Ser Arg Asp
            100                 105                 110

Asn Ser Lys Asn Thr Leu Tyr Leu Gln Met Asn Ser Leu Arg Ala Glu
        115                 120                 125

Asp Thr Ala Val Tyr Tyr Cys Ala Arg Ala Leu Thr Tyr Tyr Asp Tyr
    130                 135                 140

Glu Phe Ala Tyr Trp Gly Gln Gly Thr Thr Val Thr Val Ser Ser Gly
145                 150                 155                 160

Gly Gly Gly Ser Gly Gly Gly Ser Gly Gly Gly Ser Asp Ile
                165                 170                 175

Gln Leu Thr Gln Ser Pro Ser Phe Leu Ser Ala Ser Val Gly Asp Arg
            180                 185                 190

Val Thr Ile Thr Cys Arg Ala Ser Gln Ser Ile Gly Thr Asn Ile His
        195                 200                 205

Trp Tyr Gln Gln Lys Pro Gly Lys Ala Pro Lys Leu Leu Ile Lys Tyr
    210                 215                 220

Ala Ser Glu Ser Ile Ser Gly Val Pro Ser Arg Phe Ser Gly Ser Gly
225                 230                 235                 240

Ser Gly Thr Glu Phe Thr Leu Thr Ile Ser Ser Leu Gln Pro Glu Asp
                245                 250                 255

-continued

Phe Ala Thr Tyr Tyr Cys Gln Gln Asn Asn Asn Trp Pro Thr Thr Phe
                260                 265                 270

Gly Ala Gly Thr Lys Leu Glu Ile Lys Arg Ala Ala Gly Gly Ser
        275                 280                 285

Gly Gly Asp Phe Thr Pro Pro Thr Val Lys Ile Leu Gln Ser Ser Cys
        290                 295                 300

Asp Gly Gly Gly His Phe Pro Pro Thr Ile Gln Leu Leu Cys Leu Val
305                 310                 315                 320

Ser Gly Tyr Thr Pro Gly Thr Ile Asn Ile Thr Trp Leu Glu Asp Gly
                325                 330                 335

Gln Val Met Asp Val Asp Leu Ser Thr Ala Ser Thr Thr Gln Glu Gly
            340                 345                 350

Glu Leu Ala Ser Thr Gln Ser Glu Leu Thr Leu Ser Gln Lys His Trp
            355                 360                 365

Leu Ser Asp Arg Thr Tyr Thr Cys Gln Val Thr Tyr Gln Gly His Thr
            370                 375                 380

Phe Glu Asp Ser Thr Lys Lys Cys Ala Asp Ser Asn Gly Gly Ser Gly
385                 390                 395                 400

Gly Glu Phe Thr Arg Gly Thr Ser Glu Thr Ile Ser Thr Val Gln
                405                 410                 415

Glu Lys Gln Gln Asn Ile Ser Pro Leu Val Arg Glu Arg Gly Pro Gln
            420                 425                 430

Arg Val Ala Ala His Ile Thr Gly Thr Arg Gly Arg Ser Asn Thr Leu
            435                 440                 445

Ser Ser Pro Asn Ser Lys Asn Glu Lys Ala Leu Gly Arg Lys Ile Asn
450                 455                 460

Ser Trp Glu Ser Ser Arg Ser Gly His Ser Phe Leu Ser Asn Leu His
465                 470                 475                 480

Leu Arg Asn Gly Glu Leu Val Ile His Glu Lys Gly Phe Tyr Tyr Ile
                485                 490                 495

Tyr Ser Gln Thr Tyr Phe Arg Phe Gln Glu Glu Ile Lys Glu Asn Thr
            500                 505                 510

Lys Asn Asp Lys Gln Met Val Gln Tyr Ile Tyr Lys Tyr Thr Ser Tyr
            515                 520                 525

Pro Asp Pro Ile Leu Leu Met Lys Ser Ala Arg Asn Ser Cys Trp Ser
            530                 535                 540

Lys Asp Ala Glu Tyr Gly Leu Tyr Ser Ile Tyr Gln Gly Gly Ile Phe
545                 550                 555                 560

Glu Leu Lys Glu Asn Asp Arg Ile Phe Val Ser Val Thr Asn Glu His
                565                 570                 575

Leu Ile Asp Met Asp His Glu Ala Ser Phe Phe Gly Ala Phe Leu Val
            580                 585                 590

Gly Gly Gly Gly Ser Gly Gly Gly Ser Thr Ser Glu Glu Thr Ile Ser
            595                 600                 605

Thr Val Gln Glu Lys Gln Gln Asn Ile Ser Pro Leu Val Arg Glu Arg
            610                 615                 620

Gly Pro Gln Arg Val Ala Ala His Ile Thr Gly Thr Arg Gly Arg Ser
625                 630                 635                 640

Asn Thr Leu Ser Ser Pro Asn Ser Lys Asn Glu Lys Ala Leu Gly Arg
                645                 650                 655

Lys Ile Asn Ser Trp Glu Ser Ser Arg Ser Gly His Ser Phe Leu Ser
            660                 665                 670

Asn Leu His Leu Arg Asn Gly Glu Leu Val Ile His Glu Lys Gly Phe

-continued

```
                675                 680                 685
Tyr Tyr Ile Tyr Ser Gln Thr Tyr Phe Arg Phe Gln Glu Glu Ile Lys
            690                 695                 700

Glu Asn Thr Lys Asn Asp Lys Gln Met Val Gln Tyr Ile Tyr Lys Tyr
705                 710                 715                 720

Thr Ser Tyr Pro Asp Pro Ile Leu Leu Met Lys Ser Ala Arg Asn Ser
                725                 730                 735

Cys Trp Ser Lys Asp Ala Glu Tyr Gly Leu Tyr Ser Ile Tyr Gln Gly
            740                 745                 750

Gly Ile Phe Glu Leu Lys Glu Asn Asp Arg Ile Phe Val Ser Val Thr
        755                 760                 765

Asn Glu His Leu Ile Asp Met Asp His Glu Ala Ser Phe Phe Gly Ala
770                 775                 780

Phe Leu Val Gly Gly Gly Ser Gly Gly Gly Ser Thr Ser Glu Glu
785                 790                 795                 800

Thr Ile Ser Thr Val Gln Glu Lys Gln Gln Asn Ile Ser Pro Leu Val
                805                 810                 815

Arg Glu Arg Gly Pro Gln Arg Val Ala Ala His Ile Thr Gly Thr Arg
            820                 825                 830

Gly Arg Ser Asn Thr Leu Ser Ser Pro Asn Ser Lys Asn Glu Lys Ala
        835                 840                 845

Leu Gly Arg Lys Ile Asn Ser Trp Glu Ser Ser Arg Ser Gly His Ser
    850                 855                 860

Phe Leu Ser Asn Leu His Leu Arg Asn Gly Glu Leu Val Ile His Glu
865                 870                 875                 880

Lys Gly Phe Tyr Tyr Ile Tyr Ser Gln Thr Tyr Phe Arg Phe Gln Glu
                885                 890                 895

Glu Ile Lys Glu Asn Thr Lys Asn Asp Lys Gln Met Val Gln Tyr Ile
            900                 905                 910

Tyr Lys Tyr Thr Ser Tyr Pro Asp Pro Ile Leu Leu Met Lys Ser Ala
        915                 920                 925

Arg Asn Ser Cys Trp Ser Lys Asp Ala Glu Tyr Gly Leu Tyr Ser Ile
    930                 935                 940

Tyr Gln Gly Gly Ile Phe Glu Leu Lys Glu Asn Asp Arg Ile Phe Val
945                 950                 955                 960

Ser Val Thr Asn Glu His Leu Ile Asp Met Asp His Glu Ala Ser Phe
                965                 970                 975

Phe Gly Ala Phe Leu Val Gly
            980
```

<210> SEQ ID NO 18
<211> LENGTH: 5
<212> TYPE: PRT
<213> ORGANISM: Artificial Sequence
<220> FEATURE:
<223> OTHER INFORMATION: peptide linker 1

<400> SEQUENCE: 18

```
Gly Gly Gly Gly Ser
1               5
```

<210> SEQ ID NO 19
<211> LENGTH: 10
<212> TYPE: PRT
<213> ORGANISM: Artificial Sequence
<220> FEATURE:
<223> OTHER INFORMATION: peptide linker 2

<400> SEQUENCE: 19

Gly Gly Gly Gly Ser Gly Gly Gly Gly Ser
1               5                   10

<210> SEQ ID NO 20
<211> LENGTH: 15
<212> TYPE: PRT
<213> ORGANISM: Artificial Sequence
<220> FEATURE:
<223> OTHER INFORMATION: peptide linker 3

<400> SEQUENCE: 20

Gly Gly Gly Gly Ser Gly Gly Gly Gly Ser Gly Gly Gly Gly Ser
1               5                   10                  15

<210> SEQ ID NO 21
<211> LENGTH: 8
<212> TYPE: PRT
<213> ORGANISM: Artificial Sequence
<220> FEATURE:
<223> OTHER INFORMATION: peptide linker 4

<400> SEQUENCE: 21

Gly Ser Leu Gly Gly Ser Gly Gly
1               5

<210> SEQ ID NO 22
<211> LENGTH: 8
<212> TYPE: PRT
<213> ORGANISM: Artificial Sequence
<220> FEATURE:
<223> OTHER INFORMATION: peptide linker 5

<400> SEQUENCE: 22

Gly Gly Gly Ser Gly Gly Gly Thr
1               5

<210> SEQ ID NO 23
<211> LENGTH: 10
<212> TYPE: PRT
<213> ORGANISM: Artificial Sequence
<220> FEATURE:
<223> OTHER INFORMATION: peptide linker 6

<400> SEQUENCE: 23

Gly Gly Gly Ser Gly Gly Gly Thr Gly Ser
1               5                   10

<210> SEQ ID NO 24
<211> LENGTH: 12
<212> TYPE: PRT
<213> ORGANISM: Artificial Sequence
<220> FEATURE:
<223> OTHER INFORMATION: peptide linker 7

<400> SEQUENCE: 24

Gly Gly Gly Ser Gly Gly Gly Thr Gly Ser Gly Gly
1               5                   10

<210> SEQ ID NO 25
<211> LENGTH: 8
<212> TYPE: PRT
<213> ORGANISM: Artificial Sequence
<220> FEATURE:
<223> OTHER INFORMATION: peptide linker 8

```
<400> SEQUENCE: 25

Gly Gly Gly Ser Gly Gly Gly Ser
1               5

<210> SEQ ID NO 26
<211> LENGTH: 5
<212> TYPE: PRT
<213> ORGANISM: Artificial Sequence
<220> FEATURE:
<223> OTHER INFORMATION: peptide linker 9

<400> SEQUENCE: 26

Glu Phe Thr Arg Gly
1               5

<210> SEQ ID NO 27
<211> LENGTH: 3
<212> TYPE: PRT
<213> ORGANISM: Artificial Sequence
<220> FEATURE:
<223> OTHER INFORMATION: peptide linker 10

<400> SEQUENCE: 27

Ala Ala Ala
1

<210> SEQ ID NO 28
<211> LENGTH: 405
<212> TYPE: PRT
<213> ORGANISM: Artificial Sequence
<220> FEATURE:
<223> OTHER INFORMATION: Anti-CEA scFv-EHD2

<400> SEQUENCE: 28

Met Glu Thr Asp Thr Leu Leu Leu Trp Val Leu Leu Leu Trp Val Pro
1               5                   10                  15

Gly Ser Thr Gly Asp Ala Ala Gln Pro Ala Met Ala Gln Val Lys Leu
            20                  25                  30

Gln Gln Ser Gly Ala Glu Leu Val Arg Ser Gly Thr Ser Val Lys Leu
        35                  40                  45

Ser Cys Thr Ala Ser Gly Phe Asn Ile Lys Asp Ser Tyr Met His Trp
    50                  55                  60

Leu Arg Gln Gly Pro Glu Gln Gly Leu Glu Trp Ile Gly Trp Ile Asp
65                  70                  75                  80

Pro Glu Asn Gly Asp Thr Glu Tyr Ala Pro Lys Phe Gln Gly Lys Ala
                85                  90                  95

Thr Phe Thr Thr Asp Thr Ser Ser Asn Thr Ala Tyr Leu Gln Leu Ser
            100                 105                 110

Ser Leu Thr Ser Glu Asp Thr Ala Val Tyr Tyr Cys Asn Glu Gly Thr
        115                 120                 125

Pro Thr Gly Pro Tyr Tyr Phe Asp Tyr Trp Gly Gln Gly Thr Thr Val
    130                 135                 140

Thr Val Ser Ser Gly Gly Gly Ser Gly Gly Gly Ser Gly Gly
145                 150                 155                 160

Gly Gly Ser Asp Ile Glu Leu Thr Gln Ser Pro Ala Ile Met Ser Ala
                165                 170                 175

Ser Pro Gly Glu Lys Val Thr Ile Thr Cys Ser Ala Ser Ser Ser Val
            180                 185                 190

Ser Tyr Met His Trp Phe Gln Gln Lys Pro Gly Thr Ser Pro Lys Leu
        195                 200                 205
```

```
Trp Ile Tyr Ser Thr Ser Asn Leu Ala Ser Gly Val Pro Ala Arg Phe
    210                 215                 220
Ser Gly Ser Gly Ser Gly Thr Ser Tyr Ser Leu Thr Ile Ser Arg Met
225                 230                 235                 240
Glu Ala Glu Asp Ala Ala Thr Tyr Tyr Cys Gln Gln Arg Ser Ser Tyr
                245                 250                 255
Pro Leu Thr Phe Gly Ala Gly Thr Lys Leu Glu Leu Lys Arg Gly Ser
            260                 265                 270
Leu Gly Gly Ser Gly Gly Asp Phe Thr Pro Thr Val Lys Ile Leu
        275                 280                 285
Gln Ser Ser Cys Asp Gly Gly His Phe Pro Pro Thr Ile Gln Leu
    290                 295                 300
Leu Cys Leu Val Ser Gly Tyr Thr Pro Gly Thr Ile Asn Ile Thr Trp
305                 310                 315                 320
Leu Glu Asp Gly Gln Val Met Asp Val Asp Leu Ser Thr Ala Ser Thr
                325                 330                 335
Thr Gln Glu Gly Glu Leu Ala Ser Thr Gln Ser Glu Leu Thr Leu Ser
            340                 345                 350
Gln Lys His Trp Leu Ser Asp Arg Thr Tyr Thr Cys Gln Val Thr Tyr
        355                 360                 365
Gln Gly His Thr Phe Glu Asp Ser Thr Lys Lys Cys Ala Asp Ser Asn
    370                 375                 380
Gly Gly Gly Ser Gly Gly Gly Thr Gly Ser Glu Phe Ala Ala Ala His
385                 390                 395                 400
His His His His His
            405

<210> SEQ ID NO 29
<211> LENGTH: 391
<212> TYPE: PRT
<213> ORGANISM: Artificial Sequence
<220> FEATURE:
<223> OTHER INFORMATION: Anti-HER2 scFv-EHD2

<400> SEQUENCE: 29

Met Glu Thr Asp Thr Leu Leu Leu Trp Val Leu Leu Leu Trp Val Pro
1               5                   10                  15
Gly Ser Thr Gly Glu Val Gln Leu Val Glu Ser Gly Gly Gly Leu Val
            20                  25                  30
Gln Pro Gly Gly Ser Leu Arg Leu Ser Cys Ala Ala Ser Gly Phe Asn
        35                  40                  45
Ile Lys Asp Thr Tyr Ile His Trp Val Arg Gln Ala Pro Gly Lys Gly
    50                  55                  60
Leu Glu Trp Val Ala Arg Ile Tyr Pro Thr Asn Gly Tyr Thr Arg Tyr
65                  70                  75                  80
Ala Asp Ser Val Lys Gly Arg Phe Thr Ile Ser Ala Asp Thr Ser Lys
                85                  90                  95
Asn Thr Ala Tyr Leu Gln Met Asn Ser Leu Arg Ala Glu Asp Thr Ala
            100                 105                 110
Val Tyr Tyr Cys Ser Arg Trp Gly Gly Asp Gly Phe Tyr Ala Met Asp
        115                 120                 125
Tyr Trp Gly Gln Gly Thr Leu Val Thr Val Ser Ser Gly Gly Gly Gly
    130                 135                 140
Ser Gly Gly Gly Gly Ser Gly Gly Gly Gly Ser Asp Ile Gln Met Thr
145                 150                 155                 160
```

-continued

```
Gln Ser Pro Ser Ser Leu Ser Ala Ser Val Gly Asp Arg Val Thr Ile
                165                 170                 175

Thr Cys Arg Ala Ser Gln Asp Val Asn Thr Ala Val Ala Trp Tyr Gln
            180                 185                 190

Gln Lys Pro Gly Lys Ala Pro Lys Leu Leu Ile Tyr Ser Ala Ser Phe
        195                 200                 205

Leu Tyr Ser Gly Val Pro Ser Arg Phe Ser Gly Ser Arg Ser Gly Thr
    210                 215                 220

Asp Phe Thr Leu Thr Ile Ser Ser Leu Gln Pro Glu Asp Phe Ala Thr
225                 230                 235                 240

Tyr Tyr Cys Gln Gln His Tyr Thr Thr Pro Pro Thr Phe Gly Gln Gly
                245                 250                 255

Thr Lys Val Glu Ile Lys Arg Ala Ala Ala Gly Gly Ser Gly Gly Asp
            260                 265                 270

Phe Thr Pro Pro Thr Val Lys Ile Leu Gln Ser Ser Cys Asp Gly Gly
        275                 280                 285

Gly His Phe Pro Pro Thr Ile Gln Leu Leu Cys Leu Val Ser Gly Tyr
    290                 295                 300

Thr Pro Gly Thr Ile Asn Ile Thr Trp Leu Glu Asp Gly Gln Val Met
305                 310                 315                 320

Asp Val Asp Leu Ser Thr Ala Ser Thr Thr Gln Glu Gly Glu Leu Ala
                325                 330                 335

Ser Thr Gln Ser Glu Leu Thr Leu Ser Gln Lys His Trp Leu Ser Asp
            340                 345                 350

Arg Thr Tyr Thr Cys Gln Val Thr Tyr Gln Gly His Thr Phe Glu Asp
        355                 360                 365

Ser Thr Lys Lys Cys Ala Asp Ser Asn Gly Gly Ser Gly Gly Ala Ser
    370                 375                 380

Ser His His His His His His
385                 390

<210> SEQ ID NO 30
<211> LENGTH: 393
<212> TYPE: PRT
<213> ORGANISM: Artificial Sequence
<220> FEATURE:
<223> OTHER INFORMATION: Anti-HER3 scFv-EHD2

<400> SEQUENCE: 30

Met Glu Thr Asp Thr Leu Leu Leu Trp Val Leu Leu Leu Trp Val Pro
1               5                   10                  15

Gly Ser Thr Gly Glu Val Gln Leu Leu Glu Ser Gly Gly Gly Leu Val
            20                  25                  30

Gln Pro Gly Gly Ser Leu Arg Leu Ser Cys Ala Ala Ser Gly Phe Thr
        35                  40                  45

Phe Ser His Tyr Val Met Ala Trp Val Arg Gln Ala Pro Gly Lys Gly
    50                  55                  60

Leu Glu Trp Val Ser Ser Ile Ser Ser Gly Gly Trp Thr Leu Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Thr Arg Gly Leu Lys Met Ala Thr Ile Phe Asp Tyr
        115                 120                 125
```

Trp Gly Gln Gly Thr Leu Val Thr Val Ser Ser Gly Gly Gly Ser
            130                 135                 140

Gly Gly Gly Ser Gly Gly Gly Ser Gln Ser Ala Leu Thr Gln
145                 150                 155                 160

Pro Ala Ser Val Ser Gly Ser Pro Gly Gln Ser Ile Thr Ile Ser Cys
                165                 170                 175

Thr Gly Thr Ser Ser Asp Val Gly Ser Tyr Asn Val Ser Trp Tyr
                180                 185                 190

Gln Gln His Pro Gly Lys Ala Pro Lys Leu Ile Ile Tyr Glu Val Ser
            195                 200                 205

Gln Arg Pro Ser Gly Val Ser Asn Arg Phe Ser Gly Ser Lys Ser Gly
210                 215                 220

Asn Thr Ala Ser Leu Thr Ile Ser Gly Leu Gln Thr Glu Asp Glu Ala
225                 230                 235                 240

Asp Tyr Tyr Cys Ser Ser Tyr Ala Gly Ser Ser Ile Phe Val Ile Phe
                245                 250                 255

Gly Gly Gly Thr Lys Val Thr Val Leu Ala Ala Ala Gly Gly Ser Gly
                260                 265                 270

Gly Asp Phe Thr Pro Pro Thr Val Lys Ile Leu Gln Ser Ser Cys Asp
            275                 280                 285

Gly Gly Gly His Phe Pro Pro Thr Ile Gln Leu Leu Cys Leu Val Ser
290                 295                 300

Gly Tyr Thr Pro Gly Thr Ile Asn Ile Thr Trp Leu Glu Asp Gly Gln
305                 310                 315                 320

Val Met Asp Val Asp Leu Ser Thr Ala Ser Thr Thr Gln Glu Gly Glu
                325                 330                 335

Leu Ala Ser Thr Gln Ser Glu Leu Thr Leu Ser Gln Lys His Trp Leu
                340                 345                 350

Ser Asp Arg Thr Tyr Thr Cys Gln Val Thr Tyr Gln Gly His Thr Phe
            355                 360                 365

Glu Asp Ser Thr Lys Lys Cys Ala Asp Ser Asn Gly Gly Ser Gly Gly
            370                 375                 380

Ala Ser Ser His His His His His His
385                 390

<210> SEQ ID NO 31
<211> LENGTH: 645
<212> TYPE: PRT
<213> ORGANISM: Artificial Sequence
<220> FEATURE:
<223> OTHER INFORMATION: Anti-CEAxCD3 scDb-EHD2

<400> SEQUENCE: 31

Met Glu Thr Asp Thr Leu Leu Leu Trp Val Leu Leu Leu Trp Val Pro
1               5                   10                  15

Gly Ser Thr Gly Asp Ala Ala Gln Pro Ala Met Ala Gln Val Lys Leu
                20                  25                  30

Gln Gln Ser Gly Ala Glu Leu Val Arg Ser Gly Thr Ser Val Lys Leu
            35                  40                  45

Ser Cys Thr Ala Ser Gly Phe Asn Ile Lys Asp Ser Tyr Met His Trp
50                  55                  60

Leu Arg Gln Gly Pro Glu Gln Gly Leu Glu Trp Ile Gly Trp Ile Asp
65                  70                  75                  80

Pro Glu Asn Gly Asp Thr Glu Tyr Ala Pro Lys Phe Gln Gly Lys Ala
                85                  90                  95

```
Thr Phe Thr Thr Asp Thr Ser Ser Asn Thr Ala Tyr Leu Gln Leu Ser
            100                 105                 110

Ser Leu Thr Ser Glu Asp Thr Ala Val Tyr Tyr Cys Asn Glu Gly Thr
        115                 120                 125

Pro Thr Gly Pro Tyr Tyr Phe Asp Tyr Trp Gly Gln Gly Thr Thr Val
    130                 135                 140

Thr Val Ser Ser Gly Gly Gly Ser Asp Ile Gln Met Thr Gln Ser
145                 150                 155                 160

Pro Ser Ser Leu Ser Ala Ser Val Gly Asp Arg Val Thr Ile Thr Cys
                165                 170                 175

Arg Ala Ser Gln Asp Ile Arg Asn Tyr Leu Asn Trp Tyr Gln Gln Lys
            180                 185                 190

Pro Gly Lys Ala Pro Lys Leu Leu Ile Tyr Tyr Thr Ser Arg Leu Glu
        195                 200                 205

Ser Gly Val Pro Ser Arg Phe Ser Gly Ser Gly Ser Gly Thr Asp Tyr
    210                 215                 220

Thr Leu Thr Ile Ser Ser Leu Gln Pro Glu Asp Phe Ala Thr Tyr Tyr
225                 230                 235                 240

Cys Gln Gln Gly Asn Thr Leu Pro Trp Thr Phe Gly Gln Gly Thr Lys
                245                 250                 255

Val Glu Ile Lys Arg Gly Gly Gly Ser Gly Gly Arg Ala Ser Gly
            260                 265                 270

Gly Gly Gly Ser Glu Val Gln Leu Val Glu Ser Gly Gly Gly Leu Val
        275                 280                 285

Gln Pro Gly Gly Ser Leu Arg Leu Ser Cys Ala Ala Ser Gly Tyr Ser
    290                 295                 300

Phe Thr Gly Tyr Thr Met Asn Trp Val Arg Gln Ala Pro Gly Lys Gly
305                 310                 315                 320

Leu Glu Trp Val Ala Leu Ile Asn Pro Tyr Lys Gly Val Ser Thr Tyr
                325                 330                 335

Asn Gln Lys Phe Lys Asp Arg Phe Thr Ile Ser Val Asp Lys Ser Lys
            340                 345                 350

Asn Thr Ala Tyr Leu Gln Met Asn Ser Leu Arg Ala Glu Asp Thr Ala
        355                 360                 365

Val Tyr Tyr Cys Ala Arg Ser Gly Tyr Gly Asp Ser Asp Trp Tyr
    370                 375                 380

Phe Asp Val Trp Gly Gln Gly Thr Leu Val Thr Val Ser Ser Gly Gly
385                 390                 395                 400

Gly Gly Ser Asp Ile Glu Leu Thr Gln Ser Pro Ala Ile Met Ser Ala
            405                 410                 415

Ser Pro Gly Glu Lys Val Thr Ile Thr Cys Ser Ala Ser Ser Ser Val
        420                 425                 430

Ser Tyr Met His Trp Phe Gln Gln Lys Pro Gly Thr Ser Pro Lys Leu
    435                 440                 445

Trp Ile Tyr Ser Thr Ser Asn Leu Ala Ser Gly Val Pro Ala Arg Phe
450                 455                 460

Ser Gly Ser Gly Ser Gly Thr Ser Tyr Ser Leu Thr Ile Ser Arg Met
465                 470                 475                 480

Glu Ala Glu Asp Ala Ala Thr Tyr Tyr Cys Gln Gln Arg Ser Ser Tyr
            485                 490                 495

Pro Leu Thr Phe Gly Ala Gly Thr Lys Leu Glu Leu Lys Arg Gly Ser
        500                 505                 510
```

```
Leu Gly Gly Ser Gly Gly Asp Phe Thr Pro Pro Thr Val Lys Ile Leu
            515                 520                 525

Gln Ser Ser Cys Asp Gly Gly His Phe Pro Pro Thr Ile Gln Leu
        530                 535                 540

Leu Cys Leu Val Ser Gly Tyr Thr Pro Gly Thr Ile Asn Ile Thr Trp
545                 550                 555                 560

Leu Glu Asp Gly Gln Val Met Asp Val Asp Leu Ser Thr Ala Ser Thr
                565                 570                 575

Thr Gln Glu Gly Glu Leu Ala Ser Thr Gln Ser Glu Leu Thr Leu Ser
            580                 585                 590

Gln Lys His Trp Leu Ser Asp Arg Thr Tyr Thr Cys Gln Val Thr Tyr
        595                 600                 605

Gln Gly His Thr Phe Glu Asp Ser Thr Lys Lys Cys Ala Asp Ser Asn
    610                 615                 620

Gly Gly Gly Ser Gly Gly Gly Thr Gly Ser Glu Phe Ala Ala Ala His
625                 630                 635                 640

His His His His His
            645

<210> SEQ ID NO 32
<211> LENGTH: 394
<212> TYPE: PRT
<213> ORGANISM: Artificial Sequence
<220> FEATURE:
<223> OTHER INFORMATION: Anti-EGFR scFv-L3-EHD2

<400> SEQUENCE: 32

Met Glu Thr Asp Thr Leu Leu Leu Trp Val Leu Leu Leu Trp Val Pro
1               5                   10                  15

Gly Ser Thr Gly Gln Val Gln Leu Lys Gln Ser Gly Ala Glu Leu Val
            20                  25                  30

Lys Pro Gly Ala Ser Val Lys Leu Ser Cys Lys Thr Ser Gly Tyr Thr
        35                  40                  45

Phe Thr Glu Asn Ile Ile His Trp Val Lys Gln Arg Ser Gly Gln Gly
    50                  55                  60

Leu Glu Trp Ile Gly Trp Phe His Pro Gly Ser Gly Ser Ile Lys Tyr
65                  70                  75                  80

Asn Glu Lys Phe Lys Asp Lys Ala Thr Leu Thr Ala Asp Lys Ser Ser
                85                  90                  95

Ser Thr Val Tyr Met Glu Leu Ser Arg Leu Thr Ser Glu Asp Ser Ala
            100                 105                 110

Val Tyr Phe Cys Ala Arg His Gly Gly Thr Gly Arg Gly Ala Met Asp
        115                 120                 125

Tyr Trp Gly Gln Gly Thr Ser Val Thr Val Ser Ser Gly Gly Cys Gly
    130                 135                 140

Ser Gly Gly Gly Ser Gly Gly Ser Ala Gln Ile Leu Met Thr Gln
145                 150                 155                 160

Ser Pro Ala Ser Ser Val Val Ser Leu Gly Gln Arg Ala Thr Ile Ser
                165                 170                 175

Cys Arg Ala Ser Lys Ser Val Ser Thr Ser Ala Tyr Ser Tyr Met His
            180                 185                 190

Trp Tyr Gln Gln Lys Pro Gly Gln Pro Pro Lys Leu Leu Ile Tyr Leu
        195                 200                 205

Ala Ser Asn Leu Glu Ser Gly Val Pro Pro Arg Phe Ser Gly Ser Gly
    210                 215                 220
```

-continued

```
Ser Gly Thr Asp Phe Thr Leu Asn Ile His Pro Val Glu Glu Asp
225                 230                 235                 240

Ala Ala Thr Tyr Tyr Cys Gln His Ser Arg Glu Leu Pro Tyr Thr Phe
            245                 250                 255

Gly Gly Gly Thr Lys Leu Glu Ile Lys Arg Ala Ala Ala Gly Gly Ser
        260                 265                 270

Gly Gly Asp Phe Thr Pro Pro Thr Val Lys Ile Leu Gln Ser Ser Cys
    275                 280                 285

Asp Gly Gly His Phe Pro Pro Thr Ile Gln Leu Leu Cys Leu Val
290                 295                 300

Ser Gly Tyr Thr Pro Gly Thr Ile Asn Ile Thr Trp Leu Glu Asp Gly
305                 310                 315                 320

Gln Val Met Asp Val Asp Leu Ser Thr Ala Ser Thr Thr Gln Glu Gly
            325                 330                 335

Glu Leu Ala Ser Thr Gln Ser Glu Leu Thr Leu Ser Gln Lys His Trp
        340                 345                 350

Leu Ser Asp Arg Thr Tyr Thr Cys Gln Val Thr Tyr Gln Gly His Thr
    355                 360                 365

Phe Glu Asp Ser Thr Lys Lys Cys Ala Asp Ser Asn Gly Gly Ser Gly
370                 375                 380

Gly Ala Ser Ser His His His His His His
385                 390
```

<210> SEQ ID NO 33
<211> LENGTH: 645
<212> TYPE: PRT
<213> ORGANISM: Artificial Sequence
<220> FEATURE:
<223> OTHER INFORMATION: Anti-EGFR scFv-L3-EHD2-scFv

<400> SEQUENCE: 33

```
Met Glu Thr Asp Thr Leu Leu Leu Trp Val Leu Leu Leu Trp Val Pro
1               5                   10                  15

Gly Ser Thr Gly Gln Val Gln Leu Lys Gln Ser Gly Ala Glu Leu Val
            20                  25                  30

Lys Pro Gly Ala Ser Val Lys Leu Ser Cys Lys Thr Ser Gly Tyr Thr
        35                  40                  45

Phe Thr Glu Asn Ile Ile His Trp Val Lys Gln Arg Ser Gly Gln Gly
    50                  55                  60

Leu Glu Trp Ile Gly Trp Phe His Pro Gly Ser Gly Ser Ile Lys Tyr
65                  70                  75                  80

Asn Glu Lys Phe Lys Asp Lys Ala Thr Leu Thr Ala Asp Lys Ser Ser
                85                  90                  95

Ser Thr Val Tyr Met Glu Leu Ser Arg Leu Thr Ser Glu Asp Ser Ala
            100                 105                 110

Val Tyr Phe Cys Ala Arg His Gly Gly Thr Gly Arg Gly Ala Met Asp
        115                 120                 125

Tyr Trp Gly Gln Gly Thr Ser Val Thr Val Ser Ser Gly Gly Cys Gly
    130                 135                 140

Ser Gly Gly Gly Ser Gly Gly Ser Ala Gln Ile Leu Met Thr Gln
145                 150                 155                 160

Ser Pro Ala Ser Ser Val Val Ser Leu Gly Gln Arg Ala Thr Ile Ser
                165                 170                 175

Cys Arg Ala Ser Lys Ser Val Ser Thr Ser Ala Tyr Ser Tyr Met His
            180                 185                 190
```

-continued

```
Trp Tyr Gln Gln Lys Pro Gly Gln Pro Pro Lys Leu Leu Ile Tyr Leu
            195                 200                 205
Ala Ser Asn Leu Glu Ser Gly Val Pro Pro Arg Phe Ser Gly Ser Gly
    210                 215                 220
Ser Gly Thr Asp Phe Thr Leu Asn Ile His Pro Val Glu Glu Glu Asp
225                 230                 235                 240
Ala Ala Thr Tyr Tyr Cys Gln His Ser Arg Glu Leu Pro Tyr Thr Phe
                245                 250                 255
Gly Gly Gly Thr Lys Leu Glu Ile Lys Arg Ala Ala Gly Gly Ser
            260                 265                 270
Gly Gly Asp Phe Thr Pro Pro Thr Val Lys Ile Leu Gln Ser Ser Cys
            275                 280                 285
Asp Gly Gly His Phe Pro Pro Thr Ile Gln Leu Leu Cys Leu Val
    290                 295                 300
Ser Gly Tyr Thr Pro Gly Thr Ile Asn Ile Thr Trp Leu Glu Asp Gly
305                 310                 315                 320
Gln Val Met Asp Val Asp Leu Ser Thr Ala Ser Thr Thr Gln Glu Gly
                325                 330                 335
Glu Leu Ala Ser Thr Gln Ser Glu Leu Thr Leu Ser Gln Lys His Trp
            340                 345                 350
Leu Ser Asp Arg Thr Tyr Thr Cys Gln Val Thr Tyr Gln Gly His Thr
            355                 360                 365
Phe Glu Asp Ser Thr Lys Lys Cys Ala Asp Ser Asn Gly Gly Ser Gly
    370                 375                 380
Gly Ala Ser Ser Glu Phe Gln Val Gln Leu Lys Gln Ser Gly Ala Glu
385                 390                 395                 400
Leu Val Lys Pro Gly Ala Ser Val Lys Leu Ser Cys Lys Thr Ser Gly
                405                 410                 415
Tyr Thr Phe Thr Glu Asn Ile Ile His Trp Val Lys Gln Arg Ser Gly
            420                 425                 430
Gln Gly Leu Glu Trp Ile Gly Trp Phe His Pro Gly Ser Gly Ser Ile
            435                 440                 445
Lys Tyr Asn Glu Lys Phe Lys Asp Lys Ala Thr Leu Thr Ala Asp Lys
    450                 455                 460
Ser Ser Ser Thr Val Tyr Met Glu Leu Ser Arg Leu Thr Ser Glu Asp
465                 470                 475                 480
Ser Ala Val Tyr Phe Cys Ala Arg His Gly Thr Gly Arg Gly Ala
                485                 490                 495
Met Asp Tyr Trp Gly Gln Gly Thr Ser Val Thr Val Ser Ser Gly Gly
            500                 505                 510
Gly Gly Ser Gly Gly Gly Gly Ser Gly Gly Ser Ala Gln Ile Leu Met
            515                 520                 525
Thr Gln Ser Pro Ala Ser Ser Val Val Ser Leu Gly Gln Arg Ala Thr
    530                 535                 540
Ile Ser Cys Arg Ala Ser Lys Ser Val Ser Thr Ser Ala Tyr Ser Tyr
545                 550                 555                 560
Met His Trp Tyr Gln Gln Lys Pro Gly Gln Pro Pro Lys Leu Leu Ile
                565                 570                 575
Tyr Leu Ala Ser Asn Leu Glu Ser Gly Val Pro Pro Arg Phe Ser Gly
            580                 585                 590
Ser Gly Ser Gly Thr Asp Phe Thr Leu Asn Ile His Pro Val Glu Glu
            595                 600                 605
Glu Asp Ala Ala Thr Tyr Tyr Cys Gln His Ser Arg Glu Leu Pro Tyr
```

```
                  610                 615                 620
Thr Phe Gly Gly Gly Thr Lys Leu Glu Ile Lys Arg Ala Ala Ala His
625                 630                 635                 640

His His His His His
                645

<210> SEQ ID NO 34
<211> LENGTH: 652
<212> TYPE: PRT
<213> ORGANISM: Artificial Sequence
<220> FEATURE:
<223> OTHER INFORMATION: MHD2-scTNFR2

<400> SEQUENCE: 34

Met Glu Thr Asp Thr Leu Leu Leu Trp Val Leu Leu Leu Trp Val Pro
1               5                   10                  15

Gly Ser Thr Gly Asp Ala Ala Gln Pro Ala Gly Gly Ala Ala Ala
            20                  25                  30

His His His His His His Gly Gly Thr Gly Gly Gly Ser Gly Gly
                35                  40                  45

Lys Leu Gly Gly Ser Gly Gly Ala Glu Leu Pro Pro Lys Val Ser Val
    50                  55                  60

Phe Val Pro Pro Arg Asp Gly Phe Phe Gly Asn Pro Arg Lys Ser Lys
65                  70                  75                  80

Leu Ile Cys Gln Ala Thr Gly Phe Ser Pro Arg Gln Ile Gln Val Ser
                85                  90                  95

Trp Leu Arg Glu Gly Lys Gln Val Gly Ser Gly Val Thr Thr Asp Gln
            100                 105                 110

Val Gln Ala Glu Ala Lys Glu Ser Gly Pro Thr Thr Tyr Lys Val Thr
        115                 120                 125

Ser Thr Leu Thr Ile Lys Glu Ser Asp Trp Leu Gly Gln Ser Met Phe
130                 135                 140

Thr Cys Arg Val Asp His Arg Gly Leu Thr Phe Gln Gln Asn Ala Ser
145                 150                 155                 160

Ser Met Cys Val Pro Asp Gly Gly Ser Gly Gly Gly Thr Gly Ser
                165                 170                 175

Glu Phe Leu Ala Ser Ser Arg Thr Pro Ser Asp Lys Pro Val Ala His
            180                 185                 190

Val Val Ala Asn Pro Gln Ala Glu Gly Gln Leu Gln Trp Leu Asn Arg
        195                 200                 205

Arg Ala Asn Ala Leu Leu Ala Asn Gly Val Glu Leu Arg Asp Asn Gln
210                 215                 220

Leu Val Val Pro Ser Glu Gly Leu Tyr Leu Ile Tyr Ser Gln Val Leu
225                 230                 235                 240

Phe Lys Gly Gln Gly Cys Pro Ser Thr His Val Leu Leu Thr His Thr
                245                 250                 255

Ile Ser Arg Ile Ala Val Ser Tyr Gln Thr Lys Val Asn Leu Leu Ser
            260                 265                 270

Ala Ile Lys Ser Pro Cys Gln Arg Glu Thr Pro Glu Gly Ala Glu Ala
        275                 280                 285

Lys Pro Trp Tyr Glu Pro Ile Tyr Leu Gly Gly Val Phe Gln Leu Glu
    290                 295                 300

Lys Gly Asp Arg Leu Ser Ala Glu Ile Asn Arg Pro Asp Tyr Leu Asn
305                 310                 315                 320

Phe Arg Glu Ser Gly Gln Val Tyr Phe Gly Ile Ile Ala Leu Gly Gly
```

```
                    325                 330                 335
Gly Gly Ser Ser Ser Arg Thr Pro Ser Asp Lys Pro Val Ala His Val
                340                 345                 350

Val Ala Asn Pro Gln Ala Glu Gly Gln Leu Gln Trp Leu Asn Arg Arg
                355                 360                 365

Ala Asn Ala Leu Leu Ala Asn Gly Val Glu Leu Arg Asp Asn Gln Leu
            370                 375                 380

Val Val Pro Ser Glu Gly Leu Tyr Leu Ile Tyr Ser Gln Val Leu Phe
385                 390                 395                 400

Lys Gly Gln Gly Cys Pro Ser Thr His Val Leu Leu Thr His Thr Ile
                405                 410                 415

Ser Arg Ile Ala Val Ser Tyr Gln Thr Lys Val Asn Leu Leu Ser Ala
                420                 425                 430

Ile Lys Ser Pro Cys Gln Arg Glu Thr Pro Glu Gly Ala Glu Ala Lys
                435                 440                 445

Pro Trp Tyr Glu Pro Ile Tyr Leu Gly Gly Val Phe Gln Leu Glu Lys
                450                 455                 460

Gly Asp Arg Leu Ser Ala Glu Ile Asn Arg Pro Asp Tyr Leu Asn Phe
465                 470                 475                 480

Arg Glu Ser Gly Gln Val Tyr Phe Gly Ile Ile Ala Leu Gly Gly Gly
                485                 490                 495

Gly Ser Ser Ser Arg Thr Pro Ser Asp Lys Pro Val Ala His Val Val
                500                 505                 510

Ala Asn Pro Gln Ala Glu Gly Gln Leu Gln Trp Leu Asn Arg Arg Ala
                515                 520                 525

Asn Ala Leu Leu Ala Asn Gly Val Glu Leu Arg Asp Asn Gln Leu Val
            530                 535                 540

Val Pro Ser Glu Gly Leu Tyr Leu Ile Tyr Ser Gln Val Leu Phe Lys
545                 550                 555                 560

Gly Gln Gly Cys Pro Ser Thr His Val Leu Leu Thr His Thr Ile Ser
                565                 570                 575

Arg Ile Ala Val Ser Tyr Gln Thr Lys Val Asn Leu Leu Ser Ala Ile
                580                 585                 590

Lys Ser Pro Cys Gln Arg Glu Thr Pro Glu Gly Ala Glu Ala Lys Pro
                595                 600                 605

Trp Tyr Glu Pro Ile Tyr Leu Gly Gly Val Phe Gln Leu Glu Lys Gly
                610                 615                 620

Asp Arg Leu Ser Ala Glu Ile Asn Arg Pro Asp Tyr Leu Asn Phe Arg
625                 630                 635                 640

Glu Ser Gly Gln Val Tyr Phe Gly Ile Ile Ala Leu
                645                 650

<210> SEQ ID NO 35
<211> LENGTH: 647
<212> TYPE: PRT
<213> ORGANISM: Artificial Sequence
<220> FEATURE:
<223> OTHER INFORMATION: EHD2-scTNFR2-L16aa

<400> SEQUENCE: 35

Met Glu Thr Asp Thr Leu Leu Leu Trp Val Leu Leu Leu Trp Val Pro
1               5                   10                  15

Gly Ser Thr Gly Asp Ala Ala Gln Pro Ala Gly Gly Ala Ala Ala
                20                  25                  30

His His His His His His Gly Gly Thr Gly Gly Gly Gly Ser Gly Gly
```

```
                35                  40                  45
Lys Leu Gly Gly Ser Gly Gly Asp Phe Thr Pro Thr Val Lys Ile
 50                  55                  60
Leu Gln Ser Ser Cys Asp Gly Gly His Phe Pro Pro Thr Ile Gln
65                   70                  75                  80
Leu Leu Cys Leu Val Ser Gly Tyr Thr Pro Gly Thr Ile Asn Ile Thr
                 85                  90                  95
Trp Leu Glu Asp Gly Gln Val Met Asp Val Asp Leu Ser Thr Ala Ser
                100                 105                 110
Thr Thr Gln Glu Gly Glu Leu Ala Ser Thr Gln Ser Glu Leu Thr Leu
                115                 120                 125
Ser Gln Lys His Trp Leu Ser Asp Arg Thr Tyr Thr Cys Gln Val Thr
130                 135                 140
Tyr Gln Gly His Thr Phe Glu Asp Ser Thr Lys Lys Cys Ala Asp Ser
145                 150                 155                 160
Asn Gly Gly Ser Gly Gly Gly Thr Gly Ser Glu Phe Leu Ala Ser
                165                 170                 175
Ser Arg Thr Pro Ser Asp Lys Pro Val Ala His Val Val Ala Asn Pro
                180                 185                 190
Gln Ala Glu Gly Gln Leu Gln Trp Leu Asn Arg Arg Ala Asn Ala Leu
                195                 200                 205
Leu Ala Asn Gly Val Glu Leu Arg Asp Asn Gln Leu Val Val Pro Ser
210                 215                 220
Glu Gly Leu Tyr Leu Ile Tyr Ser Gln Val Leu Phe Lys Gly Gln Gly
225                 230                 235                 240
Cys Pro Ser Thr His Val Leu Leu Thr His Thr Ile Ser Arg Ile Ala
                245                 250                 255
Val Ser Tyr Gln Thr Lys Val Asn Leu Leu Ser Ala Ile Lys Ser Pro
                260                 265                 270
Cys Gln Arg Glu Thr Pro Glu Gly Ala Glu Ala Lys Pro Trp Tyr Glu
                275                 280                 285
Pro Ile Tyr Leu Gly Gly Val Phe Gln Leu Glu Lys Gly Asp Arg Leu
290                 295                 300
Ser Ala Glu Ile Asn Arg Pro Asp Tyr Leu Asn Phe Arg Glu Ser Gly
305                 310                 315                 320
Gln Val Tyr Phe Gly Ile Ile Ala Leu Gly Gly Gly Ser Ser Ser
                325                 330                 335
Arg Thr Pro Ser Asp Lys Pro Val Ala His Val Val Ala Asn Pro Gln
                340                 345                 350
Ala Glu Gly Gln Leu Gln Trp Leu Asn Arg Arg Ala Asn Ala Leu Leu
                355                 360                 365
Ala Asn Gly Val Glu Leu Arg Asp Asn Gln Leu Val Val Pro Ser Glu
                370                 375                 380
Gly Leu Tyr Leu Ile Tyr Ser Gln Val Leu Phe Lys Gly Gln Gly Cys
385                 390                 395                 400
Pro Ser Thr His Val Leu Leu Thr His Thr Ile Ser Arg Ile Ala Val
                405                 410                 415
Ser Tyr Gln Thr Lys Val Asn Leu Leu Ser Ala Ile Lys Ser Pro Cys
                420                 425                 430
Gln Arg Glu Thr Pro Glu Gly Ala Glu Ala Lys Pro Trp Tyr Glu Pro
                435                 440                 445
Ile Tyr Leu Gly Gly Val Phe Gln Leu Glu Lys Gly Asp Arg Leu Ser
450                 455                 460
```

```
Ala Glu Ile Asn Arg Pro Asp Tyr Leu Asn Phe Arg Glu Ser Gly Gln
465                 470                 475                 480

Val Tyr Phe Gly Ile Ile Ala Leu Gly Gly Gly Ser Ser Arg
                485                 490                 495

Thr Pro Ser Asp Lys Pro Val Ala His Val Val Ala Asn Pro Gln Ala
            500                 505                 510

Glu Gly Gln Leu Gln Trp Leu Asn Arg Arg Ala Asn Ala Leu Leu Ala
            515                 520                 525

Asn Gly Val Glu Leu Arg Asp Asn Gln Leu Val Val Pro Ser Glu Gly
            530                 535                 540

Leu Tyr Leu Ile Tyr Ser Gln Val Leu Phe Lys Gly Gln Gly Cys Pro
545                 550                 555                 560

Ser Thr His Val Leu Leu Thr His Thr Ile Ser Arg Ile Ala Val Ser
                565                 570                 575

Tyr Gln Thr Lys Val Asn Leu Leu Ser Ala Ile Lys Ser Pro Cys Gln
            580                 585                 590

Arg Glu Thr Pro Glu Gly Ala Glu Ala Lys Pro Trp Tyr Glu Pro Ile
            595                 600                 605

Tyr Leu Gly Gly Val Phe Gln Leu Glu Lys Gly Asp Arg Leu Ser Ala
610                 615                 620

Glu Ile Asn Arg Pro Asp Tyr Leu Asn Phe Arg Glu Ser Gly Gln Val
625                 630                 635                 640

Tyr Phe Gly Ile Ile Ala Leu
                645

<210> SEQ ID NO 36
<211> LENGTH: 660
<212> TYPE: PRT
<213> ORGANISM: Artificial Sequence
<220> FEATURE:
<223> OTHER INFORMATION: EHD2-scTNFR2-L28aa

<400> SEQUENCE: 36

Met Glu Thr Asp Thr Leu Leu Leu Trp Val Leu Leu Leu Trp Val Pro
1               5                   10                  15

Gly Ser Thr Gly Asp Ala Ala Gln Pro Ala Gly Gly Ala Ala Ala
                20                  25                  30

His His His His His Gly Gly Thr Gly Gly Gly Ser Gly Gly
                35                  40                  45

Lys Leu Gly Gly Ser Gly Gly Asp Phe Thr Pro Pro Thr Val Lys Ile
            50                  55                  60

Leu Gln Ser Ser Cys Asp Gly Gly His Phe Pro Pro Thr Ile Gln
65                  70                  75                  80

Leu Leu Cys Leu Val Ser Gly Tyr Thr Pro Gly Thr Ile Asn Ile Thr
                85                  90                  95

Trp Leu Glu Asp Gly Gln Val Met Asp Val Asp Leu Ser Thr Ala Ser
                100                 105                 110

Thr Thr Gln Glu Gly Glu Leu Ala Ser Thr Gln Ser Glu Leu Thr Leu
            115                 120                 125

Ser Gln Lys His Trp Leu Ser Asp Arg Thr Tyr Thr Cys Gln Val Thr
            130                 135                 140

Tyr Gln Gly His Thr Phe Glu Asp Ser Thr Lys Lys Cys Ala Asp Ser
145                 150                 155                 160

Asn Gly Gly Gly Ser Gly Gly Gly Ser Gly Gly Ser Gly Gly Gly
                165                 170                 175
```

```
Ser Gly Gly Gly Ser Gly Ser Glu Phe Leu Ala Ser Ser Arg Thr
            180                 185                 190
Pro Ser Asp Lys Pro Val Ala His Val Val Ala Asn Pro Gln Ala Glu
        195                 200                 205
Gly Gln Leu Gln Trp Leu Asn Arg Arg Ala Asn Ala Leu Leu Ala Asn
    210                 215                 220
Gly Val Glu Leu Arg Asp Asn Gln Leu Val Val Pro Ser Glu Gly Leu
225                 230                 235                 240
Tyr Leu Ile Tyr Ser Gln Val Leu Phe Lys Gly Gln Gly Cys Pro Ser
                245                 250                 255
Thr His Val Leu Leu Thr His Thr Ile Ser Arg Ile Ala Val Ser Tyr
            260                 265                 270
Gln Thr Lys Val Asn Leu Leu Ser Ala Ile Lys Ser Pro Cys Gln Arg
        275                 280                 285
Glu Thr Pro Glu Gly Ala Glu Ala Lys Pro Trp Tyr Glu Pro Ile Tyr
    290                 295                 300
Leu Gly Gly Val Phe Gln Leu Glu Lys Gly Asp Arg Leu Ser Ala Glu
305                 310                 315                 320
Ile Asn Arg Pro Asp Tyr Leu Asn Phe Arg Glu Ser Gly Gln Val Tyr
                325                 330                 335
Phe Gly Ile Ile Ala Leu Gly Gly Gly Ser Ser Ser Arg Thr Pro
            340                 345                 350
Ser Asp Lys Pro Val Ala His Val Val Ala Asn Pro Gln Ala Glu Gly
        355                 360                 365
Gln Leu Gln Trp Leu Asn Arg Arg Ala Asn Ala Leu Leu Ala Asn Gly
    370                 375                 380
Val Glu Leu Arg Asp Asn Gln Leu Val Val Pro Ser Glu Gly Leu Tyr
385                 390                 395                 400
Leu Ile Tyr Ser Gln Val Leu Phe Lys Gly Gln Gly Cys Pro Ser Thr
                405                 410                 415
His Val Leu Leu Thr His Thr Ile Ser Arg Ile Ala Val Ser Tyr Gln
            420                 425                 430
Thr Lys Val Asn Leu Leu Ser Ala Ile Lys Ser Pro Cys Gln Arg Glu
        435                 440                 445
Thr Pro Glu Gly Ala Glu Ala Lys Pro Trp Tyr Glu Pro Ile Tyr Leu
    450                 455                 460
Gly Gly Val Phe Gln Leu Glu Lys Gly Asp Arg Leu Ser Ala Glu Ile
465                 470                 475                 480
Asn Arg Pro Asp Tyr Leu Asn Phe Arg Glu Ser Gly Gln Val Tyr Phe
                485                 490                 495
Gly Ile Ile Ala Leu Gly Gly Gly Ser Ser Ser Arg Thr Pro Ser
            500                 505                 510
Asp Lys Pro Val Ala His Val Val Ala Asn Pro Gln Ala Glu Gly Gln
        515                 520                 525
Leu Gln Trp Leu Asn Arg Arg Ala Asn Ala Leu Leu Ala Asn Gly Val
    530                 535                 540
Glu Leu Arg Asp Asn Gln Leu Val Val Pro Ser Glu Gly Leu Tyr Leu
545                 550                 555                 560
Ile Tyr Ser Gln Val Leu Phe Lys Gly Gln Gly Cys Pro Ser Thr His
                565                 570                 575
Val Leu Leu Thr His Thr Ile Ser Arg Ile Ala Val Ser Tyr Gln Thr
            580                 585                 590
```

```
Lys Val Asn Leu Leu Ser Ala Ile Lys Ser Pro Cys Gln Arg Glu Thr
            595                 600                 605

Pro Glu Gly Ala Glu Ala Lys Pro Trp Tyr Pro Ile Tyr Leu Gly
    610                 615                 620

Gly Val Phe Gln Leu Glu Lys Gly Asp Arg Leu Ser Ala Glu Ile Asn
625                 630                 635                 640

Arg Pro Asp Tyr Leu Asn Phe Arg Glu Ser Gly Gln Val Tyr Phe Gly
                645                 650                 655

Ile Ile Ala Leu
            660

<210> SEQ ID NO 37
<211> LENGTH: 795
<212> TYPE: DNA
<213> ORGANISM: Artificial Sequence
<220> FEATURE:
<223> OTHER INFORMATION: anti-HER2 scFvs (4D5)

<400> SEQUENCE: 37
atgaaatacc tattgcctac ggcagccgct ggattgttat tactcgcggc ccagccggcc      60
atggccgaag tgcagctcgt cgaaagtggc ggtggacttg tgcagcctgg cggttccctc     120
agactgtcct gtgccgcgtc aggcttcaac atcaaggaca cgtacatcca ctgggtgagg     180
caagctcctg gaaagggctt ggagtgggtc gctaggatct acccgacgaa cggctacacc     240
aggtacgctg actcagtgaa gggaaggttc acgatcagtg cagacaccag caagaacacc     300 gcataccctcc aaatgaactc cctgagagcc gaggacaccg ccgtgtacta ctgctctcgt     360
tggggtggag atggcttcta cgctatggac tactgggtc aaggcacact ggtgaccgtg      420
tccagtggtg gcggaggcag tggcggaggt ggctcaggag gcggaaccgg tgacatccag     480
atgacccagt caccctcaag cctcagtgcc agcgtcggag atagagtgac cataacgtgc     540
cgagcttctc aggatgtgaa cacggcagtg gcttggtatc agcaaaagcc tgggaaagcc     600
ccaaagctgc tcatctactc cgcatccttc ctgtatagcg gagttccatc taggttctca     660
ggctctaggt ctgggaccga cttcacgctg acgatctcct ccctgcaacc tgaggacttc     720
gccacgtact actgccagca gcactacacg actcctccaa ccttcggtca gggaacgaag     780
gtcgagatca agcgt                                                      795

<210> SEQ ID NO 38
<211> LENGTH: 792
<212> TYPE: DNA
<213> ORGANISM: Artificial Sequence
<220> FEATURE:
<223> OTHER INFORMATION: anti-EGFR scFvs (hu225)

<400> SEQUENCE: 38
atgaaatacc tattgcctac ggcagccgct ggattgttat tactcgcggc ccagccggcc      60
atggcggaag tgcagctggt tgaaagcggc ggtggtctgg ttcagccggg tgcagcctg      120 cgtctgagct gtgcggcgag cggctttagc ctgaccaact atggcgtgca ttgggtgcgt     180
caggcaccgg gcaaaggcct ggaatggctg ggcgtgattt ggagcggcgg caacaccgat     240
tataacaccc cgtttaccag ccgttttacc attagccgtg ataacagcaa aaacaccctg     300
tatctgcaga tgaacagcct gcgtgcggaa gataccgcgg tgtattattg cgcgcgtgcg     360
ctgacctatt atgattacga atttgcgtat tggggccagg gcaccaccgt tacggtctcg     420
agcggtggcg gtggtagcgg tggtggcggc tctggcggtg gtggatccga tattcagctg     480
```

```
acccagagcc cgagctttct gagcgcgagc gtgggcgatc gtgttaccat tacctgtcgt    540
gcaagccaga gcattggcac caacattcat tggtatcagc agaaaccggg caaagcgccg    600
aaactgctga ttaaatatgc gagcgaaagc attagcggcg tgccgagccg ttttagcggc    660
agcggtagcg gcaccgaatt taccctgacc attagcagcc tgcagccgga agattttgcg    720
acctattatt gccagcagaa caacaactgg ccgaccacct ttggtgcggg caccaaactg    780
gaaattaaac gt                                                       792
```

<210> SEQ ID NO 39
<211> LENGTH: 1416
<212> TYPE: DNA
<213> ORGANISM: Artificial Sequence
<220> FEATURE:
<223> OTHER INFORMATION: scTNF

<400> SEQUENCE: 39

```
tcttctcgta ccccgtctga caaaccggtt gctcacgttg ttgcaaaccc gcaggctgaa     60
ggtcaactgc aatggctgaa ccgtcgtgct aacgctctgc tggctaacgg tgttgaactg    120
cgtgacaacc agctggttgt tccgtctgaa ggcctgtacc tgatctactc ccaggttctg    180
ttcaaaggcc agggctgccc gtccacccac gttctgctga cccacaccat ctctcgtatc    240 gctgttttcct accagaccaa agtaaacctg ctgtctgcaa tcaaatctcc gtgccagcgt    300
gaaaccccgg aaggtgctga agctaaaccg tggtacgaac cgatctacct gggtggcgtt    360
tttcaactgg agaaaggtga ccgtctgtct gcagaaatta accgtccgga ctacctggac    420
ttcgcagaat ctggtcaggt ttacttcggt atcatagcgc tgggtggagg tggttcctct    480
tctcgtaccc cgtctgacaa accggttgct cacgttgttg caaacccgca ggctgaaggt    540
caactgcaat ggctgaaccg tcgtgctaac gctctgctgg ctaacggtgt tgaactgcgt    600
gacaaccagc tggttgttcc gtctgaaggc ctgtacctga tctactccca ggttctgttc    660
aaaggccagg gctgcccgtc cacccacgtt ctgctgaccc acaccatctc tcgtatcgct    720
gtttcctacc agaccaaagt aaacctgctg tctgcaatca aatctccgtg ccagcgtgaa    780
accccggaag gtgctgaagc taaaccgtgg tacgaaccga tctacctggg tggcgttttt    840
caactggaga aaggtgaccg tctgtctgca gaaattaacc gtccggacta cctggacttc    900
gcagaatctg gtcaggttta cttcggtatc atcgctctgg tggtggagga tcctcttct    960 cgtaccccgt ctgacaaacc ggttgctcac gttgttgcaa acccgcaggc tgaaggtcaa   1020
ctgcaatggc tgaaccgtcg tgctaacgct ctgctggcta acggtgttga actgcgtgac   1080
aaccagctgg ttgttccgtc tgaaggcctg tacctgatct actcccaggt tctgttcaaa   1140
ggccagggct gcccgtccac ccacgttctg ctgacccaca ccatctctcg tatcgctgtt   1200
tcctaccaga ccaaagtaaa cctgctgtct gcaatcaaat ctccgtgcca gcgtgaaacc   1260
ccggaaggtg ctgaagctaa accgtggtac gaaccgatct acctgggtgg cgttttcaa   1320 ctggagaaag gtgaccgtct gtctgcagaa attaaccgtc cggactacct ggacttcgca   1380
gaatctggtc aggtttactt cggtatcatc gctctg                             1416
```

<210> SEQ ID NO 40
<211> LENGTH: 1743
<212> TYPE: DNA
<213> ORGANISM: Artificial Sequence
<220> FEATURE:
<223> OTHER INFORMATION: scTRAIL

<400> SEQUENCE: 40

```
acgcgtggca ccagcgagga aaccattagc accgtccagg aaaagcagca gaacatcagc    60 ccccctggtcc gggagagagg ccccccagaga gtcgccgccc acatcaccgg cacccggggc   120
agaagcaaca ccctgagcag ccccaacagc aagaacgaga aggccctggg ccggaagatc   180
aacagctggg agagcagcag aagcggccac agctttctga gcaacctgca cctgcggaac   240
ggcgagctgg tcatccacga gaagggcttc tactacatct acagccagac ctacttcaga   300
ttccaagaag agatcaaaga gaacaccaag aacgacaagc agatggtgca gtacatctac   360
aagtacacca gctaccccga ccccatcctg ctgatgaagt ccgcccggaa cagctgctgg   420
tccaaggacg ccgagtacgg cctgtacagc atctaccagg gcggcatctt cgagctgaaa   480
gagaacgacc ggatcttcgt gagcgtgacc aacgagcacc tgatcgacat ggaccacgag   540
gccagctttt tcggcgcatt cctggtcggc ggagggggat ccggcggagg aagcacctcc   600
gaagagacta tctctacagt ccaggaaaaa cagcagaata tctcccctct cgtgcgggag   660
cggggacctc agcgggtggc cgcccatatt acaggcacaa gaggccggtc caacaccctg   720
tcctccccca actctaagaa tgaaaaggcc ctcgggagaa agatcaactc ctgggagtcc   780
agccgctccg ccactccttt tctgtccaat ctgcacctga aaatggggga gctggtcatt   840
cacgaaaagg ggttttacta tatctactct cagacatact ttaggtttca ggaagaaatt   900
aaagaaaata caaagaatga taaacagatg gtccagtata tctataaata cacttcctac   960
cctgatccta ttctgctgat gaaaagcgcc agaaacagct gttggagcaa ggatgccgaa  1020
tatgggctct actctatcta ccagggggg atttttgaac ttaaggagaa tgacagaatc  1080
tttgtgtctg tgacaaatga gcatctgatt gatatggatc acgaagcctc attctttgga  1140
gcctttcttg tgggagggg cggatctggt ggcggatcca cctctgagga acaatatcc  1200 accgtccagg agaagcaaca aaacatttcc cccctcgtgc gcgaacgggg cccacagagg  1260
gtcgccgctc acattacagg gaccaggggc cgcagcaata ccctgtccag cccgaactcc  1320
aaaaatgaga agcgctgggg cggaagatt aattcctggg aaagctccag aagcgggcac  1380
tccttcctca gcaatctgca tctgcgcaac ggggaactcg tgattcatga gaagggattc  1440
tattatatct attcccagac atacttccgc ttccaagagg aaattaaaga gaacactaaa  1500
aacgataaac aaatggttca atacatctac aaatatacct cttacccaga tcccatcctc  1560
ctcatgaaga gtgccagaaa ctcctgctgg tctaaggatg cggaatacgg attgtactcc  1620
atctatcaag ggggaatctt tgagttgaaa gaaaatgatc gcattttcgt gtccgtcacg  1680
aatgagcacc tcatagacat ggatcatgaa gcgagtttct tcggggcttt cctcgtgggt  1740
tga                                                                1743
```

<210> SEQ ID NO 41
<211> LENGTH: 1233
<212> TYPE: DNA
<213> ORGANISM: Artificial Sequence
<220> FEATURE:
<223> OTHER INFORMATION: scFvEGFR-MHD2

<400> SEQUENCE: 41

```
atggagacag acacactcct gctatgggta ctgctgctct ggttccagg ttccactggt    60 gacgcggccc agccggccat ggcggaagtg cagctggttg aaagcggcgg tggtctggtt   120
cagccgggtg gcagcctgcg tctgagctgt ggggcgagcg gctttagcct gaccaactat   180
ggcgtgcatt gggtgcgtca ggcaccgggc aaaggcctgg aatggctggg cgtgatttgg   240
```

| | |
|---|---:|
| agcggcggca acaccgatta taacaccccg tttaccagcc gttttaccat tagccgtgat | 300 |
| aacagcaaaa acaccctgta tctgcagatg aacagcctgc gtgcggaaga taccgcggtg | 360 |
| tattattgcg cgcgtgcgct gacctattat gattacgaat ttgcgtattg gggccagggc | 420 |
| accaccgtta cggtctcgag cggtggcggt ggtagcggtg gtggcggctc tggcggtggt | 480 |
| ggatccgata ttcagctgac ccagagcccg agctttctga gcgcgagcgt gggcgatcgt | 540 |
| gttaccatta cctgtcgtgc aagccagagc attggcacca acattcattg gtatcagcag | 600 |
| aaaccgggca aagcgccgaa actgctgatt aaatatgcga gcgaaagcat tagcggcgtg | 660 |
| ccgagccgtt ttagcggcag cggtagcggc accgaattta ccctgaccat tagcagcctg | 720 |
| cagccggaag attttgcgac ctattattgc cagcagaaca caactggcc gaccacctttt | 780 |
| ggtgcgggca ccaaactgga aattaaacgt ggaagcttag gaggctctgg cggagccgag | 840 |
| ctgccccta aggtgtccgt gttcgtgccc cccagggacg gcttcttcgg caaccccaga | 900 |
| aagagcaagc tgatctgcca ggccaccggc ttcagcccca gacagatcca ggtgtcctgg | 960 |
| ctgcgcgagg gcaaacaggt cggaagcggc gtgaccaccg accaggtgca ggccgaggcc | 1020 |
| aaagagagcg gccccaccac ctacaaagtg accagcaccc tgaccatcaa agagtccgac | 1080 |
| tggctgggcc agagcatgtt cacctgtcgg gtggaccacc ggggcctgac cttccagcag | 1140 |
| aacgccagct ctatgtgcgt gcccgacggc ggagggtccg gcggaggtac cggatccgaa | 1200 |
| ttcgcggccg cccaccatca tcaccatcac tga | 1233 |

<210> SEQ ID NO 42
<211> LENGTH: 1242
<212> TYPE: DNA
<213> ORGANISM: Artificial Sequence
<220> FEATURE:
<223> OTHER INFORMATION: MHD2-scFvHER2

<400> SEQUENCE: 42

| | |
|---|---:|
| atggagacag acacactcct gctatgggta ctgctgctct ggttccagg ttccactggt | 60 |
| gacgcggccc agccggccag cgctggcgcc ggaagcttag gaggctctgg cggagccgag | 120 |
| ctgccccta aggtgtccgt gttcgtgccc cccagggacg gcttcttcgg caaccccaga | 180 |
| aagagcaagc tgatctgcca ggccaccggc ttcagcccca gacagatcca ggtgtcctgg | 240 |
| ctgcgcgagg gcaaacaggt cggaagcggc gtgaccaccg accaggtgca ggccgaggcc | 300 |
| aaagagagcg gccccaccac ctacaaagtg accagcaccc tgaccatcaa agagtccgac | 360 |
| tggctgggcc agagcatgtt cacctgtcgg gtggaccacc ggggcctgac cttccagcag | 420 |
| aacgccagct ctatgtgcgt gcccgacggc ggagggtccg gcggaggtac cggatccggc | 480 |
| ggagaagtgc agctcgtcga agtggcggt ggacttgtgc agcctggcgg ttccctcaga | 540 |
| ctgtcctgtg ccgcgtcagg cttcaacatc aaggacacgt acatccactg ggtgaggcaa | 600 |
| gctcctggaa agggcttgga gtgggtcgct aggatctacc cgacgaacgg ctacaccagg | 660 |
| tacgctgact cagtgaaggg aaggttcacg atcagtgcag acaccagcaa gaacaccgca | 720 |
| tacctccaaa tgaactccct gagagccgag gacaccgccg tgtactactg ctctcgttgg | 780 |
| ggtggagatg gcttctacgc tatggactac tggggtcaag gcacactggt gaccgtgtcc | 840 |
| agtggtggcg gaggcagtgg cggaggtggc tcaggaggcg aaccggtga catccagatg | 900 |
| acccagtcac cctcaagcct cagtgccagc gtcggagata gagtgaccat aacgtgccga | 960 |
| gcttctcagg atgtgaacac ggcagtggct tggtatcagc aaaagccgg gaaagcccca | 1020 |
| aagctgctca tctactccgc atccttcctg tatagcggag ttccatctag gttctcaggc | 1080 |

```
tctaggtctg ggaccgactt cacgctgacg atctcctccc tgcaacctga ggacttcgcc      1140
acgtactact gccagcagca ctacacgact cctccaacct tcggtcaggg aacgaaggtc      1200
gagatcaagc gtgcggccgc ccaccatcat caccatcact aa                        1242
```

<210> SEQ ID NO 43
<211> LENGTH: 1962
<212> TYPE: DNA
<213> ORGANISM: Artificial Sequence
<220> FEATURE:
<223> OTHER INFORMATION: scFvEGFR-MHD2-scFvHER2

<400> SEQUENCE: 43

```
atggagacag acacactcct gctatgggta ctgctgctct gggttccagg ttccactggt        60
gacgcggccc agccggccat ggcggaagtg cagctggttg aaagcggcgg tggtctggtt       120
cagccgggtg gcagcctgcg tctgagctgt gcggcgagcg gctttagcct gaccaactat       180
ggcgtgcatt gggtgcgtca ggcaccgggc aaaggcctgg aatggctggg cgtgatttgg       240
agcggcggca acaccgatta taacaccccg tttaccagcc gttttaccat tagccgtgat       300
aacagcaaaa acaccctgta tctgcagatg aacagcctgc gtgcggaaga taccgcggtg       360
tattattgcg cgcgtgcgct gacctattat gattacgaat ttgcgtattg gggccagggc       420
accaccgtta cggtctcgag cggtggcggt ggtagcggtg gtggcggctc tggcggtggt       480
ggatccgata ttcagctgac ccagagcccg agctttctga gcgcgagcgt gggcgatcgt       540
gttaccatta cctgtcgtgc aagccagagc attggcacca acattcattg gtatcagcag       600
aaaccgggca aagcgccgaa actgctgatt aaatatgcga gcgaaagcat tagcggcgtg       660
ccgagccgtt ttagcggcag cggtagcggc accgaattta ccctgaccat tagcagcctg       720
cagccggaag attttgcgac ctattattgc agcagaaaca caactggcc gaccaccttt       780 ggtgcgggca ccaaactgga aattaaacgt ggaagcttag gaggctctgg cggagccgag       840 ctgccccta aggtgtccgt gttcgtgccc cccagggacg gcttcttcgg caaccccaga       900
aagagcaagc tgatctgcca ggccaccggc ttcagcccca cagagatcca ggtgtcctgg       960
ctgcgcgagg gcaaacaggt cggaagcggc gtgaccaccc accaggtgca ggccgaggcc      1020
aaagagagcg gccccaccac ctacaaagtg accagcaccc tgaccatcaa agagtccgac      1080
tggctgggcc agagcatgtt cacctgtcgg gtggaccacc ggggcctgac cttccagcag      1140
aacgccagct ctatgtgcgt gcccgacggc ggagggtccg gcggaggtac cggatccggc      1200
ggagaagtgc agctcgtcga aagtggcggt ggacttgtgc agcctggcgg ttccctcaga      1260
ctgtcctgtg ccgcgtcagg cttcaacatc aaggacacgt acatccactg ggtgaggcaa      1320
gctcctggaa agggcttgga gtgggtcgct aggatctacc cgacgaacgg ctacaccagg      1380
tacgctgact cagtgaaggg aaggttcacg atcagtgcag acaccagcaa gaacaccgca      1440
tacctccaaa tgaactccct gagagccgag acaccgccg tgtactactg ctctcgttgg      1500
ggtggagatg gcttctacgc tatggactac tggggtcaag gcacactggt gaccgtgtcc      1560
agtggtggcg gaggcagtgg cggaggtggc tcaggaggcg gaaccggtga catccagatg      1620
acccagtcac cctcaagcct cagtgccagc gtcggagata gtgtgaccat aacgtgccga      1680
gcttctcagg atgtgaacac ggcagtggct tggtatcagc aaaagcctgg gaaagcccca      1740
aagctgctca tctactccgc atccttcctg tatagcggag ttccatctag gttctcaggc      1800
tctaggtctg ggaccgactt cacgctgacg atctcctccc tgcaacctga ggacttcgcc      1860
```
acgtactact gccagcagca ctacacgact cctccaacct tcggtcaggg aacgaaggtc    1920
gagatcaagc gtgcggccgc ccaccatcat caccatcact ga    1962

<210> SEQ ID NO 44
<211> LENGTH: 1947
<212> TYPE: DNA
<213> ORGANISM: Artificial Sequence
<220> FEATURE:
<223> OTHER INFORMATION: MHD2-scTNF

<400> SEQUENCE: 44
atggagacag acacactcct gctatgggta ctgctgctct ggttccagg ttccactggt    60 gacgcggccc agccggccag cgctggcgcc ggaagcttag gaggctctgg cggagccgag    120
ctgcccccta aggtgtccgt gttcgtgccc cccagggacg gcttcttcgg caaccccaga    180
aagagcaagc tgatctgcca ggccaccggc ttcagcccca gacagatcca ggtgtcctgg    240
ctgcgcgagg gcaaacaggt cggaagcggc gtgaccaccg accaggtgca ggccgaggcc    300
aaagagagcg gccccaccac ctacaaagtg accagcaccc tgaccatcaa agagtccgac    360
tggctgggcc agagcatgtt cacctgtcgg gtggaccacc ggggcctgac cttccagcag    420
aacgccagct ctatgtgcgt gcccgacggc ggagggtccg gcggaggtac cggatccgaa    480
ttcatgagag atcgcatca ccatcaccat cacggatcag cgtcgtcttc ttctcgtacc    540
ccgtctgaca aaccggttgc tcacgttgtt gcaaacccgc aggctgaagg tcaactgcaa    600
tggctgaacc gtcgtgctaa cgctctgctg gctaacggtg ttgaactgcg tgacaaccag    660
ctggttgttc cgtctgaagg cctgtacctg atctactccc aggttctgtt caaaggccag    720
ggctgcccgt ccacccacgt tctgctgacc cacaccatct ctcgtatcgc tgtttcctac    780
cagaccaaag taaacctgct gtctgcaatc aaatctccgt gccagcgtga accccggaa    840 ggtgctgaag ctaaaccgtg gtacgaaccg atctacctgg tggcgttttt caactggag    900 aaaggtgacc gtctgtctgc agaaattaac cgtccggact acctggactt cgcagaatct    960
ggtcaggttt acttcggtat catagcgctg gtggaggtg ttcctcttc tcgtaccccg    1020 tctgacaaac cggttgctca cgttgttgca aacccgcagg ctgaaggtca actgcaatgg    1080
ctgaaccgtc gtgctaacgc tctgctggct aacggtgttg aactgcgtga caaccagctg    1140
gttgttccgt ctgaaggcct gtacctgatc tactcccagg ttctgttcaa aggccagggc    1200
tgcccgtcca cccacgttct gctgacccac accatctctc gtatcgctgt tcctaccag    1260 accaaagtaa acctgctgtc tgcaatcaaa tctccgtgcc agcgtgaaac cccggaaggt    1320
gctgaagcta aaccgtggta cgaaccgatc tacctgggtg gcgttttca actggagaaa    1380 ggtgaccgtc tgtctgcaga aattaaccgt ccggactacc tggacttcgc agaatctggt    1440
caggtttact tcggtatcat cgctctgggt ggtggaggat cctcttctcg taccccgtct    1500
gacaaaccgg ttgctcacgt tgttgcaaac ccgcaggctg aaggtcaact gcaatggctg    1560
aaccgtcgtg ctaacgctct gctggctaac ggtgttgaac tgcgtgacaa ccagctggtt    1620
gttccgtctg aaggcctgta cctgatctac tcccaggttc tgttcaaagg ccagggctgc    1680
ccgtccaccc acgttctgct gacccacacc atctctcgta tcgctgtttc ctaccagacc    1740
aaagtaaacc tgctgtctgc aatcaaatct ccgtgccagc gtgaaacccc ggaaggtgct    1800
gaagctaaac cgtggtacga accgatctac ctgggtggcg ttttcaact ggagaaaggt    1860 gaccgtctgt ctgcagaaat taaccgtccg gactacctgg acttcgcaga atctggtcag    1920
gtttacttcg gtatcatcgc tctgtga    1947

<210> SEQ ID NO 45
<211> LENGTH: 2667
<212> TYPE: DNA
<213> ORGANISM: Artificial Sequence
<220> FEATURE:
<223> OTHER INFORMATION: scFvEGFR-MHD2-scTNF

<400> SEQUENCE: 45

```
atggagacag acacactcct gctatgggta ctgctgctct gggttccagg ttccactggt      60
gacgcggccc agccggccat ggcggaagtg cagctggttg aaagcggcgg tggtctggtt     120
cagccgggtg gcagcctgcg tctgagctgt gcggcgagcg gctttagcct gaccaactat     180
ggcgtgcatt gggtgcgtca ggcaccgggc aaaggcctgg aatggctggg cgtgatttgg     240
agcggcggca acaccgatta taacaccccg tttaccagcc gttttaccat tagccgtgat     300
aacagcaaaa acaccctgta tctgcagatg aacagcctgc gtgcggaaga taccgcggtg     360
tattattgcg cgcgtgcgct gacctattat gattacgaat ttgcgtattg gggccagggc     420
accaccgtta cggtctcgag cggtggcggt ggtagcggtg gtggcggctc tggcggtggt     480
ggatccgata ttcagctgac ccagagcccg agctttctga gcgcgagcgt gggcgatcgt     540
gttaccatta cctgtcgtgc aagccagagc attggcacca acattcattg gtatcagcag     600
aaaccgggca aagcgccgaa actgctgatt aaatatgcga cgaaagcat tagcggcgtg     660
ccgagccgtt ttagcggcag cggtagcggc accgaattta ccctgaccat tagcagcctg     720
cagccggaag attttgcgac ctattattgc cagcagaaca caactggcc gaccaccttt     780
ggtgcgggca ccaaactgga aattaaacgt ggaagcttag gaggctctgg cggagccgag     840
ctgcccccta aggtgtccgt gttcgtgccc ccagggacg gcttcttcgg caaccccaga     900
aagagcaagc tgatctgcca ggccaccggc ttcagcccca cagatccag gtgtcctgg     960
ctgcgcgagg gcaaacaggt cggaagcggc gtgaccaccg accaggtgca ggccgaggcc    1020
aaagagagcg ccccaccac ctacaaagtg accagcaccc tgaccatcaa agagtccgac    1080
tggctgggcc agagcatgtt cacctgtcgg gtggaccacc ggggcctgac cttccagcag    1140
aacgccagct ctatgtgcgt gcccgacggc ggagggtccg gcggaggtac cggatccgaa    1200
ttcatgagag atcgcatca ccatcaccat cacggatcag cgtcgtcttc ttctcgtacc    1260
ccgtctgaca aaccggttgc tcacgttgtt gcaaacccgc aggctgaagg tcaactgcaa    1320
tggctgaacc gtcgtgctaa cgctctgctg gctaacggtg ttgaactgcg tgacaaccag    1380
ctggttgttc cgtctgaagg cctgtacctg atctactccc caggttctgtt caaaggccag    1440
ggctgcccgt ccacccacgt tctgctgacc cacaccatct ctcgtatcgc tgtttcctac    1500
cagaccaaag taaacctgct gtctgcaatc aaatctccgt gccagcgtga accccggaa    1560
ggtgctgaag ctaaaccgtg gtacgaaccg atctacctgg gtggcgtttt tcaactggag    1620
aaaggtgacc gtctgtctgc agaaattaac cgtccggact acctggactt cgcagaatct    1680
ggtcaggttt acttcggtat catagcgctg ggtggaggtg gttcctcttc tcgtaccccg    1740
tctgacaaac cggttgctca cgttgttgca aacccgcagg ctgaaggtca actgcaatgg    1800
ctgaaccgtc gtgctaacgc tctgctggct aacggtgttg aactgcgtga caaccagctg    1860
gttgttccgt ctgaaggcct gtacctgatc tactcccagg ttctgttcaa aggccagggc    1920
tgcccgtcca cccacgttct gctgacccac accatctctc gtatcgctgt ttcctaccag    1980
accaaagtaa acctgctgtc tgcaatcaaa tctccgtgcc agcgtgaaac cccggaaggt    2040
```

```
gctgaagcta aaccgtggta cgaaccgatc tacctgggtg gcgtttttca actggagaaa    2100
ggtgaccgtc tgtctgcaga aattaaccgt ccggactacc tggacttcgc agaatctggt    2160
caggtttact tcggtatcat cgctctgggt ggtggaggat cctcttctcg tacccgtct     2220 gacaaaccgg ttgctcacgt tgttgcaaac ccgcaggctg aaggtcaact gcaatggctg    2280
aaccgtcgtg ctaacgctct gctggctaac ggtgttgaac tgcgtgacaa ccagctggtt    2340
gttccgtctg aaggcctgta cctgatctac tcccaggttc tgttcaaagg ccagggctgc    2400
ccgtccaccc acgttctgct gacccacacc atctctcgta tcgctgtttc ctaccagacc    2460
aaagtaaacc tgctgtctgc aatcaaatct ccgtgccagc gtgaaacccc ggaaggtgct    2520
gaagctaaac cgtggtacga accgatctac ctgggtggcg ttttcaact ggagaaaggt     2580 gaccgtctgt ctgcagaaat taaccgtccg gactacctgg acttcgcaga atctggtcag    2640
gtttacttcg gtatcatcgc tctgtga                                        2667

<210> SEQ ID NO 46
<211> LENGTH: 2175
<212> TYPE: DNA
<213> ORGANISM: Artificial Sequence
<220> FEATURE:
<223> OTHER INFORMATION: MHD2-scTRAIL

<400> SEQUENCE: 46
atggactgga cctggcgcgt gttttgcctg ctcgccgtgg ctcctggggc ccacagcctc      60
gacgattaca agacgatga cgataaagaa ttcgccgagc tgccccctaa ggtgtccgtg     120
ttcgtgcccc ccagggacgg cttcttcggc aaccccagaa agagcaagct gatctgccag     180
gccaccggct tcagccccag acagatccag gtgtcctggc tgcgcgaggg caaacaggtc     240
ggaagcggcg tgaccaccga ccaggtgcag gccgaggcca agagagcgg ccccaccacc      300 tacaaagtga ccagcaccct gaccatcaaa gagtccgact ggctgggcca gagcatgttc     360
acctgtcggg tggaccaccg gggcctgacc ttccagcaga cgccagctc tatgtgcgtg     420 cccgacgaat tcacgcgtgg caccagcgag gaaaccatta gcaccgtcca ggaaaagcag     480
cagaacatca gccccctggt ccgggagaga ggccccagaa gagtcgccgc ccacatcacc     540
ggcacccggg gcagaagcaa cacccctgagc agccccaaca gcaagaacga aaggccctg     600 ggccggaaga tcaacagctg ggagagcagc agaagcggcc acagctttct gagcaacctg     660
cacctgcgga acggcgagct ggtcatccac gagaagggct tctactacat ctacagccag     720
acctacttca gattccaaga agagatcaaa gagaacacca gaacgacaa gcagatggtg     780 cagtacatct acaagtacac cagctacccc gaccccatcc tgctgatgaa gtccgcccgg    840
aacagctgct ggtccaagga cgccgagtac ggcctgtaca gcatctacca gggcggcatc    900
ttcgagctga agagaacga ccggatcttc gtgagcgtga ccaacgagca cctgatcgac    960
atggaccacg aggccagctt tttcggcgca ttcctggtcg gcgaggggg atccggcgga   1020 ggaagcacct ccgaagagac tatctctaca gtccaggaaa acagcagaa tatctcccct   1080 ctcgtgcggg agcggggacc tcagcgggtg ccgcccata ttacaggcac aagaggccgg     1140
tccaacaccc tgtcctcccc caactctaag aatgaaaagg ccctcgggag aaagatcaac    1200
tcctgggagt ccagccgctc cggccactcc tttctgtcca atctgcacct gagaaatggg     1260
gagctggtca ttcacgaaaa gggggtttttac tatatctact ctcagacata ctttaggttt    1320
caggaagaaa ttaagaaaaa tacaagaat gataaacaga tggtccagta tatctataaa     1380
tacacttcct accctgatcc tattctgctg atgaaaagcg ccagaaacag ctgttggagc    1440
```

```
aaggatgccg aatatgggct ctactctatc taccagggggg ggattttttga acttaaggag    1500 aatgacagaa tctttgtgtc tgtgacaaat gagcatctga ttgatatgga tcacgaagcc    1560
tcattctttg gagcctttct tgtgggaggg ggcggatctg gtggcggatc cacctctgag    1620
gaaacaatat ccaccgtcca ggagaagcaa caaaacattt cccccctcgt gcgcgaacgg    1680
ggcccacaga gggtcgccgc tcacattaca gggaccaggg gccgcagcaa taccctgtcc    1740
agcccgaact ccaaaaatga aaagcgctg ggcggaaga ttaattcctg gaaagctcc    1800 agaagcgggc actccttcct cagcaatctg catctgcgca acggggaact cgtgattcat    1860
gagaagggat tctattatat ctattcccag acatacttcc gcttccaaga ggaaattaaa    1920
gagaacacta aaaacgataa acaaatggtt caatacatct acaaatatac ctcttaccca    1980
gatcccatcc tcctcatgaa gagtgccaga aactcctgct ggtctaagga tgcggaatac    2040
ggattgtact ccatctatca agggggaatc tttgagttga agaaaatga tcgcattttc    2100 gtgtccgtca cgaatgagca cctcatagac atggatcatg aagcgagttt cttcggggct    2160
ttcctcgtgg gttga                                                    2175

<210> SEQ ID NO 47
<211> LENGTH: 2937
<212> TYPE: DNA
<213> ORGANISM: Artificial Sequence
<220> FEATURE:
<223> OTHER INFORMATION: scFvEGFR-MHD2-scTRAIL

<400> SEQUENCE: 47
atggagacag acacactcct gctatgggta ctgctgctct gggttccagg ttccaccggt      60
gactacaaag acgatgacga taaaggcggt ggcggatcag cggcccagcc ggccatggcg    120
gaagtgcagc tggttgaaag cggcggtggt ctggttcagc cgggtggcag cctgcgtctg    180
agctgtgcgg cgagcggctt tagcctgacc aactatggcg tgcattgggt gcgtcaggca    240
ccgggcaaag gcctggaatg gctgggcgtg atttggagcg gcggcaacac cgattataac    300
accccgttta ccagccgttt taccattagc cgtgataaca gcaaaaacac cctgtatctg    360
cagatgaaca gcctgcgtgc ggaagatacc gcggtgtatt attgcgcgcg tgcgctgacc    420
tattatgatt acgaatttgc gtattggggc cagggcacca ccgttacggt ctcgagcggt    480
ggcggtggta gcggtggtgg cggctctggc ggtggtggat ccgatattca gctgacccag    540
agcccgagct ttctgagcgc gagcgtgggc gatcgtgtta ccattacctg tcgtgcaagc    600
cagagcattg caccaacat tcattggtat cagcagaaac cgggcaaagc gccgaaactg    660
ctgattaaat atgcgagcga aagcattagc ggcgtgccga ccgttttag cggcagcggt    720 agcggcaccg aatttaccct gaccattagc agcctgcagc cggaagattt tgcgacctat    780
tattgccagc agaacaacaa ctggccgacc acctttggtg cgggcaccaa actggaaatt    840
aaacgtgcgg ccgcagccga gctgccccct aaggtgtccg tgttcgtgcc cccagggac    900 ggcttcttcg caaccccag aaagagcaag ctgatctgcc aggccaccgg cttcagcccc    960
agacagatcc aggtgtcctg gctgcgcgag ggcaaacagg tcggaagcgg cgtgaccacc   1020
gaccaggtgc aggccgaggc caaagagagc ggccccacca cctacaaagt gaccagcacc   1080
ctgaccatca agagtccga ctggctgggc cagagcatgt tcacctgtcg ggtggaccac   1140
cggggcctga ccttccagca gaacgccagc tctatgtgcg tgcccgacga attcacgcgt   1200
ggcaccagcg aggaaaccat tagcaccgtc caggaaaagc agcagaacat cagcccctg   1260
```

| | |
|---|---:|
| gtccgggaga gaggccccca gagagtcgcc gcccacatca ccggcacccg ggcagaagc | 1320 |
| aacaccctga gcagcccaa cagcaagaac gagaaggccc tgggccggaa gatcaacagc | 1380 |
| tgggagagca gcagaagcgg ccacagcttt ctgagcaacc tgcacctgcg aacggcgag | 1440 |
| ctggtcatcc acgagaaggg cttctactac atctacagcc agacctactt cagattccaa | 1500 |
| gaagagatca aagagaacac caagaacgac aagcagatgg tgcagtacat ctacaagtac | 1560 |
| accagctacc ccgaccccat cctgctgatg aagtccgccc ggaacagctg ctggtccaag | 1620 |
| gacgccgagt acggcctgta cagcatctac cagggcggca tcttcgagct gaaagagaac | 1680 |
| gaccggatct tcgtgagcgt gaccaacgag caccctgatcg acatggacca cgaggccagc | 1740 |
| tttttcggcg cattcctggt cggcggaggg ggatccggcg aggaagcac ctccgaagag | 1800 |
| actatctcta cagtccagga aaaacagcag aatatctccc ctctcgtgcg ggagcgggga | 1860 |
| cctcagcggg tggccgccca tattacaggc acaagaggcc ggtccaacac cctgtcctcc | 1920 |
| cccaactcta agaatgaaaa ggccctcggg agaaagatca actcctggga gtccagccgc | 1980 |
| tccggccact cctttctgtc caatctgcac ctgagaaatg gggagctggt cattcacgaa | 2040 |
| aaggggtttt actatatcta ctctcagaca tactttaggt ttcaggaaga aattaaagaa | 2100 |
| aatacaaaga atgataaaca gatggtccag tatatctata atacacttc ctaccctgat | 2160 |
| cctattctgc tgatgaaaag cgccagaaac agctgttgga gcaaggatgc cgaatatggg | 2220 |
| ctctactcta tctaccaggg ggggattttt gaacttaagg agaatgacag aatctttgtg | 2280 |
| tctgtgacaa atgagcatct gattgatatg gatcacgaag cctcattctt tggagccttt | 2340 |
| cttgtgggag gggcggatc tggtggcgga tccacctctg aggaaacaat atccaccgtc | 2400 |
| caggagaagc aacaaaacat ttccccctc gtgcgcgaac ggggcccaca gagggtcgcc | 2460 |
| gctcacatta cagggaccag gggccgcagc aatatccctgt ccagcccgaa ctccaaaaat | 2520 |
| gagaaagcgc tggggcggaa gattaattcc tgggaaagct ccagaagcgg gcactccttc | 2580 |
| ctcagcaatc tgcatctgcg caacggggaa tcgtgattc atgagaaggg attctattat | 2640 |
| atctattccc agacatactt ccgcttccaa gaggaaatta agagaacac taaaaacgat | 2700 |
| aaacaaatgg ttcaatacat ctacaaatat acctcttacc cagatcccat cctcctcatg | 2760 |
| aagagtgcca gaaactcctg ctggtctaag gatgcggaat acggattgta ctccatctat | 2820 |
| caagggggaa tctttgagtt gaagaaaaat gatcgcattt tcgtgtccgt cacgaatgag | 2880 |
| cacctcatag acatggatca tgaagcgagt ttcttcgggg ctttcctcgt gggttga | 2937 |

<210> SEQ ID NO 48
<211> LENGTH: 3654
<212> TYPE: DNA
<213> ORGANISM: Artificial Sequence
<220> FEATURE:
<223> OTHER INFORMATION: scDbEpCAMxEGFR-MHD2-scTRAIL

<400> SEQUENCE: 48

| | |
|---|---:|
| atggagacag acacactcct gctatgggta ctgctgctct ggttccagg ttccaccggt | 60 |
| gactacaaag acgatgacga taaaggcggt ggcggatcag cggcccagcc ggccatggct | 120 |
| gaagtgcagc tggtgcagag cggacctggc ctggtgcagc tggcggatc tgtgcggatc | 180 |
| agctgtgccg ccagcggcta caccttcacc aactacggca tgaactgggt caagcaggct | 240 |
| ccaggcaagg gcctggaatg gatgggctgg atcaacacct acaccggcga gagcacctac | 300 |
| gccgacagct tcaagggccg gttcaccttc agcctggaca cctctgccag cgccgcctac | 360 |
| ctgcagatca actctctgcg ggccgaggac accgccgtgt actactgcgc cagattcgcc | 420 |

```
atcaagggcg actactgggg ccagggcacc ctgctgacag tctcgagtgg cggtggcgga    480
tcggatattc agctgaccca gagcccgagc tttctgagcg cgagcgtggg cgatcgtgtt    540
accattacct gtcgtgcaag ccagagcatt ggcaccaaca ttcattggta tcagcagaaa    600
ccgggcaaag cgccgaaact gctgattaaa tatgcgagcg aaagcattag cggcgtgccg    660
agccgtttta gcggcagcgg tagcggcacc gaatttaccc tgaccattag cagcctgcag    720
ccggaagatt ttgcgaccta ttattgccag cagaacaaca actggccgac cacctttggt    780
gcgggcacca aactggaaat taaacgtgga ggcggtggca gcggtgggcg cgcctcgggc    840
ggaggtggct cagaagtgca gctggttgaa gccggcggtg gtctggttca gccgggtggc    900
agcctgcgtc tgagctgtgc ggcgagcggc tttagcctga ccaactatgg cgtgcattgg    960
gtgcgtcagg caccgggcaa aggcctggaa tggctgggcg tgatttggag cggcggcaac   1020
accgattata cacccgtt taccagccgt tttaccatta gccgtgataa cagcaaaaac    1080
accctgtatc tgcagatgaa cagcctgcgt gcggaagata ccgcggtgta ttattgcgcg   1140
cgtgcgctga cctattatga ttacgaattt gcgtattggg gccagggcac caccgttacg   1200
gtctctagcg gaggcggggg atccgacatc cagatgaccc agagcccag cagcctgagc    1260 gccagcgtgg gcgacagagt gaccatcacc tgtcggagca ccaagagcct gctgcacagc   1320
aacggcatca cctacctgta ctggtatcag cagaagcccg gcaaggcccc caagctgctg   1380
atctaccaga tgagcaacct ggccagcggc gtgcccagca gattcagcag cagcggcagc   1440
ggcaccgact caccctgac catcagcagc ctgcagcctg aggacttcgc cacctactac    1500
tgtgcccaga acctggaaat ccccggacc ttcggacagg gcaccaaggt ggaactgaag    1560
agagcggccg cagccgagct gccccctaag gtgtccgtgt tcgtgccccc cagggacggc   1620
ttcttcggca accccagaaa gagcaagctg atctgccagg ccaccggctt cagccccaga   1680
cagatccagg tgtcctggct gcgcgagggc aaacaggtcg aagcggcgt gaccaccgac    1740 caggtgcagg ccgaggccaa agagagcggc cccaccacct acaaagtgac cagcaccctg   1800
accatcaaag agtccgactg gctgggccag agcatgttca cctgtcgggt ggaccaccgg   1860
ggcctgacct tccagcagaa cgccagctct atgtgcgtgc ccgacgaatt cacgcgtggc   1920
accagcgagg aaaccattag caccgtccag gaaaagcagc agaacatcag cccctggtc    1980 cgggagagag cccccagag agtcgccgcc cacatcaccg gcacccgggg cagaagcaac   2040
accctgagca gccccaacag caagaacgag aaggccctgg ccggaagat caacagctgg    2100 gagagcagca gaagcggcca cagctttctg agcaacctgc acctgcggaa cggcgagctg   2160
gtcatccacg agaagggctt ctactacatc tacagccaga cctacttcag attccaagaa   2220
gagatcaaag agaacaccaa gaacgacaag cagatggtgc agtacatcta caagtacacc   2280
agctaccccg accccatcct gctgatgaag tccgcccgga acagctgctg gtccaaggac   2340
gccgagtacg gcctgtacag catctaccag ggcggcatct tcgagctgaa agagaacgac   2400
cggatcttcg tgagcgtgac caacgagcac ctgatcgaca tggaccacga ggccagcttt   2460
ttcggcgcat tcctggtcgg cggagggga tccggcggag aagcacctc cgaagagact    2520 atctctacag tccaggaaaa acagcagaat atctcccctc tcgtgcggga gcgggacct    2580 cagcgggtgg ccgcccatat tacaggcaca agaggccggt ccaacaccct gtcctcccc    2640 aactctaaga atgaaaaggc cctcgggaga aagatcaact cctgggagtc cagccgctcc   2700
ggccactcct ttctgtccaa tctgcacctg agaaatgggg agctggtcat tcacgaaaag   2760
```

| | |
|---|---|
| gggttttact atatctactc tcagacatac tttaggtttc aggaagaaat taaagaaaat | 2820 |
| acaaagaatg ataaacagat ggtccagtat atctataaat acacttccta ccctgatcct | 2880 |
| attctgctga tgaaaagcgc cagaaacagc tgttggagca aggatgccga atatgggctc | 2940 |
| tactctatct accaggggg gattttttgaa cttaaggaga atgacagaat ctttgtgtct | 3000 |
| gtgacaaatg agcatctgat tgatatggat cacgaagcct cattctttgg agcctttctt | 3060 |
| gtgggagggg gcggatctgg tggcggatcc acctctgagg aaacaatatc caccgtccag | 3120 |
| gagaagcaac aaaacatttc ccccctcgtg cgcgaacggg gcccacagag ggtcgccgct | 3180 |
| cacattacag ggaccagggg ccgcagcaat accctgtcca gcccgaactc caaaaatgag | 3240 |
| aaagcgctgg ggcggaagat taattcctgg gaaagctcca gaagcgggca ctccttcctc | 3300 |
| agcaatctgc atctgcgcaa cggggaactc gtgattcatg agaagggatt ctattatatc | 3360 |
| tattcccaga catacttccg cttccaagag gaaattaaag agaacactaa aaacgataaa | 3420 |
| caaatggttc aatacatcta caaatatacc tcttacccag atcccatcct cctcatgaag | 3480 |
| agtgccagaa actcctgctg gtctaaggat gcggaatacg gattgtactc catctatcaa | 3540 |
| gggggaatct ttgagttgaa agaaaatgat cgcattttcg tgtccgtcac gaatgagcac | 3600 |
| ctcatagaca tggatcatga agcgagtttc ttcggggctt cctcgtggg ttga | 3654 |

<210> SEQ ID NO 49
<211> LENGTH: 1218
<212> TYPE: DNA
<213> ORGANISM: Artificial Sequence
<220> FEATURE:
<223> OTHER INFORMATION: scFvEGFR-EHD2

<400> SEQUENCE: 49

| | |
|---|---|
| atggagacag acacactcct gctatgggta ctgctgctct ggttccagg ttccactggt | 60 |
| gacgcggccc agccggccat ggcggaagtg cagctggttg aaagcggcgg tggtctggtt | 120 |
| cagccgggtg gcagcctgcg tctgagctgt gcggcgagcg gctttagcct gaccaactat | 180 |
| ggcgtgcatt gggtgcgtca ggcaccgggc aaaggcctgg aatggctggg cgtgatttgg | 240 |
| agcggcggca acaccgatta taacaccccg tttaccagcc gttttaccat tagccgtgat | 300 |
| aacagcaaaa acaccctgta tctgcagatg aacagcctgc gtgcggaaga taccgcggtg | 360 |
| tattattgcg cgcgtgcgct gacctattat gattacgaat ttgcgtattg gggccagggc | 420 |
| accaccgtta cggtctcgag cggtggcggt ggtagcggtg gtgcggctc tggcggtggt | 480 |
| ggatccgata ttcagctgac ccagagcccg agctttctga cgcgagcgt gggcgatcgt | 540 |
| gttaccatta cctgtcgtgc aagccagagc attggcacca acattcattg gtatcagcag | 600 |
| aaaccgggca agcgccgaa actgctgatt aaatatgcga cgaaagcat tagcggcgtg | 660 |
| ccgagccgtt ttagcggcag cggtagcggc accgaattta ccctgaccat tagcagcctg | 720 |
| cagccggaag attttgcgac ctattattgc cagcagaaca caactggcc gaccaccttt | 780 |
| ggtgcgggca ccaaactgga aattaaacgt ggaagcttag gcggctctgg cggcgatttc | 840 |
| accccccccca cagtgaagat cctccagagc agctgtgacg gcggaggcca cttcccacct | 900 |
| accatccagc tgctgtgtct ggtgtccggc tacacccccg gcaccatcaa catcacctgg | 960 |
| ctggaagatg gacaagtgat ggacgtggac ctgagcaccg ccagcaccac acaggaaggc | 1020 |
| gagctggcct ctacccagag cgagctgaca ctgagccaga agcactggct gagcgaccgg | 1080 |
| acctacacct gtcaagtgac ctaccagggc cacaccttcg aggacagcac caagaagtgc | 1140 |
| gccgacagca acggggagg atctggcgga ggtaccggat ccgaattcgc ggccgcccac | 1200 | catcatcacc atcactaa                                                      1218

<210> SEQ ID NO 50
<211> LENGTH: 2196
<212> TYPE: DNA
<213> ORGANISM: Artificial Sequence
<220> FEATURE:
<223> OTHER INFORMATION: EHD2-scTRAIL

<400> SEQUENCE: 50

```
atggagacag acacactcct gctatgggta ctgctgctct gggttccagg ttccaccggt      60
gactacaaag acgatgacga taaaggcggt ggcggatcag cggcccagcc ggccgatttc     120
accccccca cagtgaagat cctccagagc agctgtgacg gcggaggcca cttcccacct     180
accatccagc tgctgtgtct ggtgtccggc tacacccccg caccatcaa catcacctgg     240
ctggaagatg acaagtgat ggacgtggac ctgagcaccg ccagcaccac acaggaaggc     300
gagctggcct ctacccagag cgagctgaca ctgagccaga agcactggct gagcgaccgg     360
acctacacct gtcaagtgac ctaccagggc cacaccttcg aggacagcac caagaagtgc     420
gccgacagca cggggggaag cggcggtgaa ttcacgcgtg caccagcga ggaaaccatt     480
agcaccgtcc aggaaaagca gcagaacatc agcccctgg tccgggagag aggcccccag     540
agagtcgccg cccacatcac cggcacccgg ggcagaagca cacccctgag cagccccaac     600
agcaagaacg agaaggccct gggccggaag atcaacagct gggagagcag cagaagcggc     660
cacagctttc tgagcaacct gcacctgcgg aacggcgagc tggtcatcca cgagaagggc     720
ttctactaca tctacagcca gacctacttc agattccaag aagagatcaa agagaacacc     780
aagaacgaca gcagatggt gcagtacatc tacaagtaca ccagctaccc cgaccccatc     840
ctgctgatga agtccgcccg aacagctgc tggtccaagg acgccgagta cggcctgtac     900
agcatctacc agggcggcat cttcgagctg aaagagaacg accggatctt cgtgagcgtg     960
accaacgagc acctgatcga catggaccac gaggccagct ttttcggcgc attcctggtc    1020
ggcgaggg gatccggcgg aggaagcacc tccgaagaga ctatctctac agtccaggaa    1080
aaacagcaga atatctcccc tctcgtgcgg gagcgggac ctcagcgggt ggccgcccat    1140
attacaggca agaggccg gtccaacacc ctgtcctccc ccaactctaa gaatgaaaag    1200
gccctcggga gaaagatcaa ctcctgggag tccagccgct ccggccactc ctttctgtcc    1260
aatctgcacc tgagaaatgg ggagctggtc attcacgaaa agggttttta ctatatctac    1320
tctcagacat actttaggtt tcaggaagaa attaaagaaa tacaaagaa tgataaacag    1380
atggtccagt atatctataa atacacttcc taccctgatc ctattctgct gatgaaaagc    1440
gccagaaaca gctgttggag caaggatgcc gaatatgggc tctactctat ctaccagggg    1500
gggattttg aacttaagga gaatgacaga atctttgtgt ctgtgacaaa tgagcatctg    1560
attgatatgg atcacgaagc ctcattcttt ggagcctttc ttgtgggagg ggcggatct    1620
ggtggcggat ccacctctga ggaaacaata tccaccgtcc aggagaagca caaaacatt    1680
tcccccctcg tgcgcgaacg gggcccacag agggtcgccg ctcacattac agggaccagg    1740
ggccgcagca tacccctgtc cagcccgaac tccaaaaatg agaaagcgct ggggcggaag    1800
attaattcct gggaaagctc cagaagcggg cactccttcc tcagcaatct gcatctgcgc    1860
aacgggaac tcgtgattca tgagaaggga ttctattata tctattccca gacatacttc    1920
cgcttccaag aggaaattaa agagaacact aaaaacgata aacaaatggt tcaatacatc    1980
```

| | |
|---|---|
| tacaaatata cctcttaccc agatcccatc ctcctcatga agagtgccag aaactcctgc | 2040 |
| tggtctaagg atgcggaata cggattgtac tccatctatc aagggggaat ctttgagttg | 2100 |
| aaagaaaatg atcgcatttt cgtgtccgtc acgaatgagc acctcataga catggatcat | 2160 |
| gaagcgagtt tcttcggggc tttcctcgtg ggttga | 2196 |

<210> SEQ ID NO 51
<211> LENGTH: 2952
<212> TYPE: DNA
<213> ORGANISM: Artificial Sequence
<220> FEATURE:
<223> OTHER INFORMATION: scFvEGFR-EHD2-scTRAIL

<400> SEQUENCE: 51

| | |
|---|---|
| atggagacag acacactcct gctatgggta ctgctgctct ggttccagg ttccaccggt | 60 |
| gactacaaag acgatgacga taaaggcggt ggcggatcag cggcccagcc ggccatggcg | 120 |
| gaagtgcagc tggttgaaag cggcggtggt ctggttcagc cgggtggcag cctgcgtctg | 180 |
| agctgtgcgg cgagcggctt tagcctgacc aactatggcg tgcattgggt gcgtcaggca | 240 |
| ccgggcaaag gcctggaatg gctgggcgtg atttggagcg gcggcaacac cgattataac | 300 |
| accccgttta ccagccgttt taccattagc cgtgataaca gcaaaaacac cctgtatctg | 360 |
| cagatgaaca gcctgcgtgc ggaagatacc gcggtgtatt attgcgcgcg tgcgctgacc | 420 |
| tattatgatt acgaatttgc gtattggggc cagggcacca ccgttacggt ctcgagcggt | 480 |
| ggcggtggta gcggtggtgg cggctctggc ggtggtggat ccgatattca gctgacccag | 540 |
| agcccgagct ttctgagcgc gagcgtgggc gatcgtgtta ccattacctg tcgtgcaagc | 600 |
| cagagcattg gcaccaacat tcattggtat cagcagaaac cgggcaaagc gccgaaactg | 660 |
| ctgattaaat atgcgagcga aagcattagc ggcgtgccga ccgttttag cggcagcggt | 720 |
| agcggcaccg aatttaccct gaccattagc agcctgcagc cggaagattt tgcgacctat | 780 |
| tattgccagc agaacaacaa ctggccgacc acctttggtg cgggcaccaa actggaaatt | 840 |
| aaacgtgcgg ccgcaggagg ctctggcggt gatttcaccc cccccacagt gaagatcctc | 900 |
| cagagcagct gtgacggcgg aggccacttc ccacctacca tccagctgct gtgtctggtg | 960 |
| tccggctaca cccccggcac catcaacatc acctggctgg aagatggaca agtgatggac | 1020 |
| gtggacctga gcaccgccag caccacacag gaaggcgagc tggcctctac ccagagcgag | 1080 |
| ctgacactga gccagaagca ctggctgagc gaccggacct acacctgtca agtgacctac | 1140 |
| cagggccaca ccttcgagga cagcaccaag aagtgcgccg acagcaacgg ggaagcggc | 1200 |
| ggtgaattca cgcgtggcac cagcgaggaa accattagca ccgtccagga aaagcagcag | 1260 |
| aacatcagcc cctggtccg ggagagaggc cccagagag tcgccgccca catcaccggc | 1320 |
| acccggggca gaagcaacac cctgagcagc cccaacagca gaacgagaa ggccctgggc | 1380 |
| cggaagatca cagctggga gagcagcaga agcggccaca gctttctgag caacctgcac | 1440 |
| ctgcggaacg gcgagctggt catccacgag aagggcttct actacatcta cagccagacc | 1500 |
| tacttcagat tccaagaaga gatcaaagag aacaccaaga acgacaagca gatggtgcag | 1560 |
| tacatctaca gtacaccag ctaccccgac cccatcctgc tgatgaagtc cgcccggaac | 1620 |
| agctgctggt ccaaggacgc cgagtacggc ctgtacagca tctaccaggg cggcatcttc | 1680 |
| gagctgaaag agaacgaccg gatcttcgtg agcgtgacca acgagcacct gatcgacatg | 1740 |
| gaccacgagg ccagcttttt cggcgcattc ctggtcggcg aggggggatc cggcggagga | 1800 |
| agcacctccg aagagactat ctctacagtc caggaaaaac agcagaatat ctcccctctc | 1860 |

```
gtgcgggagc gggaccctca gcggtggcc gcccatatta caggcacaag aggccggtcc    1920
aacaccctgt cctcccccaa ctctaagaat gaaaaggccc tcgggagaaa gatcaactcc    1980
tgggagtcca gccgctccgg ccactccttt ctgtccaatc tgcacctgag aaatggggag    2040
ctggtcattc acgaaaaggg gttttactat atctactctc agacatactt taggtttcag    2100
gaagaaatta agaaaatac aaagaatgat aaacagatgg tccagtatat ctataaatac    2160
acttcctacc ctgatcctat tctgctgatg aaaagcgcca gaaacagctg ttggagcaag    2220
gatgccgaat atgggctcta ctctatctac caggggggga ttttgaact taaggagaat    2280 gacagaatct ttgtgtctgt gacaaatgag catctgattg atatggatca cgaagcctca    2340
ttctttggag cctttcttgt gggagggggc ggatctggtg gcggatccac ctctgaggaa    2400
acaatatcca ccgtccagga gaagcaacaa aacatttccc ccctcgtgcg cgaacggggc    2460
ccacagaggg tcgccgctca cattacaggg accaggggcc gcagcaatac cctgtccagc    2520
ccgaactcca aaaatgagaa agcgctgggg cggaagatta ttcctggga aagctccaga    2580 agcgggcact ccttcctcag caatctgcat ctgcgcaacg gggaactcgt gattcatgag    2640
aagggattct attatatcta ttcccagaca tacttccgct tccaagagga aattaaagag    2700
aacactaaaa acgataaaca aatggttcaa tacatctaca aatatacctc ttacccagat    2760
cccatcctcc tcatgaagag tgccagaaac tcctgctggt ctaaggatgc ggaatacgga    2820
ttgtactcca tctatcaagg gggaatcttt gagttgaaag aaaatgatcg cattttcgtg    2880
tccgtcacga atgagcacct catagacatg gatcatgaag cgagtttctt cggggctttc    2940
ctcgtgggtt ga                                                        2952

<210> SEQ ID NO 52
<211> LENGTH: 14
<212> TYPE: PRT
<213> ORGANISM: Artificial Sequence
<220> FEATURE:
<223> OTHER INFORMATION: Linker

<400> SEQUENCE: 52

Gly Gly Cys Gly Ser Gly Gly Gly Ser Gly Gly Ser Ala
1               5                   10

<210> SEQ ID NO 53
<211> LENGTH: 1218
<212> TYPE: DNA
<213> ORGANISM: Artificial Sequence
<220> FEATURE:
<223> OTHER INFORMATION: Anti-CEA scFv-EHD2

<400> SEQUENCE: 53
atggagacag acacactcct gctatgggta ctgctgctct gggttccagg ttccactggt      60
gacgcggccc agccggccat ggcccaggtg aaactgcagc agtctggggc agaacttgtg     120
aggtcaggga cctcagtcaa gttgtcctgc acagcttctg cttcaacat aaagactcc      180 tatatgcact ggttgaggca ggggcctgaa cagggcctgg agtggattgg atggattgat     240
cctgagaatg gtgatactga atatgcccg aagttccagg caaggccac ttttactaca      300 gacacatcct ccaacacagc ctacctgcag ctcagcagcc tgacatctga ggacactgcc    360
gtctattatt gtaatgaggg gactccgact gggccgtact actttgacta ctggggccaa    420
gggaccacgg tcaccgtctc ctcaggtgga ggcggttcag gggaggtgg atccggtgga    480 ggcggttcag acatcgagct cacccagtct ccagcaatca tgtctgcatc tccaggggag    540
```

```
aaagtcacca taacctgcag tgccagctca agtgtaagtt acatgcactg gttccagcag    600
aagccaggca cttctcccaa actctggatt tatagcacat ccaacctggc ttctggagtc    660
cctgctcgct tcagtggcag tggatctggg acctcttact ctctcacaat cagccgaatg    720
gaggctgaag atgctgccac ttattactgc agcaaagga gtagttaccc actcacgttc    780
ggtgctggca ccaagctgga gctgaaacgg ggaagcttag gcggctctgg cggcgatttc    840 accccccca cagtgaagat cctccagagc agctgtgacg gcggaggcca cttcccacct    900
accatccagc tgctgtgtct ggtgtccggc tacaccccg gcaccatcaa catcacctgg    960
ctggaagatg gacaagtgat ggacgtggac ctgagcaccg ccagcaccac acaggaaggc    1020
gagctggcct ctacccagag cgagctgaca ctgagccaga agcactggct gagcgaccgg    1080
acctacacct gtcaagtgac ctaccagggc cacaccttcg aggacagcac caagaagtgc    1140
gccgacagca acggggagg atctggcgga ggtaccggat ccgaattcgc ggccgcccac    1200
catcatcacc atcactaa                                                  1218
```

<210> SEQ ID NO 54
<211> LENGTH: 405
<212> TYPE: PRT
<213> ORGANISM: Artificial Sequence
<220> FEATURE:
<223> OTHER INFORMATION: Anti-CEA scFv-EHD2

<400> SEQUENCE: 54

```
Met Glu Thr Asp Thr Leu Leu Leu Trp Val Leu Leu Leu Trp Val Pro
1               5                   10                  15

Gly Ser Thr Gly Asp Ala Ala Gln Pro Ala Met Ala Gln Val Lys Leu
            20                  25                  30

Gln Gln Ser Gly Ala Glu Leu Val Arg Ser Gly Thr Ser Val Lys Leu
        35                  40                  45

Ser Cys Thr Ala Ser Gly Phe Asn Ile Lys Asp Ser Tyr Met His Trp
    50                  55                  60

Leu Arg Gln Gly Pro Glu Gln Gly Leu Glu Trp Ile Gly Trp Ile Asp
65                  70                  75                  80

Pro Glu Asn Gly Asp Thr Glu Tyr Ala Pro Lys Phe Gln Gly Lys Ala
                85                  90                  95

Thr Phe Thr Thr Asp Thr Ser Ser Asn Thr Ala Tyr Leu Gln Leu Ser
            100                 105                 110

Ser Leu Thr Ser Glu Asp Thr Ala Val Tyr Tyr Cys Asn Glu Gly Thr
        115                 120                 125

Pro Thr Gly Pro Tyr Tyr Phe Asp Tyr Trp Gly Gln Gly Thr Thr Val
    130                 135                 140

Thr Val Ser Ser Gly Gly Gly Gly Ser Gly Gly Gly Gly Ser Gly Gly
145                 150                 155                 160

Gly Gly Ser Asp Ile Glu Leu Thr Gln Ser Pro Ala Ile Met Ser Ala
                165                 170                 175

Ser Pro Gly Glu Lys Val Thr Ile Thr Cys Ser Ala Ser Ser Ser Val
            180                 185                 190

Ser Tyr Met His Trp Phe Gln Gln Lys Pro Gly Thr Ser Pro Lys Leu
        195                 200                 205

Trp Ile Tyr Ser Thr Ser Asn Leu Ala Ser Gly Val Pro Ala Arg Phe
    210                 215                 220

Ser Gly Ser Gly Ser Gly Thr Ser Tyr Ser Leu Thr Ile Ser Arg Met
225                 230                 235                 240
```

```
Glu Ala Glu Asp Ala Ala Thr Tyr Tyr Cys Gln Gln Arg Ser Ser Tyr
                245                 250                 255
Pro Leu Thr Phe Gly Ala Gly Thr Lys Leu Glu Leu Lys Arg Gly Ser
            260                 265                 270
Leu Gly Gly Ser Gly Gly Asp Phe Thr Pro Pro Thr Val Lys Ile Leu
        275                 280                 285
Gln Ser Ser Cys Asp Gly Gly His Phe Pro Pro Thr Ile Gln Leu
    290                 295                 300
Leu Cys Leu Val Ser Gly Tyr Thr Pro Gly Thr Ile Asn Ile Thr Trp
305                 310                 315                 320
Leu Glu Asp Gly Gln Val Met Asp Val Asp Leu Ser Thr Ala Ser Thr
                325                 330                 335
Thr Gln Glu Gly Glu Leu Ala Ser Thr Gln Ser Glu Leu Thr Leu Ser
            340                 345                 350
Gln Lys His Trp Leu Ser Asp Arg Thr Tyr Thr Cys Gln Val Thr Tyr
        355                 360                 365
Gln Gly His Thr Phe Glu Asp Ser Thr Lys Lys Cys Ala Asp Ser Asn
    370                 375                 380
Gly Gly Gly Ser Gly Gly Gly Thr Gly Ser Glu Phe Ala Ala Ala His
385                 390                 395                 400

His His His His His
            405

<210> SEQ ID NO 55
<211> LENGTH: 1176
<212> TYPE: DNA
<213> ORGANISM: Artificial Sequence
<220> FEATURE:
<223> OTHER INFORMATION: Anti-HER2 scFv-EHD2

<400> SEQUENCE: 55
atggagacag acacactcct gctatgggta ctgctgctct gggttccagg ttccaccggt         60
gaagtgcagc tcgtcgaaag tggcggtgga cttgtgcagc ctggcggttc cctcagactg        120
tcctgtgccg cgtcaggctt caacatcaag gacacgtaca tccactgggt gaggcaagct        180
cctggaaagg gcttggagtg ggtcgctagg atctacccga cgaacggcta caccaggtac        240
gctgactcag tgaagggaag gttcacgatc agtgcagaca ccagcaagaa caccgcatac        300
ctccaaatga actccctgag agccgaggac accgccgtgt actactgctc tcgttggggt        360
ggagatggct ctacgctat ggactactgg ggtcaaggca cactggtgac cgtgtccagt        420
ggtggcggag gcagtggcgg aggtggctca ggaggcggag gatccgacat ccagatgacc        480
cagtcaccct caagcctcag tgccagcgtc ggagatagag tgaccataac gtgccgagct        540
tctcaggatg tgaacacggc agtggcttgg tatcagcaaa agcctgggaa agccccaaag        600
ctgctcatct actccgcatc cttcctgtat agcggagttc catctaggtt ctcaggctct        660
aggtctggga ccgacttcac gctgacgatc tcctccctgc aacctgagga cttcgccacg        720
tactactgcc agcagcacta cacgactcct ccaaccttcg gtcagggaac gaaggtcgag        780
atcaagcgtg cggccgccgg gggaagcggc ggtgatttca ccccccccac agtgaagatc        840
ctccagagca gctgtgacgg cggaggccac ttcccaccta ccatccagct gctgtgtctg        900
gtgtccggct acaccccgg caccatcaac atcacctggc tggaagatgg acaagtgatg        960
gacgtggacc tgagcaccgc cagcaccaca caggaaggcg agctggcctc tacccagagc       1020
gagctgacac tgagccagaa gcactggctg agcgaccgga cctacacctg tcaagtgacc       1080
```
taccagggcc acaccttcga ggacagcacc aagaagtgcg ccgacagcaa cggaggttca    1140
gggggcgcct cgagccacca tcatcaccat cactaa                              1176

<210> SEQ ID NO 56
<211> LENGTH: 391
<212> TYPE: PRT
<213> ORGANISM: Artificial Sequence
<220> FEATURE:
<223> OTHER INFORMATION: Anti-HER2 scFv-EHD2

<400> SEQUENCE: 56

Met Glu Thr Asp Thr Leu Leu Leu Trp Val Leu Leu Leu Trp Val Pro
1               5                   10                  15

Gly Ser Thr Gly Glu Val Gln Leu Val Glu Ser Gly Gly Gly Leu Val
            20                  25                  30

Gln Pro Gly Gly Ser Leu Arg Leu Ser Cys Ala Ala Ser Gly Phe Asn
        35                  40                  45

Ile Lys Asp Thr Tyr Ile His Trp Val Arg Gln Ala Pro Gly Lys Gly
    50                  55                  60

Leu Glu Trp Val Ala Arg Ile Tyr Pro Thr Asn Gly Tyr Thr Arg Tyr
65                  70                  75                  80

Ala Asp Ser Val Lys Gly Arg Phe Thr Ile Ser Ala Asp Thr Ser Lys
                85                  90                  95

Asn Thr Ala Tyr Leu Gln Met Asn Ser Leu Arg Ala Glu Asp Thr Ala
            100                 105                 110

Val Tyr Tyr Cys Ser Arg Trp Gly Gly Asp Gly Phe Tyr Ala Met Asp
        115                 120                 125

Tyr Trp Gly Gln Gly Thr Leu Val Thr Val Ser Ser Gly Gly Gly Gly
    130                 135                 140

Ser Gly Gly Gly Gly Ser Gly Gly Gly Ser Asp Ile Gln Met Thr
145                 150                 155                 160

Gln Ser Pro Ser Ser Leu Ser Ala Ser Val Gly Asp Arg Val Thr Ile
                165                 170                 175

Thr Cys Arg Ala Ser Gln Asp Val Asn Thr Ala Val Ala Trp Tyr Gln
            180                 185                 190

Gln Lys Pro Gly Lys Ala Pro Lys Leu Leu Ile Tyr Ser Ala Ser Phe
        195                 200                 205

Leu Tyr Ser Gly Val Pro Ser Arg Phe Ser Gly Ser Arg Ser Gly Thr
    210                 215                 220

Asp Phe Thr Leu Thr Ile Ser Ser Leu Gln Pro Glu Asp Phe Ala Thr
225                 230                 235                 240

Tyr Tyr Cys Gln Gln His Tyr Thr Thr Pro Pro Thr Phe Gly Gln Gly
                245                 250                 255

Thr Lys Val Glu Ile Lys Arg Ala Ala Ala Gly Gly Ser Gly Gly Asp
            260                 265                 270

Phe Thr Pro Pro Thr Val Lys Ile Leu Gln Ser Ser Cys Asp Gly Gly
        275                 280                 285

Gly His Phe Pro Pro Thr Ile Gln Leu Leu Cys Leu Val Ser Gly Tyr
    290                 295                 300

Thr Pro Gly Thr Ile Asn Ile Thr Trp Leu Glu Asp Gly Gln Val Met
305                 310                 315                 320

Asp Val Asp Leu Ser Thr Ala Ser Thr Thr Gln Glu Gly Glu Leu Ala
                325                 330                 335

Ser Thr Gln Ser Glu Leu Thr Leu Ser Gln Lys His Trp Leu Ser Asp

```
               340           345           350
Arg Thr Tyr Thr Cys Gln Val Thr Tyr Gln Gly His Thr Phe Glu Asp
        355                   360                   365

Ser Thr Lys Lys Cys Ala Asp Ser Asn Gly Gly Ser Gly Gly Ala Ser
    370                   375                   380

Ser His His His His His His
385               390

<210> SEQ ID NO 57
<211> LENGTH: 1182
<212> TYPE: DNA
<213> ORGANISM: Artificial Sequence
<220> FEATURE:
<223> OTHER INFORMATION: Anti-HER3 scFv-EHD2

<400> SEQUENCE: 57
atggagacag acacactcct gctatgggta ctgctgctct ggttccagg ttccaccggt      60 gaagtgcagc tgctggaaag cggaggcggc ctggtgcagc ctggcggctc tctgagactg    120
agctgtgccg ccagcggctt caccttcagc cactacgtga tggcctgggt ccgacaggcc    180
cctggcaagg gactggaatg ggtgtccagc atcagcagca gcggcggctg gaccctgtac    240
gccgatagcg tgaagggccg gtttaccatc agccgggaca acagcaagaa caccctgtac    300
ctgcagatga acagcctgcg ggccgaggac accgccgtgt actactgcac cagaggcctg    360
aagatggcca ccatcttcga ctactggggg cagggcaccc tggtcacagt ctcgagtggc    420 ggggaggat ctgggggagg tggaagtggc ggcggtggat cccagtctgc cctgacacag    480
cctgccagcg tgtccggcag ccctggccag agcatcacaa tcagctgcac cggcaccagc    540
agcgacgtgg gcagctacaa cgtggtgtcc tggtatcagc agcacccgg caaggccccc    600 aagctgatca tctacgaggt gtcccagcgg cccagcggcg tgtccaacag attcagcggc    660
agcaagagcg gcaacaccgc cagcctgacc atcagcgggc tgcagaccga ggacgaggcc    720
gactactact gctccagcta cgccggcagc agcatcttcg tgatcttcgg aggtggcacc    780
aaagtgaccg tgctggcggc cgccggggga agcggcggtg atttcacccc cccacagtg    840 aagatcctcc agagcagctg tgacggcgga ggccacttcc cacctaccat ccagctgctg    900
tgtctggtgt ccggctacac ccccggcacc atcaacatca cctggctgga agatggacaa    960
gtgatggacg tggacctgag caccgccagc accacacagg aaggcgagct ggcctctacc   1020
cagagcgagc tgacactgag ccagaagcac tggctgagcg accggaccta cacctgtcaa   1080
gtgacctacc agggccacac cttcgaggac agcaccaaga gtgcgccga cagcaacgga   1140 ggttcagggg gcgcctcgag ccaccatcat caccatcact aa                      1182

<210> SEQ ID NO 58
<211> LENGTH: 393
<212> TYPE: PRT
<213> ORGANISM: Artificial Sequence
<220> FEATURE:
<223> OTHER INFORMATION: Anti-HER3 scFv-EHD2

<400> SEQUENCE: 58

Met Glu Thr Asp Thr Leu Leu Leu Trp Val Leu Leu Leu Trp Val Pro
1               5                   10                  15

Gly Ser Thr Gly Glu Val Gln Leu Leu Glu Ser Gly Gly Gly Leu Val
            20                  25                  30

Gln Pro Gly Gly Ser Leu Arg Leu Ser Cys Ala Ala Ser Gly Phe Thr
        35                  40                  45
```

```
Phe Ser His Tyr Val Met Ala Trp Val Arg Gln Ala Pro Gly Lys Gly
 50                  55                  60
Leu Glu Trp Val Ser Ser Ile Ser Ser Gly Gly Trp Thr Leu Tyr
 65                  70                  75                  80
Ala Asp Ser Val Lys Gly Arg Phe Thr Ile Ser Arg Asp Asn Ser Lys
                 85                  90                  95
Asn Thr Leu Tyr Leu Gln Met Asn Ser Leu Arg Ala Glu Asp Thr Ala
                100                 105                 110
Val Tyr Tyr Cys Thr Arg Gly Leu Lys Met Ala Thr Ile Phe Asp Tyr
                115                 120                 125
Trp Gly Gln Gly Thr Leu Val Thr Val Ser Ser Gly Gly Gly Ser
130                 135                 140
Gly Gly Gly Gly Ser Gly Gly Gly Ser Gln Ser Ala Leu Thr Gln
145                 150                 155                 160
Pro Ala Ser Val Ser Gly Ser Pro Gly Gln Ser Ile Thr Ile Ser Cys
                165                 170                 175
Thr Gly Thr Ser Ser Asp Val Gly Ser Tyr Asn Val Val Ser Trp Tyr
                180                 185                 190
Gln Gln His Pro Gly Lys Ala Pro Lys Leu Ile Ile Tyr Glu Val Ser
                195                 200                 205
Gln Arg Pro Ser Gly Val Ser Asn Arg Phe Ser Gly Ser Lys Ser Gly
210                 215                 220
Asn Thr Ala Ser Leu Thr Ile Ser Gly Leu Gln Thr Glu Asp Glu Ala
225                 230                 235                 240
Asp Tyr Tyr Cys Ser Ser Tyr Ala Gly Ser Ile Phe Val Ile Phe
                245                 250                 255
Gly Gly Gly Thr Lys Val Thr Val Leu Ala Ala Ala Gly Gly Ser Gly
                260                 265                 270
Gly Asp Phe Thr Pro Pro Thr Val Lys Ile Leu Gln Ser Ser Cys Asp
                275                 280                 285
Gly Gly Gly His Phe Pro Pro Thr Ile Gln Leu Leu Cys Leu Val Ser
290                 295                 300
Gly Tyr Thr Pro Gly Thr Ile Asn Ile Thr Trp Leu Glu Asp Gly Gln
305                 310                 315                 320
Val Met Asp Val Asp Leu Ser Thr Ala Ser Thr Thr Gln Glu Gly Glu
                325                 330                 335
Leu Ala Ser Thr Gln Ser Glu Leu Thr Leu Ser Gln Lys His Trp Leu
                340                 345                 350
Ser Asp Arg Thr Tyr Thr Cys Gln Val Thr Tyr Gln Gly His Thr Phe
                355                 360                 365
Glu Asp Ser Thr Lys Lys Cys Ala Asp Ser Asn Gly Gly Ser Gly Gly
                370                 375                 380
Ala Ser Ser His His His His His
385                 390

<210> SEQ ID NO 59
<211> LENGTH: 1938
<212> TYPE: DNA
<213> ORGANISM: Artificial Sequence
<220> FEATURE:
<223> OTHER INFORMATION: Anti-CEAxCD3 scDb-EHD2

<400> SEQUENCE: 59
atggagacag acacactcct gctatgggta ctgctgctct gggttccagg ttccactggt      60
```

```
gacgcggccc agccggccat ggcccaggtg aaactgcagc agtctggggc agaacttgtg      120
aggtcaggga cctcagtcaa gttgtcctgc acagcttctg gcttcaacat taaagactcc      180
tatatgcact ggttgaggca ggggcctgaa cagggcctgg agtggattgg atggattgat      240
cctgagaatg gtgatactga atatgccccg aagttccagg gcaaggccac ttttactaca      300
gacacatcct ccaacacagc ctacctgcag ctcagcagcc tgacatctga ggacactgcc      360
gtctattatt gtaatgaggg gactccgact gggccgtact actttgacta ctggggccaa      420
gggaccacgg tcaccgtctc ctcaggcggt ggcggatcgg atatccagat gacccagtcc      480
ccgagttccc tgtccgcctc tgtgggcgat agagtcacca tcacctgtcg tgccagtcag      540
gacatccgta attatctgaa ctggtatcaa cagaaaccag gaaaagctcc gaaactactg      600
atttactata cctcccgcct ggagtctgga gtcccttctc gcttctctgg ttctggttct      660
gggacggatt acactctcac catcagcagt ctgcaaccgg aggacttcgc aacctattac      720
tgtcagcaag gtaatactct gccgtggacg ttcggacagg gcaccaaggt ggagatcaaa      780
cgtggaggcg gtggcagcgg tgggcgcgcc tcggcggag gtggctcaga ggttcagctg      840
gtggagtctg gcggtggcct ggtgcagcca ggggctcac tccgtttgtc ctgtgcagct      900
tctggctact cctttaccgg ctacactatg aactgggtgc gtcaggcccc aggtaagggc      960
ctggaatggg ttgcactgat taatccttat aaaggtgttt ccacctataa ccagaaattc     1020
aaggatcgtt tcacgatatc cgtagataaa tccaaaaaca cagcctacct gcaaatgaac     1080
agcctgcgtg ctgaggacac tgcagtctat tattgtgcta aagcggata ctacggcgat     1140
agcgactggt attttgacgt ctggggtcaa ggaaccctag tcaccgtctc ctcgggaggc     1200
gggggttcgg acatcgagct cacccagtct ccagcaatca tgtctgcatc tccaggggag     1260
aaagtcacca taacctgcag tgccagctca agtgtaagtt acatgcactg gttccagcag     1320
aagccaggca cttctcccaa actctggatt tatagcacat ccaacctggc ttctggagtc     1380
cctgctcgct tcagtggcag tggatctggg acctcttact ctctcacaat cagccgaatg     1440
gaggctgaag atgctgccac ttattactgc cagcaaagga gtagttaccc actcacgttc     1500
ggtgctggca ccaagctgga gctgaaacgg gaagcttag gcggctctgg cggcgatttc     1560
acccccccca cagtgaagat cctccagagc agctgtgacg gcggaggcca cttcccacct     1620
accatccagc tgctgtgtct ggtgtccggc tacccccccg gcaccatcaa catcacctgg     1680
ctggaagatg gacaagtgat ggacgtggac ctgagcaccg ccagcaccac acaggaaggc     1740
gagctggcct ctacccagag cgagctgaca ctgagccaga agcactggct gagcgaccgg     1800
acctacacct gtcaagtgac ctaccagggc cacaccttcg aggacagcac caagaagtgc     1860
gccgacagca cgggggagg atctggcgga ggtaccggat ccgaattcgc ggccgcccac     1920
catcatcacc atcactaa                                                   1938
```

<210> SEQ ID NO 60
<211> LENGTH: 645
<212> TYPE: PRT
<213> ORGANISM: Artificial Sequence
<220> FEATURE:
<223> OTHER INFORMATION: Anti-CEAxCD3 scDb-EHD2

<400> SEQUENCE: 60

Met Glu Thr Asp Thr Leu Leu Leu Trp Val Leu Leu Leu Trp Val Pro
1               5                   10                  15

Gly Ser Thr Gly Asp Ala Ala Gln Pro Ala Met Ala Gln Val Lys Leu
            20                  25                  30

```
Gln Gln Ser Gly Ala Glu Leu Val Arg Ser Gly Thr Ser Val Lys Leu
        35                  40                  45

Ser Cys Thr Ala Ser Gly Phe Asn Ile Lys Asp Ser Tyr Met His Trp
 50                  55                  60

Leu Arg Gln Gly Pro Glu Gln Gly Leu Glu Trp Ile Gly Trp Ile Asp
 65                  70                  75                  80

Pro Glu Asn Gly Asp Thr Glu Tyr Ala Pro Lys Phe Gln Gly Lys Ala
                 85                  90                  95

Thr Phe Thr Thr Asp Thr Ser Ser Asn Thr Ala Tyr Leu Gln Leu Ser
                100                 105                 110

Ser Leu Thr Ser Glu Asp Thr Ala Val Tyr Tyr Cys Asn Glu Gly Thr
        115                 120                 125

Pro Thr Gly Pro Tyr Tyr Phe Asp Tyr Trp Gly Gln Gly Thr Thr Val
        130                 135                 140

Thr Val Ser Ser Gly Gly Gly Ser Asp Ile Gln Met Thr Gln Ser
145                 150                 155                 160

Pro Ser Ser Leu Ser Ala Ser Val Gly Asp Arg Val Thr Ile Thr Cys
                165                 170                 175

Arg Ala Ser Gln Asp Ile Arg Asn Tyr Leu Asn Trp Tyr Gln Gln Lys
                180                 185                 190

Pro Gly Lys Ala Pro Lys Leu Leu Ile Tyr Tyr Thr Ser Arg Leu Glu
        195                 200                 205

Ser Gly Val Pro Ser Arg Phe Ser Gly Ser Gly Ser Gly Thr Asp Tyr
        210                 215                 220

Thr Leu Thr Ile Ser Ser Leu Gln Pro Glu Asp Phe Ala Thr Tyr Tyr
225                 230                 235                 240

Cys Gln Gln Gly Asn Thr Leu Pro Trp Thr Phe Gly Gln Gly Thr Lys
                245                 250                 255

Val Glu Ile Lys Arg Gly Gly Gly Ser Gly Gly Arg Ala Ser Gly
                260                 265                 270

Gly Gly Gly Ser Glu Val Gln Leu Val Glu Ser Gly Gly Gly Leu Val
        275                 280                 285

Gln Pro Gly Gly Ser Leu Arg Leu Ser Cys Ala Ala Ser Gly Tyr Ser
        290                 295                 300

Phe Thr Gly Tyr Thr Met Asn Trp Val Arg Gln Ala Pro Gly Lys Gly
305                 310                 315                 320

Leu Glu Trp Val Ala Leu Ile Asn Pro Tyr Lys Gly Val Ser Thr Tyr
                325                 330                 335

Asn Gln Lys Phe Lys Asp Arg Phe Thr Ile Ser Val Asp Lys Ser Lys
                340                 345                 350

Asn Thr Ala Tyr Leu Gln Met Asn Ser Leu Arg Ala Glu Asp Thr Ala
        355                 360                 365

Val Tyr Tyr Cys Ala Arg Ser Gly Tyr Gly Asp Ser Asp Trp Tyr
        370                 375                 380

Phe Asp Val Trp Gly Gln Gly Thr Leu Val Thr Val Ser Ser Gly Gly
385                 390                 395                 400

Gly Gly Ser Asp Ile Glu Leu Thr Gln Ser Pro Ala Ile Met Ser Ala
                405                 410                 415

Ser Pro Gly Glu Lys Val Thr Ile Thr Cys Ser Ala Ser Ser Ser Val
                420                 425                 430

Ser Tyr Met His Trp Phe Gln Gln Lys Pro Gly Thr Ser Pro Lys Leu
        435                 440                 445
```

```
Trp Ile Tyr Ser Thr Ser Asn Leu Ala Ser Gly Val Pro Ala Arg Phe
    450                 455                 460
Ser Gly Ser Gly Ser Gly Thr Ser Tyr Ser Leu Thr Ile Ser Arg Met
465                 470                 475                 480
Glu Ala Glu Asp Ala Ala Thr Tyr Tyr Cys Gln Gln Arg Ser Ser Tyr
                485                 490                 495
Pro Leu Thr Phe Gly Ala Gly Thr Lys Leu Glu Leu Lys Arg Gly Ser
            500                 505                 510
Leu Gly Gly Ser Gly Gly Asp Phe Thr Pro Thr Val Lys Ile Leu
        515                 520                 525
Gln Ser Ser Cys Asp Gly Gly His Phe Pro Thr Ile Gln Leu
    530                 535                 540
Leu Cys Leu Val Ser Gly Tyr Thr Pro Gly Thr Ile Asn Ile Thr Trp
545                 550                 555                 560
Leu Glu Asp Gly Gln Val Met Asp Val Asp Leu Ser Thr Ala Ser Thr
                565                 570                 575
Thr Gln Glu Gly Glu Leu Ala Ser Thr Gln Ser Glu Leu Thr Leu Ser
            580                 585                 590
Gln Lys His Trp Leu Ser Asp Arg Thr Tyr Thr Cys Gln Val Thr Tyr
    595                 600                 605
Gln Gly His Thr Phe Glu Asp Ser Thr Lys Lys Cys Ala Asp Ser Asn
    610                 615                 620
Gly Gly Gly Ser Gly Gly Gly Thr Gly Ser Glu Phe Ala Ala Ala His
625                 630                 635                 640
His His His His His
            645

<210> SEQ ID NO 61
<211> LENGTH: 1185
<212> TYPE: DNA
<213> ORGANISM: Artificial Sequence
<220> FEATURE:
<223> OTHER INFORMATION: Anti-EGFR scFv-L3-EHD2

<400> SEQUENCE: 61
atggagacag acacactcct gctatgggta ctgctgctct gggttccagg ttccaccggt       60
caggtgcagc tgaagcagtc tggagctgaa ctggtaaaac ccggggcatc agtgaagctg      120
tcctgcaaga cttctggcta caccttcact gaaaatatta cactgggt aaagcagagg       180 tctgggcagg tcttgagtg gattgggtgg tttcaccctg aagtggtag tataaagtac       240 aatgagaaat tcaaggacaa ggccacattg actgcggaca atcctccag cacagtctat      300 atggagctta gtagattgac atctgaagac tctgcggtct atttctgtgc aagacacgga      360
ggaactgggc gaggagctat ggactactgg ggtcaaggaa cctcagtcac cgtctcgagt      420
ggtggatgcg gttcaggcgg aggtggctct ggcggtagtg cacaaattct gatgacccag      480
tctcctgctt cctcagttgt atctctgggg cagagggcca ccatctcatg cagggccagc      540
aaaagtgtca gtacatctgc ctatagttat atgcactggt accaacagaa accaggacag      600
ccacccaaac tcctcatcta tcttgcatcc aacctagaat ctggggtccc tccaggttc       660 agtggcagtg gtctgggac agacttcacc ctcaacatcc accctgtgga ggaggaggat      720
gctgcaacct attactgtca gcacagtagg gagcttccgt acacgttcgg agggggggacc      780 aagctggaaa taaaacgggc ggccgccggg ggaagcggcg tgatttcac cccccccaca       840 gtgaagatcc tccagagcag ctgtgacggc ggaggccact tccccacctac catccagctg      900
```

```
ctgtgtctgg tgtccggcta cacccccggc accatcaaca tcacctggct ggaagatgga      960
caagtgatgg acgtggacct gagcaccgcc agcaccacac aggaaggcga gctggcctct     1020
acccagagcg agctgacact gagccagaag cactggctga gcgaccggac ctacacctgt     1080
caagtgacct accagggcca caccttcgag gacagcacca agaagtgcgc cgacagcaac     1140
ggaggttcag ggggcgcctc gagccaccat catcaccatc actaa                     1185
```

<210> SEQ ID NO 62
<211> LENGTH: 394
<212> TYPE: PRT
<213> ORGANISM: Artificial Sequence
<220> FEATURE:
<223> OTHER INFORMATION: Anti-EGFR scFv-L3-EHD2

<400> SEQUENCE: 62

```
Met Glu Thr Asp Thr Leu Leu Leu Trp Val Leu Leu Leu Trp Val Pro
1               5                   10                  15

Gly Ser Thr Gly Gln Val Gln Leu Lys Gln Ser Gly Ala Glu Leu Val
            20                  25                  30

Lys Pro Gly Ala Ser Val Lys Leu Ser Cys Lys Thr Ser Gly Tyr Thr
        35                  40                  45

Phe Thr Glu Asn Ile Ile His Trp Val Lys Gln Arg Ser Gly Gln Gly
    50                  55                  60

Leu Glu Trp Ile Gly Trp Phe His Pro Gly Ser Gly Ser Ile Lys Tyr
65                  70                  75                  80

Asn Glu Lys Phe Lys Asp Lys Ala Thr Leu Thr Ala Asp Lys Ser Ser
                85                  90                  95

Ser Thr Val Tyr Met Glu Leu Ser Arg Leu Thr Ser Glu Asp Ser Ala
            100                 105                 110

Val Tyr Phe Cys Ala Arg His Gly Gly Thr Gly Arg Gly Ala Met Asp
        115                 120                 125

Tyr Trp Gly Gln Gly Thr Ser Val Thr Val Ser Ser Gly Gly Cys Gly
    130                 135                 140

Ser Gly Gly Gly Gly Ser Gly Gly Ser Ala Gln Ile Leu Met Thr Gln
145                 150                 155                 160

Ser Pro Ala Ser Ser Val Val Ser Leu Gly Gln Arg Ala Thr Ile Ser
                165                 170                 175

Cys Arg Ala Ser Lys Ser Val Ser Thr Ser Ala Tyr Ser Tyr Met His
            180                 185                 190

Trp Tyr Gln Gln Lys Pro Gly Gln Pro Pro Lys Leu Leu Ile Tyr Leu
        195                 200                 205

Ala Ser Asn Leu Glu Ser Gly Val Pro Pro Arg Phe Ser Gly Ser Gly
    210                 215                 220

Ser Gly Thr Asp Phe Thr Leu Asn Ile His Pro Val Glu Glu Glu Asp
225                 230                 235                 240

Ala Ala Thr Tyr Tyr Cys Gln His Ser Arg Glu Leu Pro Tyr Thr Phe
                245                 250                 255

Gly Gly Gly Thr Lys Leu Glu Ile Lys Arg Ala Ala Ala Gly Gly Ser
            260                 265                 270

Gly Gly Asp Phe Thr Pro Pro Thr Val Lys Ile Leu Gln Ser Ser Cys
        275                 280                 285

Asp Gly Gly Gly His Phe Pro Pro Thr Ile Gln Leu Leu Cys Leu Val
    290                 295                 300

Ser Gly Tyr Thr Pro Gly Thr Ile Asn Ile Thr Trp Leu Glu Asp Gly
305                 310                 315                 320
```

```
Gln Val Met Asp Val Asp Leu Ser Thr Ala Ser Thr Thr Gln Glu Gly
                325                 330                 335

Glu Leu Ala Ser Thr Gln Ser Glu Leu Thr Leu Ser Gln Lys His Trp
            340                 345                 350

Leu Ser Asp Arg Thr Tyr Thr Cys Gln Val Thr Tyr Gln Gly His Thr
        355                 360                 365

Phe Glu Asp Ser Thr Lys Lys Cys Ala Asp Ser Asn Gly Gly Ser Gly
    370                 375                 380

Gly Ala Ser Ser His His His His His His
385                 390

<210> SEQ ID NO 63
<211> LENGTH: 1938
<212> TYPE: DNA
<213> ORGANISM: Artificial Sequence
<220> FEATURE:
<223> OTHER INFORMATION: Anti-EGFR scFv-L3-EHD2-scFv

<400> SEQUENCE: 63
atggagacag acacactcct gctatgggta ctgctgctct ggttccagg  ttccaccggt      60 caggtgcagc tgaagcagtc tggagctgaa ctggtgaaac ccggggcatc agtgaagctg     120
tcctgcaaga cttctggcta caccttcact gaaaatatta cactgggt  aaagcagagg     180 tctgggcagg tcttgagtg gattggtgg tttcaccctg aagtggtag  tataaagtac     240 aatgagaaat tcaaggacaa ggccacattg actgcggaca atcctccag cacagtctat     300 atggagctta gtagattgac atctgaagac tctgcggtct atttctgtgc aagacacgga     360
ggaactgggc gaggagctat ggactactgg ggtcaaggaa cctcagtcac cgtctcgagt     420
ggtggatgcg gttcaggcgg aggtggctct ggcggtagtg cacaaattct gatgacccag     480
tctcctgctt cctcagttgt atctctgggg cagagggcca ccatctcatg cagggccagc     540
aaaagtgtca gtacatctgc ctatagttat atgcactggt accaacgaaa ccaggacag     600 ccacccaaac tcctcatcta tcttgcatcc aacctagaat ctggggtccc tcccaggttc     660
agtggcagtg gtctgggac agacttcacc ctcaacatcc accctgtgga ggaggaggat     720
gctgcaacct attactgtca gcacagtagg gagcttccgt acacgttcgg aggggggacc     780
aagctggaaa taaaacgggc ggccgccggg ggaagcggcg tgatttcac ccccccaca      840 gtgaagatcc tccagagcag ctgtgacggc ggaggccact cccacctac atccagctg     900 ctgtgtctgg tgtccggcta cacccccggc accatcaaca tcacctggct ggaagatgga     960
caagtgatgg acgtggacct gagcaccgcc agcaccacac aggaaggcga gctggcctct    1020
acccagagcg agctgacact gagccagaag cactggctga cgaccggac ctacacctgt    1080 caagtgacct accagggcca caccttcgag gacagcacca gaagtgcgc cgacagcaac    1140 ggaggttcag gggcgcctc gagcgaattc aggtgcagc tgaagcagtc tggagctgaa    1200
ctggtgaaac ccggggcatc agtgaagctg tcctgcaaga cttctggcta caccttcact    1260
gaaaatatta cactgggt  aaagcagagg tctgggcagg tcttgagtg gattggtgg    1320 tttcaccctg aagtggtag  tataaagtac aatgagaaat tcaaggacaa ggccacattg    1380
actgcggaca atcctccag cacagtctat atggagctta gtagattgac atctgaagac    1440
tctgcggtct atttctgtgc aagacacgga ggaactgggc gaggagctat ggactactgg    1500
ggtcaaggaa cctcagtcac cgtctcgagt ggtggaggcg gttcaggcgg aggtggctct    1560
ggcggtagtg cacaaattct gatgacccag tctcctgctt cctcagttgt atctctgggg    1620
```

```
cagagggcca ccatctcatg cagggccagc aaaagtgtca gtacatctgc ctatagttat    1680
atgcactggt accaacagaa accaggacag ccacccaaac tcctcatcta tcttgcatcc    1740
aacctagaat ctggggtccc tcccaggttc agtggcagtg ggtctgggac agacttcacc    1800
ctcaacatcc accctgtgga ggaggaggat gctgcaacct attactgtca gcacagtagg    1860
gagcttccgt acacgttcgg aggggggacc aagctggaaa taaaacgggc ggccgcccac    1920
catcatcacc atcactaa                                                  1938
```

<210> SEQ ID NO 64
<211> LENGTH: 645
<212> TYPE: PRT
<213> ORGANISM: Artificial Sequence
<220> FEATURE:
<223> OTHER INFORMATION: Anti-EGFR scFv-L3-EHD2-scFv

<400> SEQUENCE: 64

```
Met Glu Thr Asp Thr Leu Leu Leu Trp Val Leu Leu Leu Trp Val Pro
1               5                   10                  15

Gly Ser Thr Gly Gln Val Gln Leu Lys Gln Ser Gly Ala Glu Leu Val
            20                  25                  30

Lys Pro Gly Ala Ser Val Lys Leu Ser Cys Lys Thr Ser Gly Tyr Thr
        35                  40                  45

Phe Thr Glu Asn Ile Ile His Trp Val Lys Gln Arg Ser Gly Gln Gly
    50                  55                  60

Leu Glu Trp Ile Gly Trp Phe His Pro Gly Ser Gly Ser Ile Lys Tyr
65                  70                  75                  80

Asn Glu Lys Phe Lys Asp Lys Ala Thr Leu Thr Ala Asp Lys Ser Ser
                85                  90                  95

Ser Thr Val Tyr Met Glu Leu Ser Arg Leu Thr Ser Glu Asp Ser Ala
            100                 105                 110

Val Tyr Phe Cys Ala Arg His Gly Gly Thr Gly Arg Gly Ala Met Asp
        115                 120                 125

Tyr Trp Gly Gln Gly Thr Ser Val Thr Val Ser Ser Gly Gly Cys Gly
    130                 135                 140

Ser Gly Gly Gly Gly Ser Gly Gly Ser Ala Gln Ile Leu Met Thr Gln
145                 150                 155                 160

Ser Pro Ala Ser Ser Val Val Ser Leu Gly Gln Arg Ala Thr Ile Ser
                165                 170                 175

Cys Arg Ala Ser Lys Ser Val Ser Thr Ser Ala Tyr Ser Tyr Met His
            180                 185                 190

Trp Tyr Gln Gln Lys Pro Gly Gln Pro Pro Lys Leu Leu Ile Tyr Leu
        195                 200                 205

Ala Ser Asn Leu Glu Ser Gly Val Pro Pro Arg Phe Ser Gly Ser Gly
    210                 215                 220

Ser Gly Thr Asp Phe Thr Leu Asn Ile His Pro Val Glu Glu Glu Asp
225                 230                 235                 240

Ala Ala Thr Tyr Tyr Cys Gln His Ser Arg Glu Leu Pro Tyr Thr Phe
                245                 250                 255

Gly Gly Gly Thr Lys Leu Glu Ile Lys Arg Ala Ala Ala Gly Gly Ser
            260                 265                 270

Gly Gly Asp Phe Thr Pro Pro Thr Val Lys Ile Leu Gln Ser Ser Cys
        275                 280                 285

Asp Gly Gly Gly His Phe Pro Pro Thr Ile Gln Leu Leu Cys Leu Val
    290                 295                 300
```

Ser Gly Tyr Thr Pro Gly Thr Ile Asn Ile Thr Trp Leu Glu Asp Gly
305                 310                 315                 320

Gln Val Met Asp Val Asp Leu Ser Thr Ala Ser Thr Gln Glu Gly
            325                 330                 335

Glu Leu Ala Ser Thr Gln Ser Glu Leu Thr Leu Ser Gln Lys His Trp
            340                 345                 350

Leu Ser Asp Arg Thr Tyr Thr Cys Gln Val Thr Tyr Gln Gly His Thr
            355                 360                 365

Phe Glu Asp Ser Thr Lys Lys Cys Ala Asp Ser Asn Gly Gly Ser Gly
370                 375                 380

Gly Ala Ser Ser Glu Phe Gln Val Gln Leu Lys Gln Ser Gly Ala Glu
385                 390                 395                 400

Leu Val Lys Pro Gly Ala Ser Val Lys Leu Ser Cys Lys Thr Ser Gly
            405                 410                 415

Tyr Thr Phe Thr Glu Asn Ile Ile His Trp Val Lys Gln Arg Ser Gly
            420                 425                 430

Gln Gly Leu Glu Trp Ile Gly Trp Phe His Pro Gly Ser Gly Ser Ile
            435                 440                 445

Lys Tyr Asn Glu Lys Phe Lys Asp Lys Ala Thr Leu Thr Ala Asp Lys
450                 455                 460

Ser Ser Ser Thr Val Tyr Met Glu Leu Ser Arg Leu Thr Ser Glu Asp
465                 470                 475                 480

Ser Ala Val Tyr Phe Cys Ala Arg His Gly Gly Thr Gly Arg Gly Ala
            485                 490                 495

Met Asp Tyr Trp Gly Gln Gly Thr Ser Val Thr Val Ser Ser Gly Gly
            500                 505                 510

Gly Gly Ser Gly Gly Gly Gly Ser Gly Gly Ser Ala Gln Ile Leu Met
            515                 520                 525

Thr Gln Ser Pro Ala Ser Ser Val Val Ser Leu Gly Gln Arg Ala Thr
            530                 535                 540

Ile Ser Cys Arg Ala Ser Lys Ser Val Ser Thr Ser Ala Tyr Ser Tyr
545                 550                 555                 560

Met His Trp Tyr Gln Gln Lys Pro Gly Gln Pro Pro Lys Leu Leu Ile
            565                 570                 575

Tyr Leu Ala Ser Asn Leu Glu Ser Gly Val Pro Pro Arg Phe Ser Gly
            580                 585                 590

Ser Gly Ser Gly Thr Asp Phe Thr Leu Asn Ile His Pro Val Glu Glu
            595                 600                 605

Glu Asp Ala Ala Thr Tyr Tyr Cys Gln His Ser Arg Glu Leu Pro Tyr
            610                 615                 620

Thr Phe Gly Gly Gly Thr Lys Leu Glu Ile Lys Arg Ala Ala Ala His
625                 630                 635                 640

His His His His His
            645

<210> SEQ ID NO 65
<211> LENGTH: 1959
<212> TYPE: DNA
<213> ORGANISM: Artificial Sequence
<220> FEATURE:
<223> OTHER INFORMATION: MHD2-scTNFR2

<400> SEQUENCE: 65
atggagacag acacactcct gctatgggta ctgctgctct gggttccagg ttccaccggt    60

| | |
|---|---|
| gacgcggccc agccggccgg aggcggtgcg gccgcacacc atcatcacca tcacggaggt | 120 |
| accggcgggg gaggttcagg cggaaagctt ggaggctctg gcggagccga gctgcccct | 180 |
| aaggtgtccg tgttcgtgcc ccccagggac ggcttcttcg gcaaccccag aaagagcaag | 240 |
| ctgatctgcc aggccaccgg cttcagcccc agacagatcc aggtgtcctg gctgcgcgag | 300 |
| ggcaaacagg tcggaagcgg cgtgaccacc gaccaggtgc aggccgaggc caaagagagc | 360 |
| ggccccacca cctacaaagt gaccagcacc ctgaccatca agagtccga ctggctgggc | 420 |
| cagagcatgt tcacctgtcg ggtggaccac cggggcctga ccttccagca gaacgccagc | 480 |
| tctatgtgcg tgcccgacgg cggagggtcc ggcggaggta ccggatccga attcctcgcc | 540 |
| agcagccgga cccctagcga taagcccgtg gcccacgtgg tggccaatcc tcaggccgag | 600 |
| ggccagctgc agtggctgaa cagacgggcc aacgccctgc tggccaacgg cgtggagctg | 660 |
| cgggacaacc agctggtcgt gcccagcgag ggcctgtacc tgatctacag ccaggtgctg | 720 |
| ttcaagggcc agggctgccc ttctaccac gtgctgctga cccacaccat cagccggatc | 780 |
| gccgtgagct accagaccaa agtgaacctg ctgtccgcca tcaagagccc tgccagaga | 840 |
| gagacacctg agggcgccga ggccaagcct tggtacgagc ccatctacct gggcggcgtg | 900 |
| ttccagctgg aaaagggcga ccggctgtcc gccgagatca accggcccga ctacctgaac | 960 |
| ttccgggaga gcggccaggt gtacttcggc atcatagcgc tgggcggagg gggcagcagc | 1020 |
| agcagaaccc cctccgacaa gcctgtggct catgtggtgg ctaaccccca ggctgaagga | 1080 |
| cagctgcagt ggctgaatcg gagagctaat gctctgctgg ctaatggggt ggaactgaga | 1140 |
| gataatcagc tggtcgtgcc ttctgagggg ctgtatctga tctattctca ggtgctgttt | 1200 |
| aaaggacagg ggtgtcccag cacacatgtg ctgctgacac atacaatctc cagaatcgcc | 1260 |
| gtgtcttatc agacaaaagt gaatctgctg agtgccatca gtcccccctg tcagcgggaa | 1320 |
| acccctgaag gggccgaagc taaaccttgg tatgaaccta tctatctggg gggagtgttt | 1380 |
| cagctggaaa aagggacag actgagcgcc gagattaaca gacctgatta cctgaatttc | 1440 |
| agagaatccg gcaggtgta ctttgggatt atcgccctgg aggggggcgg atccagctcc | 1500 |
| agaaccccca gtgacaaacc agtggcccat gtggtggcca acccacaggc tgaggggcag | 1560 |
| ctgcagtggc tgaaccgcag agccaatgcc ctgctggcca atggcgtgga actgcgcgac | 1620 |
| aatcagctgg tcgtgccatc cgaaggactg tacctgatct actcacaggt gctgtttaag | 1680 |
| gggcagggat gcccctccac tcatgtgctg ctgactcaca ctatctctcg gattgctgtg | 1740 |
| tcctaccaga ctaaagtgaa tctgctgtct gctattaagt ctccttgcca gcgcgagact | 1800 |
| ccagaggggg ctgaagccaa gccctggtat gagccaatct atctgggagg ggtgttccag | 1860 |
| ctggaaaagg gggatcgcct gagcgccgaa atcaatagac agactatct gaactttcgc | 1920 |
| gagtctggac aggtgtactt tggaatcatt gctctgtga | 1959 |

<210> SEQ ID NO 66
<211> LENGTH: 652
<212> TYPE: PRT
<213> ORGANISM: Artificial Sequence
<220> FEATURE:
<223> OTHER INFORMATION: MHD2-scTNFR2

<400> SEQUENCE: 66

Met Glu Thr Asp Thr Leu Leu Leu Trp Val Leu Leu Trp Val Pro
1               5                   10                  15

Gly Ser Thr Gly Asp Ala Ala Gln Pro Ala Gly Gly Ala Ala Ala
            20                  25                  30

```
His His His His His His Gly Gly Thr Gly Gly Gly Ser Gly Gly
            35                  40                  45

Lys Leu Gly Gly Ser Gly Gly Ala Glu Leu Pro Pro Lys Val Ser Val
     50                  55                  60

Phe Val Pro Pro Arg Asp Gly Phe Phe Gly Asn Pro Arg Lys Ser Lys
 65              70                  75                  80

Leu Ile Cys Gln Ala Thr Gly Phe Ser Pro Arg Gln Ile Gln Val Ser
                 85                  90                  95

Trp Leu Arg Glu Gly Lys Gln Val Gly Ser Gly Val Thr Thr Asp Gln
             100                 105                 110

Val Gln Ala Glu Ala Lys Glu Ser Gly Pro Thr Thr Tyr Lys Val Thr
             115                 120                 125

Ser Thr Leu Thr Ile Lys Glu Ser Asp Trp Leu Gly Gln Ser Met Phe
             130                 135                 140

Thr Cys Arg Val Asp His Arg Gly Leu Thr Phe Gln Gln Asn Ala Ser
145                 150                 155                 160

Ser Met Cys Val Pro Asp Gly Gly Ser Gly Gly Thr Gly Ser
                 165                 170                 175

Glu Phe Leu Ala Ser Ser Arg Thr Pro Ser Asp Lys Pro Val Ala His
             180                 185                 190

Val Val Ala Asn Pro Gln Ala Glu Gly Gln Leu Gln Trp Leu Asn Arg
             195                 200                 205

Arg Ala Asn Ala Leu Leu Ala Asn Gly Val Glu Leu Arg Asp Asn Gln
        210                 215                 220

Leu Val Val Pro Ser Glu Gly Leu Tyr Leu Ile Tyr Ser Gln Val Leu
225                 230                 235                 240

Phe Lys Gly Gln Gly Cys Pro Ser Thr His Val Leu Leu Thr His Thr
                 245                 250                 255

Ile Ser Arg Ile Ala Val Ser Tyr Gln Thr Lys Val Asn Leu Leu Ser
             260                 265                 270

Ala Ile Lys Ser Pro Cys Gln Arg Glu Thr Pro Glu Gly Ala Glu Ala
        275                 280                 285

Lys Pro Trp Tyr Glu Pro Ile Tyr Leu Gly Gly Val Phe Gln Leu Glu
        290                 295                 300

Lys Gly Asp Arg Leu Ser Ala Glu Ile Asn Arg Pro Asp Tyr Leu Asn
305                 310                 315                 320

Phe Arg Glu Ser Gly Gln Val Tyr Phe Gly Ile Ile Ala Leu Gly Gly
                 325                 330                 335

Gly Gly Ser Ser Ser Arg Thr Pro Ser Asp Lys Pro Val Ala His Val
             340                 345                 350

Val Ala Asn Pro Gln Ala Glu Gly Gln Leu Gln Trp Leu Asn Arg Arg
             355                 360                 365

Ala Asn Ala Leu Leu Ala Asn Gly Val Glu Leu Arg Asp Asn Gln Leu
        370                 375                 380

Val Val Pro Ser Glu Gly Leu Tyr Leu Ile Tyr Ser Gln Val Leu Phe
385                 390                 395                 400

Lys Gly Gln Gly Cys Pro Ser Thr His Val Leu Leu Thr His Thr Ile
                 405                 410                 415

Ser Arg Ile Ala Val Ser Tyr Gln Thr Lys Val Asn Leu Leu Ser Ala
             420                 425                 430

Ile Lys Ser Pro Cys Gln Arg Glu Thr Pro Glu Gly Ala Glu Ala Lys
        435                 440                 445
```

Pro Trp Tyr Glu Pro Ile Tyr Leu Gly Gly Val Phe Gln Leu Glu Lys
            450                 455                 460

Gly Asp Arg Leu Ser Ala Glu Ile Asn Arg Pro Asp Tyr Leu Asn Phe
465                 470                 475                 480

Arg Glu Ser Gly Gln Val Tyr Phe Gly Ile Ile Ala Leu Gly Gly Gly
                485                 490                 495

Gly Ser Ser Ser Arg Thr Pro Ser Asp Lys Pro Val Ala His Val Val
            500                 505                 510

Ala Asn Pro Gln Ala Glu Gly Gln Leu Gln Trp Leu Asn Arg Arg Ala
            515                 520                 525

Asn Ala Leu Leu Ala Asn Gly Val Glu Leu Arg Asp Asn Gln Leu Val
530                 535                 540

Val Pro Ser Glu Gly Leu Tyr Leu Ile Tyr Ser Gln Val Leu Phe Lys
545                 550                 555                 560

Gly Gln Gly Cys Pro Ser Thr His Val Leu Leu Thr His Thr Ile Ser
                565                 570                 575

Arg Ile Ala Val Ser Tyr Gln Thr Lys Val Asn Leu Leu Ser Ala Ile
                580                 585                 590

Lys Ser Pro Cys Gln Arg Glu Thr Pro Glu Gly Ala Glu Ala Lys Pro
                595                 600                 605

Trp Tyr Glu Pro Ile Tyr Leu Gly Gly Val Phe Gln Leu Glu Lys Gly
610                 615                 620

Asp Arg Leu Ser Ala Glu Ile Asn Arg Pro Asp Tyr Leu Asn Phe Arg
625                 630                 635                 640

Glu Ser Gly Gln Val Tyr Phe Gly Ile Ile Ala Leu
                645                 650

<210> SEQ ID NO 67
<211> LENGTH: 1944
<212> TYPE: DNA
<213> ORGANISM: Artificial Sequence
<220> FEATURE:
<223> OTHER INFORMATION: EHD2-scTNFR2-L16aa

<400> SEQUENCE: 67
atggagacag acacactcct gctatgggta ctgctgctct gggttccagg ttccaccggt      60
gacgcggccc agccggccgg aggcggtgcg gccgcacacc atcatcacca tcacggaggt    120
accggcgggg gaggttcagg cggaaagctt ggcggtctg gcggcgattt cacccccccc     180
acagtgaaga tcctccagag cagctgtgac ggcggaggcc acttcccacc taccatccag    240
ctgctgtgtc tggtgtccgg ctacaccccc ggcaccatca acatcacctg ctgaagat      300 ggacaagtga tggacgtgga cctgagcacc gccagcacca cacaggaagg cgagctggcc    360
tctacccaga gcgagctgac actgagccag aagcactggc tgagcgaccg gacctacacc    420
tgtcaagtga cctaccaggg ccacaccttc aggacagca ccaagaagtg cgccgacagc     480
aacgggggag gatctggcgg aggtaccgga tccgaattcc tcgccagcag ccggaccccct   540 agcgataagc ccgtggccca cgtggtggcc aatcctcagg ccgagggcca gctgcagtgg    600
ctgaacagac gggccaacgc cctgctggcc aacggcgtgg agctgcggga caaccagctg    660
gtcgtgccca gcgagggcct gtacctgatc tacagccagg tgctgttcaa gggccagggc    720
tgcccttcta cccacgtgct gctgacccac accatcagcc ggatcgccgt gagctaccag    780
accaaagtga acctgctgtc cgccatcaag agccctgcc agagagagac acctgagggc    840
gccgaggcca agccttggta cgagcccatc tacctgggcg gcgtgttcca gctggaaaag    900

```
ggcgaccggc tgtccgccga gatcaaccgg cccgactacc tgaacttccg ggagagcggc    960
caggtgtact tcggcatcat agcgctgggc ggaggggggca gcagcagcag aaccccctcc   1020
gacaagcctg tggctcatgt ggtggctaac ccccaggctg aaggacagct gcagtggctg   1080
aatcggagag ctaatgctct gctggctaat ggggtggaac tgagagataa tcagctggtc   1140
gtgccttctg aggggctgta tctgatctat tctcaggtgc tgtttaaagg acaggggtgt   1200
cccagcacac atgtgctgct gacacataca atctccagaa tcgccgtgtc ttatcagaca   1260
aaagtgaatc tgctgagtgc catcaagtcc cctgtcagc gggaaacccc tgaaggggcc    1320
gaagctaaac cttggtatga acctatctat ctggggggag tgtttcagct ggaaaaaggg   1380
gacagactga gcgccgagat taacagacct gattacctga atttcagaga atccgggcag   1440
gtgtactttg ggattatcgc cctgggaggg ggcggatcca gctccagaac ccccagtgac   1500
aaaccagtgg cccatgtggt ggccaaccca caggctgagg ggcagctgca gtggctgaac   1560
cgcagagcca atgccctgct ggccaatggc gtggaactgc gcgacaatca gctggtcgtg   1620
ccatccgaag gactgtacct gatctactca caggtgctgt ttaaggggca gggatgcccc   1680
tccactcatg tgctgctgac tcacactatc tctcggattg ctgtgtccta ccagactaaa   1740
gtgaatctgc tgtctgctat taagtctcct tgccagcgcg agactccaga gggggctgaa   1800
gccaagccct ggtatgagcc aatctatctg gaggggtgt tccagctgga aaggggggat    1860
cgcctgagcg ccgaaatcaa tagaccagac tatctgaact tcgcgagtc tggacaggtg    1920 tactttggaa tcattgctct gtga                                          1944
```

<210> SEQ ID NO 68
<211> LENGTH: 647
<212> TYPE: PRT
<213> ORGANISM: Artificial Sequence
<220> FEATURE:
<223> OTHER INFORMATION: EHD2-scTNFR2-L16aa

<400> SEQUENCE: 68

```
Met Glu Thr Asp Thr Leu Leu Leu Trp Val Leu Leu Leu Trp Val Pro
1               5                   10                  15

Gly Ser Thr Gly Asp Ala Ala Gln Pro Ala Gly Gly Ala Ala Ala
            20                  25                  30

His His His His His His Gly Gly Thr Gly Gly Gly Ser Gly Gly
        35                  40                  45

Lys Leu Gly Gly Ser Gly Gly Asp Phe Thr Pro Pro Thr Val Lys Ile
    50                  55                  60

Leu Gln Ser Ser Cys Asp Gly Gly His Phe Pro Pro Thr Ile Gln
65                  70                  75                  80

Leu Leu Cys Leu Val Ser Gly Tyr Thr Pro Gly Thr Ile Asn Ile Thr
                85                  90                  95

Trp Leu Glu Asp Gly Gln Val Met Asp Val Asp Leu Ser Thr Ala Ser
            100                 105                 110

Thr Thr Gln Glu Gly Glu Leu Ala Ser Thr Gln Ser Glu Leu Thr Leu
        115                 120                 125

Ser Gln Lys His Trp Leu Ser Asp Arg Thr Tyr Thr Cys Gln Val Thr
    130                 135                 140

Tyr Gln Gly His Thr Phe Glu Asp Ser Thr Lys Lys Cys Ala Asp Ser
145                 150                 155                 160

Asn Gly Gly Gly Ser Gly Gly Gly Thr Gly Ser Glu Phe Leu Ala Ser
                165                 170                 175
```

```
Ser Arg Thr Pro Ser Asp Lys Pro Val Ala His Val Val Ala Asn Pro
                180                 185                 190
Gln Ala Glu Gly Gln Leu Gln Trp Leu Asn Arg Arg Ala Asn Ala Leu
            195                 200                 205
Leu Ala Asn Gly Val Glu Leu Arg Asp Asn Gln Leu Val Val Pro Ser
        210                 215                 220
Glu Gly Leu Tyr Leu Ile Tyr Ser Gln Val Leu Phe Lys Gly Gln Gly
225                 230                 235                 240
Cys Pro Ser Thr His Val Leu Leu Thr His Thr Ile Ser Arg Ile Ala
                245                 250                 255
Val Ser Tyr Gln Thr Lys Val Asn Leu Leu Ser Ala Ile Lys Ser Pro
            260                 265                 270
Cys Gln Arg Glu Thr Pro Glu Gly Ala Glu Ala Lys Pro Trp Tyr Glu
        275                 280                 285
Pro Ile Tyr Leu Gly Gly Val Phe Gln Leu Glu Lys Gly Asp Arg Leu
290                 295                 300
Ser Ala Glu Ile Asn Arg Pro Asp Tyr Leu Asn Phe Arg Glu Ser Gly
305                 310                 315                 320
Gln Val Tyr Phe Gly Ile Ile Ala Leu Gly Gly Gly Ser Ser Ser
                325                 330                 335
Arg Thr Pro Ser Asp Lys Pro Val Ala His Val Val Ala Asn Pro Gln
                340                 345                 350
Ala Glu Gly Gln Leu Gln Trp Leu Asn Arg Arg Ala Asn Ala Leu Leu
            355                 360                 365
Ala Asn Gly Val Glu Leu Arg Asp Asn Gln Leu Val Val Pro Ser Glu
        370                 375                 380
Gly Leu Tyr Leu Ile Tyr Ser Gln Val Leu Phe Lys Gly Gln Gly Cys
385                 390                 395                 400
Pro Ser Thr His Val Leu Leu Thr His Thr Ile Ser Arg Ile Ala Val
                405                 410                 415
Ser Tyr Gln Thr Lys Val Asn Leu Leu Ser Ala Ile Lys Ser Pro Cys
            420                 425                 430
Gln Arg Glu Thr Pro Glu Gly Ala Glu Ala Lys Pro Trp Tyr Glu Pro
        435                 440                 445
Ile Tyr Leu Gly Gly Val Phe Gln Leu Glu Lys Gly Asp Arg Leu Ser
450                 455                 460
Ala Glu Ile Asn Arg Pro Asp Tyr Leu Asn Phe Arg Glu Ser Gly Gln
465                 470                 475                 480
Val Tyr Phe Gly Ile Ile Ala Leu Gly Gly Gly Gly Ser Ser Ser Arg
                485                 490                 495
Thr Pro Ser Asp Lys Pro Val Ala His Val Val Ala Asn Pro Gln Ala
            500                 505                 510
Glu Gly Gln Leu Gln Trp Leu Asn Arg Arg Ala Asn Ala Leu Leu Ala
        515                 520                 525
Asn Gly Val Glu Leu Arg Asp Asn Gln Leu Val Val Pro Ser Glu Gly
530                 535                 540
Leu Tyr Leu Ile Tyr Ser Gln Val Leu Phe Lys Gly Gln Gly Cys Pro
545                 550                 555                 560
Ser Thr His Val Leu Leu Thr His Thr Ile Ser Arg Ile Ala Val Ser
                565                 570                 575
Tyr Gln Thr Lys Val Asn Leu Leu Ser Ala Ile Lys Ser Pro Cys Gln
            580                 585                 590
Arg Glu Thr Pro Glu Gly Ala Glu Ala Lys Pro Trp Tyr Glu Pro Ile
```

595                 600                 605
        Tyr Leu Gly Gly Val Phe Gln Leu Glu Lys Gly Asp Arg Leu Ser Ala
            610                 615                 620
        Glu Ile Asn Arg Pro Asp Tyr Leu Asn Phe Arg Glu Ser Gly Gln Val
        625                 630                 635                 640
        Tyr Phe Gly Ile Ile Ala Leu
                        645

<210> SEQ ID NO 69
<211> LENGTH: 1983
<212> TYPE: DNA
<213> ORGANISM: Artificial Sequence
<220> FEATURE:
<223> OTHER INFORMATION: EHD2-scTNFR2-L28aa

<400> SEQUENCE: 69

| | | | | | | |
|---|---|---|---|---|---|---|
| atggagacag | acacactcct | gctatgggta | ctgctgctct | gggttccagg | ttccaccggt | 60 |
| gacgcggccc | agccggccgg | aggcggtgcg | gccgcacacc | atcatcacca | tcacggaggt | 120 |
| accggcgggg | gaggttcagg | cggaaagctt | ggcggctctg | gcggcgattt | caccccccc | 180 |
| acagtgaaga | tcctccagag | cagctgtgac | ggcggaggcc | acttcccacc | taccatccag | 240 |
| ctgctgtgtc | tggtgtccgg | ctacaccccc | ggcaccatca | acatcacctg | gctggaagat | 300 |
| ggacaagtga | tggacgtgga | cctgagcacc | gccagcacca | cacaggaagg | cgagctggcc | 360 |
| tctacccaga | gcgagctgac | actgagccag | aagcactggc | tgagcgaccg | gacctacacc | 420 |
| tgtcaagtga | cctaccaggg | ccacaccttc | gaggacagca | ccaagaagtg | cgccgacagc | 480 |
| aacgggggag | gatctggggg | aggatctggg | ggaggatctg | ggggaggatc | tggcggaggt | 540 |
| tctgggggat | ccgaattcct | cgccagcagc | cggacccta | gcgataagcc | cgtggcccac | 600 |
| gtggtggcca | tcctcaggc | cgagggccag | ctgcagtggc | tgaacagacg | ggccaacgcc | 660 |
| ctgctggcca | acggcgtgga | gctgcgggac | aaccagctgg | tcgtgcccag | cgagggcctg | 720 |
| tacctgatct | acagccaggt | gctgttcaag | ggccagggct | gcccttctac | ccacgtgctg | 780 |
| ctgacccaca | ccatcagccg | gatcgccgtg | agctaccaga | ccaaagtgaa | cctgctgtcc | 840 |
| gccatcaaga | gccctgcca | gagagagaca | cctgagggcg | ccgaggccaa | gccttggtac | 900 |
| gagcccatct | acctgggcgg | cgtgttccag | ctggaaaagg | gcgaccggct | gtccgccgag | 960 |
| atcaaccggc | ccgactacct | gaacttccgg | gagagcggcc | aggtgtactt | cggcatcata | 1020 |
| gcgctgggcg | gagggggcag | cagcagcaga | accccctccg | acaagcctgt | ggctcatgtg | 1080 |
| gtggctaacc | ccaggctga | aggacagctg | cagtggctga | atcggagagc | taatgctctg | 1140 |
| ctggctaatg | ggtggaact | gagagataat | cagctggtcg | tgccttctga | ggggctgtat | 1200 |
| ctgatctatt | ctcaggtgct | gtttaaagga | caggggtgtc | ccagcacaca | tgtgctgctg | 1260 |
| acacatacaa | tctccagaat | cgccgtgtct | tatcagacaa | agtgaatct | gctgagtgcc | 1320 |
| atcaagtccc | cctgtcagcg | ggaaacccct | gaaggggccg | aagctaaacc | ttggtatgaa | 1380 |
| cctatctatc | tggggggagt | gtttcagctg | gaaaaggggg | acagactgag | cgccgagatt | 1440 |
| aacagacctg | attacctgaa | tttcagagaa | tccgggcagg | tgtactttgg | gattatcgcc | 1500 |
| ctgggagggg | gcggatccag | ctccagaacc | cccagtgaca | aaccagtggc | ccatgtggtg | 1560 |
| gccaacccac | aggctgaggg | gcagctgcag | tggctgaacc | gcagagccaa | tgccctgctg | 1620 |
| gccaatggcg | tggaactgcg | cgacaatcag | ctggtcgtgc | catccgaagg | actgtacctg | 1680 |
| atctactcac | aggtgctgtt | taaggggcag | ggatgcccct | ccactcatgt | gctgctgact | 1740 |

```
cacactatct ctcggattgc tgtgtcctac cagactaaag tgaatctgct gtctgctatt    1800
aagtctcctt gccagcgcga gactccagag ggggctgaag ccaagccctg gtatgagcca    1860
atctatctgg gagggtgtt ccagctggaa aaggggatc gcctgagcgc cgaaatcaat     1920
agaccagact atctgaactt tcgcgagtct ggacaggtgt actttggaat cattgctctg    1980
tga                                                                  1983
```

```
<210> SEQ ID NO 70
<211> LENGTH: 660
<212> TYPE: PRT
<213> ORGANISM: Artificial Sequence
<220> FEATURE:
<223> OTHER INFORMATION: EHD2-scTNFR2-L28aa

<400> SEQUENCE: 70
```

Met Glu Thr Asp Thr Leu Leu Leu Trp Val Leu Leu Trp Val Pro
1               5                   10                  15

Gly Ser Thr Gly Asp Ala Ala Gln Pro Ala Gly Gly Ala Ala Ala
            20                  25                  30

His His His His His His Gly Gly Thr Gly Gly Gly Ser Gly Gly
            35                  40                  45

Lys Leu Gly Gly Ser Gly Gly Asp Phe Thr Pro Thr Val Lys Ile
50                  55                  60

Leu Gln Ser Ser Cys Asp Gly Gly His Phe Pro Pro Thr Ile Gln
65                  70                  75                  80

Leu Leu Cys Leu Val Ser Gly Tyr Thr Pro Gly Thr Ile Asn Ile Thr
            85                  90                  95

Trp Leu Glu Asp Gly Gln Val Met Asp Val Asp Leu Ser Thr Ala Ser
            100                 105                 110

Thr Thr Gln Glu Gly Glu Leu Ala Ser Thr Gln Ser Gly Leu Thr Leu
            115                 120                 125

Ser Gln Lys His Trp Leu Ser Asp Arg Thr Tyr Thr Cys Gln Val Thr
130                 135                 140

Tyr Gln Gly His Thr Phe Glu Asp Ser Thr Lys Lys Cys Ala Asp Ser
145                 150                 155                 160

Asn Gly Gly Gly Ser Gly Gly Gly Ser Gly Gly Ser Gly Gly Gly
            165                 170                 175

Ser Gly Gly Gly Ser Gly Gly Ser Glu Phe Leu Ala Ser Ser Arg Thr
            180                 185                 190

Pro Ser Asp Lys Pro Val Ala His Val Val Ala Asn Pro Gln Ala Glu
            195                 200                 205

Gly Gln Leu Gln Trp Leu Asn Arg Arg Ala Asn Ala Leu Leu Ala Asn
            210                 215                 220

Gly Val Glu Leu Arg Asp Asn Gln Leu Val Val Pro Ser Glu Gly Leu
225                 230                 235                 240

Tyr Leu Ile Tyr Ser Gln Val Leu Phe Lys Gly Gln Gly Cys Pro Ser
            245                 250                 255

Thr His Val Leu Leu Thr His Thr Ile Ser Arg Ile Ala Val Ser Tyr
            260                 265                 270

Gln Thr Lys Val Asn Leu Leu Ser Ala Ile Lys Ser Pro Cys Gln Arg
            275                 280                 285

Glu Thr Pro Glu Gly Ala Glu Ala Lys Pro Trp Tyr Glu Pro Ile Tyr
            290                 295                 300

Leu Gly Gly Val Phe Gln Leu Glu Lys Gly Asp Arg Leu Ser Ala Glu
305                 310                 315                 320

-continued

```
Ile Asn Arg Pro Asp Tyr Leu Asn Phe Arg Glu Ser Gly Gln Val Tyr
            325                 330                 335
Phe Gly Ile Ile Ala Leu Gly Gly Gly Ser Ser Arg Thr Pro
            340             345             350
Ser Asp Lys Pro Val Ala His Val Val Ala Asn Pro Gln Ala Glu Gly
            355                 360                 365
Gln Leu Gln Trp Leu Asn Arg Arg Ala Asn Ala Leu Leu Ala Asn Gly
        370                 375                 380
Val Glu Leu Arg Asp Asn Gln Leu Val Val Pro Ser Glu Gly Leu Tyr
385                 390                 395                 400
Leu Ile Tyr Ser Gln Val Leu Phe Lys Gly Gln Gly Cys Pro Ser Thr
                405                 410                 415
His Val Leu Leu Thr His Thr Ile Ser Arg Ile Ala Val Ser Tyr Gln
                420                 425                 430
Thr Lys Val Asn Leu Leu Ser Ala Ile Lys Ser Pro Cys Gln Arg Glu
            435                 440                 445
Thr Pro Glu Gly Ala Glu Ala Lys Pro Trp Tyr Glu Pro Ile Tyr Leu
        450                 455                 460
Gly Gly Val Phe Gln Leu Glu Lys Gly Asp Arg Leu Ser Ala Glu Ile
465                 470                 475                 480
Asn Arg Pro Asp Tyr Leu Asn Phe Arg Glu Ser Gly Gln Val Tyr Phe
                485                 490                 495
Gly Ile Ile Ala Leu Gly Gly Gly Ser Ser Ser Arg Thr Pro Ser
                500                 505                 510
Asp Lys Pro Val Ala His Val Val Ala Asn Pro Gln Ala Glu Gly Gln
            515                 520                 525
Leu Gln Trp Leu Asn Arg Arg Ala Asn Ala Leu Leu Ala Asn Gly Val
        530                 535                 540
Glu Leu Arg Asp Asn Gln Leu Val Val Pro Ser Glu Gly Leu Tyr Leu
545                 550                 555                 560
Ile Tyr Ser Gln Val Leu Phe Lys Gly Gln Gly Cys Pro Ser Thr His
                565                 570                 575
Val Leu Leu Thr His Thr Ile Ser Arg Ile Ala Val Ser Tyr Gln Thr
                580                 585                 590
Lys Val Asn Leu Leu Ser Ala Ile Lys Ser Pro Cys Gln Arg Glu Thr
            595                 600                 605
Pro Glu Gly Ala Glu Ala Lys Pro Trp Tyr Glu Pro Ile Tyr Leu Gly
        610                 615                 620
Gly Val Phe Gln Leu Glu Lys Gly Asp Arg Leu Ser Ala Glu Ile Asn
625                 630                 635                 640
Arg Pro Asp Tyr Leu Asn Phe Arg Glu Ser Gly Gln Val Tyr Phe Gly
                645                 650                 655
Ile Ile Ala Leu
            660
```